US008835607B2

(12) United States Patent
Dreier et al.

(10) Patent No.: US 8,835,607 B2
(45) Date of Patent: *Sep. 16, 2014

(54) HUMANIZED ANTIBODIES

(75) Inventors: Torten Dreier, Saint-Martens Latem (BE); Johannes Joseph Wilhelmus De Haard, Oudelande (NL)

(73) Assignee: arGEN-X B.V., Breda (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/984,402

(22) Filed: Jan. 4, 2011

(65) Prior Publication Data

US 2011/0165621 A1    Jul. 7, 2011

Related U.S. Application Data

(60) Provisional application No. 61/292,028, filed on Jan. 4, 2010.

(30) Foreign Application Priority Data

Jan. 4, 2010  (GB) .................................. 1000064.4

(51) Int. Cl.
- *C12P 21/08* (2006.01)
- *C07K 16/24* (2006.01)
- *C07K 16/46* (2006.01)

(52) U.S. Cl.
CPC ........... *C07K 16/245* (2013.01); *C07K 2317/24* (2013.01); *C07K 2317/56* (2013.01); *C07K 2317/76* (2013.01); *C07K 16/467* (2013.01); *C07K 16/461* (2013.01); *C07K 2317/22* (2013.01); *C07K 2316/96* (2013.01); *C07K 2317/567* (2013.01); *C07K 2317/55* (2013.01)
USPC ..................................................... 530/387.3

(58) Field of Classification Search
None
See application file for complete search history.

(56) References Cited

U.S. PATENT DOCUMENTS

2005/0070692 A1   3/2005   Beals
2009/0130123 A1*  5/2009   Fikrig et al. ............... 424/159.1

FOREIGN PATENT DOCUMENTS

| | | |
|---|---|---|
| GB | 2461546 | 7/2010 |
| WO | WO 2008070344 A2 * | 6/2008 |
| WO | WO 2008/142165 | 11/2008 |
| WO | WO 2009/004065 | 1/2009 |
| WO | WO2009/135953 | 11/2009 |
| WO | WO 2010/001251 | 1/2010 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Pelat T et al: "Germline Humanization of a Non-human Primate Antibody that Neutralizes the Anthrax Toxin, by in Vitro and in Silico Engineering", Journal of Molecular Biology, London, GB, vol. 384, No. 5, Dec. 31, 2008, pp. 1400-1407, XP025744838.
Morea V et al: "Antibody Modeling: Implications for Engineering and Design", Methods : A Companion to Methods in Enzymology, Academic Press Inc., New York, NY, US, vol. 20, No. 3, Mar. 1, 2000, pp. 267-279, XP004466884.
Legssyer I: "The camel (*Camelus dromedarius*) immunoglobulin light chains", Jun. 1, 2002, Thesis Urije Uniuersiteit Brussel, Brussels, pp. 1-59, XP002562099.
Vu K B et al: "Comparison of llama VH sequences from conventional and heavy chain antibodies.", Molecular Immunology Nov.-Dec. 1997 LNKD-PUBMED:9566760, vol. 34, No. 16-17, Nov. 1997, pp. 1121-1131, XP002628905.
Scaviner D: "Protein display: Llama (*Lama glama*) IGH U-REGIONs", Internet Citation, Feb. 5, 2002, p. 1, XP002562101, Retrieved from the Internet: URL:http://www.imgt.org/textes/IMGTrepertoire/Proteins/protein/Lama/IGH/IGHU/Lg IGHUallgenes.html.
Scaviner D: "Protein display: Llama (*Lama glama*) IGH J-REGIONs", Internet Citation, Jul. 1, 2002, p. 1, XP002562100, Retrieved from the Internet: URL:http://imgt.cines.fr/textes/IMGTrepertoire/Proteins/protein/Lama/IGH/IGHJ/LgIGHJallgenes.html.
Martinez-Jean C and Jabado-Michaloud J: "Protein display: Arabian camel (*Camelus dromedarius*) IGH C-REGIONs", Internet Citation, Jul. 1, 2002, p. 1, XP002562103, Retrieved from the Internet: URL:http://www.imgt.org/textes/IMGTrepertoire/Proteins/protein/camel/IGH/IGHC/Cd IGHCallgenes.html.
Vincke C et al: "General Strategy to Humanize a Camelid Single-domain Antibody and Identification of a Universal Humanized Nanobody Scaffold", Journal of Biological Chemistry 284 (2009), pp. 3273-3284, PREV200900151404.
Conrath K et al: "Antigen Binding and Solubility Effects upon the Veneering of a Camel VHH in Framework-2 to Mimic a VH", Journal of Molecular Biology 350 (2005), pp. 112-125, XP004918534.
Achour I et al: "Tetrameric and Homodimeric Camelid IgGs Originate from the Same IgH Locus", J Immunol 2008 181: 2001-2009.
Combined Search and Examination Report from GB1000064.4 dated May 5, 2012.
International Search Report & Written Opinion from PCT/EP2011/050071, dated Mar. 18, 2011.

* cited by examiner

*Primary Examiner* — Hong Sang
(74) *Attorney, Agent, or Firm* — Lathrop & Gage LLP; James H. Velema, Esq.; Andrew T. Wilkins, Esq.

(57) ABSTRACT

The invention relates to novel humanized antibodies derived from the conventional antibody repertoire of species in the family Camelidae.

33 Claims, 124 Drawing Sheets

Fig. 2A

Sequences of fully human and safe variants of Fab 1E2 and 1F2

TABLE 1: COMPARISON OF LLAMA GLAMA MATURE CONSENSUS SEQUENCES WITH HUMAN GERMLINE CONSENSUS SEQUENCES

Lama glama VH4-30-4 germlined towards human VH6; Framework Region 1)

| NUMBERING | H1 | H2 | H3 | H4 | H5 | H6 | H7 | H8 | H9 | H10 | H11 | H12 | H13 | H14 | H15 | H16 | H17 | H18 | H19 | H20 | H21 | H22 | H23 | H24 | H25 | H26 | H27 | H28 | H29 | H30 |
|---|---|---|---|---|---|---|---|---|---|---|---|---|---|---|---|---|---|---|---|---|---|---|---|---|---|---|---|---|---|---|
| VH4-30-1 LAMA GLAMA Consensus | | V | Q | L | Q | E | S | G | P | G | L | V | K | P | S | Q | T | L | S | L | T | C | T | V | S | G | G | S | Y | T |
| VH6 HUMAN Consensus | Q | V | Q | L | Q | Q | S | G | P | G | L | V | K | P | S | Q | T | L | S | L | T | C | A | I | S | G | D | S | V | S |

Lama glama VH4-30-4 germlined towards human VH7; Framework Region 1)

| NUMBERING | H1 | H2 | H3 | H4 | H5 | H6 | H7 | H8 | H9 | H10 | H11 | H12 | H13 | H14 | H15 | H16 | H17 | H18 | H19 | H20 | H21 | H22 | H23 | H24 | H25 | H26 | H27 | H28 | H29 | H30 |
|---|---|---|---|---|---|---|---|---|---|---|---|---|---|---|---|---|---|---|---|---|---|---|---|---|---|---|---|---|---|---|
| VH4-30-4 LAMA GLAMA Consensus | - | V | Q | L | Q | E | S | G | P | G | L | V | K | P | S | Q | T | L | S | L | T | C | T | V | S | G | G | S | I | T |
| VH7 HUMAN Consensus | Q | V | Q | L | V | Q | S | G | S | E | L | K | K | P | G | A | S | V | K | V | S | C | K | A | S | G | Y | T | F | T |

*Fig. 6J*

TABLE 2: COMPARISON OF LLAMA GLAMA MATURE CONSENSUS SEQUENCES WITH HUMAN GERMLINE CONSENSUS SEQUENCES

Lama glama VH1-46 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA GLAMA Consensus | W | V | R | Q | A | P | G | Q | G | L | E | W | M | G |
| VH1 | HUMAN Consensus | W | V | R | Q | A | P | G | Q | G | L | E | W | M | G |

Lama glama VH1-46 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA GLAMA Consensus | W | V | R | Q | A | P | G | Q | G | L | E | W | M | G |
| VH2 | HUMAN Consensus | W | I | R | Q | P | P | G | K | A | L | E | W | L | A |

Lama glama VH1-46 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA GLAMA Consensus | W | V | R | Q | A | P | G | Q | G | L | E | W | M | G |
| VH3 | HUMAN Consensus | W | V | R | Q | A | P | G | K | G | L | E | W | V | S |

Lama glama VH1-46 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA GLAMA Consensus | W | V | R | Q | A | P | G | Q | G | L | E | W | M | G |
| VH4 | HUMAN Consensus | W | I | R | Q | P | P | G | K | G | L | E | W | I | G |

Lama glama VH1-46 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA GLAMA Consensus | W | V | R | Q | A | P | G | Q | G | L | E | W | M | G |
| VH5 | HUMAN Consensus | W | V | R | Q | M | P | G | K | G | L | E | W | M | G |

Lama glama VH1-46 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA GLAMA Consensus | W | V | R | Q | A | P | G | Q | G | L | E | W | M | G |
| VH6 | HUMAN Consensus | W | I | R | Q | S | P | S | R | G | L | E | W | L | G |

*Fig. 7A*

TABLE 2: COMPARISON OF LLAMA GLAMA MATURE CONSENSUS SEQUENCES WITH HUMAN GERMLINE CONSENSUS SEQUENCES
Lama glama VH1-46 germlined towards human VH7 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA GLAMA Consensus | W | V | R | Q | A | P | G | Q | G | L | E | W | M | G |
| VH7 | HUMAN Consensus | W | V | R | Q | A | P | G | Q | G | L | E | W | M | G |

COMPARISON OF LAMA GLAMA VH3-11 CONSENSUS SEQUENCE TO HUMAN CONSENSUS GERMLINES OF VH

Lama glama VH3-11 germlined towards human VH1 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-11 | LAMA GLAMA Consensus | W | V | R | Q | A | P | G | K | G | L | E | W | V | S |
| VH1 | HUMAN Consensus | W | V | R | Q | A | P | G | Q | G | L | E | W | M | G |

Lama glama VH3-11 germlined towards human VH2 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-11 | LAMA GLAMA Consensus | W | V | R | Q | A | P | G | K | G | L | E | W | V | S |
| VH2 | HUMAN Consensus | W | I | R | Q | P | P | G | K | A | L | E | W | L | A |

Lama glama VH3-11 germlined towards human VH3 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-11 | LAMA GLAMA Consensus | W | V | R | Q | A | P | G | K | G | L | E | W | V | S |
| VH3 | HUMAN Consensus | W | V | R | Q | A | P | G | K | G | L | E | W | V | S |

Lama glama VH3-11 germlined towards human VH4 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-11 | LAMA GLAMA Consensus | W | V | R | Q | A | P | G | K | G | L | E | W | V | S |
| VH4 | HUMAN Consensus | W | I | R | Q | P | P | G | K | G | L | E | W | I | G |

Lama glama VH3-11 germlined towards human VH5 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-11 | LAMA GLAMA Consensus | W | V | R | Q | A | P | G | K | G | L | E | W | V | S |
| VH5 | HUMAN Consensus | W | V | R | Q | M | P | G | K | G | L | E | W | M | G |

Fig. 7B

TABLE 2: COMPARISON OF LLAMA GLAMA MATURE CONSENSUS SEQUENCES WITH HUMAN GERMLINE CONSENSUS SEQUENCES

Lama glama VH3-11 germlined towards human VH6 (Framework Region 2)

|  |  |  |  |  |  |  |  |  |  |  |  |  |  |  |
|---|---|---|---|---|---|---|---|---|---|---|---|---|---|---|
|  |  |  |  |  |  | x |  | x | x |  |  |  |  | x x |
|  | NUMBERING | H36 | H37 | H38 | H39 | H40 | H41 | H42 | H43 | H44 | H45 | H46 | H47 | H48 H49 |
| VH3-11 | LAMA GLAMA Consensus | W | V | R | Q | A | P | G | K | G | L | E | W | V S |
| VH6 | HUMAN Consensus | W | I | R | Q | S | P | S | R | G | L | E | W | L G |

Lama glama VH3-11 germlined towards human VH7 (Framework Region 2)

|  |  |  |  |  |  |  |  |  |  |  |  |  |  |  |
|---|---|---|---|---|---|---|---|---|---|---|---|---|---|---|
|  |  |  |  |  |  |  |  |  | x |  |  |  |  | x x |
|  | NUMBERING | H36 | H37 | H38 | H39 | H40 | H41 | H42 | H43 | H44 | H45 | H46 | H47 | H48 H49 |
| VH3-11 | LAMA GLAMA Consensus | W | V | R | Q | A | P | G | K | G | L | E | W | V S |
| VH7 | HUMAN Consensus | W | V | R | Q | A | P | G | Q | G | L | E | W | M G |

COMPARISON OF LAMA GLAMA VH3-21 CONSENSUS SEQUENCE TO HUMAN CONSENSUS GERMLINES OF VH

Lama glama VH3-21 germlined towards human VH1 (Framework Region 2)

|  |  |  |  |  |  |  |  |  |  |  |  |  |  |  |
|---|---|---|---|---|---|---|---|---|---|---|---|---|---|---|
|  |  |  |  |  |  |  |  |  | x |  |  |  |  | x x |
|  | NUMBERING | H36 | H37 | H38 | H39 | H40 | H41 | H42 | H43 | H44 | H45 | H46 | H47 | H48 H49 |
| VH3-21 | LAMA GLAMA Consensus | W | V | R | Q | A | P | G | K | G | L | E | W | V S |
| VH1 | HUMAN Consensus | W | V | R | Q | A | P | G | Q | G | L | E | W | M G |

Lama glama VH3-21 germlined towards human VH2 (Framework Region 2)

|  |  |  |  |  |  |  |  |  |  |  |  |  |  |  |
|---|---|---|---|---|---|---|---|---|---|---|---|---|---|---|
|  |  |  | x |  |  | x |  |  |  | x |  |  |  | x x |
|  | NUMBERING | H36 | H37 | H38 | H39 | H40 | H41 | H42 | H43 | H44 | H45 | H46 | H47 | H48 H49 |
| VH3-21 | LAMA GLAMA Consensus | W | V | R | Q | A | P | G | K | G | L | E | W | V S |
| VH2 | HUMAN Consensus | W | I | R | Q | P | P | G | K | A | L | E | W | L A |

Lama glama VH3-21 germlined towards human VH3 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|---|
| VH3-21 | LAMA GLAMA Consensus | W | V | R | Q | A | P | G | K | G | L | E | W | V | S |
| VH3 | HUMAN Consensus | W | V | R | Q | A | P | G | K | G | L | E | W | V | S |

Lama glama VH3-21 germlined towards human VH4 (Framework Region 2)

|  |  |  |  |  |  |  |  |  |  |  |  |  |  |  |
|---|---|---|---|---|---|---|---|---|---|---|---|---|---|---|
|  |  |  | x |  |  | x |  |  |  |  |  |  |  | x x |
|  | NUMBERING | H36 | H37 | H38 | H39 | H40 | H41 | H42 | H43 | H44 | H45 | H46 | H47 | H48 H49 |
| VH3-21 | LAMA GLAMA Consensus | W | V | R | Q | A | P | G | K | G | L | E | W | V S |
| VH4 | HUMAN Consensus | W | I | R | Q | P | P | G | K | G | L | E | W | I G |

Fig. 7C

TABLE 2: COMPARISON OF LLAMA GLAMA MATURE CONSENSUS SEQUENCES WITH HUMAN GERMLINE CONSENSUS SEQUENCES

Lama glama VH3-21 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-21 | LAMA GLAMA Consensus | W | V | R | Q | A | P | G | K | G | L | E | W | V | S |
| VH5 | HUMAN Consensus | W | V | R | Q | M | P | G | K | G | L | E | W | M | G |

Lama glama VH3-21 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-21 | LAMA GLAMA Consensus | W | V | R | Q | A | P | G | K | G | L | E | W | V | S |
| VH6 | HUMAN Consensus | W | I | R | Q | S | P | S | R | G | L | E | W | L | G |

Lama glama VH3-21 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-21 | LAMA GLAMA Consensus | W | V | R | Q | A | P | G | K | G | L | E | W | V | S |
| VH7 | HUMAN Consensus | W | V | R | Q | A | P | G | Q | G | L | E | W | M | G |

COMPARISON OF LAMA GLAMA VH3-23 CONSENSUS SEQUENCE TO HUMAN CONSENSUS GERMLINES OF VH

Lama glama VH3-23 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-23 | LAMA GLAMA Consensus | W | V | R | Q | A | P | G | K | G | L | E | W | V | S |
| VH1 | HUMAN Consensus | W | V | R | Q | A | P | G | Q | G | L | E | W | M | G |

Lama glama VH3-23 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-23 | LAMA GLAMA Consensus | W | V | R | Q | A | P | G | K | G | L | E | W | V | S |
| VH2 | HUMAN Consensus | W | I | R | Q | P | P | G | K | A | L | E | W | L | A |

Lama glama VH3-23 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-23 | LAMA GLAMA Consensus | W | V | R | Q | A | P | G | K | G | L | E | W | V | S |
| VH3 | HUMAN Consensus | W | V | R | Q | A | P | G | K | G | L | E | W | V | S |

Fig. 7D

TABLE 2: COMPARISON OF LLAMA GLAMA MATURE CONSENSUS SEQUENCES WITH HUMAN GERMLINE CONSENSUS SEQUENCES

Lama glama VH3-23 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-23 | LAMA GLAMA Consensus | W | V | R | Q | A | P | G | K | G | L | E | W | V | S |
| VH4 | HUMAN Consensus | W | I | R | Q | P | P | G | K | G | L | E | W | I | G |

Lama glama VH3-23 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-23 | LAMA GLAMA Consensus | W | V | R | Q | A | P | G | K | G | L | E | W | V | S |
| VH5 | HUMAN Consensus | W | V | R | Q | M | P | G | K | G | L | E | W | M | G |

Lama glama VH3-23 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-23 | LAMA GLAMA Consensus | W | V | R | Q | A | P | G | K | G | L | E | W | V | S |
| VH6 | HUMAN Consensus | W | I | R | Q | S | P | S | R | G | L | E | W | L | G |

Lama glama VH3-23 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-23 | LAMA GLAMA Consensus | W | V | R | Q | A | P | G | K | G | L | E | W | V | S |
| VH7 | HUMAN Consensus | W | V | R | Q | A | P | G | Q | G | L | E | W | M | G |

COMPARISON OF LAMA GLAMA VH3-48 CONSENSUS SEQUENCE TO HUMAN CONSENSUS GERMLINES OF VH

Lama glama VH3-48 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA GLAMA Consensus | W | V | R | Q | A | P | G | K | G | L | E | W | V | S |
| VH1 | HUMAN Consensus | W | V | R | Q | A | P | G | Q | G | L | E | W | M | G |

Lama glama VH3-48 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA GLAMA Consensus | W | V | R | Q | A | P | G | K | G | L | E | W | V | S |
| VH2 | HUMAN Consensus | W | I | R | Q | P | P | G | K | A | L | E | W | L | A |

Fig. 7E

TABLE 2: COMPARISON OF LLAMA GLAMA MATURE CONSENSUS SEQUENCES WITH HUMAN GERMLINE CONSENSUS SEQUENCES

Lama glama VH3-48 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA GLAMA Consensus | W | V | R | Q | A | P | G | K | G | L | E | W | V | S |
| VH3 | HUMAN Consensus | W | V | R | Q | A | P | G | K | G | L | E | W | V | S |

Lama glama VH3-48 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| | | | x | | | | | | | | | | | x | x |
| VH3-48 | LAMA GLAMA Consensus | W | V | R | Q | A | P | G | K | G | L | E | W | V | S |
| VH4 | HUMAN Consensus | W | I | R | Q | P | P | G | K | G | L | E | W | I | G |

Lama glama VH3-48 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| | | | | | | x | | | | | | | | x | x |
| VH3-48 | LAMA GLAMA Consensus | W | V | R | Q | A | P | G | K | G | L | E | W | V | S |
| VH5 | HUMAN Consensus | W | V | R | Q | M | P | G | K | G | L | E | W | M | G |

Lama glama VH3-48 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| | | | x | | | x | | x | x | | | | | x | |
| VH3-48 | LAMA GLAMA Consensus | W | V | R | Q | A | P | G | K | G | L | E | W | V | S |
| VH6 | HUMAN Consensus | W | I | R | Q | S | P | S | R | G | L | E | W | L | G |

Lama glama VH3-48 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| | | | | | | | | | x | | | | | x | x |
| VH3-48 | LAMA GLAMA Consensus | W | V | R | Q | A | P | G | K | G | L | E | W | V | S |
| VH7 | HUMAN Consensus | W | V | R | Q | A | P | G | Q | G | L | E | W | M | G |

COMPARISON OF LAMA GLAMA VH3-66 CONSENSUS SEQUENCE TO HUMAN CONSENSUS GERMLINES OF VH

Lama glama VH3-66 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| | | | | | | | | | x | | | | | x | x |
| VH3-66 | LAMA GLAMA Consensus | W | V | R | Q | A | P | G | K | G | L | E | W | V | S |
| VH1 | HUMAN Consensus | W | V | R | Q | A | P | G | Q | G | L | E | W | M | G |

*Fig. 7F*

TABLE 2: COMPARISON OF LLAMA GLAMA MATURE CONSENSUS SEQUENCES WITH HUMAN GERMLINE CONSENSUS SEQUENCES
Lama glama VH3-66 germlined towards human VH2 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA GLAMA Consensus | W | V | R | Q | A | P | G | K | G | L | E | W | V | S |
| VH2 | HUMAN Consensus | W | I | R | Q | P | P | G | K | A | L | E | W | L | A |

Lama glama VH3-66 germlined towards human VH3 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA GLAMA Consensus | W | V | R | Q | A | P | G | K | G | L | E | W | V | S |
| VH3 | HUMAN Consensus | W | V | R | Q | A | P | G | K | G | L | E | W | V | S |

Lama glama VH3-66 germlined towards human VH4 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA GLAMA Consensus | W | V | R | Q | A | P | G | K | G | L | E | W | V | S |
| VH4 | HUMAN Consensus | W | I | R | Q | P | P | G | K | G | L | E | W | I | G |

Lama glama VH3-66 germlined towards human VH5 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA GLAMA Consensus | W | V | R | Q | A | P | G | K | G | L | E | W | V | S |
| VH5 | HUMAN Consensus | W | V | R | Q | M | P | G | K | G | L | E | W | M | G |

Lama glama VH3-66 germlined towards human VH6 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA GLAMA Consensus | W | V | R | Q | A | P | G | K | G | L | E | W | V | S |
| VH6 | HUMAN Consensus | W | I | R | Q | S | P | S | R | G | L | E | W | L | G |

Lama glama VH3-66 germlined towards human VH7 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA GLAMA Consensus | W | V | R | Q | A | P | G | K | G | L | E | W | V | S |
| VH7 | HUMAN Consensus | W | V | R | Q | A | P | G | Q | G | L | E | W | M | G |

Fig. 7G

TABLE 2: COMPARISON OF LLAMA GLAMA MATURE CONSENSUS SEQUENCES WITH HUMAN GERMLINE CONSENSUS SEQUENCES
COMPARISON OF LAMA GLAMA VH3-48 CONSENSUS SEQUENCE TO HUMAN CONSENSUS GERMLINES OF VH

Lama glama VH3 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA GLAMA Consensus | W | V | R | Q | A | P | G | K | G | L | E | W | V | S |
| VH1 | HUMAN Consensus | W | V | R | Q | A | P | G | Q | G | L | E | W | M | G |

Lama glama VH3 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA GLAMA Consensus | W | V | R | Q | A | P | G | K | G | L | E | W | V | S |
| VH2 | HUMAN Consensus | W | I | R | Q | P | P | G | K | A | L | E | W | L | A |

Lama glama VH3 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA GLAMA Consensus | W | V | R | Q | A | P | G | K | G | L | E | W | V | S |
| VH3 | HUMAN Consensus | W | V | R | Q | A | P | G | K | G | L | E | W | V | S |

Lama glama VH3 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA GLAMA Consensus | W | V | R | Q | A | P | G | K | G | L | E | W | V | S |
| VH4 | HUMAN Consensus | W | I | R | Q | P | P | G | K | G | L | E | W | I | G |

Lama glama VH3 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA GLAMA Consensus | W | V | R | Q | A | P | G | K | G | L | E | W | V | S |
| VH5 | HUMAN Consensus | W | V | R | Q | M | P | G | K | G | L | E | W | M | G |

Lama glama VH3 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA GLAMA Consensus | W | V | R | Q | A | P | G | K | G | L | E | W | V | S |
| VH6 | HUMAN Consensus | W | I | R | Q | S | P | S | R | G | L | E | W | L | G |

*Fig. 7H*

TABLE 2: COMPARISON OF LLAMA GLAMA MATURE CONSENSUS SEQUENCES WITH HUMAN GERMLINE CONSENSUS SEQUENCES

Lama glama VH3 germlined towards human VH7 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  |  |  |  |  |  |  | x |  |  |  |  | x | x |
| VH3 | LAMA GLAMA Consensus | W | V | R | Q | A | P | G | K | G | L | E | W | V | S |
| VH7 | HUMAN Consensus | W | V | R | Q | A | P | G | Q | G | L | E | W | M | G |

COMPARISON OF LAMA GLAMA VH4-30-4 CONSENSUS SEQUENCE TO HUMAN CONSENSUS GERMLINES OF VH

Lama glama VH4-30-4 germlined towards human VH1 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  | x |  |  | x |  |  | x |  |  |  |  |  |  |
| VH4-30-4 | LAMA GLAMA Consensus | W | I | R | Q | P | P | G | K | G | L | E | W | M | G |
| VH1 | HUMAN Consensus | W | V | R | Q | A | P | G | Q | G | L | E | W | M | G |

Lama glama VH4-30-4 germlined towards human VH2 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  |  |  |  |  |  |  |  | x |  |  |  | x | x |
| VH4-30-4 | LAMA GLAMA Consensus | W | I | R | Q | P | P | G | K | G | L | E | W | M | G |
| VH2 | HUMAN Consensus | W | I | R | Q | P | P | G | K | A | L | E | W | L | A |

Lama glama VH4-30-4 germlined towards human VH3 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  | x |  |  | x |  |  |  |  |  |  |  | x | x |
| VH4-30-4 | LAMA GLAMA Consensus | W | I | R | Q | P | P | G | K | G | L | E | W | M | G |
| VH3 | HUMAN Consensus | W | V | R | Q | A | P | G | K | G | L | E | W | V | S |

Lama glama VH4-30-4 germlined towards human VH4 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  |  |  |  |  |  |  |  |  |  |  |  | x |  |
| VH4-30-4 | LAMA GLAMA Consensus | W | I | R | Q | P | P | G | K | G | L | E | W | M | G |
| VH4 | HUMAN Consensus | W | I | R | Q | P | P | G | K | G | L | E | W | I | G |

Lama glama VH4-30-4 germlined towards human VH5 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  | x |  |  | x |  |  |  |  |  |  |  |  |  |
| VH4-30-4 | LAMA GLAMA Consensus | W | I | R | Q | P | P | G | K | G | L | E | W | M | G |
| VH5 | HUMAN Consensus | W | V | R | Q | M | P | G | K | G | L | E | W | M | G |

*Fig. 7I*

TABLE 2: COMPARISON OF LLAMA GLAMA MATURE CONSENSUS SEQUENCES WITH HUMAN GERMLINE CONSENSUS SEQUENCES

Lama glama VH4-30-4 germlined towards human VH6 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  |  |  |  | X |  | X | X |  |  |  |  | X |  |
| VH4-30-4 | LAMA GLAMA Consensus | W | I | R | Q | P | P | G | K | G | L | E | W | M | G |
| VH6 | HUMAN Consensus | W | I | R | Q | S | P | S | R | G | L | E | W | L | G |

Lama glama VH4-30-4 germlined towards human VH7 (Framework Region 2)

|  | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
|  |  |  | X |  |  | X |  |  | X |  |  |  |  |  |  |
| VH4-30-4 | LAMA GLAMA Consensus | W | I | R | Q | P | P | G | K | G | L | E | W | M | G |
| VH7 | HUMAN Consensus | W | V | R | Q | A | P | G | Q | G | L | E | W | M | G |

*Fig. 7J*

TABLE 3: COMPARISON OF LLAMA GLAMA MATURE CONSENSUS SEQUENCES WITH HUMAN GERMLINE CONSENSUS SEQUENCES

L. glama VH1-46 germlined towards human VH1 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | | | x | | x | | | | | | | | | x | | | | | | | | | | | | | | | | | |
| VH1-46 L. glama Consensus | R | V | T | F | T | A | D | T | S | T | S | T | A | Y | V | E | L | S | S | L | R | S | E | D | T | A | V | Y | Y | C | A | R |
| VH1 HUMAN Consensus | R | V | T | I | T | R | D | T | S | T | S | T | A | Y | M | E | L | S | S | L | R | S | E | D | T | A | V | Y | Y | C | A | R |

L. glama VH1-46 germlined towards human VH2 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|---|---|---|---|---|---|---|---|---|---|---|---|---|---|---|---|
| | | x | x | x | x | x | | | x | x | x | x | x | x | x | x | x | x | x | x | x | x | x | | | x | x | | | | | x | |
| VH1-46 L. glama Consensus | R | V | T | F | T | A | D | T | S | T | S | T | A | Y | V | E | L | S | S | L | R | S | E | D | T | A | V | Y | Y | C | A | R | |
| VH2 HUMAN Consensus | R | L | T | I | S | K | D | T | S | K | N | Q | V | V | L | T | M | T | N | M | D | P | V | D | T | A | T | Y | Y | C | A | R | - |

L. glama VH1-46 germlined towards human VH3 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | | x | x | x | x | x | | | x | x | x | x | | | x | | x | x | | | x | x | | | | | | | | | |
| VH1-46 L. glama Consensus | R | V | T | F | T | A | D | T | S | T | S | T | A | Y | V | E | L | S | S | L | R | S | E | D | T | A | V | Y | Y | C | A | R |
| VH3 HUMAN Consensus | R | F | T | I | S | R | D | N | S | K | N | T | L | Y | L | Q | M | N | S | L | R | A | E | D | T | A | V | Y | Y | C | A | R |

L. glama VH1-46 germlined towards human VH4 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | | x | x | x | x | x | | | x | x | x | x | | | x | x | | | x | x | x | x | x | | | | | | | | |
| VH1-46 L. glama Consensus | R | V | T | F | T | A | D | T | S | T | S | T | A | Y | V | E | L | S | S | L | R | S | E | D | T | A | V | Y | Y | C | A | R |
| VH4 HUMAN Consensus | R | V | T | I | S | V | D | T | S | K | N | Q | F | S | L | K | L | S | S | V | T | A | A | D | T | A | V | Y | Y | C | A | R |

*Fig. 8A*

TABLE 3: COMPARISON OF LLAMA GLAMA MATURE CONSENSUS SEQUENCES WITH HUMAN GERMLINE CONSENSUS SEQUENCES

L. glama VH1-46 germlined towards human VH5 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | x | | | | | | x | | | x | | | | | x | x | x | | | | x | x | x | | | | x | | | | | |
| VH1-46 L. glama Consensus | R | V | T | F | T | A | D | T | S | T | S | T | A | Y | V | L | S | S | S | L | R | S | E | D | T | A | V | Y | Y | C | A | R |
| VH5 HUMAN Consensus | H/Q | V | | I | S | A | D | K | S | I | S | T | A | Y | L | Q | W | S | S | L | K | A | S | D | T | A | M | Y | Y | C | A | R |

L. glama VH1-46 germlined towards human VH6 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | x | x | | | | | x | x | x | x | x | x | x | x | | x | | | x | x | x | | | | | | | | | |
| VH1-46 L. glama Consensus | R | V | T | T | A | D | T | S | T | S | T | A | Y | V | E | L | S | S | S | L | R | S | E | D | T | A | V | Y | Y | C | A | R |
| VH6 HUMAN Consensus | R | I | T | I | N | P | D | T | S | K | N | Q | F | S | L | Q | L | N | S | V | T | P | E | D | T | A | M | Y | Y | C | A | R |

L. glama VH1-46 germlined towards human VH7 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | x | x | | | | x | | | | | x | x | | | | | x | x | x | | | | | | | | | |
| VH1-46 L. glama Consensus | R | V | T | F | T | A | D | T | S | T | S | T | A | Y | V | E | L | S | S | S | L | R | S | E | D | T | A | V | Y | Y | C | A | R |
| VH7 HUMAN Consensus | R | F | V | F | S | L | D | T | S | V | S | T | A | Y | L | Q | I | C | S | L | K | A | E | D | T | A | V | Y | Y | C | A | R |

COMPARISON OF L. glama VH3-11 CONSENSUS SEQUENCE TO HUMAN CONSENSUS GERMLINES OF VH L. glama VH3-11 germlined towards human VH1 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | x | | | | | | | x | x | x | x | x | | x | | x | x | | | | x | x | | | | | | | | | x | x |
| VH3-11 L. glama Consensus | R | F | T | I | S | R | D | N | A | K | N | T | V | Y | L | Q | M | N | S | L | K | P/S | E | D | T | A | V | Y | Y | C | A | K |
| VH1 HUMAN Consensus | R | V | T | I | T | R | D | T | S | T | S | T | A | Y | M | E | L | S | S | L | R | S | E | D | T | A | V | Y | Y | C | A | R |

TABLE 3: COMPARISON OF LLAMA GLAMA MATURE CONSENSUS SEQUENCES WITH HUMAN GERMLINE CONSENSUS SEQUENCES

L. glama VH3-21 germlined towards human VH3 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | | | | | | | | x | | | | | | | | | | | | x | x | | | | | | | | | | |
| VH3-21 L. glama Consensus | R | F | T | I | S | R | D | N | A | K | N | T | L | Y | L | Q | M | N | S | L | K | P | E | D | T | A | V | Y | Y | C | A | R |
| VH3 HUMAN Consensus | R | F | T | I | S | R | D | N | S | K | N | T | L | Y | L | Q | M | N | S | L | R | A | E | D | T | A | V | Y | Y | C | A | R |

L. glama VH3-21 germlined towards human VH4 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | | x | | | x | | | x | x | | | x | x | x | | | x | x | x | | | | | | | | | | |
| VH3-21 L. glama Consensus | R | F | T | I | S | R | D | N | A | K | N | T | L | Y | L | Q | M | N | S | L | K | P | E | D | T | A | V | Y | Y | C | A | R |
| VH4 HUMAN Consensus | R | V | T | I | S | V | D | T | S | K | N | Q | F | S | L | K | L | S | S | V | T | A | A | D | T | A | V | Y | Y | C | A | R |

L. glama VH3-21 germlined towards human VH5 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | | | | | x | | | x | | | x | | | | x | | x | | | x | x | | | | | x | x | | | | |
| VH3-21 L. glama Consensus | R | F | T | I | S | R | D | N | A | K | N | T | L | Y | L | Q | M | N | S | L | K | P | E | D | T | A | V | Y | Y | C | A | R |
| VH5 HUMAN Consensus | R | I | T | I | S | A | D | K | S | I | S | T | A | Y | L | Q | W | S | S | L | K | A | S | D | T | A | M | Y | Y | C | A | R |

L. glama VH3-21 germlined towards human VH6 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | | | | | x | x | | | | | x | | | | | x | | | | x | x | | | | | | | | | | |
| VH3-21 L. glama Consensus | R | F | T | I | S | R | D | N | A | K | N | T | L | Y | L | Q | M | N | S | L | K | P | E | D | T | A | V | Y | Y | C | A | R |
| VH6 HUMAN Consensus | R | I | T | I | N | P | D | T | S | K | N | Q | F | S | L | Q | L | N | S | V | T | P | E | D | T | A | V | Y | Y | C | A | R |

*Fig. 8E*

TABLE 3: COMPARISON OF LLAMA GLAMA MATURE CONSENSUS SEQUENCES WITH HUMAN GERMLINE CONSENSUS SEQUENCES

L.glama VH3-21 germlined towards human VH7 (Framework Region 3)

| | NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| | | | | | | | x | | x | x | x | x | | x | | | | x | x | | | | | x | | | | | | | | | | |
| VH3-21 | L. glama Consensus | R | F | T | I | S | R | D | N | A | K | N | T | L | Y | L | Q | M | N | S | L | K | P | E | D | T | A | V | Y | Y | C | A | R |
| VH7 | HUMAN Consensus | R | F | V | F | S | L | D | T | S | V | S | T | A | Y | L | Q | I | C | S | L | K | A | E | D | T | A | V | Y | Y | C | A | R |

COMPARISON OF L. glama VH3-23 CONSENSUS SEQUENCE TO HUMAN CONSENSUS GERMLINES OF VH L.glama VH3-23 germlined towards human VH1 (Framework Region 3)

| | NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| | | | x | | | | x | | | x | | x | x | x | | x | x | x | x | | | | x | x | | | | | | | | | x | |
| VH3-23 | L. glama Consensus | R | F | T | I | S | R | D | N | A | K | N | T | L | Y | L | Q | M | N | S | L | K | P | E | D | T | A | V | Y | Y | C | A | K |
| VH1 | HUMAN Consensus | R | V | T | I | T | R | D | T | S | I | S | T | A | Y | M | E | L | S | S | L | R | S | E | D | T | A | V | Y | Y | C | A | R |

L.glama VH3-23 germlined towards human VH2 (Framework Region 3)

| | NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| | | x | | | | | x | | x | x | | x | x | x | x | x | x | x | x | | | | x | x | x | | | | x | x | | | | x |
| VH3-23 | L. glama Consensus | R | F | T | I | S | R | D | N | A | K | N | T | L | Y | L | Q | M | N | S | L | K | P | E | D | T | A | V | Y | Y | C | A | K |
| VH2 | HUMAN Consensus | L | F | L | Q | M | K | D | T | S | I | N | Q | V | V | L | T | M | T | N | M | D | P | V | D | T | A | T | Y | Y | C | A | R |

L.glama VH3-23 germlined towards human VH3 (Framework Region 3)

| | NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| | | | | | | | | | | x | | | | | | | | | | | | | x | x | | | | | | | | | | x |
| VH3-23 | L. glama Consensus | R | F | T | I | S | R | D | N | A | K | N | T | L | Y | L | Q | M | N | S | L | K | P | E | D | T | A | V | Y | Y | C | A | K |
| VH3 | HUMAN Consensus | R | F | T | I | S | R | D | N | S | K | N | T | L | Y | L | Q | M | N | S | L | R | A | E | D | T | A | V | Y | Y | C | A | R |

TABLE 3: COMPARISON OF LLAMA GLAMA MATURE CONSENSUS SEQUENCES WITH HUMAN GERMLINE CONSENSUS SEQUENCES
COMPARISON OF L. glama VH3-48 CONSENSUS SEQUENCE TO HUMAN CONSENSUS GERMLINES OF VH L. glama VH3-48 germlined towards human VH1 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  |  | x |  |  | x |  |  | x | x |  |  | x | x | x |  | x | x | x |  |  | x | x |  |  |  | x | x |  |  |  |  |  |
| VH3-48 L. glama Consensus | R | F | T | I | S | R | D | N | A | K | N | T | L | Y | L | Q | M | N | S | L | K | P | E | D | T | A | L/V | Y | Y | C | A | R |
| VH1 HUMAN Consensus | R | V | T | I | T | R | D | T | S | I | S | T | A | Y | M | E | L | S | S | L | R | S | E | D | T | A | V | Y | Y | C | A | R |

L. glama VH3-48 germlined towards human VH2 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  | x |  |  |  |  |  | x | x |  |  |  |  |  |  |  | x | x | x |  |  | x |  |  |  |  | x | x |  |  |  |  |  |
| VH3-48 L. glama Consensus | R | F | T | I | S | R | D | N | A | K | N | T | L | Y | L | Q | M | N | S | L | K | P | E | D | T | A | L/V | Y | Y | C | A | R |
| VH2 HUMAN Consensus | R | L | T | I | S | K | D | T | S | K | N | Q | V | V | L | T | M | T | N | M | D | P | V | D | T | A | T | Y | Y | C | A | R |

L. glama VH3-48 germlined towards human VH3 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  |  |  |  |  |  |  |  | x |  |  |  |  |  |  |  |  |  |  |  |  |  | x | x | x |  | x | x |  |  |  |  |  |
| VH3-48 L. glama Consensus | R | F | T | I | S | R | D | N | A | K | N | T | L | Y | L | Q | M | N | S | L | K | P | E | D | T | A | L/V | Y | Y | C | A | R |
| VH3 HUMAN Consensus | R | F | T | I | S | R | D | N | S | K | N | T | L | Y | L | Q | M | N | S | L | R | A | E | D | T | A | V | Y | Y | C | A | R |

L. glama VH3-48 germlined towards human VH4 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  |  | x |  |  | x |  |  | x | x |  |  | x | x | x | x |  |  |  |  |  | x | x |  |  |  | x | x |  |  |  |  |  |
| VH3-48 L. glama Consensus | R | F | T | I | S | R | D | N | A | K | N | T | L | Y | L | Q | M | N | S | L | K | P | E | D | T | A | L/V | Y | Y | C | A | R |
| VH4 HUMAN Consensus | R | V | T | I | T | R | D | T | S | K | N | Q | F | S | L | K | L | S | S | V | T | A | A | D | T | A | V | Y | Y | C | A | R |

Fig. 8H

TABLE 3: COMPARISON OF LLAMA GLAMA MATURE CONSENSUS SEQUENCES WITH HUMAN GERMLINE CONSENSUS SEQUENCES

L.glama VH3-48 germlined towards human VH5 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | x | | | x | | x | x | | x | | | | | x | | | | x | x | | | | x | | | | | |
| VH3-48 L. glama Consensus | R | F | T | I | S | R | D | N | A | K | N | T | L | Y | L | Q | M | N | S | L | K | P | E | D | T | A | L/V | Y | Y | C | A | R |
| VH5 HUMAN Consensus | H/Q | V | T | I | S | A | D | K | S | I | S | T | A | Y | L | Q | W | S | S | L | K | A | S | D | T | A | M | Y | Y | C | A | R |

L.glama VH3-48 germlined towards human VH6 (Framework Region 3)

| NUMBERING H- | 65 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | x | x | | | | x | | | x | x | x | | | x | | | | x | | | | | x | | | | | |
| VH3-48 L. glama Consensus | R | F | T | I | S | R | D | N | A | K | N | T | L | Y | L | Q | M | N | S | L | K | P | E | D | T | A | L/V | Y | Y | C | A | R |
| VH6 HUMAN Consensus | R | I | T | I | N | P | D | T | S | K | N | Q | F | S | L | Q | L | N | S | V | T | P | E | D | T | A | V | Y | Y | C | A | R |

L.glama VH3-48 germlined towards human VH7 (Framework Region 3)

| NUMBERING H- | 65 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | x | x | | | | x | x | | x | x | | | | x | | | | x | | | | | x | | | | | |
| VH3-48 L. glama Consensus | R | F | T | I | G | R | D | N | A | K | N | T | L | Y | L | Q | M | N | S | L | R | P | E | D | T | A | L/V | Y | Y | C | A | R |
| VH7 HUMAN Consensus | R | V | V | I | S | R | D | T | S | K | N | Q | L | S | L | Q | L | N | S | L | R | A | E | D | T | A | V | Y | Y | C | A | R |

COMPARISON OF L. glama VH3-66 CONSENSUS SEQUENCE TO HUMAN CONSENSUS GERMLINES OF VH L.glama VH3-66 germlined towards human VH1 (Framework Region 3)

| NUMBERING H- | 65 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | | | | | | | | | x | | x | x | x | x | x | | | x | x | | | | | | | | | x |
| VH3-66 L. glama Consensus | R | F | T | I | S | R | D | N | D | T | S | I | A | Y | L | Q | M | N | S | L | R | S | E | D | T | A | V | Y | Y | C | A | K |
| VH1 HUMAN Consensus | R | V | T | I | T | R | D | T | S | T | S | T | A | Y | M | E | L | S | S | L | R | S | E | D | T | A | V | Y | Y | C | A | R |

TABLE 3: COMPARISON OF LLAMA GLAMA MATURE CONSENSUS SEQUENCES WITH HUMAN GERMLINE CONSENSUS SEQUENCES

L. glama VH3 germlined towards human VH3 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  |  |  |  |  |  |  |  |  | x |  |  |  |  |  |  |  |  |  |  |  | x | x |  |  |  |  |  |  |  |  |  | x |
| VH3 L. glama Consensus | R | F | T | I | S | R | D | N | A | K | N | T | L | Y | L | Q | M | N | S | L | K | P | E | D | T | A | V | Y | Y | C | A | K |
| VH3 HUMAN Consensus | R | F | T | I | S | R | D | N | S | K | N | T | L | Y | L | Q | M | N | S | L | R | A | E | D | T | A | V | Y | Y | C | A | R |

L. glama VH3 germlined towards human VH4 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  |  | x |  |  |  |  |  |  | x |  |  | x |  |  |  | x |  | x |  |  | x | x |  |  |  |  |  |  |  |  |  | x |
| VH3 L. glama Consensus | R | F | T | I | S | R | D | N | A | K | N | T | L | Y | L | Q | M | N | S | L | K | P | E | D | T | A | V | Y | Y | C | A | K |
| VH4 HUMAN Consensus | R | V | T | I | S | V | D | T | S | K | N | Q | F | S | L | K | L | S | S | V | T | A | A | D | T | A | V | Y | Y | C | A | R |

L. glama VH3 germlined towards human VH5 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  |  |  |  |  |  | x |  |  | x | x |  | x | x |  |  |  |  |  |  |  | x | x |  |  |  |  |  |  |  |  |  | x |
| VH3 L. glama Consensus | R | F | T | I | S | R | D | N | A | K | N | T | L | Y | L | Q | M | N | S | L | K | P | E | D | T | A | V | Y | Y | C | A | K |
| VH5 HUMAN Consensus | H/Q | V | T | I | S | A | D | K | S | I | S | T | A | Y | L | Q | W | S | S | L | K | A | S | D | T | A | M | Y | Y | C | A | R |

L. glama VH3 germlined towards human VH6 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
|  |  | x |  | x | x | x |  |  | x |  |  | x | x |  |  |  | x |  |  |  | x |  |  |  |  |  | x |  |  |  |  | x |
| VH3 L. glama Consensus | R | F | T | I | S | R | D | N | A | K | N | T | L | Y | L | Q | M | N | S | L | K | P | E | D | T | A | V | Y | Y | C | A | K |
| VH6 HUMAN Consensus | R | I | T | I | N | P | D | T | S | K | N | Q | F | S | L | Q | L | N | S | V | T | P | E | D | T | A | M | Y | Y | C | A | R |

*Fig. 8L*

TABLE 3: COMPARISON OF LLAMA GLAMA MATURE CONSENSUS SEQUENCES WITH HUMAN GERMLINE CONSENSUS SEQUENCES

L. glama VH3 germlined towards human VH7 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | | | | | x | x | x | x | x | x | | x | | | | x | x | | | | x | x | | | | | | | | | | x |
| VH3 L. glama Consensus | R | F | T | I | S | R | D | N | A | K | N | T | L | Y | L | Q | M | N | S | L | K | P | E | D | T | A | V | Y | Y | C | A | K |
| VH7 HUMAN Consensus | R | F | V | F | S | L | D | T | S | V | S | T | A | Y | L | Q | I | C | S | L | K | A | E | D | T | A | V | Y | Y | C | A | R |

COMPARISON OF L. glama VH4-30-4 CONSENSUS SEQUENCE TO HUMAN CONSENSUS GERMLINES OF VH L. glama VH4-30-4 germlined towards human VH1 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | | x | | | | x | x | x | x | x | x | x | x | | | x | x | x | | | | | | | | | | |
| VH4-30-4 L. glama Consensus | R | T | S | I | S | R | D | T | S | K | N | Q | F | S | L | Q | L | S | S | V | T | P | E | D | T | A | V | Y | Y | C | A | R |
| VH1 HUMAN Consensus | R | V | T | I | T | R | D | T | S | I | S | T | A | Y | M | E | L | S | S | L | R | S | E | D | T | A | V | Y | Y | C | A | R |

L. glama VH4-30-4 germlined towards human VH2 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | | | | x | | | | | | x | x | x | x | x | x | | | x | x | x | | x | | | x | | | | | | |
| VH4-30-4 L. glama Consensus | R | T | S | I | S | R | D | T | S | K | N | Q | F | S | L | Q | L | S | S | V | T | P | E | D | T | A | V | Y | Y | C | A | R |
| VH2 HUMAN Consensus | R | L | T | I | S | K | D | T | S | K | N | Q | V | V | L | T | M | T | N | M | D | P | V | D | T | A | T | Y | Y | C | A | R |

L. glama VH4-30-4 germlined towards human VH3 (Framework Region 3)

| NUMBERING H- | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| | | x | x | | | | x | | | | x | x | | | | | x | | | x | x | x | | | | | | | | | | |
| VH4-30-4 L. glama Consensus | R | T | S | I | S | R | D | T | S | K | N | Q | F | S | L | Q | L | S | S | V | T | P | E | D | T | A | V | Y | Y | C | A | R |
| VH3 HUMAN Consensus | R | F | T | I | S | R | D | N | S | K | N | T | L | Y | L | Q | M | N | S | L | R | A | E | D | T | A | V | Y | Y | C | A | R |

TABLE 4: COMPARISON OF L. PACOS MATURE CONSENSUS SEQUENCES WITH HUMAN GERMLINE CONSENSUS SEQUENCES

COMPARISON OF L. pacos VH1-46 CONSENSUS SEQUENCE TO HUMAN CONSENSUS GERMLINES OF VH L. pacos VH1-46 germlined towards human VH1 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH1-46 | L. PACOS Consensus | E | V | Q | L | V | Q | P | G | A | E | L | R | K | P | G | A | S | V | K | V | S | C | K | A | S | G | Y | T | F | T |
| VH1 | HUMAN Consensus | Q | V | Q | L | V | Q | S | G | A | E | V | K | K | P | G | A | S | V | K | V | S | C | K | A | S | G | Y | T | F | T |

L. pacos VH1-46 germlined towards human VH2 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH1-46 | L. PACOS Consensus | E | V | Q | L | V | Q | P | G | A | E | L | R | K | P | G | A | S | V | K | V | S | C | K | A | S | G | Y | T | F | T |
| VH2 | HUMAN Consensus | Q | V | T | L | K | E | S | G | P | A/T/V | L | V | K | P | T | Q | T | L | T | L | T | C | T | F | S | G | F | S | L | S |

L. pacos VH1-46 germlined towards human VH3 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH1-46 | L. PACOS Consensus | E | V | Q | L | V | Q | P | G | A | E | L | R | K | P | G | A | S | V | K | V | S | C | K | A | S | G | Y | T | F | T |
| VH3 | HUMAN Consensus | E | V | Q | L | V | E | S | G | G | G | L | V | Q | P | G | G | S | L | R | L | S | C | A | A | S | G | F | T | F | S |

L. pacos VH1-46 germlined towards human VH4 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH1-46 | L. PACOS Consensus | E | V | Q | L | V | Q | P | G | A | E | L | R | K | P | G | A | S | V | K | V | S | C | K | A | S | G | Y | T | F | T |
| VH4 | HUMAN Consensus | Q | L | Q | L | Q | E | S | G | P | G | L | V | K | P | S | E | T | L | S | L | T | C | A | V | S | G | G | S | I | S |

L. pacos VH1-46 germlined towards human VH5 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH1-46 | L. PACOS Consensus | E | V | Q | L | V | Q | P | G | A | E | V | K | K | P | G | E | S | V | K/R | V | S | C | A/T | G | S | G | Y | T | F | T | T |
| VH5 | HUMAN Consensus | E | V | Q | L | V | Q | S | G | A | E | V | K | K | P | G | E | S | L | K | V | S | C | K | V | S | G | Y | S | F | T |

L. pacos VH1-46 germlined towards human VH6 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH1-46 | L. PACOS Consensus | E | V | Q | L | V | Q | P | G | A | E | L | V | K | P | G | A | S | V | K | V | S | C | K | A | S | G | Y | T | F | T |
| VH6 | HUMAN Consensus | Q | V | Q | L | Q | Q | S | G | P | G | L | V | K | P | S | Q | T | L | S | L | T | C | A | I | S | G | D | S | V | S |

*Fig. 9A*

TABLE 4: COMPARISON OF L. PACOS MATURE CONSENSUS SEQUENCES WITH HUMAN GERMLINE CONSENSUS SEQUENCES

L. pacos VH1-46 germlined towards human VH7 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH1-46 | L. PACOS Consensus | E | V | Q | L | V | Q | P | G | A | E | L | R | K | P | G | A | S | V | V | K | S | C | K | A | S | G | Y | T | F | T |
| VH7 | HUMAN Consensus | Q | V | Q | L | V | Q | S | G | S | E | L | K | K | P | G | A | S | V | K | V | S | C | K | A | S | G | Y | T | F | T |

COMPARISON OF L. pacos VH3-66 CONSENSUS SEQUENCE TO HUMAN CONSENSUS GERMLINES OF VH L. pacos VH3-66 germlined towards human VH1 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-66 | L. PACOS Consensus | Q | V | Q | L | V | E | S | G | G | G | L | V | Q | P | G | G | S | L | R | L | S | C | A | A | S | G | F | T | F | S |
| VH1 | HUMAN Consensus | Q | V | Q | L | V | Q | S | G | A | E | V | K | K | P | G | A | S | V | K | V | S | C | K | A | S | G | Y | T | F | T |

L. pacos VH3-66 germlined towards human VH2 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-66 | L. PACOS Consensus | Q | V | T | L | K | E | S | G | P | A/T/V | L | V | K | P | T | Q | T | L | T | L | T | C | T | F | S | G | F | S | L | S |
| VH2 | HUMAN Consensus | Q | V | Q | L | V | Q | S | G | G | G | L | V | K | P | G | G | S | L | R | L | S | C | A | A | S | G | F | T | F | S |

L. pacos VH3-66 germlined towards human VH3 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-66 | L. PACOS Consensus | Q | V | Q | L | V | E | S | G | G | G | L | V | Q | P | G | G | S | L | R | L | S | C | A | A | S | G | F | T | F | S |
| VH3 | HUMAN Consensus | E | V | Q | L | V | E | S | G | G | G | L | V | K | P | G | G | S | L | R | L | S | C | A | A | S | G | F | T | F | S |

L. pacos VH3-66 germlined towards human VH4 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-66 | L. PACOS Consensus | Q | V | Q | L | Q | E | S | G | P | G | L | V | K | P | S | E | T | L | S | L | T | C | A/T | V | S | G | F | S | L | S |
| VH4 | HUMAN Consensus | Q | V | Q | L | V | Q | S | G | G | G | L | V | K | P | G | G | S | L | R | L | S | C | A | A | S | G | F | T | F | S |

L. pacos VH3-66 germlined towards human VH5 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-66 | L. PACOS Consensus | E | V | Q | L | V | Q | S | G | A | E | V | K | K | P | G | E | S | L | K/R | I | S | C | K | G | S | G | Y | S | F | T |
| VH5 | HUMAN Consensus | E | V | Q | L | V | Q | S | G | A | E | V | K | K | P | G | E | S | L | R | I | S | C | K | G | S | G | Y | S | F | T |

TABLE 4: COMPARISON OF L. PACOS MATURE CONSENSUS SEQUENCES WITH HUMAN GERMLINE CONSENSUS SEQUENCES

L. pacos VH3-48 germlined towards human VH5 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-48 | L. PACOS Consensus | Q | V | Q | L | V | E | S | G | G | G | L | V | Q | P | G | G | S | L | R | L | S | C | A | A | S | G | F | T | F | S |
| VH5 | HUMAN Consensus | E | V | Q | L | V | Q | S | G | A | E | V | K | K | P | G | E | S | L | K/R | I | S | C | K | G | S | G | Y | S | F | T |

L. pacos VH3-48 germlined towards human VH6 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-48 | L. PACOS Consensus | Q | V | Q | L | Q | Q | S | G | G | G | L | V | Q | P | G | G | S | L | R | L | S | C | A | A | S | G | F | T | F | S |
| VH6 | HUMAN Consensus | Q | V | Q | L | Q | Q | S | G | P | G | L | V | K | P | S | Q | T | L | S | L | T | C | A | I | S | G | D | S | V | S |

L. pacos VH3-48 germlined towards human VH7 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3-48 | L. PACOS Consensus | Q | V | Q | L | V | E | S | G | G | G | L | V | Q | P | G | G | S | L | R | L | S | C | A | A | S | G | F | T | F | S |
| VH7 | HUMAN Consensus | Q | V | Q | L | V | Q | S | G | S | E | L | K | K | P | G | A | S | V | K | V | S | C | K | A | S | G | Y | T | F | T |

COMPARISON OF L. pacos VH3 CONSENSUS SEQUENCE TO HUMAN CONSENSUS GERMLINES OF VH L. pacos VH3 germlined towards human VH1 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3 | L. PACOS Consensus | Q | V | Q | L | V | E | S | G | G | G | L | V | Q | P | G | G | S | L | R | L | S | C | A | A | S | G | F | T | F | S |
| VH1 | HUMAN Consensus | Q | V | Q | L | V | Q | S | G | A | E | V | K | K | P | G | A | S | V | K | V | S | C | K | A | S | G | Y | T | F | T |

L. pacos VH3 germlined towards human VH2 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3 | L. PACOS Consensus | Q | V | T | L | K | E | S | G | P | A/V | L | V | K | P | T | Q | T | L | T | L | T | C | T | F | S | G | F | S | L | S |
| VH2 | HUMAN Consensus | Q | V | Q | L | V | E | S | G | G | G | L | V | Q | P | G | G | S | L | R | L | S | C | A | A | S | G | F | T | F | S |

L. pacos VH3 germlined towards human VH3 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH3 | L. PACOS Consensus | Q | V | Q | L | V | E | S | G | G | G | L | V | Q | P | G | G | S | L | R | L | S | C | A | A | S | G | F | T | F | S |
| VH3 | HUMAN Consensus | E | V | Q | L | V | E | S | G | G | G | L | V | Q | P | G | G | S | L | R | L | S | C | A | A | S | G | F | T | F | S |

TABLE 4: COMPARISON OF L. PACOS MATURE CONSENSUS SEQUENCES WITH HUMAN GERMLINE CONSENSUS SEQUENCES

L. pacos vH4-30-4 germlined towards human VH3 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH4-30-4 | L. PACCS Consensus | Q | V | Q | L | Q | E | S | G | P | G | L | V | K | P | S | Q | T | L | S | L | T | C | T | V | S | G | G | S | I | T |
| VH3 | HUMAN Consensus | E | V | Q | L | V | E | S | G | G | G | L | V | Q | P | G | G | S | L | R | L | S | C | A | A | S | G | F | T | F | S |

L. pacos vH4-30-4 germlined towards human VH4 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH4-30-4 | L. PACCS Consensus | Q | V | Q | L | Q | E | S | G | P | G | L | V | K | P | S | Q | T | L | S | L | T | C | T | V | S | G | G | S | I | T |
| VH4 | HUMAN Consensus | Q | V | Q | L | Q | E | S | G | P | G | L | V | K | P | S | E | T | L | S | L | T | C | T | V | S | G | G | S | I | S |

L. pacos vH4-30-4 germlined towards human VH5 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH4-30-4 | L. PACCS Consensus | Q | V | Q | L | Q | E | S | G | P | G | L | V | K | P | S | Q | T | L | S | L | T | C | T | V | S | G | G | S | I | T |
| VH5 | HUMAN Consensus | V | V | Q | L | V | Q | S | G | A | E | V | K | K | P | G | L | S | L | K/R | L | S | C | K | G | S | G | Y | S | F | T |

L. pacos vH4-30-4 germlined towards human VH6 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH4-30-4 | L. PACCS Consensus | Q | V | Q | L | Q | E | S | G | P | G | L | V | K | P | S | Q | T | L | S | L | T | C | A | I | S | G | G | S | L | T |
| VH6 | HUMAN Consensus | Q | V | Q | L | Q | Q | S | G | A | E | V | K | K | P | G | A | S | V | K | V | S | C | K | A | S | G | Y | T | F | T |

L. pacos vH4-30-4 germlined towards human VH7 (Framework Region 1)

| | NUMBERING H- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| VH4-30-4 | L. PACCS Consensus | Q | V | Q | L | Q | E | S | G | P | G | L | L | K | P | S | Q | T | L | S | L | T | C | T | V | S | G | G | S | I | T |
| VH7 | HUMAN Consensus | Q | V | Q | L | V | Q | S | G | S | E | L | K | K | P | G | A | S | V | K | V | S | C | K | A | S | G | Y | T | F | T |

*Fig. 9F*

TABLE 5: COMPARISON OF LLAMA PACOS MATURE CONSENSUS SEQUENCES WITH HUMAN GERMLINE CONSENSUS SEQUENCES

COMPARISON OF LAMA pacos VH1-46 CONSENSUS SEQUENCE TO HUMAN CONSENSUS GERMLINES OF VH Lama pacos VH1-46 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA PACOS Consensus | W | V | R | Q | A | P | G | Q | G | L | E | W | M | G |
| VH1 | HUMAN Consensus | W | V | R | Q | A | P | G | Q | G | L | E | W | M | G |

Lama pacos VH1-46 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA PACOS Consensus | W | V | R | Q | A | P | G | Q | G | L | E | W | M | G |
| VH2 | HUMAN Consensus | W | I | R | Q | P | P | G | K | A | L | E | W | L | A |

Lama pacos VH1-46 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA PACOS Consensus | W | V | R | Q | A | P | G | Q | G | L | E | W | M | G |
| VH3 | HUMAN Consensus | W | V | R | Q | A | P | G | K | G | L | E | W | V | S |

Lama pacos VH1-46 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA PACOS Consensus | W | V | R | Q | A | P | G | Q | G | L | E | W | M | G |
| VH4 | HUMAN Consensus | W | I | R | Q | P | P | G | K | G | L | E | W | I | G |

TABLE 5: COMPARISON OF LLAMA PACOS MATURE CONSENSUS SEQUENCES WITH HUMAN GERMLINE CONSENSUS SEQUENCES

Lama pacos VH1-46 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA PACOS Consensus | W | V | R | Q | A | P | G | Q | G | L | E | W | M | G |
| VH5 | HUMAN Consensus | W | V | R | Q | M | P | G | K | G | L | E | W | M | G |

*Fig. 10A*

TABLE 5: COMPARISON OF LLAMA PACOS MATURE CONSENSUS SEQUENCES WITH HUMAN GERMLINE CONSENSUS SEQUENCES

Lama pacos VH1-46 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA PACOS Consensus | W | V | R | Q | A | P | G | Q | G | L | E | W | M | G |
| VH6 | HUMAN Consensus | W | I | R | Q | S | P | S | R | G | L | E | W | L | G |

Lama pacos VH1-46 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH1-46 | LAMA PACOS Consensus | W | V | R | Q | A | P | G | Q | G | L | E | W | M | G |
| VH7 | HUMAN Consensus | W | V | R | Q | A | P | G | Q | G | L | E | W | M | G |

COMPARISON OF LAMA pacos VH3-66 CONSENSUS SEQUENCE TO HUMAN CONSENSUS GERMLINES OF VH Lama pacos VH3-66 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA PACOS Consensus | W | A | R | Q | V | P | G | K | G | L | E | W | V | S |
| VH1 | HUMAN Consensus | W | V | R | Q | A | P | G | Q | G | L | E | W | M | G |

*Fig. 10B*

TABLE 5: COMPARISON OF LLAMA PACOS MATURE CONSENSUS SEQUENCES WITH HUMAN GERMLINE CONSENSUS SEQUENCES

Lama pacos VH3-66 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA PACOS Consensus | W | A | R | Q | V | P | G | K | G | L | E | W | V | S |
| VH2 | HUMAN Consensus | W | I | R | Q | P | P | G | K | A | L | E | W | L | A |

Lama pacos VH3-66 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA PACOS Consensus | W | A | R | Q | V | P | G | K | G | L | E | W | V | S |
| VH3 | HUMAN Consensus | W | V | R | Q | A | P | G | K | G | L | E | W | V | S |

Lama pacos VH3-66 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA PACOS Consensus | W | A | R | Q | V | P | G | K | G | L | E | W | V | S |
| VH4 | HUMAN Consensus | W | I | R | Q | P | P | G | K | G | L | E | W | I | G |

Lama pacos VH3-66 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA PACOS Consensus | W | A | R | Q | V | P | G | K | G | L | E | W | V | S |
| VH5 | HUMAN Consensus | W | V | R | Q | M | P | G | K | G | L | E | W | M | G |

Lama pacos VH3-66 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA PACOS Consensus | W | A | R | Q | V | P | G | K | G | L | E | W | V | S |
| VH6 | HUMAN Consensus | W | I | R | Q | S | P | S | R | G | L | E | W | L | G |

Lama pacos VH3-66 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-66 | LAMA PACOS Consensus | W | A | R | Q | V | P | G | K | G | L | E | W | V | S |
| VH7 | HUMAN Consensus | W | V | R | Q | A | P | G | Q | G | L | E | W | M | G |

Fig. 10C

TABLE 5: COMPARISON OF LLAMA PACOS MATURE CONSENSUS SEQUENCES WITH HUMAN GERMLINE CONSENSUS SEQUENCES

COMPARISON OF LAMA pacos VH3-48 CONSENSUS SEQUENCE TO HUMAN CONSENSUS GERMLINES OF VH Lama pacos VH3-48 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA PACOS Consensus | W | V | R | Q | A | P | G | K | G | L | E | W | V | S |
| VH1 | HUMAN Consensus | W | V | R | Q | A | P | G | Q | G | L | E | W | M | G |

Lama pacos VH3-48 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA PACOS Consensus | W | V | R | Q | A | P | G | K | G | L | E | W | V | S |
| VH2 | HUMAN Consensus | W | I | R | Q | P | P | G | K | A | L | E | W | L | A |

Lama pacos VH3-48 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA PACOS Consensus | W | V | R | Q | A | P | G | K | G | L | E | W | V | S |
| VH3 | HUMAN Consensus | W | V | R | Q | A | P | G | K | G | L | E | W | V | S |

TABLE 5: COMPARISON OF LLAMA PACOS MATURE CONSENSUS SEQUENCES WITH HUMAN GERMLINE CONSENSUS SEQUENCES

Lama pacos VH3-48 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA PACOS Consensus | W | V | R | Q | A | P | G | K | G | L | E | W | V | S |
| VH4 | HUMAN Consensus | W | I | R | Q | P | P | G | K | G | L | E | W | I | G |

Fig. 10D

TABLE 5: COMPARISON OF LLAMA PACOS MATURE CONSENSUS SEQUENCES WITH HUMAN GERMLINE CONSENSUS SEQUENCES

Lama pacos VH3-48 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA PACOS Consensus | W | V | R | Q | A | P | G | K | G | L | E | W | V | S |
| VH5 | HUMAN Consensus | W | V | R | Q | M | P | G | K | G | L | E | W | M | G |

Lama pacos VH3-48 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA PACOS Consensus | W | V | R | Q | A | P | G | K | G | L | E | W | V | S |
| VH6 | HUMAN Consensus | W | I | R | Q | S | P | S | R | G | L | E | W | L | G |

Lama pacos VH3-48 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3-48 | LAMA PACOS Consensus | W | V | R | Q | A | P | G | K | G | L | E | W | V | S |
| VH7 | HUMAN Consensus | W | V | R | Q | A | P | G | Q | G | L | E | W | M | G |

COMPARISON OF LAMA pacos VH3 CONSENSUS SEQUENCE TO HUMAN CONSENSUS GERMLINES OF VH Lama pacos VH3 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA PACOS Consensus | W | V | R | Q | A | P | G | K | G | L | E | W | V | S |
| VH1 | HUMAN Consensus | W | V | R | Q | A | P | G | Q | G | L | E | W | M | G |

*Fig. 10E*

TABLE 5: COMPARISON OF LLAMA PACOS MATURE CONSENSUS SEQUENCES WITH HUMAN GERMLINE CONSENSUS SEQUENCES

Lama pacos VH3 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA PACOS Consensus | W | V | R | Q | A | P | G | K | G | L | E | W | V | S |
| VH2 | HUMAN Consensus | W | I | R | Q | P | P | G | K | A | L | E | W | L | A |

Lama pacos VH3 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA PACOS Consensus | W | V | R | Q | A | P | G | K | G | L | E | W | V | S |
| VH3 | HUMAN Consensus | W | V | R | Q | A | P | G | K | G | L | E | W | V | S |

Lama pacos VH3 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA PACOS Consensus | W | V | R | Q | A | P | G | K | G | L | E | W | V | S |
| VH4 | HUMAN Consensus | W | I | R | Q | P | P | G | K | G | L | E | W | I | G |

Lama pacos VH3 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA PACOS Consensus | W | V | R | Q | A | P | G | K | G | L | E | W | V | S |
| VH5 | HUMAN Consensus | W | V | R | Q | M | P | G | K | G | L | E | W | M | G |

Lama pacos VH3 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA PACOS Consensus | W | V | R | Q | A | P | G | K | G | L | E | W | V | S |
| VH6 | HUMAN Consensus | W | I | R | Q | S | P | S | R | G | L | E | W | L | G |

*Fig. 10F*

TABLE 5: COMPARISON OF LLAMA PACOS MATURE CONSENSUS SEQUENCES WITH HUMAN GERMLINE CONSENSUS SEQUENCES

Lama pacos VH3 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH3 | LAMA PACOS Consensus | W | V | R | Q | A | P | G | K | G | L | E | W | V | S |
| VH7 | HUMAN Consensus | W | V | R | Q | A | P | G | Q | G | L | E | W | M | G |

COMPARISON OF LAMA pacos VH4-30-4 CONSENSUS SEQUENCE TO HUMAN CONSENSUS GERMLINES OF VH

Lama pacos VH4-30-4 germlined towards human VH1 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH4-30-4 | LAMA PACOS Consensus | W | I | R | Q | P | P | G | K | G | L | E | W | M | G |
| VH1 | HUMAN Consensus | W | V | R | Q | A | P | G | Q | G | L | E | W | M | G |

Lama pacos VH4-30-4 germlined towards human VH2 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH4-30-4 | LAMA PACOS Consensus | W | I | R | Q | P | P | G | K | G | L | E | W | M | G |
| VH2 | HUMAN Consensus | W | I | R | Q | P | P | G | K | A | L | E | W | L | A |

Lama pacos VH4-30-4 germlined towards human VH3 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH4-30-4 | LAMA PACOS Consensus | W | I | R | Q | P | P | G | K | G | L | E | W | M | G |
| VH3 | HUMAN Consensus | W | V | R | Q | A | P | G | K | G | L | E | W | V | S |

Lama pacos VH4-30-4 germlined towards human VH4 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH4-30-4 | LAMA PACOS Consensus | W | I | R | Q | P | P | G | K | G | L | E | W | M | G |
| VH4 | HUMAN Consensus | W | I | R | Q | P | P | G | K | G | L | E | W | I | G |

*Fig. 10G*

TABLE 5: COMPARISON OF LLAMA PACOS MATURE CONSENSUS SEQUENCES WITH HUMAN GERMLINE CONSENSUS SEQUENCES

Lama pacos VH4-30-4 germlined towards human VH5 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH4-30-4 | LAMA PACOS Consensus | W | I | R | Q | P | P | G | K | G | L | E | W | M | G |
| VH5 | HUMAN Consensus | W | V | R | Q | M | P | G | K | G | L | E | W | M | G |

Lama pacos VH4-30-4 germlined towards human VH6 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH4-30-4 | LAMA PACOS Consensus | W | I | R | Q | P | P | G | K | G | L | E | W | M | G |
| VH6 | HUMAN Consensus | W | I | R | Q | S | P | S | R | G | L | E | W | L | G |

Lama pacos VH4-30-4 germlined towards human VH7 (Framework Region 2)

| | NUMBERING | H36 | H37 | H38 | H39 | H40 | H41 | H42 | H43 | H44 | H45 | H46 | H47 | H48 | H49 |
|---|---|---|---|---|---|---|---|---|---|---|---|---|---|---|---|
| VH4-30-4 | LAMA PACOS Consensus | W | I | R | Q | P | P | G | K | G | L | E | W | M | G |
| VH7 | HUMAN Consensus | W | V | R | Q | A | P | G | Q | G | L | E | W | M | G |

TABLE 6: COMPARISON OF LLAMA PACOS MATURE CONSENSUS SEQUENCES WITH HUMAN GERMLINE CONSENSUS SEQUENCES

Lama pacos VH1-46 germlined towards human VH6 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH1-46 | L. PACOS Cons. | R | V | T | F | T | A | D | T | S | K | S | T | A | Y | V | E | L | S | S | L | R | S | E | G | T | A | V | Y | Y | C | A | R |
| VH6 | HUMAN Cons. | R | I | T | I | N | P | D | T | S | K | N | Q | F | S | L | Q | L | N | S | V | T | P | E | D | T | A | V | Y | Y | C | A | R |

Lama pacos VH1-46 germlined towards human VH7 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH1-46 | L. PACOS Cons. | R | V | T | F | T | A | D | T | S | T | S | T | A | Y | V | E | L | S | S | L | R | S | E | G | T | A | V | Y | Y | C | A | R |
| VH7 | HUMAN Cons. | R | F | V | F | S | L | D | T | S | V | S | T | A | Y | L | Q | I | C | S | L | K | A | E | D | T | A | V | Y | Y | C | A | R |

COMPARISON OF LAMA pacos VH3-66 CONSENSUS SEQUENCE TO HUMAN CONSENSUS GERMLINES OF VH Lama pacos VH3-66 germlined towards human VH1 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-66 | L. PACOS Cons. | R | F | T | I | S | R | D | N | A | K | N | T | V | V | L | Q | M | N | S | L | K | P | E | G | T | A | V | Y | Y | C | A | R |
| VH1 | HUMAN Cons. | R | V | T | I | T | R | D | T | S | T | N | T | A | Y | M | E | L | S | S | L | R | S | E | D | T | A | V | Y | Y | C | A | R |

Lama pacos VH3-66 germlined towards human VH2 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-66 | L. PACOS Cons. | R | L | T | I | S | K | D | T | S | K | N | Q | V | V | L | T | M | T | N | M | D | P | V | D | T | A | T | Y | Y | C | A | R |
| VH2 | HUMAN Cons. | R | F | T | I | S | R | D | N | S | K | N | Q | V | V | L | Q | M | N | S | L | R | S | E | D | T | A | V | Y | Y | C | A | R |

Lama pacos VH3-66 germlined towards human VH3 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-66 | L. PACOS Cons. | R | F | T | I | S | R | D | N | S | K | N | T | L | Y | L | Q | M | N | S | L | R | A | E | D | T | A | T | Y | Y | C | A | R |
| VH3 | HUMAN Cons. | R | F | T | I | S | R | D | N | N | K | N | T | L | Y | L | Q | M | N | S | L | R | A | E | D | T | A | V | Y | Y | C | A | R |

Fig. 11C

TABLE 6: COMPARISON OF LLAMA PACOS MATURE CONSENSUS SEQUENCES WITH HUMAN GERMLINE CONSENSUS SEQUENCES

Lama pacos VH3-48 germlined towards human VH2 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-48 | L. PACOS Cons. | R | F | T | I | S | R | D | N | A | K | N | T | L | Y | L | Q | M | N | S | L | K | P | E | G | T | A | V | Y | Y | C | A | R |
| VH2 | HUMAN Cons. | R | L | T | I | S | K | D | T | S | K | N | Q | V | V | L | T | M | T | N | M | D | P | V | D | T | A | T | Y | Y | C | A | R |

Lama pacos VH3-48 germlined towards human VH3 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-48 | L. PACOS Cons. | R | F | T | I | S | R | D | N | A | K | N | T | L | Y | L | Q | M | N | S | L | K | P | E | G | T | A | V | Y | Y | C | A | R |
| VH3 | HUMAN Cons. | R | F | T | I | S | R | D | N | S | K | N | T | L | Y | L | Q | M | N | S | L | R | A | E | D | T | A | V | Y | Y | C | A | R |

Lama pacos VH3-48 germlined towards human VH4 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-48 | L. PACOS Cons. | R | F | T | I | S | R | D | N | A | K | N | T | L | Y | L | Q | M | N | S | L | K | P | E | G | T | A | V | Y | Y | C | A | R |
| VH4 | HUMAN Cons. | R | V | T | I | S | V | D | T | S | K | N | Q | F | S | L | K | L | S | S | V | T | A | A | D | T | A | V | Y | Y | C | A | R |

Lama pacos VH3-48 germlined towards human VH5 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-48 | L. PACOS Cons. | R | F | T | I | S | R | D | N | A | K | N | T | L | Y | L | Q | M | N | S | L | K | P | E | G | T | A | V | Y | Y | C | A | R |
| VH5 | HUMAN Cons. | R | F | T | I | S | A | D | K | S | I | S | T | A | Y | L | Q | W | S | S | L | K | A | S | D | T | A | M | Y | Y | C | A | R |

Lama pacos VH3-48 germlined towards human VH6 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3-48 | L. PACOS Cons. | R | F | T | I | S | R | D | N | A | K | N | T | L | Y | L | Q | M | N | S | L | K | P | E | G | T | A | V | Y | Y | C | A | R |
| VH6 | HUMAN Cons. | H/Q | I | T | I | N | P | D | T | S | K | N | Q | F | S | L | Q | L | N | S | V | T | P | E | D | T | A | V | Y | Y | C | A | R |

TABLE 6: COMPARISON OF LLAMA PACOS MATURE CONSENSUS SEQUENCES WITH HUMAN GERMLINE CONSENSUS SEQUENCES

Lama pacos VH3 germlined towards human VH5 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3 | L. PACOS Cons. | R | F | T | I | S | R | D | N | A | K | N | T | L | Y | L | Q | M | N | S | L | K | P | E | G | T | A | V | Y | Y | C | A | R |
| VH5 | HUMAN Cons. | H/Q | V | T | I | | | | K | S | I | S | T | A | Y | L | Q | W | S | | L | K | A | S | D | T | A | M | Y | Y | C | A | R |

Lama pacos VH3 germlined towards human VH6 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3 | L. PACOS Cons. | R | F | T | I | S | R | D | N | A | K | N | T | L | Y | L | Q | M | N | S | L | K | P | E | G | T | A | V | Y | Y | C | A | R |
| VH6 | HUMAN Cons. | R | F | T | I | N | P | D | T | S | K | N | Q | F | S | L | Q | L | | S | V | T | P | E | D | T | A | V | Y | Y | C | A | R |

Lama pacos VH3 germlined towards human VH7 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH3 | L. PACOS Cons. | R | F | T | I | S | R | D | N | A | K | N | T | L | Y | L | Q | M | N | S | L | K | P | E | G | T | A | V | Y | Y | C | A | R |
| VH7 | HUMAN Cons. | R | V | T | V | F | S | L | D | T | S | V | T | A | Y | L | Q | I | C | S | V | K | A | E | D | T | A | T | Y | Y | C | A | R |

COMPARISON OF LAMA pacos VH4-30-4 CONSENSUS SEQUENCE TO HUMAN CONSENSUS GERMLINES OF VH Lama pacos VH4-30-4 germlined towards human VH1 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH4-30-4 | L. PACOS Cons. | R | T | S | I | T | R | D | T | S | K | N | Q | F | S | L | Q | L | S | S | V | T | P | E | D | T | A | V | Y | Y | C | A | R |
| VH1 | HUMAN Cons. | R | V | T | | | | | T | A | Y | M | E | L | | | | | | | | | | | | | | | | | | | |

Lama pacos VH4-30-4 germlined towards human VH2 (Framework Region 3)

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH4-30-4 | L. PACOS Cons. | R | T | S | I | T | R | D | T | S | K | N | Q | F | S | L | Q | L | S | S | V | T | P | E | D | T | A | V | Y | Y | C | A | R |
| VH2 | HUMAN Cons. | R | L | T | I | S | K | D | T | S | K | N | Q | V | V | L | T | M | T | N | M | D | P | V | D | T | A | T | Y | Y | C | A | R |

*Fig. 11F*

TABLE 6: COMPARISON OF LLAMA PACOS MATURE CONSENSUS SEQUENCES WITH HUMAN GERMLINE CONSENSUS SEQUENCES

Lama pacos VH4-30-4 germlined towards human VH3 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH4-30-4 | L. PACOS Cons. | R | T | S | I | S | R | D | T | S | K | N | Q | F | S | L | Q | L | S | S | V | T | P | E | G | T | A | V | Y | Y | C | A | R |
| VH3 | HUMAN Cons. | R | F | T | I | S | R | D | N | S | K | N | T | L | Y | L | Q | M | N | S | L | R | A | E | D | T | A | V | Y | Y | C | A | R |

Lama pacos VH4-30-4 germlined towards human VH4 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH4-30-4 | L. PACOS Cons. | R | T | S | I | S | R | D | T | S | K | N | Q | F | S | L | Q | L | S | S | V | T | P | E | G | T | A | V | Y | Y | C | A | R |
| VH4 | HUMAN Cons. | R | V | T | I | S | V | D | T | S | K | N | Q | F | S | L | K | L | S | S | V | T | A | A | D | T | A | V | Y | Y | C | A | R |

Lama pacos VH4-30-4 germlined towards human VH5 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH4-30-4 | L. PACOS Cons. | R | T | S | I | S | R | D | T | S | K | N | Q | F | S | L | Q | L | S | S | V | T | P | E | G | T | A | V | Y | Y | C | A | R |
| VH5 | HUMAN Cons. | R | V | T | I | S | A | D | K | S | I | S | T | A | Y | L | Q | W | S | S | L | K | A | S | D | T | A | M | Y | Y | C | A | R |

Lama pacos VH4-30-4 germlined towards human VH6 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH4-30-4 | L. PACOS Cons. | R | T | S | I | S | R | D | T | S | K | N | Q | F | S | L | Q | L | S | S | V | T | P | E | G | T | A | V | Y | Y | C | A | R |
| VH6 | HUMAN Cons. | R | I | T | I | N | P | D | T | S | K | N | Q | F | S | L | Q | L | N | S | V | T | P | E | D | T | A | V | Y | Y | C | A | R |

Lama pacos VH4-30-4 germlined towards human VH7 [Framework Region 3]

| | NUMBERING | 66 | 67 | 68 | 69 | 70 | 71 | 72 | 73 | 74 | 75 | 76 | 77 | 78 | 79 | 80 | 81 | 82 | 82A | 82B | 82C | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|
| VH4-30-4 | L. PACOS Cons. | R | T | S | I | S | R | D | T | S | K | N | Q | F | S | L | Q | L | S | S | V | T | P | E | G | T | A | V | Y | Y | C | A | R |
| VH7 | HUMAN Cons. | R | V | F | S | L | D | T | S | V | S | T | A | Y | L | Q | L | C | S | L | I | K | A | E | D | T | A | V | Y | Y | C | A | R |

Fig. 11G

TABLE 7: COMPARISON OF LLAMA GLAMA VL1 CONSENSUS SEQUENCES WITH HUMAN GERMLINE CONSENSUS SEQUENCES (Framework Region 1)

COMPARISON OF LAMA GLAMA VL1-44 CONSENSUS SEQUENCE TO HUMAN CONSENSUS GERMLINES OF VL1-10

Lama glama VL1 germlined towards human VL1 (Framework Region 1)

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | F | T | I | S | C |
| VL1 HUMAN Cons. | Q | S | V | L | T | Q | P | P | S | - | V | S | G | A | P | G | Q | R | V | T | I | S | C |

Lama glama VL1 germlined towards human VL2

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | T | I | S | C |  |
| VL2 HUMAN Cons. | Q | S | A | I | T | Q | P | A/P | S | - | V | S | G | S | P | G | Q | S | V | T | I | S | C |

Lama glama VL1 germlined towards human VL3

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | F | T | I | S | C |
| VL3 HUMAN Cons. | S | Y | E | L | T | Q | P | P | S | - | V | S | V | S | P | G | Q | T | A | R | I | T | C |

Lama glama VL1 germlined towards human VL4

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | I | P | S | - | V | S | G | S | P | G | Q | K | T | T | S | C |  |
| VL4 HUMAN Cons. | Q | P | V | L | T | Q | S | P | S | - | A | S | A | S | P | G | Q | A | S | V | K | L | T |

Lama glama VL1 germlined towards human VL5

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | T | T | S | C |  |
| VL5 HUMAN Cons. | Q | P | V | L | T | Q | P | A/P/S/T | S | - | L | S | A | L | P | G | Q | A | S | A | R | L | T |

Lama glama VL1 germlined towards human VL6

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | F | T | I | S | C |
| VL6 HUMAN Cons. | N | F | M | L | T | Q | P | H | S | - | V | S | E | S | P | G | Q | K | T | V | T | I | S | C |

*Fig. 12A*

TABLE 7: COMPARISON OF LLAMA GLAMA VL1 CONSENSUS SEQUENCES WITH HUMAN GERMLINE CONSENSUS SEQUENCES (Framework Region 1)I Lama glama VL1 germlined towards human VL7

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | F | T | I | S | C |
| VL7 HUMAN Cons. | Q | A/T | V | V | T | Q | E | P | S | - | L | T | V | S | P | G | G | T | V | T | L | T | C |

Lama glama VL1 germlined towards human VL8

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | F | T | I | S | C |
| VL8 HUMAN Cons. | Q | T | V | V | T | Q | E | P | S | - | F | S | V | S | P | G | G | T | V | T | L | T | C |

Lama glama VL1 germlined towards human VL9

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | F | T | I | S | C |
| VL9 HUMAN Cons. | Q | P | V | L | T | Q | P | P | S | - | A | S | A | S | L | G | A | S | V | T | L | T | C |

Lama glama VL1 germlined towards human VL10

| NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| VL1 LAMA glama Cons. | N/Q | F | M/V | L | T | Q | P | P | S | - | V | S | G | S | P | G | Q | K | F | T | I | S | C |
| VL10 HUMAN Cons. | Q | A | G | L | T | Q | P | P | S | - | V | S | K | G | L | R | Q | T | A | T | L | T | C |

*Fig. 12B*

TABLE 8: COMPARISON OF LAMA GLAMA VL1 CONSENSUS SEQUENCES WITH HUMAN GERMLINE CONSENSUS SEQUENCES (Framework Region 2)

COMPARISON OF LAMA GLAMA VL1-44 CONSENSUS SEQUENCE TO HUMAN CONSENSUS GERMLINES OF VL1-10

Lama glama VL1 germlined towards human VL1 (Framework Region 2)

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL1 | HUMAN Cons. | W | Y | Q | Q | L | P | G | K | A | P | K | L | L | I | Y |

Lama glama VL1 germlined towards human VL2

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL2 | HUMAN Cons. | W | Y | Q | Q | H | P | G | Q | A | P | K | L | L | I | Y |

Lama glama VL1 germlined towards human VL3

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL3 | HUMAN Cons. | W | Y | Q | Q | K | P | G | Q | A | P | V | L | V | I | Y |

Lama glama VL1 germlined towards human VL4

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | V | Q | H | I | P | G | T | A | P | K | I | L | M | Y |
| VL4 | HUMAN Cons. | W | H | Q | Q | Q | P | G | K | G/A/S | Q | R | Y | L | K | X |

Lama glama VL1 germlined towards human VL5

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL5 | HUMAN Cons. | W | Y | Q | Q | K | P | G | S | P | P | R | Y | L | L | Y/R |

Lama glama VL1 germlined towards human VL6

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL6 | HUMAN Cons. | W | Y | Q | Q | R | P | G | S | S | P | T | T | V | L | Y |

Fig. 13A

TABLE 8: COMPARISON OF LLAMA GLAMA VL1 CONSENSUS SEQUENCES WITH HUMAN GERMLINE CONSENSUS SEQUENCES (Framework Region 2)

Lama glama VL1 germlined towards human VL7

| | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL7 | HUMAN Cons. | W | F | Q | Q | K | P | G | Q | A | P | R | A/T | L | I | Y |

Lama glama VL1 germlined towards human VL8

| | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL8 | HUMAN Cons. | W | Y | Q | Q | T | P | G | Q | A | P | R | T | L | I | Y |

Lama glama VL1 germlined towards human VL9

| | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL9 | HUMAN Cons. | W | Y | Q | Q | R | P | G | K | G | P | R | F | V | M | R |

Lama glama VL1 germlined towards human VL10

| | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| VL1 | LAMA glama Cons. | W | Y | Q | H | L | P | G | T | A | P | K | L | L | I | Y |
| VL10 | HUMAN Cons. | W | L | Q | Q | H | Q | G | H | P | P | K | L | L | S | Y |

TABLE 9: COMPARISON OF LLAMA GLAMA VL1 CONSENSUS SEQUENCES WITH HUMAN GERMLINE CONSENSUS SEQUENCES (Framework Region 3)

Lama glama VL1 germlined towards human VL9

| NUMBERING L- | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|
| VL1 L.glama Cons. | P | D | R | F | S | G | S | K | - | - | S | G | S | S | A | S | L | T | I | T | G | L | Q | A | E | D | E | A | D | Y | Y | C |
| VL9 HUMAN Cons. | P | D | R | F | S | V | L | G | - | - | S | G | L | N | R | Y | L | T | I | K | N | I | Q | E | E | D | E | S | D | Y | H | C |

Lama glama VL1 germlined towards human VL10

| NUMBERING L- | 59 | 60 | 61 | 62 | 63 | 64 | 65 | 66 | | | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|
| VL1 L.glama Cons. | P | D | R | F | S | G | S | K | | | S | G | S | S | A | S | L | T | I | T | G | L | Q | A | E | D | E | A | D | Y | Y | C |
| VL10 HUMAN Cons. | S | E | R | F | S | A | S | R | | | S | G | N | T | A | S | L | T | I | T | G | L | Q | P | E | D | E | A | D | Y | Y | C |

*Fig. 14B*

TABLE 10: COMPARISON OF LLAMA GLAMA VL2 CONSENSUS SEQUENCES WITH HUMAN GERMLINE CONSENSUS SEQUENCES (Framework Region 1)
COMPARISON OF LAMA GLAMA VL2-11 CONSENSUS SEQUENCE TO HUMAN CONSENSUS GERMLINES OF VK1-10

Lama glama VL2 germlined towards human VL1

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL1 | HUMAN Cons. | Q | S | V | L | T | Q | P | P | S | - | V | S | G | A | P | G | Q | R | V | T | I | S | C |

Lama glama VL2 germlined towards human VL2 (preferred for sequence homology and length of CDRs)

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL2 | HUMAN Cons. | Q | S | A | L | T | Q | P | A/P | S | - | V | S | G | S | P | G | Q | S | V | T | I | S | C |

Lama glama VL2 germlined towards human VL3

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL3 | HUMAN Cons. | S | Y | E | L | T | Q | P | P | S | - | V | S | V | S | P | G | Q | T | A | R | I | T | C |

Lama glama VL2 germlined towards human VL4

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL4 | HUMAN Cons. | Q | P | V | L | T | Q | S | P | S | - | A | S | A | S | L | G | A | S | V | K | L | T | C |

Lama glama VL2 germlined towards human VL5

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL5 | HUMAN Cons. | Q | P | V | L | T | Q | P | A/P/S/T | S | - | L | S | A | S | P | G | A | S | A | R | L | T | C |

Lama glama VL2 germlined towards human VL6

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL6 | HUMAN Cons. | N | F | M | L | T | Q | P | H | S | - | V | S | E | S | P | G | K | T | V | T | I | S | C |

Lama glama VL2 germlined towards human VL7

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL7 | HUMAN Cons. | Q | A/T | V | V | T | Q | E | P | S | - | L | T | V | S | P | G | G | T | V | T | L | T | C |

Lama glama VL2 germlined towards human VL8

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL8 | HUMAN Cons. | Q | T | V | V | T | Q | E | P | S | - | F | S | V | S | P | G | G | T | V | T | L | T | C |

Fig. 15A

TABLE 10: COMPARISON OF LLAMA GLAMA VL2 CONSENSUS SEQUENCES WITH HUMAN GERMLINE CONSENSUS SEQUENCES (Framework Region 1)

Lama glama VL2 germlined towards human VL9

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL9 | HUMAN Cons. | Q | P | V | L | T | Q | P | P | S | - | A | S | A | S | L | G | A | S | V | T | L | T | C |

Lama glama VL2 germlined towards human VL10

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-11 | LAMA glama Cons. | Q | S | A | L | T | Q | P | P | S | - | V | S | G | S | P | G | K | T | V | T | I | S | C |
| VL10 | HUMAN Cons. | Q | A | G | L | T | Q | P | P | S | - | V | S | K | G | L | R | Q | T | A | T | L | T | C |

COMPARISON OF LAMA GLAMA VL2-18 CONSENSUS SEQUENCE TO HUMAN CONSENSUS GERMLINES OF VK1-10

Lama glama VL2 germlined towards human VL1

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-18 | LAMA glama Cons. | Q | S | V | L | T | Q | P | P | S | - | V | S | G | T | L | G | K | T | V | T | I | S | C |
| VL1 | HUMAN Cons. | Q | S | V | L | T | Q | P | P | S | - | V | S | G | A | P | G | Q | R | V | T | I | S | C |

Lama glama VL2 germlined towards human VL2 (preferred for sequence homology and length of CDRs)

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-18 | LAMA glama Cons. | Q | S | V | L | T | Q | P | P | S | - | V | S | G | T | L | G | K | T | V | T | I | S | C |
| VL2 | HUMAN Cons. | Q | S | A | L | T | Q | P | A/P | S | - | V | S | G | S | P | G | Q | S | V | T | I | S | C |

Lama glama VL2 germlined towards human VL3

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-18 | LAMA glama Cons. | Q | S | V | L | T | Q | P | P | S | - | V | S | G | T | L | G | K | T | V | T | I | S | C |
| VL3 | HUMAN Cons. | S | Y | E | L | T | Q | P | P | S | - | V | S | V | S | P | G | Q | T | A | R | I | T | C |

Lama glama VL2 germlined towards human VL4

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-18 | LAMA glama Cons. | Q | S | V | L | T | Q | P | P | S | - | V | S | G | T | L | G | K | T | V | T | I | S | C |
| VL4 | HUMAN Cons. | Q | P | V | L | T | Q | S | P | S | - | A | S | A | S | L | G | A | S | V | K | L | T | C |

Lama glama VL2 germlined towards human VL5

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-18 | LAMA glama Cons. | Q | S | V | L | T | Q | P | P | S | - | V | S | G | T | L | G | K | T | V | T | I | S | C |
| VL5 | HUMAN Cons. | Q | P | V | L | T | Q | P | A/P/S/T | S | - | L | S | A | S | P | G | A | S | A | R | L | T | C |

Lama glama VL2 germlined towards human VL6

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL2-18 | LAMA glama Cons. | Q | S | V | L | T | Q | P | P | S | - | V | S | G | T | L | G | K | T | V | T | I | S | C |
| VL6 | HUMAN Cons. | N | F | M | L | T | Q | P | H | S | - | V | S | E | S | P | G | K | T | V | T | I | S | C |

Fig. 15B

TABLE 10: COMPARISON OF LLAMA GLAMA VL2 CONSENSUS SEQUENCES WITH HUMAN GERMLINE CONSENSUS SEQUENCES (Framework Region 1)

Lama glama vL2 germlined towards human VL7

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL2-1B LAMA glama Cons. | Q | S | V | L | T | Q | P | P | S | - | V | S | G | T | L | G | K | T | V | T | I | S | C |
| VL7 HUMAN Cons. | Q | A/T | V | V | T | Q | E | P | S | - | L | T | V | S | P | G | G | T | V | T | L | T | C |

Lama glama vL2 germlined towards human VL8

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL2-1R LAMA glama Cons. | Q | S | V | V | T | Q | P | P | S | - | V | S | G | T | L | G | K | T | V | T | I | S | C |
| VL8 HUMAN Cons. | Q | T | V | V | T | Q | E | P | S | - | F | S | V | S | P | G | G | T | V | T | L | T | C |

Lama glama vL2 germlined towards human VL9

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL2-1B LAMA glama Cons. | Q | S | V | L | T | Q | P | P | S | - | V | S | G | T | L | G | K | T | V | T | I | S | C |
| VL9 HUMAN Cons. | Q | P | V | L | T | Q | P | P | S | - | A | S | A | S | L | G | A | S | V | T | L | T | C |

Lama glama vL2 germlined towards human VL10

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL2-1B LAMA glama Cons. | Q | S | V | L | T | Q | P | S | - | V | S | G | T | L | G | K | T | V | T | I | S | C | |
| VL10 HUMAN Cons. | Q | A | G | L | T | Q | P | P | S | - | V | S | K | G | L | R | Q | T | A | T | L | T | C |

*Fig. 15C*

TABLE 11: COMPARISON OF LLAMA GLAMA VL2 CONSENSUS SEQUENCES WITH HUMAN GERMLINE CONSENSUS SEQUENCES (Framework Region 2)
COMPARISON OF LAMA GLAMA VL2-11 CONSENSUS SEQUENCE TO HUMAN CONSENSUS GERMLINES OF VK1-10

Lama glama VL2 germlined towards human VL1

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL1 | HUMAN Cons. | W | Y | Q | Q | L | P | G | T | A | P | K | L | L | I | Y |

Lama glama VL2 germlined towards human VL2 (preferred for sequence homology and length of CDRs)

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL2 | HUMAN Cons. | W | Y | Q | Q | H | P | G | K | A | P | K | L | M | I | Y |

Lama glama VL2 germlined towards human VL3

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL3 | HUMAN Cons. | W | Y | Q | Q | K | P | G | Q | A | P | V | L | V | I | Y |

Lama glama VL2 germlined towards human VL4

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL4 | HUMAN Cons. | W | H | Q | Q | Q | P | G | K | G/A/S | P | R | Y | L | M | K |

Lama glama VL2 germlined towards human VL5

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL5 | HUMAN Cons. | W | Y | Q | Q | K | P | G | S | P | P | R | Y | L | L | Y/R |

Lama glama VL2 germlined towards human VL6

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL6 | HUMAN Cons. | W | Y | Q | Q | R | P | G | S | S | P | T | T | V | I | Y |

Lama glama VL2 germlined towards human VL7

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL7 | HUMAN Cons. | W | F | Q | Q | K | P | G | Q | A | P | R | A/T | L | I | Y |

Lama glama VL2 germlined towards human VL8

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL8 | HUMAN Cons. | W | Y | Q | Q | T | P | G | Q | A | P | R | T | L | I | Y |

*Fig. 16A*

TABLE 11: COMPARISON OF LLAMA GLAMA VL2 CONSENSUS SEQUENCES WITH HUMAN GERMLINE CONSENSUS SEQUENCES (Framework Region 2)

Lama glama VL2 germlined towards human VL9

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL9 | HUMAN Cons. | W | Y | Q | Q | R | P | G | K | G | P | R | F | V | M | R |

Lama glama VL2 germlined towards human VL10

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-11 | LAMA glama Cons. | W | Y | Q | Q | L | P | G | M | A | P | K | L | L | I | Y |
| VL10 | HUMAN Cons. | W | L | Q | Q | H | Q | G | H | P | P | K | L | L | S | Y |

COMPARISON OF LAMA GLAMA VL2-18 CONSENSUS SEQUENCE TO HUMAN CONSENSUS GERMLINES OF VK1-10

Lama glama VL2 germlined towards human VL1

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL1 | HUMAN Cons. | W | Y | Q | Q | L | P | G | T | A | P | K | L | L | I | Y |

Lama glama VL2 germlined towards human VL2 (preferred for sequence homology and length of CDRs)

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL2 | HUMAN Cons. | W | Y | Q | Q | H | P | G | K | A | P | K | L | M | I | Y |

Lama glama VL2 germlined towards human VL3

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL3 | HUMAN Cons. | W | Y | Q | Q | K | P | G | Q | A | P | V | L | V | I | Y |

Lama glama VL2 germlined towards human VL4

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL4 | HUMAN Cons. | W | H | Q | Q | Q | P | G | K | G/A/S | P | R | Y | L | M | K |

Lama glama VL2 germlined towards human VL5

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL5 | HUMAN Cons. | W | Y | Q | Q | K | P | G | S | P | P | R | Y | L | L | Y/R |

Lama glama VL2 germlined towards human VL6

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL6 | HUMAN Cons. | W | Y | Q | Q | R | P | G | S | S | P | T | T | V | I | Y |

*Fig. 16B*

TABLE 11: COMPARISON OF LLAMA GLAMA VL2 CONSENSUS SEQUENCES WITH HUMAN GERMLINE CONSENSUS SEQUENCES (Framework Region 2)

Lama glama VL2 germlined towards human VL7

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL7 | HUMAN Cons. | W | F | Q | Q | K | P | G | Q | A | P | R | A/T | L | I | Y |

Lama glama VL2 germlined towards human VL8

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL8 | HUMAN Cons. | W | Y | Q | Q | T | P | G | Q | A | P | R | T | L | I | Y |

Lama glama VL2 germlined towards human VL9

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL9 | HUMAN Cons. | W | Y | Q | Q | R | P | G | K | G | P | R | F | V | M | R |

Lama glama VL2 germlined towards human VL10

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL2-18 | LAMA glama Cons. | W | Y | Q | Q | L | P | G | T | A | P | K | L | L | I | Y |
| VL10 | HUMAN Cons. | W | L | Q | Q | H | Q | G | H | P | P | K | L | L | S | Y |

TABLE 12: COMPARISON OF LLAMA GLAMA VL2 CONSENSUS SEQUENCES WITH HUMAN GERMLINE CONSENSUS SEQUENCES (Framework Region 3)

Lama glama VL2 germlined towards human VL7

| NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|
| VL2-18 LAMA glama Cons. | G | I | P | D | R | F | S | G | S | K | - | - | S | G | N | T | A | S | L | T | I | S | G | L | Q | S | E | D | E | A | D | Y | Y | C |
| VL7 HUMAN Cons. | W | T | P | A | R | F | S | G | S | L | - | - | L | G | G | K | A | A | L | T | L | S | G | A/V | Q | P | E | D | E | A | E | Y | Y | C |

Lama glama VL2 germlined towards human VL8

| NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|
| VL2-18 LAMA glama Cons. | G | I | P | D | R | F | S | G | S | K | - | - | S | G | N | T | A | S | L | T | I | S | G | L | Q | S | E | D | E | A | D | Y | Y | C |
| VL8 HUMAN Cons. | G | V | P | D | R | F | S | G | S | I | - | - | L | G | N | K | A | A | L | T | I | T | G | A | Q | A | D | D | E | S | D | Y | Y | C |

Lama glama VL2 germlined towards human VL9

| NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|
| VL2-18 LAMA glama Cons. | G | I | P | D | R | F | S | G | S | K | - | - | S | G | N | T | A | S | L | T | I | S | G | L | Q | E | E | D | E | A | D | Y | Y | C |
| VL9 HUMAN Cons. | G | I | P | D | R | F | S | V | L | G | - | - | S | G | L | N | R | Y | L | T | I | K | N | I | Q | E | E | D | E | S | D | Y | H | C |

Lama glama VL2 germlined towards human VL10

| NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|
| VL2-18 LAMA glama Cons. | G | I | P | D | R | F | S | G | S | K | - | - | S | G | N | T | A | S | L | T | I | S | G | L | Q | S | E | D | E | A | D | Y | Y | C |
| VL10 HUMAN Cons. | G | I | S | E | R | L | S | A | S | R | - | - | S | G | N | T | A | S | L | T | I | T | G | L | Q | P | E | D | E | A | D | Y | Y | C |

Fig. 17C

TABLE 13: COMPARISON OF LLAMA GLAMA VL3 CONSENSUS SEQUENCES WITH HUMAN GERMLINE CONSENSUS SEQUENCES (Framework Region 1)
COMPARISON OF LAMA GLAMA VL3-19 CONSENSUS SEQUENCE TO HUMAN CONSENSUS GERMLINES OF VL Lama glama VL3-19 germlined towards human VL1

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | K | I | T | C |
| VL1 HUMAN Cons. | Q | S | V | L | T | Q | P | P | S | - | V | S | G | A | P | G | Q | R | V | T | I | S | C |

Lama glama VL3-19 germlined towards human VL2

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | K | I | T | C |
| VL2 HUMAN Cons. | Q | S | A | L | T | Q | P | A/P | S | - | V | S | G | S | P | G | Q | S | V | T | I | S | C |

Lama glama VL3-19 germlined towards human VL3 (preferred for sequence homology and length of CDRs)

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | K | I | T | C |
| VL3-19 HUMAN Cons. | S | Y | F | L | T | Q | P | P | S | - | V | S | V | S | L | G | A | S | A | R | L | T | C |

Lama glama VL3-19 germlined towards human VL4

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | K | I | T | C |
| VL4 HUMAN Cons. | Q | P | V | L | T | Q | P | P | S | - | A | S | A | S | L | G | A | S | V | K | L | T | C |

Lama glama VL3-19 germlined towards human VL5

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | K | I | T | C |
| VL5 HUMAN Cons. | Q | P | V | L | T | Q | P | A/P/S/T | S | - | L | S | A | S | P | G | A | S | A | R | L | T | C |

Lama glama VL3-19 germlined towards human VL6

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | R | L | T | C |
| VL6 HUMAN Cons. | N | F | M | L | T | Q | P | H | S | - | V | S | F | S | P | G | K | T | V | T | I | S | C |

Lama glama VL3-19 germlined towards human VL7

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | K | I | T | C |
| VL7 HUMAN Cons. | Q | A/T | V | T | Q | E | P | S | - | - | L | T | V | S | P | G | G | T | V | T | L | T | C |

Lama glama VL3-19 germlined towards human VL8

| | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-19 LAMA GLAMA Cons. | Q | S | A | L | T | Q | P | S | A | - | L | S | V | T | L | G | Q | T | A | K | I | T | C |
| VL8 HUMAN Cons. | Q | T | V | V | T | Q | E | P | S | - | F | S | V | S | P | G | G | T | V | T | L | T | C |

TABLE 13: COMPARISON OF LLAMA GLAMA VL3 CONSENSUS SEQUENCES WITH HUMAN GERMLINE CONSENSUS SEQUENCES (Framework Region 1)

Lama glama VL3-25 germlined towards human VL7

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-25 LAMA GLAMA Cons. | Q | A | G | L | T | Q | P | S | A | - | V | S | V | S | L | G | Q | T | A | R | I | T | C |
| VL7 HUMAN Cons. | Q | A/I | V | V | I | Q | E | P | S | - | L | I | V | S | P | G | G | T | V | I | L | T | C |

Lama glama VL3-25 germlined towards human VL8

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-25 LAMA GLAMA Cons. | Q | A | G | I | T | Q | P | S | A | - | V | S | V | S | I | G | Q | T | A | R | I | T | C |
| VL8 HUMAN Cons. | Q | T | V | V | T | Q | E | P | S | - | F | S | V | S | P | G | G | T | V | T | L | T | C |

Lama glama VL3-25 germlined towards human VL9

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-25 LAMA GLAMA Cons. | Q | A | G | L | T | Q | P | S | A | - | V | S | V | S | L | G | Q | T | A | R | I | T | C |
| VL9 HUMAN Cons. | Q | P | V | L | T | Q | P | P | S | - | A | S | A | S | L | G | A | S | V | T | L | T | C |

Lama glama VL3-25 germlined towards human VL10

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL3-25 LAMA GLAMA Cons. | Q | A | G | L | T | Q | P | S | A | - | V | S | V | S | L | G | Q | T | A | R | I | T | C |
| VL10 HUMAN Cons. | Q | A | G | L | T | Q | P | P | S | - | V | S | K | G | L | R | Q | T | A | T | L | T | C |

Fig. 18C

TABLE 14: COMPARISON OF LLAMA GLAMA VL3 CONSENSUS SEQUENCES WITH HUMAN GERMLINE CONSENSUS SEQUENCES (Framework Region 2)
COMPARISON OF LAMA GLAMA VL3-19 CONSENSUS SEQUENCE TO HUMAN CONSENSUS GERMLINES OF VL Lama glama VL3-19 germlined towards human VL1

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL1 | HUMAN Cons. | W | Y | Q | C | L | F | G | T | A | P | K | L | L | I | Y |

Lama glama VL3-19 germlined towards human VL2

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL2 | HUMAN Cons. | W | Y | Q | C | H | F | G | K | A | P | K | L | M | I | Y |

Lama glama VL3-19 germlined towards human VL3 (preferred for sequence homology and length of CDRs)

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL3-19 | HUMAN Cons. | W | Y | Q | C | K | F | G | Q | A | P | V | L | V | I | Y |

Lama glama VL3-19 germlined towards human VL4

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL4 | HUMAN Cons. | W | H | Q | C | Q | F | G | K | G/A/S | P | R | Y | L | M | K |

Lama glama VL3-19 germlined towards human VL5

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL5 | HUMAN Cons. | W | Y | Q | C | K | F | G | S | P | P | R | Y | L | L | Y/R |

Lama glama VL3-19 germlined towards human VL6

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL6 | HUMAN Cons. | W | Y | Q | C | R | F | G | S | S | P | T | T | V | I | Y |

Lama glama VL3-19 germlined towards human VL7

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL7 | HUMAN Cons. | W | F | Q | C | K | F | G | Q | A | P | R | A/T | L | I | Y |

Lama glama VL3-19 germlined towards human VL8

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-19 | LAMA GLAMA Cons. | W | Y | Q | C | K | F | G | Q | A | P | V | L | V | I | Y |
| VL8 | HUMAN Cons. | W | Y | Q | C | T | F | G | Q | A | P | R | T | L | I | Y |

*Fig. 19A*

TABLE 14: COMPARISON OF LLAMA GLAMA VL3 CONSENSUS SEQUENCES WITH HUMAN GERMLINE CONSENSUS SEQUENCES (Framework Region 2)

Lama glama VL3-19 germlined towards human VL9

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-19 | LAMA GLAMA Cons. | W | Y | Q | Q | K | P | G | Q | A | P | V | L | V | I | Y |
| V.9 | HUMAN Cons. | W | Y | Q | Q | R | P | G | K | G | P | R | F | V | M | R |

Lama glama VL3-19 germlined towards human VL10

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-19 | LAMA GLAMA Cons. | W | Y | Q | Q | K | P | G | Q | A | P | V | L | V | I | Y |
| V.10 | HUMAN Cons. | W | L | Q | Q | H | Q | G | H | P | P | K | L | L | S | Y |

COMPARISON OF LAMA GLAMA VL3-25 CONSENSUS SEQUENCE TO HUMAN CONSENSUS GERMLINES OF VL

Lama glama VL3-25 germlined towards human VL1

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-25 | LAMA GLAMA Cons. | W | Y | Q | Q | K | P | G | Q | A | P/R | V | L/Q | V | I | Y |
| V.1 | HUMAN Cons. | W | Y | Q | Q | L | P | G | T | A | P | K | L | L | I | Y |

Lama glama VL3-25 germlined towards human VL2

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-25 | LAMA GLAMA Cons. | W | Y | Q | Q | K | P | G | Q | A | P/R | V | L/Q | V | I | Y |
| V.2 | HUMAN Cons. | W | Y | Q | Q | H | P | G | K | A | P | K | L | M | I | Y |

Lama glama VL3-25 germlined towards human VL3 (preferred for sequence homology and length of CDRs)

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-25 | LAMA GLAMA Cons. | W | Y | Q | Q | K | P | G | Q | A | P/R | V | L/Q | V | I | Y |
| V.3-25 | HUMAN Cons. | W | Y | Q | Q | K | P | G | Q | A | P | V | L | V | I | Y |

Lama glama VL3-25 germlined towards human VL4

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-25 | LAMA GLAMA Cons. | W | Y | Q | Q | K | P | G | Q | A | P/R | V | L/Q | V | I | Y |
| V.4 | HUMAN Cons. | W | H | Q | Q | Q | P | G | K | G/A/S | P | R | Y | L | M | K |

Lama glama VL3-25 germlined towards human VL5

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-25 | LAMA GLAMA Cons. | W | Y | Q | Q | K | P | G | Q | A | P/R | V | L/Q | V | I | Y |
| V.5 | HUMAN Cons. | W | Y | Q | Q | K | P | G | S | P | P | R | Y | L | L | Y/R |

Lama glama VL3-25 germlined towards human VL6

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.3-25 | LAMA GLAMA Cons. | W | Y | Q | Q | K | P | G | Q | A | P/R | V | L/Q | V | I | Y |
| V.6 | HUMAN Cons. | W | Y | Q | Q | R | P | G | S | S | P | T | T | V | I | Y |

Fig. 19B

TABLE 14: COMPARISON OF LLAMA GLAMA VL3 CONSENSUS SEQUENCES WITH HUMAN GERMLINE CONSENSUS SEQUENCES (Framework Region 2)

Lama glama VL3-25 germlined towards human VL7

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-25 | LAMA GLAMA Cons. | W | Y | Q | Q | K | P | G | Q | A | P/R | V | L/Q | V | I | Y |
| VL7 | HUMAN Cons. | W | F | Q | Q | K | P | G | Q | A | P | R | A/T | L | I | Y |

Lama glama VL3-25 germlined towards human VL8

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-25 | LAMA GLAMA Cons. | W | Y | Q | Q | K | P | G | Q | A | P/R | V | L/Q | V | I | Y |
| VL8 | HUMAN Cons. | W | Y | Q | Q | T | P | G | Q | A | P | R | T | L | I | Y |

Lama glama VL3-25 germlined towards human VL9

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-25 | LAMA GLAMA Cons. | W | Y | Q | Q | K | P | G | Q | A | P/R | V | L/Q | V | I | Y |
| VL9 | HUMAN Cons. | W | Y | Q | Q | R | P | G | K | G | P | R | F | V | M | R |

Lama glama VL3-25 germlined towards human VL10

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL3-25 | LAMA GLAMA Cons. | W | Y | Q | Q | K | P | G | Q | A | P/R | V | L/Q | V | I | Y |
| VL10 | HUMAN Cons. | W | L | Q | Q | H | Q | G | H | P | P | K | L | L | S | Y |

TABLE 15: COMPARISON OF LLAMA GLAMA vL3 CONSENSUS SEQUENCES WITH HUMAN GERMLINE CONSENSUS SEQUENCES (Framework Region 3)

*Lama glama vL3-25 germlined towards human VL7*

| | NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|---|
| VL3-25 | L.GLAMA Cons. | G | I | P | E | R | F | S | G | S | R | - | - | I/S | G | G | T | A | T | L | T | I | S | G | A | Q | A | E | D | E | A | D | Y | Y | C |
| VL7 | HUMAN Cons. | W | T | P | A | R | F | S | G | S | L | - | - | L | G | G | K | A | A | L | T | L | S | G | W | Q | P | E | D | E | A | E | Y | Y | C |

*Lama glama vL3-25 germlined towards human VL8*

| | NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|---|
| VL3-25 | L.GLAMA Cons. | G | I | P | E | R | F | S | G | S | R | - | - | I/S | G | G | T | A | T | L | T | I | S | G | A | Q | A | E | D | E | A | D | Y | Y | C |
| VL8 | HUMAN Cons. | G | V | P | D | R | F | S | G | S | I | - | - | L | G | N | K | A | A | L | T | I | T | G | A | Q | A | D | D | E | S | D | Y | Y | C |

*Lama glama vL3-25 germlined towards human VL9*

| | NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|---|
| VL3-25 | L.GLAMA Cons. | G | I | P | E | R | F | S | G | S | R | - | - | I/S | G | G | T | A | T | L | T | I | S | G | A | Q | A | E | D | E | A | D | Y | Y | C |
| VL9 | HUMAN Cons. | G | I | P | D | R | F | S | G | V | L | - | - | S | G | L | N | R | Y | L | T | I | K | N | I | Q | A | E | D | E | A | D | Y | H | C |

*Lama glama vL3-25 germlined towards human VL10*

| | NUMBERING L- | 57 | 58 | 59 | 60 | 61 | 62 | 63 | 64 | 65 | 66 | 66A | 66B | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|---|---|
| VL3-25 | L.GLAMA Cons. | G | I | P | E | R | L | S | G | S | R | - | - | I/S | G | G | T | A | I | L | T | I | S | G | A | Q | A | E | D | E | A | D | Y | Y | C |
| VL10 | HUMAN Cons. | G | I | S | E | R | L | S | A | S | R | - | - | S | G | N | T | A | S | L | T | I | T | G | L | Q | P | E | D | E | A | D | Y | Y | C |

*Fig. 20C*

TABLE 16: COMPARISON OF LLAMA GLAMA VL5 CONSENSUS SEQUENCES WITH HUMAN GERMLINE CONSENSUS SEQUENCES (Framework Region 1)

COMPARISON OF LAMA GLAMA VL5 CONSENSUS SEQUENCE TO HUMAN CONSENSUS GERMLINES OF VL1-10

Lama glama VL5 germlined towards human VL1

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL1 | HUMAN Cons. | Q | S | V | L | T | Q | P | P | S | - | V | S | G | A | P | G | Q | R | V | T | I | S | C |

Lama glama VL5 germlined towards human VL2

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL2 | HUMAN Cons. | Q | S | A | L | T | Q | P | A/P | S | - | V | S | G | S | P | G | Q | S | V | T | I | S | C |

Lama glama VL5 germlined towards human VL3

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL3 | HUMAN Cons. | S | Y | E | L | T | Q | P | P | S | - | V | S | V | S | P | G | Q | T | A | R | I | T | C |

Lama glama VL5 germlined towards human VL4

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL4 | HUMAN Cons. | Q | A | V | L | T | Q | P | P | S | - | A | S | A | S | L | G | A | S | V | R | L | T | C |

Lama glama VL5 germlined towards human VL5

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P/S/ | S | - | L | S | A | S | P | G | S | S | V | R | L | T | C |
| VL5 | HUMAN Cons. | Q | P | V | L | T | Q | P | P | G | - | A | S | V | S | P | G | K | S | A | R | L | T | C |

Lama glama VL5 germlined towards human VL6

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL6 | HUMAN Cons. | N | F | M | L | T | Q | P | H | S | - | V | S | L | S | P | G | K | T | V | I | T | S | C |

*Fig. 21A*

TABLE 16: COMPARISON OF LLAMA GLAMA VL5 CONSENSUS SEQUENCES WITH HUMAN GERMLINE CONSENSUS SEQUENCES (Framework Region 1)

Lama glama VL5 germlined towards human VL7

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | - | S | A | S | P | G | S | S | V | R | L | T | C |
| VL7 | HUMAN Cons. | Q | A/T | V | V | T | Q | E | P | S | - | - | T | V | S | P | G | G | T | V | T | L | T | C |

Lama glama VL5 germlined towards human VL8

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL8 | HUMAN Cons. | Q | T | V | V | T | Q | E | P | S | - | F | S | V | S | P | G | G | T | V | T | L | T | C |

Lama glama VL5 germlined towards human VL9

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL9 | HUMAN Cons. | Q | P | V | L | T | Q | P | P | S | - | A | S | A | S | L | G | A | S | V | T | L | T | C |

Lama glama VL5 germlined towards human VL50

| | NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|---|
| VL5 | LAMA glama Cons. | Q | A | V | L | T | Q | P | P | S | - | L | S | A | S | P | G | S | S | V | R | L | T | C |
| VL10 | HUMAN Cons. | Q | A | G | L | T | Q | P | P | S | - | V | S | K | G | L | R | Q | T | A | T | L | T | C |

*Fig. 21B*

TABLE 17: COMPARISON OF LLAMA GLAMA VL5 CONSENSUS SEQUENCES WITH HUMAN GERMLINE CONSENSUS SEQUENCES (Framework Region 2)

COMPARISON OF LAMA GLAMA VL5 CONSENSUS SEQUENCE TO HUMAN CONSENSUS GERMLINES OF VL1-10

Lama glama VL5 germlined towards human VL1

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.5 | LAMA glama Cons. | W | Y | Q | Q | K | A | G | S | P | P | R | Y | L | L | Y |
| V.1 | HUMAN Cons. | W | Y | Q | Q | L | P | G | T | A | P | K | L | L | I | Y |

Lama glama VL5 germlined towards human VL2

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.5 | LAMA glama Cons. | W | Y | Q | Q | K | A | G | S | P | P | R | Y | L | L | Y |
| V.2 | HUMAN Cons. | W | Y | Q | Q | H | P | G | K | A | P | K | L | M | I | Y |

Lama glama VL5 germlined towards human VL3

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.5 | LAMA glama Cons. | W | Y | Q | Q | K | A | G | S | P | P | R | Y | L | L | Y |
| V.3 | HUMAN Cons. | W | Y | Q | Q | K | P | G | Q | A | P | V | L | V | I | Y |

Lama glama VL5 germlined towards human VL4

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.5 | LAMA glama Cons. | W | Y | Q | Q | K | A | G | S | P | P | R | Y | L | L | Y |
| V.4 | HUMAN Cons. | W | H | Q | Q | Q | P | G | K | G/A/S | P | R | Y | L | M | K |

Lama glama VL5 germlined towards human VL5

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.5 | LAMA glama Cons. | W | Y | Q | Q | K | A | G | S | P | P | R | Y | L | L | Y |
| V.5 | HUMAN Cons. | W | Y | Q | Q | K | P | G | S | P | P | R | Y | L | L | Y/R |

Lama glama VL5 germlined towards human VL6

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| V.5 | LAMA glama Cons. | W | Y | Q | Q | K | A | G | S | P | P | R | Y | L | L | Y |
| V.6 | HUMAN Cons. | W | Y | Q | Q | R | P | G | S | S | P | T | T | V | I | Y |

*Fig. 22A*

TABLE 17: COMPARISON OF LLAMA GLAMA VL5 CONSENSUS SEQUENCES WITH HUMAN GERMLINE CONSENSUS SEQUENCES (Framework Region 2)

Lama glama VL5 germlined towards human VL7

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL5 | LAMA glama Cons. | W | Y | Q | Q | K | A | G | S | P | P | R | Y | L | L | Y |
| VL7 | HUMAN Cons. | W | F | Q | Q | K | P | G | Q | A | P | R | A/T | L | I | Y |

Lama glama VL5 germlined towards human VL8

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL5 | LAMA glama Cons. | W | Y | Q | Q | K | A | G | S | P | P | R | Y | L | L | Y |
| VL8 | HUMAN Cons. | W | Y | Q | Q | T | P | G | Q | A | P | R | T | L | I | Y |

Lama glama VL5 germlined towards human VL9

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL5 | LAMA glama Cons. | W | Y | Q | Q | K | A | G | S | P | P | R | Y | L | L | Y |
| VL9 | HUMAN Cons. | W | Y | Q | Q | R | P | G | K | G | P | R | F | V | M | R |

Lama glama VL5 germlined towards human VL50

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL5 | LAMA glama Cons. | W | Y | Q | Q | K | A | G | S | P | P | R | Y | L | L | Y |
| VL10 | HUMAN Cons. | W | L | Q | Q | H | Q | G | H | P | P | K | L | L | S | Y |

Fig. 22B

TABLE 18: COMPARISON OF LLAMA GLAMA VL5 CONSENSUS SEQUENCES WITH HUMAN GERMLINE CONSENSUS SEQUENCES (Framework Region 3)

COMPARISON OF LAMA GLAMA VL5 CONSENSUS SEQUENCE TO HUMAN CONSENSUS GERMLINES OF VL1-10

Lama glama VL5 germlined towards human VL1

| | NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|---|
| VL5 | LAMA glama Cons. | V | P | S | R | F | S | G | S | K | D | - | S | A | N | A | G | L | L | L | I | S | G | L | Q | P | E | D | E | A | D | Y | Y |
| VL1 | HUMAN Cons. | V | P | D | R | F | S | G | S | K | - | - | S | G | T | S | A | S | L | A | I | S | G | L | Q | S | E | D | E | A | D | Y | Y |

Lama glama VL5 germlined towards human VL2

| | NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|---|
| VL5 | LAMA glama Cons. | V | P | S | R | F | S | G | S | K | D | - | S | A | N | A | G | L | L | L | I | S | G | L | Q | P | E | D | E | A | D | Y | Y |
| VL2 | HUMAN Cons. | V | P | E | R | F | S | G | S | K | - | - | S | G | N | A | G | L | L | T | I | S | G | L | Q | A | E | D | E | A | D | Y | Y |

Lama glama VL5 germlined towards human VL3

| | NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|---|
| VL5 | LAMA glama Cons. | V | P | S | R | F | S | G | S | K | D | - | S | A | N | A | G | L | L | L | I | S | G | L | Q | P | E | D | E | A | D | Y | Y |
| VL3 | HUMAN Cons. | I | P | E | R | F | S | G | S | S | - | - | S | G | N | T | A | T | L | T | I | S | G | L | Q | A | E | D | E | A | D | Y | Y |

Lama glama VL5 germlined towards human VL4

| | NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|---|
| VL5 | LAMA glama Cons. | V | P | S | R | F | S | G | S | K | D | - | S | A | N | A | G | L | L | L | I | S | G | L | Q | P | E | D | E | A | D | Y | Y |
| VL4 | HUMAN Cons. | V | P | D | R | F | S | G | S | K | D | - | S | A | N | T | A | T | L | T | I | S | G | L | Q | A | E | D | E | A | D | Y | Y |

Lama glama VL5 germlined towards human VL5

| | NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|---|
| VL5 | LAMA glama Cons. | V | P | S | R | F | S | G | S | K | D | - | S | A | N | A | G | L | L | L | I | S | G | L | Q | P | E | D | E | A | D | Y | Y |
| VL5 | HUMAN Cons. | V | P | D | R | F | S | G | S | S | - | - | S | A | N | A | G | R | Y | L | I | S | G | N | L | Q | A | E | D | E | A | D | Y | Y |

Lama glama VL5 germlined towards human VL6

| | NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|---|
| VL5 | LAMA glama Cons. | V | P | S | R | F | S | G | S | K | D | - | S | A | N | S | A | S | L | T | I | S | G | L | Q | K | T | D | E | A | D | Y | Y |
| VL6 | HUMAN Cons. | V | P | D | R | F | S | G | S | - | D | - | S | A | N | S | A | S | L | T | I | S | G | L | Q | K | T | D | E | A | D | Y | Y |

Fig. 23A

TABLE 18: COMPARISON O- LLAMA GLAMA VL5 CONSENSUS SEQUENCES WITH HUMAN GERMLINE CONSENSUS SEQUENCES (Framework Region 3)

Llama glama VL5 germlined towards human VL7

| NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|
| V5 LAMA glama Cons. | V | P | S | R | F | S | G | S | K | D | - | - | L | G | A | G | L | L | - | - | S | G | L | Q | P | E | D | E | A | D | Y | Y |
| V7 HUMAN Cons. | T | P | A | R | F | S | G | S | L | - | - | - | L | G | K | A | A | L | T | L | S | G | A/V | Q | P | E | D | E | A | E | Y | Y |

Llama glama VL5 germlined towards human VL8

| NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|
| V5 LAMA glama Cons. | V | P | S | R | F | S | G | S | K | D | - | - | A | S | A | N | A | G | L | L | - | - | S | G | L | Q | P | E | D | E | A | D | Y | Y |
| V8 HUMAN Cons. | V | P | D | R | F | S | G | S | I | - | - | - | L | G | N | K | A | A | L | T | I | T | G | A | Q | A | D | D | E | S | D | Y | Y |

Llama glama VL5 germlined towards human VL9

| NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|
| V5 LAMA glama Cons. | V | P | S | R | F | S | G | S | K | D | - | - | A | N | A | G | L | L | - | - | S | G | L | Q | P | E | D | E | A | D | Y | Y |
| V9 HUMAN Cons. | V | P | E | R | F | S | A | S | - | - | - | S | G | N | T | A | S | L | T | I | K | N | I | Q | E | E | D | E | S | D | Y | H |

Llama glama VL5 germlined towards human VL10

| NUMBERING | L58 | L59 | L60 | L61 | L62 | L63 | L64 | L65 | L66 | L66A | L66B | L67 | L68 | L69 | L70 | L71 | L72 | L73 | L74 | L75 | L76 | L77 | L78 | L79 | L80 | L81 | L82 | L83 | L84 | L85 | L86 | L87 |
|---|---|---|---|---|---|---|---|---|---|---|---|---|---|---|---|---|---|---|---|---|---|---|---|---|---|---|---|---|---|---|---|---|
| V5 LAMA glama Cons. | V | P | S | R | F | S | G | S | K | D | - | - | A | N | A | G | L | L | - | - | S | G | L | Q | P | E | D | E | A | D | Y | Y |
| VL10 HUMAN Cons. | I | S | E | R | L | S | A | S | R | - | - | - | S | G | N | T | A | S | L | T | I | T | G | L | Q | E | D | D | S | A | D | Y | Y |

TABLE 19: COMPARISON OF LLAMA GLAMA VL8 CONSENSUS SEQUENCES WITH HUMAN GERMLINE CONSENSUS SEQUENCES (Framework Region 1)

Lama glama VL8 germlined towards human VL9

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL8-61 LAMA GLAMA Cons. | Q | A | V | T | Q | E | P | S | - | L | S | V | S | P | G | G | T | V | T | L | T | C |
| VL9 HUMAN Cons. | Q | P | V | L | T | Q | P | P | S | - | A | S | A | S | L | G | A | S | V | T | L | T | C |

Lama glama VL8 germlined towards human VL10

| NUMBERING | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 |
|---|---|---|---|---|---|---|---|---|---|---|---|---|---|---|---|---|---|---|---|---|---|---|---|
| VL8-61 LAMA GLAMA Cons. | Q | A | V | T | Q | E | P | S | - | L | S | V | S | P | G | G | T | V | T | L | T | C |
| VL10 HUMAN Cons. | Q | A | G | L | T | Q | P | P | S | - | V | S | K | G | L | R | Q | T | A | T | L | T | C |

*Fig. 24B*

TABLE 20: COMPARISON OF LLAMA GLAMA VL8 CONSENSUS SEQUENCES WITH HUMAN GERMLINE CONSENSUS SEQUENCES (Framework Region 2)
COMPARISON OF LAMA GLAMA VL8 CONSENSUS SEQUENCE TO HUMAN CONSENSUS GERMLINES OF VL Lama glama VL8 germlined towards human VL1

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL1 | HUMAN Cons. | W | Y | Q | Q | L | P | G | T | A | P | K | L | L | I | Y |

Lama glama VL8 germlined towards human VL2

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL2 | HUMAN Cons. | W | Y | Q | Q | H | P | G | K | A | P | K | L | M | I | Y |

Lama glama VL8 germlined towards human VL3

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL3 | HUMAN Cons. | W | Y | Q | Q | K | P | G | Q | A | P | V | L | V | I | Y |

Lama glama VL8 germlined towards human VL4

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL4 | HUMAN Cons. | W | H | Q | Q | Q | P | G | K | G/A/S | P | R | Y | L | M | K |

Lama glama VL8 germlined towards human VL5

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL5 | HUMAN Cons. | W | Y | Q | Q | K | P | G | S | P | P | R | Y | L | L | Y/R |

Lama glama VL8 germlined towards human VL6

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL6 | HUMAN Cons. | W | Y | Q | Q | R | P | G | S | S | P | T | T | V | I | Y |

Lama glama VL8 germlined towards human VL7

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL7 | HUMAN Cons. | W | F | Q | Q | K | P | G | Q | A | P | R | A/T | L | I | Y |

Lama glama VL8 germlined towards human VL8 (preferred for sequence homology and length of CDRs)

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-51 | LAMA GLAMA Cons. | W | Y | Q | Q | T | P | G | Q | A | P | R | T | L | I | Y |
| VL8 | HUMAN Cons. | W | Y | Q | Q | T | P | G | Q | A | P | R | T | L | I | Y |

*Fig. 25A*

TABLE 20: COMPARISON OF LLAMA GLAMA VL8 CONSENSUS SEQUENCES WITH HUMAN GERMLINE CONSENSUS SEQUENCES (Framework Region 2)

Lama glama VL8 germlined towards human VL9

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-61 | LAMA GLAMA Cons. | W | Y | Q | Q | T | P | G | Q | A | P | R | T | L | I | Y |
| VL9 | HUMAN Cons. | W | Y | Q | Q | R | P | G | K | G | P | R | F | V | M | R |

Lama glama VL8 germlined towards human VL10

| | NUMBERING | L35 | L36 | L37 | L38 | L39 | L40 | L41 | L42 | L43 | L44 | L45 | L46 | L47 | L48 | L49 |
|---|---|---|---|---|---|---|---|---|---|---|---|---|---|---|---|---|
| VL8-61 | LAMA GLAMA Cons. | W | Y | Q | Q | T | P | G | Q | A | P | R | T | L | I | Y |
| VL10 | HUMAN Cons. | W | L | Q | Q | H | Q | G | H | P | P | K | L | L | S | Y |

TABLE 21: COMPARISON OF LLAMA GLAMA VL8 CONSENSUS SEQUENCES WITH HUMAN GERMLINE CONSENSUS SEQUENCES (Framework Region 3)

Lama glama VL8 germlined towards human VL9

| NUMBERING | L59 | L60 | L61 | L62 | L63 | L64 | L65 | L66 | L66A | L663 | L67 | L68 | L69 | L70 | L71 | L72 | L73 | L74 | L75 | L76 | L77 | L78 | L79 | L80 | L81 | L82 | L83 | L84 | L85 | L86 | L87 | L88 |
|---|---|---|---|---|---|---|---|---|---|---|---|---|---|---|---|---|---|---|---|---|---|---|---|---|---|---|---|---|---|---|---|---|
| VL8-51 L.GLAMA Cons. | P | S | R | F | S | G | S | I | - | - | S | G | N | K | A | L | T | - | - | T | G | A | Q | P | E | L | - | A | D | Y | Y | C |
| VL9 HUMAN Cons. | P | D | R | F | S | V | L | G | - | - | S | G | L | N | R | Y | L | T | - | K | N | I | Q | E | E | L | - | S | D | Y | H | C |

Lama glama VL8 germlined towards human VL10

| NUMBERING | L59 | L60 | L61 | L62 | L63 | L64 | L65 | L66 | L66A | L663 | L67 | L68 | L69 | L70 | L71 | L72 | L73 | L74 | L75 | L76 | L77 | L78 | L79 | L80 | L81 | L82 | L83 | L84 | L85 | L86 | L87 | L88 |
|---|---|---|---|---|---|---|---|---|---|---|---|---|---|---|---|---|---|---|---|---|---|---|---|---|---|---|---|---|---|---|---|---|
| VL8-51 L.GLAMA Cons. | P | S | R | F | S | G | S | I | - | - | S | G | N | K | A | L | T | - | - | T | G | A | Q | P | E | L | - | A | D | Y | Y | C |
| VL10 HUMAN Cons. | S | E | R | L | S | A | S | R | - | - | S | G | N | T | A | S | L | T | - | T | G | L | Q | P | E | L | - | A | D | Y | Y | C |

Fig. 26B

TABLE 22: COMPARISON OF LLAMA GLAMA VK CONSENSUS SEQUENCES WITH HUMAN GERMLINE CONSENSUS SEQUENCES (Framework Region 1)

COMPARISON OF LAMA GLAMA VK1 CONSENSUS SEQUENCE TO HUMAN CONSENSUS GERMLINES OF VK1-5

Lama glama VK1 germlined towards human VK1

|  | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
|  |  |  |  | x |  |  |  |  |  |  |  |  |  |  |  | x |  |  |  |  |  |  |  |  |
| VK1 | LAMA glama Consensus | D | V | V | M | T | Q | S | P | S | S | L | S | A | S | L | G | D | R | V | T | I | T | C |
| VK1 | HUMAN Consensus | D | I | Q | M | T | Q | S | P | S | S | L | S | A | S | V | G | D | R | V | T | I | T | C |

Lama glama VK1 germlined towards human VK2

|  | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
|  |  |  |  |  |  |  |  | x |  | x |  |  | x | x | x | x |  | x | x | x | x |  | x |  |
| VK1 | LAMA glama Consensus | D | I | V | M | T | Q | S | P | L | S | L | S | A | S | L | G | D | R | V | T | I | T | C |
| VK2 | HUMAN Consensus | D | I | V | M | T | Q | S | P | L | S | L | P | V | T | P | G | Q/E | P | A | S | I | S | C |

Lama glama VK1 germlined towards human VK3

|  | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| x |  |  |  |  | x |  |  |  |  | x |  |  | x | x | x | x |  | x | x | x | x |  | x |  |
| VK1 | LAMA glama Consensus | D | I | V | M | T | Q | S | P | S | S | L | S | A | S | L | G | D | R | V | T | I | T | C |
| VK3 | HUMAN Consensus | E | I | V | L | T | Q | S | P | A | T | L | P | L | S | P | G | E | R | A | T | L | S | C |

Lama glama VK1 germlined towards human VK4

|  | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
|  |  |  |  |  |  |  |  |  |  | x |  |  | x |  |  |  |  | x | x | x | x | x | x |  |
| VK1 | LAMA glama Consensus | D | I | V | M | T | Q | S | P | S | S | L | S | A | S | L | G | D | R | V | T | I | T | C |
| VK4 | HUMAN Consensus | D | I | V | M | T | Q | S | P | D | S | L | A | V | S | L | G | E | R | A | T | L | N | C |

Lama glama VK1 germlined towards human VK5

|  | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| x | x | x |  | x |  |  |  |  | x |  | x |  |  | x | x |  |  | x |  | x |  | x |  |  |
| VK1 | LAMA glama Consensus | D | I | V | M | T | Q | S | P | S | S | L | S | A | S | L | G | D | R | V | T | I | T | C |
| VK5 | HUMAN Consensus | E | T | T | L | T | Q | S | P | A | F | M | S | A | T | P | G | D | K | V | N | I | S | C |

*Fig. 27A*

TABLE 22: COMPARISON OF LLAMA GLAMA VK CONSENSUS SEQUENCES WITH HUMAN GERMLINE CONSENSUS SEQUENCES (Framework Region 1)
COMPARISON OF LAMA GLAMA VK2 CONSENSUS SEQUENCE TO HUMAN CONSENSUS GERMLINES OF VK1-5

Lama glama VK2 germlined towards human VK1

| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| | | | | x | | | | | | x | | | | x | x | x | | x | x | x | x | | x | |
| VK2 | LAMA glama Consensus | D | I | V | M | T | Q | T | P | G | S | L | S | V | V | P | G | E | S | A | S | I | S | C |
| VK1 | HUMAN Consensus | D | I | Q | M | T | Q | S | P | S | S | L | S | A | S | V | G | D | R | V | T | I | T | C |

Lama glama VK2 germlined towards human VK2

| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| | | | | | | | | | | x | | | x | | | | | | x | | | | | |
| VK2 | LAMA glama Consensus | D | I | V | M | T | Q | T | P | G | S | L | S | V | V | P | G | E | S | A | S | I | S | C |
| VK2 | HUMAN Consensus | D | I | V | M | T | Q | S | P | L | S | L | P | V | T | P | G | Q/E | P | A | S | I | S | C |

Lama glama VK2 germlined towards human VK3

| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| x | | x | | | x | | | x | | x | | | x | x | x | | | x | x | x | x | x | x | |
| VK2 | LAMA glama Consensus | D | I | V | M | T | Q | T | P | G | S | L | S | V | V | P | G | E | S | A | S | I | S | C |
| VK3 | HUMAN Consensus | E | I | V | L | T | Q | S | P | A | T | L | S | L | S | P | G | E | R | A | T | L | S | C |

Lama glama VK2 germlined towards human VK4

| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| | | | | | | | | | | x | | | x | | x | | | | x | | | x | | |
| VK2 | LAMA glama Consensus | D | I | V | M | T | Q | T | P | G | S | L | S | V | V | P | G | E | S | A | S | I | S | C |
| VK4 | HUMAN Consensus | D | I | V | M | T | Q | S | P | D | S | L | A | V | S | L | G | E | R | A | T | I | S | C |

Lama glama VK2 germlined towards human VK5

| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|
| x | x | x | | x | | | | | x | x | x | | x | x | | | x | x | x | x | | x | |
| VK2 | LAMA glama Consensus | D | I | V | M | T | Q | T | P | G | S | L | S | V | V | P | G | E | S | A | S | I | S | C |
| VK5 | HUMAN Consensus | E | T | T | L | T | Q | S | P | A | F | M | S | A | T | P | G | D | K | V | N | I | S | C |

*Fig. 27B*

TABLE 22: COMPARISON OF LLAMA GLAMA VK CONSENSUS SEQUENCES WITH HUMAN GERMLINE CONSENSUS SEQUENCES (Framework Region 1)
COMPARISON OF LLAMA GLAMA VK4 CONSENSUS SEQUENCE TO HUMAN CONSENSUS GERMLINES OF VK1-5

Lama glama VK4 germlined towards human VK1

|  |  |  |  | x |  |  |  |  |  |  |  | x |  |  |  | x |  |  | x | x |  |  | x |  |  |
|---|---|---|---|---|---|---|---|---|---|---|---|---|---|---|---|---|---|---|---|---|---|---|---|---|---|
| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| VK4 | LAMA glama Consensus | D | I | V | M | T | Q | S | P | S | S | V | T | A | S | V | G | E | K | V | T |   |   | C |
| VK1 | HUMAN Consensus | D | I | Q | M | T | Q | S | P | S | S | L | S | A | S | V | G | D | R | V | T | I | T | C |

Lama glama VK4 germlined towards human VK2

|  |  |  |  |  |  |  |  | x |  |  | x | x | x | x | x | x |  | x | x | x | x |  | x |  |  |
|---|---|---|---|---|---|---|---|---|---|---|---|---|---|---|---|---|---|---|---|---|---|---|---|---|---|
| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| VK4 | LAMA glama Consensus | D | I | V | M | T | Q | S | P | S | S | V | T | A | S | V | G | E | K | V | T |   |   | C |
| VK2 | HUMAN Consensus | D | I | V | M | T | Q | S | P | T | S | L | P | V | T | P | G | Q/E | P | A | S |   | S | G |

Lama glama VK4 germlined towards human VK3

| x |  |  | x |  |  |  |  |  |  | x | x | x | x | x | x |  | x | x | x | x | x |  | x |  |  |
|---|---|---|---|---|---|---|---|---|---|---|---|---|---|---|---|---|---|---|---|---|---|---|---|---|---|
| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| VK4 | LAMA glama Consensus | D | I | V | M | T | Q | S | P | S | S | V | T | A | S | V | G | E | K | V | T |   |   | C |
| VK3 | HUMAN Consensus | E | I | V | L | T | Q | S | P | A | T | L | S | L | S | P | G | E | R | A | T | L | S | C |

Lama glama VK4 germlined towards human VK4

|  |  |  |  |  |  |  |  |  |  |  | x | x | x | x | x | x |  | x | x | x | x |  | x |  |  |
|---|---|---|---|---|---|---|---|---|---|---|---|---|---|---|---|---|---|---|---|---|---|---|---|---|---|
| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| VK4 | LAMA glama Consensus | D | I | V | M | T | Q | S | P | S | S | V | T | A | S | V | G | E | K | V | T |   |   | C |
| VK4 | HUMAN Consensus | D | I | V | M | T | Q | S | P | D | S | L | A | V | S | L | G | E | R | A | T |   | N | C |

Lama glama VK4 germlined towards human VK5

| x | x | x |  | x |  |  |  |  |  | x | x | x | x | x | x | x | x |  | x |  | x |  |  |
|---|---|---|---|---|---|---|---|---|---|---|---|---|---|---|---|---|---|---|---|---|---|---|---|
| | NUMBERING L- | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| VK4 | LAMA glama Consensus | D | I | V | M | T | Q | S | P | S | S | V | T | A | S | V | G | E | K | V | T |   |   | C |
| VK5 | HUMAN Consensus | E | T | T | L | T | Q | S | P | A | F | M | S | A | T | P | G | D | K | V | N | I | S | C |

*Fig. 27C*

TABLE 23: COMPARISON OF LAMA GLAMA VK CONSENSUS SEQUENCES WITH HUMAN GERMLINE CONSENSUS SEQUENCES (Framework Region 2)

COMPARISON OF LAMA GLAMA VK1 CONSENSUS SEQUENCE TO HUMAN CONSENSUS GERMLINES OF VK1-5

Lama glama VK1 germlined towards human VK1

|     |                   |    |    |    |    |    |    |    |    |    | x  | x  |    |    |    |    |
|-----|-------------------|----|----|----|----|----|----|----|----|----|----|----|----|----|----|----|
|     | NUMBERING L-      | 35 | 36 | 37 | 38 | 39 | 40 | 41 | 42 | 43 | 44 | 45 | 46 | 47 | 48 | 49 |
| VK1 | LAMA glama Consensus | W | Y | Q | Q | K | P | G | Q | T | P | K | L | L | I | Y |
| VK1 | HUMAN Consensus   | W  | Y  | Q  | Q  | K  | P  | G  | K  | A  | P  | K  | L  | L  | I  | Y  |

Lama glama VK1 germlined towards human VK2

|     |                   |    |    | x  |    |    |    |    |    | x  |    | x  |    |    |    |    |
|-----|-------------------|----|----|----|----|----|----|----|----|----|----|----|----|----|----|----|
|     | NUMBERING L-      | 35 | 36 | 37 | 38 | 39 | 40 | 41 | 42 | 43 | 44 | 45 | 46 | 47 | 48 | 49 |
| VK1 | LAMA glama Consensus | W | Y | Q | Q | K | P | G | Q | T | P | K | L | L | I | Y |
| VK2 | HUMAN Consensus   | W  | Y  | L  | Q  | K  | P  | G  | Q | S | P | Q | L | L | I | Y |

Lama glama VK1 germlined towards human VK3

|     |                   |    |    |    |    |    |    |    |    | x  |    | x  |    |    |    |    |
|-----|-------------------|----|----|----|----|----|----|----|----|----|----|----|----|----|----|----|
|     | NUMBERING L-      | 35 | 36 | 37 | 38 | 39 | 40 | 41 | 42 | 43 | 44 | 45 | 46 | 47 | 48 | 49 |
| VK1 | LAMA glama Consensus | W | Y | Q | Q | K | P | G | Q | T | P | K | L | L | I | Y |
| VK3 | HUMAN Consensus   | W  | Y  | Q  | Q  | K  | P  | G  | Q  | A  | P  | R  | L  | L  | I  | Y  |

Lama glama VK1 germlined towards human VK4

|     |                   |    |    |    |    |    |    |    |    | x  |    |    |    |    |    |    |
|-----|-------------------|----|----|----|----|----|----|----|----|----|----|----|----|----|----|----|
|     | NUMBERING L-      | 35 | 36 | 37 | 38 | 39 | 40 | 41 | 42 | 43 | 44 | 45 | 46 | 47 | 48 | 49 |
| VK1 | LAMA glama Consensus | W | Y | Q | Q | K | P | G | Q | T | P | K | L | L | I | Y |
| VK4 | HUMAN Consensus   | W  | Y  | Q  | Q  | K  | P  | G  | Q  | P  | P  | K  | L  | L  | I  | Y  |

Lama glama VK1 germlined towards human VK5

|     |                   |    |    |    |    |    |    |    | x  | x  | x  | x  | x  | x  | x  | x  |
|-----|-------------------|----|----|----|----|----|----|----|----|----|----|----|----|----|----|----|
|     | NUMBERING L-      | 35 | 36 | 37 | 38 | 39 | 40 | 41 | 42 | 43 | 44 | 45 | 46 | 47 | 48 | 49 |
| VK1 | LAMA glama Consensus | W | Y | Q | Q | K | P | G | Q | T | P | K | L | L | I | Y |
| VK5 | HUMAN Consensus   | W  | Y  | Q  | Q  | K  | P  | G  | E  | A  | A  | K  | F  | L  | I  | Q  |

*Fig. 28A*

TABLE 23: COMPARISON OF LLAMA GLAMA VK CONSENSUS SEQUENCES WITH HUMAN GERMLINE CONSENSUS SEQUENCES (Framework Region 2):
COMPARISON OF LAMA GLAMA VK2 CONSENSUS SEQUENCE TO HUMAN CONSENSUS GERMLINES OF VK1-5

Lama glama VK2 germlined towards human VK1

| | | 35 | x 36 | x 37 | 38 | 39 | 40 | 41 | x 42 | x 43 | 44 | x 45 | x 46 | 47 | 48 | 49 |
|---|---|---|---|---|---|---|---|---|---|---|---|---|---|---|---|---|
| | NUMBERING L- | | | | | | | | | | | | | | | |
| VK2 | LAMA glama Consensus | W | L | L | Q | K | P | G | Q | S | P | Q | R | L | I | Y |
| VK1 | HUMAN Consensus | W | Y | Q | Q | K | P | G | K | A | P | K | L | L | I | Y |

Lama glama VK2 germlined towards human VK2

| | | 35 | x 36 | 37 | 38 | 39 | 40 | 41 | 42 | 43 | 44 | 45 | x 46 | 47 | 48 | 49 |
|---|---|---|---|---|---|---|---|---|---|---|---|---|---|---|---|---|
| | NUMBERING L- | | | | | | | | | | | | | | | |
| VK2 | LAMA glama Consensus | W | L | L | Q | K | P | G | Q | S | P | Q | R | L | I | Y |
| VK2 | HUMAN Consensus | W | Y | L | Q | K | P | G | Q | S | P | Q | L | L | I | Y |

Lama glama VK2 germlined towards human VK3

| | | 35 | x 36 | x 37 | 38 | 39 | 40 | 41 | x 42 | x 43 | 44 | x 45 | x 46 | 47 | 48 | 49 |
|---|---|---|---|---|---|---|---|---|---|---|---|---|---|---|---|---|
| | NUMBERING L- | | | | | | | | | | | | | | | |
| VK2 | LAMA glama Consensus | W | L | L | Q | K | P | G | Q | S | P | Q | R | L | I | Y |
| VK3 | HUMAN Consensus | W | Y | Q | Q | K | P | G | Q | A | P | R | L | L | I | Y |

Lama glama VK2 germlined towards human VK4

| | | 35 | x 36 | x 37 | 38 | 39 | 40 | 41 | x 42 | x 43 | 44 | x 45 | x 46 | 47 | 48 | 49 |
|---|---|---|---|---|---|---|---|---|---|---|---|---|---|---|---|---|
| | NUMBERING L- | | | | | | | | | | | | | | | |
| VK2 | LAMA glama Consensus | W | L | L | Q | K | P | G | Q | S | P | Q | R | L | I | Y |
| VK4 | HUMAN Consensus | W | Y | Q | Q | K | P | G | Q | P | P | K | L | L | I | Y |

Lama glama VK2 germlined towards human VK5

| | | 35 | x 36 | x 37 | 38 | 39 | 40 | 41 | x 42 | x 43 | 44 | x 45 | x 46 | x 47 | 48 | x 49 |
|---|---|---|---|---|---|---|---|---|---|---|---|---|---|---|---|---|
| | NUMBERING L- | | | | | | | | | | | | | | | |
| VK2 | LAMA glama Consensus | W | L | L | Q | K | P | G | Q | S | P | Q | R | L | I | Y |
| VK5 | HUMAN Consensus | W | Y | Q | Q | K | P | G | E | A | A | Q | F | I | I | Q |

*Fig. 28B*

TABLE 23: COMPARISON OF LAMA GLAMA VK CONSENSUS SEQUENCES WITH HUMAN GERMLINE CONSENSUS SEQUENCES (Framework Region 2)
COMPARISON OF LLAMA GLAMA VK4 CONSENSUS SEQUENCE TO HUMAN CONSENSUS GERMLINES OF VK1-5

Lama glama VK4 germlined towards human VK1

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
|  |  |  |  |  |  | x |  |  | x | x |  | x |  |  |  |  |
| VK4 | LAMA glama Consensus | W | Y | Q | Q | R | P | G | Q | S | P | R | L | L | I | Y |
| VK1 | HUMAN Consensus | W | Y | Q | Q | K | P | G | K | A | P | K | L | L | I | Y |

Lama glama VK4 germlined towards human VK2

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
|  |  |  |  | x |  | x |  |  |  |  |  | x |  |  |  |  |
| VK4 | LAMA glama Consensus | W | Y | Q | Q | R | P | G | Q | S | P | R | L | L | I | Y |
| VK2 | HUMAN Consensus | W | Y | L | Q | K | P | G | Q | S | P | Q | L | L | I | Y |

Lama glama VK4 germlined towards human VK3

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
|  |  |  |  |  |  | x |  |  |  | x |  |  |  |  |  |  |
| VK4 | LAMA glama Consensus | W | Y | Q | Q | R | P | G | Q | S | P | R | L | L | I | Y |
| VK3 | HUMAN Consensus | W | Y | Q | Q | K | P | G | Q | A | P | R | L | L | I | Y |

Lama glama VK4 germlined towards human VK4

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
|  |  |  |  |  |  | x |  |  |  | x |  | x |  |  |  |  |
| VK4 | LAMA glama Consensus | W | Y | Q | Q | R | P | G | Q | S | P | R | L | L | I | Y |
| VK4 | HUMAN Consensus | W | Y | Q | Q | K | P | G | Q | P | P | K | L | L | I | Y |

Lama glama VK4 germlined towards human VK5

|  | NUMBERING L- | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
|  |  |  |  |  |  | x |  |  | x | x | x | x | x | x |  | x |
| VK4 | LAMA glama Consensus | W | Y | Q | Q | R | P | G | Q | S | P | R | L | L | I | Y |
| VK5 | HUMAN Consensus | W | Y | Q | Q | K | P | G | E | A | A | I | F | L | I | Q |

*Fig. 28C*

TABLE 24: COMPARISON OF LAMA GLAMA VK CONSENSUS SEQUENCES WITH HUMAN GERMLINE CONSENSUS SEQUENCES (Framework Region 3)

COMPARISON OF LAMA GLAMA VK1 CONSENSUS SEQUENCE TO HUMAN CONSENSUS GERMLINES OF VK1-5

Lama glama VK1 germlined towards human VK1

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| VK1 | LAMA glama Consensus | G | V | P | S | R | F | S | G | S | G | S | G | T | S | F | T | L | T | I | S | G | L | E | A | E | D | L | A | T | Y | Y | C |
| VK1 | HUMAN Consensus | G | V | P | S | R | F | S | G | S | G | S | G | T | D | F | T | L | T | I | S | S | L | Q | P | E | D | F | A | T | Y | Y | C |

Lama glama VK1 germlined towards human VK2

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| VK1 | LAMA glama Consensus | G | V | P | S | R | F | S | G | S | G | S | G | T | S | F | T | L | T | I | S | G | L | E | A | E | D | L | A | T | Y | Y | C |
| VK2 | HUMAN Consensus | G | V | P | D | R | F | S | G | S | G | S | G | T | D | F | T | L | K | I | S | R | V | E | A | E | D | V | G | V | Y | Y | C |

Lama glama VK1 germlined towards human VK3

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| VK1 | LAMA glama Consensus | G | V | P | S | R | F | S | G | S | G | S | G | T | S | F | T | L | T | I | S | G | L | E | A | E | D | L | A | T | Y | Y | C |
| VK3 | HUMAN Consensus | G | I | P | A | R | F | S | G | S | G | S | G | T | D | F | T | L | T | I | S | S | L | E | P | E | D | F | A | V | Y | Y | C |

Lama glama VK1 germlined towards human VK4

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| VK1 | LAMA glama Consensus | G | V | P | S | R | F | S | G | S | G | S | G | T | S | F | T | L | T | I | S | G | L | E | A | E | D | L | A | T | Y | Y | C |
| VK4 | HUMAN Consensus | G | V | P | D | R | F | S | G | S | G | S | G | T | D | F | T | L | T | I | S | S | L | Q | A | E | D | V | A | V | Y | Y | C |

Lama glama VK1 germlined towards human VK5

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| VK1 | LAMA glama Consensus | G | V | P | S | R | F | S | G | S | G | S | G | T | S | F | T | L | T | I | S | G | L | E | A | E | D | L | A | T | Y | Y | C |
| VK5 | HUMAN Consensus | G | I | P | P | R | F | S | G | Y | G | S | G | T | D | F | T | L | T | I | S | N | I | E | S | E | D | A | A | Y | Y | F | C |

COMPARISON OF LAMA GLAMA VK2 CONSENSUS SEQUENCE TO HUMAN CONSENSUS GERMLINES OF VK1-5

Lama glama VK2 germlined towards human VK1

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| VK2 | LAMA glama Consensus | G | V | P | D | R | F | S | G | S | G | S | G | T | D | F | T | L | K | I | S | S | V | K | A | E | D | A | G | V | Y | Y | C |
| VK1 | HUMAN Consensus | G | V | P | S | R | F | S | G | S | G | S | G | T | D | F | T | L | T | I | S | S | L | Q | P | E | D | F | A | T | Y | Y | C |

TABLE 24: COMPARISON OF LLAMA GLAMA VK CONSENSUS SEQUENCES WITH HUMAN GERMLINE CONSENSUS SEQUENCES (Framework Region 3)

Lama glama VK4 germlined towards human VK3

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| | | | | | x | | | | | | | | x | | | | | | | | | | x | x | | | | x | | | | | | |
| VK4 | LAMA glama Consensus | G | I | P | D | R | F | S | G | S | G | S | T | T | D | F | T | L | T | I | S | S | V | Q | P | E | D | A | A | V | Y | Y | C |
| VK3 | HUMAN Consensus | G | I | P | A | R | F | S | G | S | G | S | G | T | D | F | T | L | T | I | S | S | L | E | P | E | D | F | A | V | Y | Y | C |

Lama glama VK4 germlined towards human VK4

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| | | | x | | | | | | | | | | x | | | | | | | | | | x | | | | | x | | | | | | |
| VK4 | LAMA glama Consensus | G | I | P | D | R | F | S | G | S | G | S | T | T | D | F | T | L | T | I | S | S | V | Q | P | E | D | A | A | V | Y | Y | C |
| VK4 | HUMAN Consensus | G | V | P | D | R | F | S | G | S | G | S | G | T | D | F | T | L | T | I | S | S | L | Q | A | E | D | V | A | V | Y | Y | C |

Lama glama VK4 germlined towards human VK5

| | NUMBERING L- | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|---|
| | | | | | x | | | | | | | x | x | | | | | | | | | | x | x | x | | | | | x | x | x | x | x |
| VK4 | LAMA glama Consensus | G | I | P | D | R | F | S | G | S | G | S | T | T | D | F | T | L | T | I | S | S | V | Q | P | E | D | A | A | V | Y | Y | C |
| VK5 | HUMAN Consensus | G | I | P | P | R | F | S | G | S | G | Y | G | T | D | F | T | L | T | I | N | N | I | E | S | E | D | A | A | Y | Y | Y | F | C |

*Fig. 29C*

Table 25

| Positions | 1 | 3 | 4 | 7 | 9 | 11 | 12 | 13 | 14 | 15 | 18 | 19 | 24 | 25 | 27C | 27D | 27E | 28 | 29 | 30 | 31 | 32 | 34 |
|---|---|---|---|---|---|---|---|---|---|---|---|---|---|---|---|---|---|---|---|---|---|---|---|
| closest glama to VK1-13 | D 94% | V 54% | M 77% | | | | K | N | | L 97% | | | Q 97% | | | | | S 74% | | S 80% | L 86% | S 94% |
| | F | Q | I | | | | | | | V | | | I | | | | | N | | D | D | A |
| | 6% | 43% | 23% | | | | | | | 3% | | | 3% | | | | | 14% | | 14% | 11% | 6% |
| | | T | | | | | | | | | | | | | | | | R | | I,V | A | |
| | | 3% | | | | | | | | | | | | | | | | 6% | | 3% | 3% | |
| | | | | | | | | | | | | | | | | | | A,T | | | | |
| | | | | | | | | | | | | | | | | | | 3% | | | | |
| human VK1-13 | A | Q | L | | | V | K | K | | V | | | R | | | | | G | | S | A | A |
| human VK1 family | D 63% | Q 84% | M 84% | | | V | K | K | | V 89% | | | R 84% | | | | | G 74% | | S 63% | V 58% | A 68% |
| | A 26% | R 11% | L 16% | | | | | | | T 11% | | | Q 11% | | | | | S 16% | | N 37% | W 21% | N 21% |
| | N 5% | | | | | | | | | | | | W 5% | | | | | D 11% | | | A,D 11% | G 11% |
| closest glama to VK2-28 | | | | T 100% | G 100% | | S 100% | | V 100% | | S 100% | | K 100% | A 100% | V 100% | | | K 100% | | K 100% | T 100% | Y 80% |
| | | | | | | | | | | | | | | | | | | | | | | S 20% |
| human VK2-28 | | | | S | L | | P | | T | P | P | | R | S | L | | | N | | Y | N | D |
| human VK2 family | | | | T 60% | L 100% | V 100% | P 70% | P 100% | T 100% | P 90% | P 100% | | R 80% | S 100% | L 70% | | | N 80% | | N 50% | T 80% | D 40% |
| | | | | S 40% | | | S 30% | | | Q 10% | | | K 20% | | V 30% | | | N 20% | | Y 30% | N 20% | Y 30% |
| | | | | | | | | | | | | | | | | | | | | K 20% | | N 20% |
| closest glama to VK4-1 | | | | S 80% | | | T 100% | A 100% | | V 69% | K 91% | Y 97% | | | V 49% | S 54% | G 51% | D 80% | Q 86% | N 50% | S 51% | Y | N 63% |
| | | | | T 9% | | | | | | A 26% | T 6% | I 3% | | | L 34% | Y 17% | S 26% | N 20% | K 6% | Y 30% | N 26% | W 21% | A 23% |
| | | | | R 6% | | | | | | I 3% | N 3% | | | | F 6% | I 9% | D 9% | | D,E,K 3% | K 20% | V 9% | A,D 11% | S 6% |
| | | | | G,N 3% | | | | | | | | | | | R,K,G 6% | W 9% | N,R 9% | | | | I 9% | | G,H,T 3% |
| | | | | | | | | | | | | | | | 3% | 6% | 6% | | | | 6% | | |
| human VK4-1 | | | | D | L | | A | V | | L | R | A | | | L | Y | | N | | N | N | | |

Fam. contains 1 member

Table 26

| glama seq to hu VL1-44 | 11 | 14 | 18 | 19 | 24 | 30 | 32 | 38 | 52 | 53 | 55 | 69 | 74 | 76 | 80 | 89 | 90 | 94 | 95A |
|---|---|---|---|---|---|---|---|---|---|---|---|---|---|---|---|---|---|---|---|
| | V | S | K | F | I | D | Y | R | N,S | N | A | S | I | T | A | S | S | N | S |
| | All | All | All | All | 89% | 33% | 78% | 11% | 33% | 67% | All | 89% | All | All | 78% | All | All | 33% | 78% |
| | | | | | S | N,E | F,S | H | D | Y | | T | | | F,V | | | S | G |
| | | | | | 11% | 22% | 11% | 56% | 22% | 11% | | 11% | | | 11% | | | 44% | 22% |
| | | | | | | A,R | | Q | T | K | | | | | | | | R,V | |
| | | | | | | 11% | | 33% | 11% | 22% | | | | | | | | 11% | |
| hu VL1-44 | A | T | R | V | S | S | T | Q | N | Q | P | T | A | S | S | A | A | A | N |
| human VL1 family | A | T | R | V | S | S,N | T,D,A | Q | N | Q | P | T | A | S | S | A | A | A | N |
| | 40% | 40% | 80% | All | 80% | 40% | 20% | All | 60% | 40% | All | All | 80% | 60% | 60% | 60% | 60% | All | 40% |
| | | | | | | G | Y | | S,D | K,N,L | | | G | T | T,A | G,Q | T,S | | S |
| | V | A | K | | T | 20% | 40% | | 20% | 20% | | | 20% | 40% | 20% | 20% | 20% | | 60% |
| | 60% | 60% | 20% | | 20% | | | | | | | | | | | | | | |

Table 27

| | | 80 | 89 | 90 | 92 | 93 | 94 | 95 | 95A | 95B |
|---|---|---|---|---|---|---|---|---|---|---|
| glama seq to hu VL2-11 | | S | A | | R | S | G | N | N | A |
| | | 91% | All | | 74% | 48% | 43% | 70% | 74% | 48% |
| | | P,V | | | R | R | Y | S | | K | V |
| | | 4% | | | 26% | 26% | 13% | 9% | 13% | 22% |
| | | | | | | T | L,S,T | N | T | N,Y |
| | | | | | | 17% | 4% | 7% | 9% | 9% |
| | | | | | | I,L | | D,E,G,L,T | D | F,I,Q |
| | | | | | | 4% | | 4% | 4% | 4% |
| human VL2-11 | | A | C | | A | G | S | Y | T | F |
| human VL2 family | | A | S | | A | G | S | S | T | F |
| | | All | 60% | | 60% | 60% | All | 60% | 80% | 60% |
| | | | C | | T | S | | Y,N | N | L |
| | | | 40% | | 40% | 40% | | 20% | 20% | 40% |

| | | 80 | 89 | 90 | 92 | 93 | 94 | 95 | 95A | 95B |
|---|---|---|---|---|---|---|---|---|---|---|
| glama seq to hu VL2-18 | | S | A | S | R | S | G | N | N | A |
| | | 92% | 81% | 92% | 81% | 35% | 32% | 62% | 65% | 43% |
| | | A | V | A | D,K | D | S | G | S,T | V |
| | | 5% | 8% | 5% | 5% | 14% | 19% | 11% | 8% | 22% |
| | | P | S | F | I,T | N | F | D | G | G,Y |
| | | 3% | 5% | 3% | 3% | 16% | 16% | 8% | 5% | 11% |
| | | | T | | | H,I,Y | T | S | A,I,R,V,Y | N |
| | | | 3% | | | 5% | 11% | 5% | 3% | 5% |
| | | | | | | R | Y | A,E,F,I,T | | F,R,W |
| | | | | | | 3% | 5% | 3% | | 3% |
| | | | | | | | D,K,P,R | | | |
| | | | | | | | 3% | | | |
| Human VL2-18 | | A | C | L | A | G | S | Y | T | F |
| Human VL2 family | | A | S | S | A | G | S | S | T | F |
| | | All | 60% | 80% | 60% | 60% | All | 60% | 80% | 60% |

*Fig. 32B*

Table 28

| glama seq to hu VL3-19 | 1 | 2 | 3 | 5 | 7 | 8 | 9 | 11 | 15 | 14 | 19 | 20 | 24 | 26 | 27 | 29 | 30 | 31 | 32 | 34 | 44 | 46 | 49 |
|---|---|---|---|---|---|---|---|---|---|---|---|---|---|---|---|---|---|---|---|---|---|---|---|
| | Q 70% | S 41% | A 33% | | P All | S All | | L 70% | | T 70% | A 93% | K 70% | | G 93% | G 93% | G 78% | | S 48% | | H 74% | | | |
| | N 26% | F 26% | M,V 26% | | | | | V 25% | | S 26% | | R 26% | | R,D | | R 11% | | Y 22% | | M 22% | | | |
| | L 4% | A 22% | G 15% | | | | | | | A 4% | | E 4% | | 4% | | E 7% | | R 15% | | S 4% | | | |
| | | P 4% | | | | | | | | | | | | | | V,W 4% | | A 7% | | | | | |
| | | | | | | | | | | | | | | | | | | G,N 6% | | | | | |
| | | | | | | | | | | | | | | | | | | 4% | | | | | |

| Human VL3-19 | | | | | | | | | | | | | | | | | | | | | | | |
|---|---|---|---|---|---|---|---|---|---|---|---|---|---|---|---|---|---|---|---|---|---|---|---|
| Human VL3 family | S All | S 10% Y 90% | E 90% V 10% | | D 80% P 10% D,L 10% | P 70% S,L,H 10% | A 75% T 25% | V V All | L All | A 40% S 60% | V 90% V 10% | R 90% S 10% | | D 60% N 30% E 10% | | R 10% P 30% G 50% A 10% | | Y 10% Y,N,Q 10% K 70% | | S Y,H 30% R,S,C,D 10% | | | |

6lama seq to hu VL3-25

| | 1 | 2 | 3 | 5 | 7 | 8 | 9 | 11 | 15 | 14 | 19 | 20 | 24 | 26 | 27 | 29 | 30 | 31 | 32 | 34 | 44 | 46 | 49 |
|---|---|---|---|---|---|---|---|---|---|---|---|---|---|---|---|---|---|---|---|---|---|---|---|
| | Q 50% N 25% | A 50% F 25% Y 25% | G 50% M 25% E 25% | T All | | S All | A All | | L All P | | | | Q,R 50% S 50% | D,G 50% | S 75% D 25% | E,G 50% R 50% | R 50% S,T 25% | Y 75% R 25% | N 50% H,T 25% | N 50% H,T 25% | P,R 50% | L,Q 50% | Y 50% F,H 25% |

| Human VL3-25 | | | | | | | | | | | | | | | | | | | | | | | |
|---|---|---|---|---|---|---|---|---|---|---|---|---|---|---|---|---|---|---|---|---|---|---|---|
| Human VL3 family | S All | S 10% Y 90% | E 90% V 10% | M 90% M 10% | P 70% D,L 10% | P 70% S,L,H 10% | S 90% A 10% | V V All | P L 60% L 30% T 10% | A 40% S 60% | V 90% V 10% | R 90% S 10% | G 60% N 30% Q 10% | D 60% N 30% E 10% | A,N 30% V 20% S,K 10% | P 10% R 10% P 30% G 50% A 10% | P 10% R 10% K,S 10% D,I 10% | Q 10% Y,N,Q 10% K 70% | Y 70% S,N,A 10% | Y V,H 30% R,S,C,D 10% | P All | L All | Y Y All |

Table 31

| Positions | 11 | 12 | 13 | 34 | 35 | 37 | 48 | 50 | 52 | 52a | 53 | 54 | 55 | 56 | 57 | 58 | 60 | 69 | 71 | 78 | 80 |
|---|---|---|---|---|---|---|---|---|---|---|---|---|---|---|---|---|---|---|---|---|---|
| glama closest to hu VH1-46 | L | R | N | I | D | | | R | D | | E | D | | G | | K | | F | A | A | V |
| | 100% | 100% | 100% | 86% | 86% | | | 100% | 100% | | 100% | 100% | | 43% | | 100% | | 100% | 100% | 100% | 100% |
| | | | | T | E | | | | | | | | | D,E | | | | | | | |
| | | | | 14% | 14% | | | | | | | | | 29% | | | | | | | |
| hu VH1-46 | V | K | K | M | H | | | I | N | | S | G | | S | | S | | M | R | V | M |
| human VH1 family | V | K | K | M | H | | | W | N | | E,G,N | N,S | | N | | N | | I | R | A | M |
| | 100% | 100% | 100% | 50% | 60% | | | 50% | 40% | | 20% | 30% | | 50% | | 50% | | 50% | 60% | 90% | 100% |
| | | | | I | S | | | G | D | | S,I,F,Y | D | | E | | I | | M | A | V | |
| | | | | 30% | 20% | | | 20% | 20% | | 10% | 20% | | 20% | | 20% | | 40% | 20% | 10% | |
| | | | | V,I | Q,N | | | I,L,R | I,T,S | | 10% | G,F | | G,T,S | | G,S | | S | E,T | | |
| | | | | 10% | 10% | | | 10% | 10% | | | 10% | | 10% | | 10% | | 10% | 10% | | |

Fig. 36

| Table 32 | | | | | Positions | | | | | |
|---|---|---|---|---|---|---|---|---|---|---|
| | 5 | 8 | 13 | 14 | 29 | 30 | 31 | 32 | 33 | 35 | 37 |
| glama closest to hu VH3-21 | | H 39% K 8% | | | | | | | A,R 38% Y 15% W 5% | Y 46% S 39% N 8% | |
| hu VH3-21 | | K | | | | | | | S | N | |
| glama closest to hu VH3-48 | | | | | | | | | A 36% R 25% Y 16.70% S 5.60% | S 41.70% T 13.90% | |
| hu VH3-48 | | | | | | | | | S | N | |
| glama closest to hu VH3-23 | V 84.50% Q 11.30% | | | | | | S 50.70% R 9.90% | | A 49.30% W 11.30% G 8.50% D,R 5.60% | | |
| hu VH3-23 | L | | | | | | S | | A | | |
| | 5 | 8 | 13 | 14 | 29 | 30 | 31 | 32 | 33 | 35 | 37 |
| glama closest to hu VH3-66 | | | | | F 88.90% S 11.10% | | T 55.60% S,N 22.20% | Y 77.80% S,H 11.10% | W 44.40% D 22.20% A,T,G 11.10% | S,Y 44.40% T 11.10% | |
| hu VH3-66 | | | | | V | | S | N | Y | S | |
| glama closest to hu VH3-11 | | | Q 100% | S 80% P 20% | | S 50% N 20% G,D,T 10% | D 30% N,S 20% M,L,K 10% | | A,W 30% Y,P,D,C 10% | N 30% T,H 20% G,F,Y 10% | V 80% I 20% |
| hu VH3-11 | | | K | P | | S | D | | Y | S | I |
| hu VH3 family | V 95.20% L 4.80% | Q 76% K 19% | Q 76% K 19% R 5% | P 100% | F 85.70% V 14.30% | S 81% D 14.30% G 4.80% | S 57% D 28.60% N 9.50% | Y 66.70% N 14.30% | A 29% W,Y 19% | S 48% H 38% N 10% | V 90.50% F,I 4.80% |

*Fig. 37A*

Table 52

| | Positions | | | | | | | | |
|---|---|---|---|---|---|---|---|---|---|
| | 50 | 52 | 52a | 53 | 54 | 55 | 56 | 57 | 58 | 60 |
| glarra closest to hu VH3-21 | A | | | S,G | G | G | | S | T | |
| | 39% | | | 38.50% | 92.30% | 53.80% | | 77% | 84.60% | |
| | R | | | N,Y,F | R | V | | T,I,D | A,S | |
| | 23% | | | 7.70% | 7.70% | 38.50% | | 7.70% | 7.70% | |
| | D,T,G,S,V | | | | | | | | | |
| | 7.70% | | | | | | | | | |
| hu VH3-21 | S | | | S | S | S | | Y | I | |
| glarra closest to hu VH3-48 | A | | | G | G | G | | S | T | |
| | 33% | | | 42% | 75% | 36% | | 61% | 86% | |
| | S | | | S | S | V | | D | A | |
| | 19% | | | 28% | 19.40% | 22% | | 17% | 5.60% | |
| | R | | | F | | I | | T | D,S | |
| | 17% | | | 11% | | 17% | | 11% | 2.80% | |
| | V,G | | | Y | | S | | | | |
| | 11% | | | 8% | | 5.60% | | | | |
| hu VH3-48 | Y | | | S | S | S | | T | I | |
| glarra closest to hu VH3-23 | A | S | A | G | | | | S | Y | |
| | 25% | 42.30% | 50.70% | 53.50% | | | | 50.70% | 46.50% | |
| | G,R | N | W | N | | | | T | S | |
| | 14% | 19.70% | 15.5 | 16.90% | | | | 12.70% | 31% | |
| | | D,T | T | S | | | | N | T | |
| | | 5.60% | 14% | 8.5 | | | | 8.50% | 7% | |
| | | | G | D | | | | | | |
| | | | 1.40% | 7% | | | | | | |
| hu VH3-23 | A | S | G | S | | | | S | Y | |
| | 50 | 52 | 52a | 53 | 54 | 55 | 56 | 57 | 58 | 60 |
| glarra closest to hu VH3-66 | T | N | S | | G | | S | | Y | A |
| | 55.60% | 55.60% | 44.40% | | 44.40% | | 44.40% | | 44.40% | 33.30% |
| | G | T | N | | A | | F | | S | V,S |
| | 22.20% | 22.20% | 22.20% | | 33.30% | | 22.20% | | 22.20% | 22.20% |
| | A | D,Y | G,A,K | | S,D | | G,L,K | | W,T,I | |
| | 11.10% | 11.10% | 11.10% | | 11.10% | | 11.10% | | 11.10% | |
| hu VH3-66 | V | Y | S | | G | | S | | Y | A |
| glarra closest to hu VH3-11 | T | N | S | G | G | G | N | | Y | A |
| | 40% | 40% | 40% | 40% | 80% | 40% | 30% | | 40% | 30% |
| | S | S,Y | W,T | N,D | I,S | S | T | | L,N,S,F,D,I | P,S |
| | 30% | 20% | 20% | 20% | 10% | 30% | 20% | | 10% | 20% |
| | A,G,R | D,F | I | L,H | | D,N,L | G,F,A,R,S | | | G,K,E |
| | 10% | 10% | 10% | 10% | | 10% | 10% | | | 10% |
| hu VH3-11 | Y | S | S | S | S | S | Y | | N | A |
| hu VH3 family | R | S | S | D | G | G | S | T | Y | A |
| | 24% | 42.9 | 42.90% | 33.30% | 71.40% | 57% | 43% | 66.70% | 61.90% | 85.70% |
| | V | K,R | W | S | S | S | T | I | G,D,E | T,V,P |
| | 19% | 14.30% | 14.30% | 28.60% | 23.30% | 33.30% | 28.60% | 19% | 9.50% | 4.80% |
| | A | Y | | N | | Y | N | K | S,A | |
| | 14% | 9.50% | | 23.80% | | 9.50% | 9.50% | 14.30% | 4.80% | |
| | Y,G,S | | | | | | | | | |
| | 9.50% | | | | | | | | | |

*Fig. 37B*

| Table 32 | Positions | | | | | | | |
|---|---|---|---|---|---|---|---|---|
| | 77 | 78 | 82b | 83 | 84 | 89 | 93 | 94 |
| glama closest to hu VH3-21 | T 100% | | | K 100% | P 100% | | | |
| | | | | | | | | |
| hu VH3-21 | S | | | R | A | | | |
| glama closest to hu VH3-48 | T 89% A 5.60% | | | K 91.70% R,L,S 2.80% | P 75% S 16.70% Q,K,L 2.80% | V,L 44.40% T,A,M 2.80% | A 41.70% K 22.20% T 16.70% V 13.90% | |
| hu VH3-48 | S | | | R | A | V | A | |
| glama closest to hu VH3-23 | | | | K 91.50% R 5.60% | P 66.20% S 28.20% | | | |
| hu VH3-23 | | | | R | A | | | |
| | 77 | 78 | 82b | 83 | 84 | 89 | 93 | 94 |
| glama closest to hu VH3-66 | | | | K 88.90% Q 11.10% | P 77.80% S 22.20% | | | K 33.30% R,N 22.20% |
| hu VH3-66 | | | | R | A | | | R |
| glama closest to hu VH3-11 | T 100% | V 60% L 40% | S 50% N 30% D,K 10% | K 80% N,E 10% | P,S 40% V,L 10% | V 50% L 30% T,R 10% | | K 50% R 30% N,T 10% |
| hu VH3-11 | S | L | S | R | A | V | | R |
| hu VH3 family | T 52.40% S 43% | L 90.50% A 9.50% | S 100% | R 76% K 24% | A 71% T 29% | V 85.70% L 14.30% | A 75% T 19% | R 71.40% K 19% T 9.50% |

*Fig. 37C*

Table 33

| | | 1 | 30 | 31 | 32 | 33 | 35 | 48 | 50 | 52 | 54 | 60 | 67 | 68 | 71 | 81 | 84 | 85 |
|---|---|---|---|---|---|---|---|---|---|---|---|---|---|---|---|---|---|---|
| glama closest to hu | | | | | | | | | | | | | | | | | | |
| VH4-30-4 | | E | T | T | S | Y | A | M | V | T,D,A | D | S | T | S | R | Q | P | E |
| | | 21% | 84% | 79% | 53% | 89.50% | 52.60% | 100% | 79% | 26.3 | 89.50% | 68.40% | 89.5 | 100% | 84.20% | 100% | 100% | 100% |
| | | Q | A,V | A | R,T | F,H | G,Y | | A | G | S | N | S | | W | | | |
| | | 21% | 5.30% | 10% | 10.50% | 5.30% | 10.50% | | 21% | 15.80% | 10.50% | 21.10% | 10.5 | | 10.50% | | | |
| | | | | V,S | D,N,H,L | | H | | | | | K,R | | | | | | |
| | | | | 5.30% | 5.30% | | 5.30% | | | | | 5.30% | | | | | | |
| hu VH4-30-4 | | Q | S | S | G | D | Y | I | Y | Y | S | N | V | T | V | K | A | A |
| hu VH4 family | | Q | S | S | G | Y | Y | I | Y | Y | S | N | V | T | V | K | A | A |
| | | 100% | 100% | 90% | 50% | 30% | 40% | 100% | 60% | 90% | 100% | 100% | 100% | 100% | 100% | 100% | 100% | 100% |
| | | | | G | S | G,N | W,S | | E,S | N | | | | | | | | |
| | | | | 10% | 30% | 20% | 30% | | 20% | 10% | | | | | | | | |
| | | | | | Y | D | | | | | | | | | | | | |
| | | | | | 20% | 10% | | | | | | | | | | | | |

*Fig. 38*

Table 34

| | | | Position | | | |
|---|---|---|---|---|---|---|
| | 100C | 100D | 100E | 101 | 102 | 108 |
| all llama glama sequences | - 80%<br>N 3%<br>D,W 2.40% | G 21.20%<br>E 15.20%<br>A 12.10%<br>M 10.90%<br>Y 6.70% | Y 25.50%<br>F 16.40%<br>M 14.50%<br>G 13.90%<br>L 13.30%<br>S 7.30% | D 68.50%<br>E 9%<br>G 6.70%<br>R 3%<br>N,S 2.40% | Y 66.70%<br>S 11.50%<br>A,F,H 3.30% | Q 69.10%<br>L 25.50%<br>R 2.40% |
| llama glama sequences closest to HJ3 | D 40%<br>W 40% | A 60%<br>S,H,L,D 10% | F 60%<br>L 20%<br>T,R 10% | D 40%<br>E 30%<br>G,L,T 10% | F 40%<br>P,S 20%<br>V,I 10% | Q 80%<br>L 20% |
| hu germline: HJ3 | D | A | F | D | V | M |
| all HJ germlines | E,W,D,N,Y,- 16% | Y 66.70%<br>A,W 16.70% | F 83.30%<br>Y 16.70% | D 83%<br>Q 17% | V 33%<br>H,L,Y,S 16.70% | L 67%<br>M,T 17% |

*Fig. 39*

Table 35

| | | 1 | 7 | 11 | 12 | 34 | 35 | 37 | 48 | 50 | 52 | 53 | 54 | 56 | 58 | 69 | 71 | 78 | 80 | 86 |
|---|---|---|---|---|---|---|---|---|---|---|---|---|---|---|---|---|---|---|---|---|
| pacos closest to hu | VH1-46 | E 100% | P 100% | L 100% | R 100% | I 100% | D 100% | | | R 100% | D 100% | E 100% | D 100% | G 100% | K 80% N 20% | F 100% | A 100% | A 100% | V 100% | G 100% |
| hu VH1-46 | | Q | S | V | K | M | H | | | I | N | S | G | S | S | M | R | V | M | D |
| human VH1 family | | Q 90% E 10% | S 100% | V 100% | K 100% | M 50% I 30% V,L 10% | H 60% S 20% Q,N 10% | | | W 50% G 20% I,L,R 10% | N 40% D 20% I,T,S 10% | E,G,N 20% S,I,F,Y 10% | N,S 30% D 20% G,F 10% | N 50% E 20% G,T,S 10% | N 50% I 20% G,S 10% | I 50% M 40% S 10% | R 60% A 20% E,T 10% | A 90% V 10% | M 100% | D 100% |

Positions

*Fig. 40*

Table 36

| | | | | | | | Positions | | | | | | | |
|---|---|---|---|---|---|---|---|---|---|---|---|---|---|---|
| | 1 | 29 | 32 | 33 | 35 | 37 | 40 | 50 | 52 | 53 | 54 | 55 | 56 | 57 |
| pacos closest to hu VH3-48 | Q 60.50% | F 100% | Y 100% | A 51.50% | S 87.90% | | | A 45.50% | N 66.70% | G 60.60% | G 81.80% | G 72.70% | S 69.70% | T 100% |
| | E 39.40% | | | D 18.20% | N 9.10% | | | S 15.20% | Y 27.30% | Y 18.20% | S 15.20% | S 27.30% | N 21.20% | |
| | | | | Y,W 12.10% | S 3% | | | Y 12.10% | S 6% | D 12.10% | D 3% | | D 9% | |
| | | | | G,V 3% | | | | G,I 9.10% | | N 6.10% | | | | |
| | | | | | | | | D 6.10% | | | | | | |
| hu VH3-48 | E | | | S | N | V | A | Y | S | S | S | S | T | I |
| pacos closest to hu VH3-66 | Q 66.60% | | | A 66.60% | G 66.60% | A 66.60% | V 66.60% | G 100% | | | D 100% | | | |
| | E 33.30% | | | D 33.30% | S 33.30% | V 33.30% | A 33.30% | | | | | | | |
| hu VH3-66 | E | V | N | Y | S | V | A | V | | | D | | | |
| hu VH3 family | E 85.70% | F 85.70% | Y 66.70% | A 29% | S 48% | V 90.50% | A 100% | R 24% | S 42.9 | D 33.30% | G 71.40% | G 57% | S 43% | T 66.70% |
| | Q 14.30% | V 14.30% | N 14.30% | W,Y 19% | H 38% | F,I 4.80% | | V 19% | K,R 14.30% | S 28.60% | S 23.80% | S 33.30% | T 28.60% | I 19% |
| | | | | | N 10% | | | A 14% | Y 9.50% | N 23.80% | | Y 9.50% | D 9.50% | K 14.30% |
| | | | | | | | | Y,G,S 9.50% | | | | | | |

*Fig. 41A*

| Table 36 | Positions | | | | | |
|---|---|---|---|---|---|---|
|  | 74 | 77 | 78 | 83 | 84 | 86 |
| pacos closest to hu VH3-48 |  | T |  | K | P | G |
|  |  | 100% |  | 100% | 84.80% | 87.90% |
|  |  |  |  |  | S | D |
|  |  |  |  |  | 15.20% | 12.10% |

| | 74 | 77 | 78 | 83 | 84 | 86 |
|---|---|---|---|---|---|---|
| hu VH3-48 |  | S |  | R | A | V |
| pacos closest to hu VH3-66 | A |  | V | K | P | G |
|  | 100% |  | 66.60% | 100% | 66.60% | 100% |
|  |  |  | L |  | S |  |
|  |  |  | 33.30% |  | 33.30% |  |
| hu VH3-66 | S |  | L | R | A | D |
| hu VH3 family | S | T | L | R | A | D |
|  | 61.90% | 52.40% | 90.50% | 76% | 71% | 100% |
|  | A | S | A | K | T |  |
|  | 38.10% | 43% | 9.50% | 24% | 29% |  |

*Fig. 41B*

Table 37

| | | | | | | | | | Positions | | | | | | | |
|---|---|---|---|---|---|---|---|---|---|---|---|---|---|---|---|---|
| | 30 | 31 | 32 | 33 | 35 | 48 | 50 | 52 | 60 | 67 | 68 | 71 | 81 | 84 | 85 | 86 |
| pacos closest to hu VH4-30-4 | T 100% | T 100% | S 100% | Y 70% C 30% | A 80% Y 20% | M 100% | A 100% | A 50% - 50% | S 100% | T 100% | S 100% | R 100% | Q 100% | P 100% | E 100% | G 100% |
| hu VH4-30-4 | S | S | G | D | Y | I | Y | Y | N | V | T | V | K | A | A | D |
| hu VH4 family | S 100% | S 90% G 10% | G 50% S 30% Y 20% | Y 30% G,N 20% D 20% 10% | Y 40% W,S 30% 30% | I 100% | Y 60% E,S 20% 20% | Y 90% N 10% | N 100% | V 100% | T 100% | V 100% | K 100% | A 100% | A 100% | D 100% |

*Fig. 42*

SEQUENCE LISTING

```
<160> NUMBER OF SEQ ID NOS: 227

<210> SEQ ID NO 1
<211> LENGTH: 98
<212> TYPE: PRT
<213> ORGANISM: Homo sapiens
<220> FEATURE:
<221> NAME/KEY: misc_feature
<223> OTHER INFORMATION: M99660, IGHV3-23 (Figure 2)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 2
<211> LENGTH: 116
<212> TYPE: PRT
<213> ORGANISM: Artificial Sequence
<220> FEATURE:
<223> OTHER INFORMATION: Synthetic peptide: 1F2 VH (Figure 2)
```

```
<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Pro Glu Trp Val
        35                  40                  45

Ser Gly Ile Asn Thr Gly Gly Ser Thr Gly Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Trp Met Ala Thr Thr Pro Trp Gly Gln Gly Thr Gln Val
            100                 105                 110

Thr Val Ser Ser
        115

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide: 1F2 VH Hum (Figure 2)

<400> SEQUENCE: 3

Leu Leu Ser Arg Ala Leu
1               5

<210> SEQ ID NO 4
<211> LENGTH: 116
<212> TYPE: PRT
<213> ORGANISM: Homo sapiens
<220> FEATURE:
<221> NAME/KEY: misc_feature
<223> OTHER INFORMATION: Wild Type VH 1F2 (Figure 2)

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Pro Glu Trp Val
        35                  40                  45

Ser Gly Ile Asn Thr Gly Gly Ser Thr Gly Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Trp Met Ala Thr Thr Pro Trp Gly Gln Gly Thr Gln Val
            100                 105                 110

Thr Val Ser Ser
        115

<210> SEQ ID NO 5
<211> LENGTH: 116
<212> TYPE: PRT
<213> ORGANISM: Artificial Sequence
```

```
<220> FEATURE:
<223> OTHER INFORMATION: Synthetic peptide: Humanized VH 1F2 (Figure 2)

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Gly Ile Asn Thr Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Met Ala Thr Thr Pro Trp Gly Gln Gly Thr Leu Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: Synthetic peptide: Safe variant VH 1F2
      (Figure 2)

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Pro Glu Trp Val
        35                  40                  45

Ser Gly Ile Asn Thr Gly Gly Ser Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Trp Met Ala Thr Thr Pro Trp Gly Gln Gly Thr Gln Val
            100                 105                 110

Thr Val Ser Ser
        115

<210> SEQ ID NO 7
<211> LENGTH: 97
<212> TYPE: PRT
<213> ORGANISM: Homo sapiens
<220> FEATURE:
<221> NAME/KEY: misc_feature
<223> OTHER INFORMATION: X92218, IGHV3-66 (Figure 2)

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
```

```
                    20                  25                  30

Tyr Met Ser Trp Val Arg Gln Ala Pro Gly Lys Gly Leu Glu Trp Val
                35                  40                  45

Ser Val Ile Tyr Ser Gly Gly Ser Thr Tyr Tyr Ala Asp Ser Val Lys
            50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 8
<211> LENGTH: 111
<212> TYPE: PRT
<213> ORGANISM: Artificial Sequence
<220> FEATURE:
<223> OTHER INFORMATION: Synthetic peptide: 1E2 VH (Figure 2)

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
                20                  25                  30

Trp Met Tyr Trp Val Arg Gln Ala Pro Gly Lys Gly Leu Glu Trp Val
                35                  40                  45

Ser Ala Ile Asn Ala Ala Gly Ser Thr Tyr Tyr Ala Asp Ser Val Lys
            50                  55                  60

Gly Arg Phe Thr Ile Ser Arg Asp Asn Ala Lys Asn Thr Leu Tyr Leu
65                  70                  75                  80

Gln Met Asn Ser Leu Gln Ser Glu Asp Thr Ala Leu Tyr Tyr Cys Ala
                85                  90                  95

Asn Leu Pro Arg Trp Gly Gln Gly Thr Gln Val Thr Val Ser Ser
            100                 105                 110

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide: 1E2 VH Hum (Figure 2)

<400> SEQUENCE: 9

Ala Ser Arg Ala Val Leu
1               5

<210> SEQ ID NO 10
<211> LENGTH: 111
<212> TYPE: PRT
<213> ORGANISM: Homo sapiens
<220> FEATURE:
<221> NAME/KEY: misc_feature
<223> OTHER INFORMATION: Wild Type VH 1E2 (Figure 2)

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
                20                  25                  30

Trp Met Tyr Trp Val Arg Gln Ala Pro Gly Lys Gly Leu Glu Trp Val
                35                  40                  45
```

Ser Ala Ile Asn Ala Ala Gly Ser Thr Tyr Tyr Ala Asp Ser Val Lys
            50                  55                  60

Gly Arg Phe Thr Ile Ser Arg Asp Asn Ala Lys Asn Thr Leu Tyr Leu
 65                  70                  75                  80

Gln Met Asn Ser Leu Gln Ser Glu Asp Thr Ala Leu Tyr Tyr Cys Ala
                85                  90                  95

Asn Leu Pro Arg Trp Gly Gln Gly Thr Gln Val Thr Val Ser Ser
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Synthetic peptide: Humanized VH 1E2 (Figure 2)

<400> SEQUENCE: 11

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Ala Ile Asn Ala Ala Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Asn Leu Pro Arg Trp Gly Gln Gly Thr Leu Val Thr Val Ser Ser
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: Synthetic peptide: Safe variant VH 1E2
      (Figure 2)

<400> SEQUENCE: 12

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Ala Ile Asn Ala Ala Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Gln Ser Glu Asp Thr Ala Val Tyr Tyr Cys Ala
                85                  90                  95

Asn Leu Pro Arg Trp Gly Gln Gly Thr Gln Val Thr Val Ser Ser
            100                 105                 110

<210> SEQ ID NO 13
<211> LENGTH: 98

<212> TYPE: PRT
<213> ORGANISM: Homo sapiens
<220> FEATURE:
<221> NAME/KEY: misc_feature
<223> OTHER INFORMATION: Z73650, IGLV8-61 (Figure 2)

<400> SEQUENCE: 13

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 14
<211> LENGTH: 113
<212> TYPE: PRT
<213> ORGANISM: Artificial Sequence
<220> FEATURE:
<223> OTHER INFORMATION: Synthetic peptide: 1F2 VL (Figure 2)

<400> SEQUENCE: 14

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Asn
            20                  25                  30

Asn Tyr Pro Gly Trp Phe Gln Gln Thr Pro Gly Gln Ala Pro Arg Thr
        35                  40                  45

Leu Ile Tyr Asn Thr Asn Asn Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Ser Ser
                85                  90                  95

Gly Ser Asn Asn Ala Val Phe Gly Gly Gly Thr His Leu Thr Val Leu
            100                 105                 110

Gly

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide: 1F2 VL Hum (Figure 2)

<400> SEQUENCE: 15

Thr Phe Tyr Ser Asp Leu Ala Asp Ser Lys
1               5                   10

<210> SEQ ID NO 16
<211> LENGTH: 113
<212> TYPE: PRT
<213> ORGANISM: Homo sapiens -continued

```
<220> FEATURE:
<221> NAME/KEY: misc_feature
<223> OTHER INFORMATION: Wild Type VL 1F2 (Figure 2)

<400> SEQUENCE: 16

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Asn
            20                  25                  30

Asn Tyr Pro Gly Trp Phe Gln Thr Pro Gly Gln Ala Pro Arg Thr
        35                  40                  45

Leu Ile Tyr Asn Thr Asn Asn Arg His Ser Gly Val Pro Ser Arg Phe
50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Ser Ser
                85                  90                  95

Gly Ser Asn Asn Ala Val Phe Gly Gly Gly Thr His Leu Thr Val Leu
            100                 105                 110

Gly

<210> SEQ ID NO 17
<211> LENGTH: 113
<212> TYPE: PRT
<213> ORGANISM: Artificial Sequence
<220> FEATURE:
<223> OTHER INFORMATION: Synthetic peptide: Humanized VL 1F2 (Figure 2)

<400> SEQUENCE: 17

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Thr Asn
            20                  25                  30

Asn Tyr Pro Gly Trp Tyr Gln Gln Thr Pro Gly Gln Ala Pro Arg Thr
        35                  40                  45

Leu Ile Tyr Asn Thr Asn Asn Arg Ser Ser Gly Val Pro Asp Arg Phe
50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Tyr Met Ser Ser
                85                  90                  95

Gly Ser Asn Asn Ala Val Phe Gly Gly Gly Thr Lys Leu Thr Val Leu
            100                 105                 110

Gly

<210> SEQ ID NO 18
<211> LENGTH: 113
<212> TYPE: PRT
<213> ORGANISM: Artificial Sequence
<220> FEATURE:
<223> OTHER INFORMATION: Synthetic peptide: Safe var VL 1F2 (Figure 2)

<400> SEQUENCE: 18

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Thr Thr Asn
            20                  25                  30

Asn Tyr Pro Gly Trp Phe Gln Gln Thr Pro Gly Gln Ala Pro Arg Thr
```

```
                35                  40                  45
Leu Ile Tyr Asn Thr Asn Asn Arg His Ser Gly Val Pro Ser Arg Phe
        50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Ala Leu Tyr Met Ser Ser
                85                  90                  95

Gly Ser Asn Asn Ala Val Phe Gly Gly Gly Thr Lys Leu Thr Val Leu
            100                 105                 110

Gly

<210> SEQ ID NO 19
<211> LENGTH: 113
<212> TYPE: PRT
<213> ORGANISM: Artificial Sequence
<220> FEATURE:
<223> OTHER INFORMATION: Synthetic peptide: 1E2 VL (Figure 2)

<400> SEQUENCE: 19

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Gly
                20                  25                  30

Asn Tyr Pro Gly Trp Tyr Gln Gln Lys Pro Gly Gln Ala Pro Arg Thr
            35                  40                  45

Leu Ile Tyr Asn Thr Asn Ser Arg Tyr Ser Gly Val Pro Asn Arg Phe
        50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Val Tyr Ile Gly Ser
                85                  90                  95

Ser Ser Tyr Pro Val Val Phe Gly Gly Gly Thr His Leu Thr Val Leu
            100                 105                 110

Gly

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide: 1E2 VL Hum (Figure 2)

<400> SEQUENCE: 20

Phe Thr Ser Asp Leu Ala Asp Ser Lys
1               5

<210> SEQ ID NO 21
<211> LENGTH: 113
<212> TYPE: PRT
<213> ORGANISM: Homo sapiens
<220> FEATURE:
<221> NAME/KEY: misc_feature
<223> OTHER INFORMATION: Wild Type VL 1E2 (Figure 2)

<400> SEQUENCE: 21

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Gly
                20                  25                  30
```

```
Asn Tyr Pro Gly Trp Tyr Gln Gln Lys Pro Gly Gln Ala Pro Arg Thr
            35                  40                  45

Leu Ile Tyr Asn Thr Asn Ser Arg Tyr Ser Gly Val Pro Asn Arg Phe
 50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ala Val Tyr Ile Gly Ser
                85                  90                  95

Ser Ser Tyr Pro Val Val Phe Gly Gly Gly Thr His Leu Thr Val Leu
            100                 105                 110

Gly
```

<210> SEQ ID NO 22
<211> LENGTH: 113
<212> TYPE: PRT
<213> ORGANISM: Artificial Sequence
<220> FEATURE:
<223> OTHER INFORMATION: Synthetic peptide: Humanized VL 1E2
      (Figure 2)

<400> SEQUENCE: 22

```
Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Thr Ser Gly
                20                  25                  30

Asn Tyr Pro Gly Trp Tyr Gln Gln Thr Pro Gly Gln Ala Pro Arg Thr
            35                  40                  45

Leu Ile Tyr Asn Thr Asn Ser Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Ala Val Tyr Ile Gly Ser
                85                  90                  95

Ser Ser Tyr Pro Val Val Phe Gly Gly Gly Thr Lys Leu Thr Val Leu
            100                 105                 110

Gly
```

<210> SEQ ID NO 23
<211> LENGTH: 113
<212> TYPE: PRT
<213> ORGANISM: Artificial Sequence
<220> FEATURE:
<223> OTHER INFORMATION: Synthetic peptide: Safe var VL 1E2 (Figure 2)

<400> SEQUENCE: 23

```
Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Thr Ser Gly
                20                  25                  30

Asn Tyr Pro Gly Trp Tyr Gln Gln Lys Pro Gly Gln Ala Pro Arg Thr
            35                  40                  45

Leu Ile Tyr Asn Thr Asn Ser Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Pro Asp Asp Glu Ser Asp Tyr Tyr Cys Ala Val Tyr Ile Gly Ser
                85                  90                  95
```

Ser Ser Tyr Pro Val Val Phe Gly Gly Gly Thr His Leu Thr Val Leu
            100                 105                 110

Gly

<210> SEQ ID NO 24
<211> LENGTH: 30
<212> TYPE: PRT
<213> ORGANISM: Artificial Sequence
<220> FEATURE:
<223> OTHER INFORMATION: Lama glama consensus sequence: VH1-46

<400> SEQUENCE: 24

Glu Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Human consensus sequence: VH1

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Human consensus sequence: VH2
<220> FEATURE:
<221> NAME/KEY: misc_feature
<222> LOCATION: (10)..(10)
<223> OTHER INFORMATION: Xaa is Ala, Thr, or Val

<400> SEQUENCE: 26

Gln Val Thr Leu Lys Glu Ser Gly Pro Xaa Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Human consensus sequence: VH3

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 28
<211> LENGTH: 30
<212> TYPE: PRT
<213> ORGANISM: Artificial Sequence
<220> FEATURE:

```
<223> OTHER INFORMATION: Human consensus sequence: VH4
<220> FEATURE:
<221> NAME/KEY: misc_feature
<222> LOCATION: (23)..(23)
<223> OTHER INFORMATION: Xaa is Ala or Thr

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Xaa Val Ser Gly Gly Ser Ile Ser
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Human consensus sequence: VH5
<220> FEATURE:
<221> NAME/KEY: misc_feature
<222> LOCATION: (19)..(19)
<223> OTHER INFORMATION: Xaa is Lys or Arg

<400> SEQUENCE: 29

Glu Val Gln Leu Val Gln Ser Gly Ala Glu Val Lys Lys Pro Gly Glu
1               5                   10                  15

Ser Leu Xaa Ile Ser Cys Lys Gly Ser Gly Tyr Ser Phe Thr
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Human consensus sequence: V6

<400> SEQUENCE: 30

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Human consensus sequence: V7

<400> SEQUENCE: 31

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 32
<211> LENGTH: 23
<212> TYPE: PRT
<213> ORGANISM: Artificial Sequence
<220> FEATURE:
<223> OTHER INFORMATION: Lama glama consensus sequence: VH3-11

<400> SEQUENCE: 32

Glu Val Gln Leu Val Gln Ser Gly Gly Ser Leu Arg Leu Ser Cys Ala
1               5                   10                  15
```

Ala Ser Gly Phe Thr Phe Ser
            20

<210> SEQ ID NO 33
<211> LENGTH: 30
<212> TYPE: PRT
<213> ORGANISM: Artificial Sequence
<220> FEATURE:
<223> OTHER INFORMATION: Lama glama consensus sequence: VH3-21

<400> SEQUENCE: 33

Glu Val Gln Leu Val Glu Ser Gly Gly Gly Leu Val His Pro Gly Gly
1               5                   10                  15

Ser Leu Arg Leu Ser Cys Ala Ala Ser Gly Phe Thr Phe Ser
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Lama glama consensus sequence: VH3-23

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Lama glama consensus sequence: VH3-48

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Lama glama consensus sequence: VH3-66

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Lama glama consensus sequence: VH3

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 38
<211> LENGTH: 29
<212> TYPE: PRT
<213> ORGANISM: Artificial Sequence
<220> FEATURE:
<223> OTHER INFORMATION: Lama glama consensus sequence: VH4-30-4

<400> SEQUENCE: 38

Val Gln Leu Gln Glu Ser Gly Pro Gly Leu Val Lys Pro Ser Gln Thr
1               5                   10                  15

Leu Ser Leu Thr Cys Thr Val Ser Gly Gly Ser Ile Thr
            20                  25

<210> SEQ ID NO 39
<211> LENGTH: 14
<212> TYPE: PRT
<213> ORGANISM: Artificial Sequence
<220> FEATURE:
<223> OTHER INFORMATION: Lama glama consensus sequence: VH1-46

<400> SEQUENCE: 39

Trp Val Arg Gln Ala Pro Gly Gln Gly Leu Glu Trp Met Gly
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Human consensus sequence: VH1

<400> SEQUENCE: 40

Trp Val Arg Gln Ala Pro Gly Gln Gly Leu Glu Trp Met Gly
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Human consensus sequence: VH2

<400> SEQUENCE: 41

Trp Ile Arg Gln Pro Pro Gly Lys Ala Leu Glu Trp Leu Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Human consensus sequence: VH3

<400> SEQUENCE: 42

Trp Val Arg Gln Ala Pro Gly Lys Gly Leu Glu Trp Val Ser
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Human consensus sequence: VH4

```
<400> SEQUENCE: 43

Trp Ile Arg Gln Pro Pro Gly Lys Gly Leu Glu Trp Ile Gly
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Human consensus sequence: VH5

<400> SEQUENCE: 44

Trp Val Arg Gln Met Pro Gly Lys Gly Leu Glu Trp Met Gly
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Human consensus sequence: VH6

<400> SEQUENCE: 45

Trp Ile Arg Gln Ser Pro Ser Arg Gly Leu Glu Trp Leu Gly
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Human consensus sequence: VH7

<400> SEQUENCE: 46

Trp Val Arg Gln Ala Pro Gly Gln Gly Leu Glu Trp Met Gly
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Lama glama consensus sequence: VH3-11

<400> SEQUENCE: 47

Trp Val Arg Gln Ala Pro Gly Lys Gly Leu Glu Trp Val Ser
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Lama glama consensus sequence: VH3-21

<400> SEQUENCE: 48

Trp Val Arg Gln Ala Pro Gly Lys Gly Leu Glu Trp Val Ser
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Lama glama consensus sequence: VH3-23
```

```
<400> SEQUENCE: 49

Trp Val Arg Gln Ala Pro Gly Lys Gly Leu Glu Trp Val Ser
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Lama glama consensus sequence: VH3-48

<400> SEQUENCE: 50

Trp Val Arg Gln Ala Pro Gly Lys Gly Leu Glu Trp Val Ser
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Lama glama consensus sequence: VH3-66

<400> SEQUENCE: 51

Trp Val Arg Gln Ala Pro Gly Lys Gly Leu Glu Trp Val Ser
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Lama glama consensus sequence: VH3

<400> SEQUENCE: 52

Trp Val Arg Gln Ala Pro Gly Lys Gly Leu Glu Trp Val Ser
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Lama glama consensus sequence: VH4-30-4

<400> SEQUENCE: 53

Trp Ile Arg Gln Pro Pro Gly Lys Gly Leu Glu Trp Met Gly
1               5                   10

<210> SEQ ID NO 54
<211> LENGTH: 32
<212> TYPE: PRT
<213> ORGANISM: Artificial Sequence
<220> FEATURE:
<223> OTHER INFORMATION: Lama glama consensus sequence: VH1-46

<400> SEQUENCE: 54

Arg Val Thr Phe Thr Ala Asp Thr Ser Thr Ser Thr Ala Tyr Val Glu
1               5                   10                  15

Leu Ser Ser Leu Arg Ser Glu Asp Thr Ala Val Tyr Tyr Cys Ala Arg
            20                  25                  30

<210> SEQ ID NO 55
<211> LENGTH: 32
<212> TYPE: PRT
<213> ORGANISM: Artificial Sequence
<220> FEATURE:
```

<223> OTHER INFORMATION: Human consensus sequence: VH1

<400> SEQUENCE: 55

Arg Val Thr Ile Thr Arg Asp Thr Ser Thr Ser Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 56
<211> LENGTH: 33
<212> TYPE: PRT
<213> ORGANISM: Artificial Sequence
<220> FEATURE:
<223> OTHER INFORMATION: Human consensus sequence: VH2

<400> SEQUENCE: 56

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

Ile

<210> SEQ ID NO 57
<211> LENGTH: 32
<212> TYPE: PRT
<213> ORGANISM: Artificial Sequence
<220> FEATURE:
<223> OTHER INFORMATION: Human consensus sequence: VH3

<400> SEQUENCE: 57

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Human consensus sequence: : VH4

<400> SEQUENCE: 58

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Human consensus sequence: : VH5
<220> FEATURE:
<221> NAME/KEY: misc_feature
<222> LOCATION: (1)..(1)
<223> OTHER INFORMATION: Xaa is His or Gln

<400> SEQUENCE: 59

Xaa Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

```
<210> SEQ ID NO 60
<211> LENGTH: 32
<212> TYPE: PRT
<213> ORGANISM: Artificial Sequence
<220> FEATURE:
<223> OTHER INFORMATION: Human consensus sequence: : VH6

<400> SEQUENCE: 60

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Val Tyr Tyr Cys Ala Arg
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Human consensus sequence: : VH7

<400> SEQUENCE: 61

Arg Phe Val Phe Ser Leu Asp Thr Ser Val Ser Thr Ala Tyr Leu Gln
1               5                   10                  15

Ile Cys Ser Leu Lys Ala Glu Asp Thr Ala Val Tyr Tyr Cys Ala Arg
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Lama glama consensus sequence: VH3-11
<220> FEATURE:
<221> NAME/KEY: misc_feature
<222> LOCATION: (22)..(22)
<223> OTHER INFORMATION: Xaa is Pro or Ser

<400> SEQUENCE: 62

Arg Phe Thr Ile Ser Arg Asp Asn Ala Lys Asn Thr Val Tyr Leu Gln
1               5                   10                  15

Met Asn Ser Leu Lys Xaa Glu Asp Thr Ala Val Tyr Tyr Cys Ala Lys
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Lama glama consensus sequence: VH3-21

<400> SEQUENCE: 63

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Arg
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Lama glama consensus sequence: VH3-23

<400> SEQUENCE: 64
```

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30
```

<210> SEQ ID NO 65
<211> LENGTH: 32
<212> TYPE: PRT
<213> ORGANISM: Artificial Sequence
<220> FEATURE:
<223> OTHER INFORMATION: Lama glama consensus sequence: VH3-48
<220> FEATURE:
<221> NAME/KEY: misc_feature
<222> LOCATION: (27)..(27)
<223> OTHER INFORMATION: Xaa is Leu or Val

<400> SEQUENCE: 65

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Xaa Tyr Tyr Cys Ala Arg
            20                  25                  30
```

<210> SEQ ID NO 66
<211> LENGTH: 32
<212> TYPE: PRT
<213> ORGANISM: Artificial Sequence
<220> FEATURE:
<223> OTHER INFORMATION: Lama glama consensus sequence: VH3-66

<400> SEQUENCE: 66

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30
```

<210> SEQ ID NO 67
<211> LENGTH: 32
<212> TYPE: PRT
<213> ORGANISM: Artificial Sequence
<220> FEATURE:
<223> OTHER INFORMATION: Lama glama consensus sequence: VH3

<400> SEQUENCE: 67

```
Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30
```

<210> SEQ ID NO 68
<211> LENGTH: 32
<212> TYPE: PRT
<213> ORGANISM: Artificial Sequence
<220> FEATURE:
<223> OTHER INFORMATION: Lama glama consensus sequence: VH4-30-4

<400> SEQUENCE: 68

```
Arg Thr Ser Ile Ser Arg Asp Thr Ser Lys Asn Gln Phe Ser Leu Gln
1               5                   10                  15

Leu Ser Ser Val Thr Pro Glu Asp Thr Ala Val Tyr Tyr Cys Ala Arg
            20                  25                  30
```

<210> SEQ ID NO 69
<211> LENGTH: 30
<212> TYPE: PRT
<213> ORGANISM: Artificial Sequence

```
<220> FEATURE:
<223> OTHER INFORMATION: Lama pacos consensus sequence: VH1-46

<400> SEQUENCE: 69

Glu Val Gln Leu Val Gln Pro Gly Ala Glu Leu Arg Lys Pro Gly Ala
1               5                   10                  15

Ser Val Lys Val Ser Cys Lys Ala Ser Gly Tyr Thr Phe Thr
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Lama pacos consensus sequence: VH3-66

<400> SEQUENCE: 70

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Lama pacos consensus sequence: VH3-48

<400> SEQUENCE: 71

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Lama pacos consensus sequence: VH3

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Lama pacos consensus sequence: VH4-30-4

<400> SEQUENCE: 73

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr
            20                  25                  30

<210> SEQ ID NO 74
<211> LENGTH: 14
<212> TYPE: PRT
```

```
<213> ORGANISM: Artificial Sequence
<220> FEATURE:
<223> OTHER INFORMATION: Lama pacos consensus sequence: VH1-46

<400> SEQUENCE: 74

Trp Val Arg Gln Ala Pro Gly Gln Gly Leu Glu Trp Met Gly
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Lama pacos consensus sequence: VH3-66

<400> SEQUENCE: 75

Trp Ala Arg Gln Val Pro Gly Lys Gly Leu Glu Trp Val Ser
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Lama pacos consensus sequence: VH3-48

<400> SEQUENCE: 76

Trp Val Arg Gln Ala Pro Gly Lys Gly Leu Glu Trp Val Ser
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Lama pacos consensus sequence: VH3

<400> SEQUENCE: 77

Trp Val Arg Gln Ala Pro Gly Lys Gly Leu Glu Trp Val Ser
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Lama pacos consensus sequence: VH4-30-4

<400> SEQUENCE: 78

Trp Ile Arg Gln Pro Pro Gly Lys Gly Leu Glu Trp Met Gly
1               5                   10

<210> SEQ ID NO 79
<211> LENGTH: 32
<212> TYPE: PRT
<213> ORGANISM: Artificial Sequence
<220> FEATURE:
<223> OTHER INFORMATION: Lama pacos consensus sequence: VH1-46

<400> SEQUENCE: 79

Arg Val Thr Phe Thr Ala Asp Thr Ser Thr Ser Thr Ala Tyr Val Glu
1               5                   10                  15

Leu Ser Ser Leu Arg Ser Glu Gly Thr Ala Val Tyr Tyr Cys Ala Arg
            20                  25                  30

<210> SEQ ID NO 80
```

```
<211> LENGTH: 32
<212> TYPE: PRT
<213> ORGANISM: Artificial Sequence
<220> FEATURE:
<223> OTHER INFORMATION: Lama pacos consensus sequence: VH3-66

<400> SEQUENCE: 80

Arg Phe Thr Ile Ser Arg Asp Asn Ala Lys Asn Thr Val Tyr Leu Gln
1               5                   10                  15

Met Asn Ser Leu Lys Pro Glu Gly Thr Ala Val Tyr Tyr Cys Ala Arg
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Lama pacos consensus sequence: VH3-48

<400> SEQUENCE: 81

Arg Phe Thr Ile Ser Arg Asp Asn Ala Lys Asn Thr Leu Tyr Leu Gln
1               5                   10                  15

Met Asn Ser Leu Lys Pro Glu Gly Thr Ala Val Tyr Tyr Cys Ala Arg
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Lama pacos consensus sequence: VH3

<400> SEQUENCE: 82

Arg Phe Thr Ile Ser Arg Asp Asn Ala Lys Asn Thr Leu Tyr Leu Gln
1               5                   10                  15

Met Asn Ser Leu Lys Pro Glu Gly Thr Ala Val Tyr Tyr Cys Ala Arg
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Lama pacos consensus sequence: VH4-30-4

<400> SEQUENCE: 83

Arg Thr Ser Ile Ser Arg Asp Thr Ser Lys Asn Gln Phe Ser Leu Gln
1               5                   10                  15

Leu Ser Ser Val Thr Pro Glu Gly Thr Ala Val Tyr Tyr Cys Ala Arg
            20                  25                  30

<210> SEQ ID NO 84
<211> LENGTH: 22
<212> TYPE: PRT
<213> ORGANISM: Artificial Sequence
<220> FEATURE:
<223> OTHER INFORMATION: Lama glama consensus sequence: VL1
<220> FEATURE:
<221> NAME/KEY: misc_feature
<222> LOCATION: (1)..(1)
<223> OTHER INFORMATION: Xaa is Asn or Gln
<220> FEATURE:
<221> NAME/KEY: misc_feature
<222> LOCATION: (3)..(3)
<223> OTHER INFORMATION: Xaa is Met or Val

<400> SEQUENCE: 84
```

```
Xaa Phe Xaa Leu Thr Gln Pro Pro Ser Val Ser Gly Ser Pro Gly Gln
1               5                   10                  15

Lys Phe Thr Ile Ser Cys
            20

<210> SEQ ID NO 85
<211> LENGTH: 22
<212> TYPE: PRT
<213> ORGANISM: Artificial Sequence
<220> FEATURE:
<223> OTHER INFORMATION: Human consensus sequence: VL1

<400> SEQUENCE: 85

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 86
<211> LENGTH: 22
<212> TYPE: PRT
<213> ORGANISM: Artificial Sequence
<220> FEATURE:
<223> OTHER INFORMATION: Human consensus sequence: VL2
<220> FEATURE:
<221> NAME/KEY: misc_feature
<222> LOCATION: (8)..(8)
<223> OTHER INFORMATION: Xaa is Ala or Pro

<400> SEQUENCE: 86

Gln Ser Ala Leu Thr Gln Pro Xaa Ser Val Ser Gly Ser Pro Gly Gln
1               5                   10                  15

Ser Val Thr Ile Ser Cys
            20

<210> SEQ ID NO 87
<211> LENGTH: 22
<212> TYPE: PRT
<213> ORGANISM: Artificial Sequence
<220> FEATURE:
<223> OTHER INFORMATION: Human consensus sequence: VL3

<400> SEQUENCE: 87

Ser Tyr Glu Leu Thr Gln Pro Pro Ser Val Val Ser Pro Gly Gln
1               5                   10                  15

Thr Ala Arg Ile Thr Cys
            20

<210> SEQ ID NO 88
<211> LENGTH: 22
<212> TYPE: PRT
<213> ORGANISM: Artificial Sequence
<220> FEATURE:
<223> OTHER INFORMATION: Human consensus sequence: VL4

<400> SEQUENCE: 88

Gln Pro Val Leu Thr Gln Ser Pro Ser Ala Ser Ala Ser Leu Gly Ala
1               5                   10                  15

Ser Val Lys Leu Thr Cys
            20

<210> SEQ ID NO 89
<211> LENGTH: 22
<212> TYPE: PRT
```

```
<213> ORGANISM: Artificial Sequence
<220> FEATURE:
<223> OTHER INFORMATION: Human consensus sequence: VL5
<220> FEATURE:
<221> NAME/KEY: misc_feature
<222> LOCATION: (8)..(8)
<223> OTHER INFORMATION: Xaa is Ala, Pro, Ser or Thr

<400> SEQUENCE: 89

Gln Pro Val Leu Thr Gln Pro Xaa Ser Leu Ser Ala Ser Pro Gly Ala
1               5                   10                  15

Ser Ala Arg Leu Thr Cys
            20

<210> SEQ ID NO 90
<211> LENGTH: 22
<212> TYPE: PRT
<213> ORGANISM: Artificial Sequence
<220> FEATURE:
<223> OTHER INFORMATION: Human consensus sequence: VL6

<400> SEQUENCE: 90

Asn Phe Met Leu Thr Gln Pro His Ser Val Ser Glu Ser Pro Gly Lys
1               5                   10                  15

Thr Val Thr Ile Ser Cys
            20

<210> SEQ ID NO 91
<211> LENGTH: 22
<212> TYPE: PRT
<213> ORGANISM: Artificial Sequence
<220> FEATURE:
<223> OTHER INFORMATION: Human consensus sequence: VL7
<220> FEATURE:
<221> NAME/KEY: misc_feature
<222> LOCATION: (2)..(2)
<223> OTHER INFORMATION: Xaa is Ala or Thr

<400> SEQUENCE: 91

Gln Xaa Val Val Thr Gln Glu Pro Ser Leu Thr Val Ser Pro Gly Gly
1               5                   10                  15

Thr Val Thr Leu Thr Cys
            20

<210> SEQ ID NO 92
<211> LENGTH: 22
<212> TYPE: PRT
<213> ORGANISM: Artificial Sequence
<220> FEATURE:
<223> OTHER INFORMATION: Human consensus sequence: VL8

<400> SEQUENCE: 92

Gln Thr Val Val Thr Gln Glu Pro Ser Phe Ser Val Ser Pro Gly Gly
1               5                   10                  15

Thr Val Thr Leu Thr Cys
            20

<210> SEQ ID NO 93
<211> LENGTH: 22
<212> TYPE: PRT
<213> ORGANISM: Artificial Sequence
<220> FEATURE:
<223> OTHER INFORMATION: Human consensus sequence: VL9

<400> SEQUENCE: 93

Gln Pro Val Leu Thr Gln Pro Pro Ser Ala Ser Ala Ser Leu Gly Ala
```

```
                 1               5                  10                 15
Ser Val Thr Leu Thr Cys
            20

<210> SEQ ID NO 94
<211> LENGTH: 22
<212> TYPE: PRT
<213> ORGANISM: Artificial Sequence
<220> FEATURE:
<223> OTHER INFORMATION: Human consensus sequence: VL10

<400> SEQUENCE: 94

Gln Ala Gly Leu Thr Gln Pro Pro Ser Val Ser Lys Gly Leu Arg Gln
1               5                  10                  15

Thr Ala Thr Leu Thr Cys
            20

<210> SEQ ID NO 95
<211> LENGTH: 15
<212> TYPE: PRT
<213> ORGANISM: Artificial Sequence
<220> FEATURE:
<223> OTHER INFORMATION: Lama glama consensus sequence: VL1

<400> SEQUENCE: 95

Trp Tyr Gln His Leu Pro Gly Thr Ala Pro Lys Leu Leu Ile Tyr
1               5                  10                  15

<210> SEQ ID NO 96
<211> LENGTH: 15
<212> TYPE: PRT
<213> ORGANISM: Artificial Sequence
<220> FEATURE:
<223> OTHER INFORMATION: Human consensus sequence: VL1

<400> SEQUENCE: 96

Trp Tyr Gln Gln Leu Pro Gly Thr Ala Pro Lys Leu Leu Ile Tyr
1               5                  10                  15

<210> SEQ ID NO 97
<211> LENGTH: 15
<212> TYPE: PRT
<213> ORGANISM: Artificial Sequence
<220> FEATURE:
<223> OTHER INFORMATION: Human consensus sequence: VL2

<400> SEQUENCE: 97

Trp Tyr Gln Gln His Pro Gly Lys Ala Pro Lys Leu Met Ile Tyr
1               5                  10                  15

<210> SEQ ID NO 98
<211> LENGTH: 15
<212> TYPE: PRT
<213> ORGANISM: Artificial Sequence
<220> FEATURE:
<223> OTHER INFORMATION: Human consensus sequence: VL3

<400> SEQUENCE: 98

Trp Tyr Gln Gln Lys Pro Gly Gln Ala Pro Val Leu Val Ile Tyr
1               5                  10                  15

<210> SEQ ID NO 99
<211> LENGTH: 15
<212> TYPE: PRT
<213> ORGANISM: Artificial Sequence
<220> FEATURE:
```

<223> OTHER INFORMATION: Human consensus sequence: VL4
<220> FEATURE:
<221> NAME/KEY: misc_feature
<222> LOCATION: (9)..(9)
<223> OTHER INFORMATION: Xaa is Gly, Ala, or Ser

<400> SEQUENCE: 99

Trp His Gln Gln Gln Pro Gly Lys Xaa Pro Arg Tyr Leu Met Lys
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Human consensus sequence: VL5
<220> FEATURE:
<221> NAME/KEY: misc_feature
<222> LOCATION: (15)..(15)
<223> OTHER INFORMATION: Xaa is Tyr or Arg

<400> SEQUENCE: 100

Trp Tyr Gln Gln Lys Pro Gly Ser Pro Pro Arg Tyr Leu Leu Xaa
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Human consensus sequence: VL6

<400> SEQUENCE: 101

Trp Tyr Gln Gln Arg Pro Gly Ser Ser Pro Thr Thr Val Ile Tyr
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Human consensus sequence: VL7
<220> FEATURE:
<221> NAME/KEY: misc_feature
<222> LOCATION: (12)..(12)
<223> OTHER INFORMATION: Xaa is Ala or Thr

<400> SEQUENCE: 102

Trp Phe Gln Gln Lys Pro Gly Gln Ala Pro Arg Xaa Leu Ile Tyr
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Human consensus sequence: VL8

<400> SEQUENCE: 103

Trp Tyr Gln Gln Thr Pro Gly Gln Ala Pro Arg Thr Leu Ile Tyr
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Human consensus sequence: VL9

```
<400> SEQUENCE: 104

Trp Tyr Gln Gln Arg Pro Gly Lys Gly Pro Arg Phe Val Met Arg
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Human consensus sequence: VL10

<400> SEQUENCE: 105

Trp Leu Gln Gln His Gln Gly His Pro Pro Lys Leu Leu Ser Tyr
1               5                   10                  15

<210> SEQ ID NO 106
<211> LENGTH: 30
<212> TYPE: PRT
<213> ORGANISM: Artificial Sequence
<220> FEATURE:
<223> OTHER INFORMATION: Lama glama consensus sequence: VL1

<400> SEQUENCE: 106

Pro Asp Arg Phe Ser Gly Ser Lys Ser Gly Ser Ala Ser Leu Thr
1               5                   10                  15

Ile Thr Gly Leu Gln Ala Glu Asp Glu Ala Asp Tyr Tyr Cys
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Human consensus sequence: VL1

<400> SEQUENCE: 107

Pro Asp Arg Phe Ser Gly Ser Lys Ser Gly Thr Ser Ala Ser Leu Ala
1               5                   10                  15

Ile Ser Gly Leu Gln Ser Glu Asp Glu Ala Asp Tyr Tyr Cys
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Human consensus sequence: VL2

<400> SEQUENCE: 108

Pro Asp Arg Phe Ser Gly Ser Lys Ser Gly Asn Thr Ala Ser Leu Thr
1               5                   10                  15

Ile Ser Gly Leu Gln Ala Glu Asp Glu Ala Asp Tyr Tyr Cys
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Human consensus sequence: VL3
<220> FEATURE:
<221> NAME/KEY: misc_feature
<222> LOCATION: (20)..(20)
<223> OTHER INFORMATION: Xaa is Ala or Val

<400> SEQUENCE: 109
```

```
Pro Glu Arg Phe Ser Gly Ser Ser Gly Asn Thr Ala Thr Leu Thr
1               5                   10                  15

Ile Ser Gly Xaa Gln Ala Glu Asp Glu Ala Asp Tyr Tyr Cys
            20                  25                  30
```

<210> SEQ ID NO 110
<211> LENGTH: 30
<212> TYPE: PRT
<213> ORGANISM: Artificial Sequence
<220> FEATURE:
<223> OTHER INFORMATION: Human consensus sequence: VL4

<400> SEQUENCE: 110

```
Pro Asp Arg Phe Ser Gly Ser Ser Gly Ala Asp Arg Tyr Leu Thr
1               5                   10                  15

Ile Ser Asn Leu Gln Ser Glu Asp Glu Ala Asp Tyr Tyr Cys
            20                  25                  30
```

<210> SEQ ID NO 111
<211> LENGTH: 32
<212> TYPE: PRT
<213> ORGANISM: Artificial Sequence
<220> FEATURE:
<223> OTHER INFORMATION: Human consensus sequence: VL5

<400> SEQUENCE: 111

```
Pro Ser Arg Phe Ser Gly Ser Lys Asp Ala Ser Ala Asn Ala Gly Ile
1               5                   10                  15

Leu Leu Ile Ser Gly Leu Gln Ser Glu Asp Glu Ala Asp Tyr Tyr Cys
            20                  25                  30
```

<210> SEQ ID NO 112
<211> LENGTH: 32
<212> TYPE: PRT
<213> ORGANISM: Artificial Sequence
<220> FEATURE:
<223> OTHER INFORMATION: Human consensus sequence: VL6

<400> SEQUENCE: 112

```
Pro Asp Arg Phe Ser Gly Ser Ile Asp Ser Ser Ser Asn Ser Ala Ser
1               5                   10                  15

Leu Thr Ile Ser Gly Leu Lys Thr Glu Asp Glu Ala Asp Tyr Tyr Cys
            20                  25                  30
```

<210> SEQ ID NO 113
<211> LENGTH: 30
<212> TYPE: PRT
<213> ORGANISM: Artificial Sequence
<220> FEATURE:
<223> OTHER INFORMATION: Human consensus sequence: VL7
<220> FEATURE:
<221> NAME/KEY: misc_feature
<222> LOCATION: (20)..(20)
<223> OTHER INFORMATION: Xaa is Ala or Val

<400> SEQUENCE: 113

```
Pro Ala Arg Phe Ser Gly Ser Leu Leu Gly Gly Lys Ala Ala Leu Thr
1               5                   10                  15

Leu Ser Gly Xaa Gln Pro Glu Asp Glu Ala Glu Tyr Tyr Cys
            20                  25                  30
```

<210> SEQ ID NO 114
<211> LENGTH: 30
<212> TYPE: PRT

<210> SEQ ID NO 114
<211> LENGTH: 30
<212> TYPE: PRT
<213> ORGANISM: Artificial Sequence
<220> FEATURE:
<223> OTHER INFORMATION: Human consensus sequence: VL8

<400> SEQUENCE: 114

Pro Asp Arg Phe Ser Gly Ser Ile Leu Gly Asn Lys Ala Ala Leu Thr
1               5                   10                  15

Ile Thr Gly Ala Gln Ala Asp Asp Glu Ser Asp Tyr Tyr Cys
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: Human consensus sequence: VL9

<400> SEQUENCE: 115

Pro Asp Arg Phe Ser Val Leu Gly Ser Gly Leu Asn Arg Tyr Leu Thr
1               5                   10                  15

Ile Lys Asn Ile Gln Glu Glu Asp Glu Ser Asp Tyr His Cys
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Human consensus sequence: VL10

<400> SEQUENCE: 116

Ser Glu Arg Leu Ser Ala Ser Arg Ser Gly Asn Thr Ala Ser Leu Thr
1               5                   10                  15

Ile Thr Gly Leu Gln Pro Glu Asp Glu Ala Asp Tyr Tyr Cys
            20                  25                  30

<210> SEQ ID NO 117
<211> LENGTH: 22
<212> TYPE: PRT
<213> ORGANISM: Artificial Sequence
<220> FEATURE:
<223> OTHER INFORMATION: Lama glama consensus sequence: VL2-11

<400> SEQUENCE: 117

Gln Ser Ala Leu Thr Gln Pro Pro Ser Val Ser Gly Ser Pro Gly Lys
1               5                   10                  15

Thr Val Thr Ile Ser Cys
            20

<210> SEQ ID NO 118
<211> LENGTH: 22
<212> TYPE: PRT
<213> ORGANISM: Artificial Sequence
<220> FEATURE:
<223> OTHER INFORMATION: Human consensus sequence: VL1

<400> SEQUENCE: 118

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 119
<211> LENGTH: 22

<212> TYPE: PRT
<213> ORGANISM: Artificial Sequence
<220> FEATURE:
<223> OTHER INFORMATION: Human consensus sequence: VL2
<220> FEATURE:
<221> NAME/KEY: misc_feature
<222> LOCATION: (8)..(8)
<223> OTHER INFORMATION: Xaa is Ala or Pro

<400> SEQUENCE: 119

Gln Ser Ala Leu Thr Gln Pro Xaa Ser Val Ser Gly Ser Pro Gly Gln
1               5                   10                  15

Ser Val Thr Ile Ser Cys
            20

<210> SEQ ID NO 120
<211> LENGTH: 22
<212> TYPE: PRT
<213> ORGANISM: Artificial Sequence
<220> FEATURE:
<223> OTHER INFORMATION: Human consensus sequence: VL3

<400> SEQUENCE: 120

Ser Tyr Glu Leu Thr Gln Pro Pro Ser Val Ser Val Ser Pro Gly Gln
1               5                   10                  15

Thr Ala Arg Ile Thr Cys
            20

<210> SEQ ID NO 121
<211> LENGTH: 22
<212> TYPE: PRT
<213> ORGANISM: Artificial Sequence
<220> FEATURE:
<223> OTHER INFORMATION: Human consensus sequence: VL4

<400> SEQUENCE: 121

Gln Pro Val Leu Thr Gln Ser Pro Ser Ala Ser Ala Ser Leu Gly Ala
1               5                   10                  15

Ser Val Lys Leu Thr Cys
            20

<210> SEQ ID NO 122
<211> LENGTH: 22
<212> TYPE: PRT
<213> ORGANISM: Artificial Sequence
<220> FEATURE:
<223> OTHER INFORMATION: Human consensus sequence: VL5
<220> FEATURE:
<221> NAME/KEY: misc_feature
<222> LOCATION: (8)..(8)
<223> OTHER INFORMATION: Xaa is Ala, Pro, Ser or Thr

<400> SEQUENCE: 122

Gln Pro Val Leu Thr Gln Pro Xaa Ser Leu Ser Ala Ser Pro Gly Ala
1               5                   10                  15

Ser Ala Arg Leu Thr Cys
            20

<210> SEQ ID NO 123
<211> LENGTH: 22
<212> TYPE: PRT
<213> ORGANISM: Artificial Sequence
<220> FEATURE:
<223> OTHER INFORMATION: Human consensus sequence: VL6

<400> SEQUENCE: 123

```
Asn Phe Met Leu Thr Gln Pro His Ser Val Ser Glu Ser Pro Gly Lys
1               5                   10                  15

Thr Val Thr Ile Ser Cys
            20
```

<210> SEQ ID NO 124
<211> LENGTH: 22
<212> TYPE: PRT
<213> ORGANISM: Artificial Sequence
<220> FEATURE:
<223> OTHER INFORMATION: Human consensus sequence: VL7
<220> FEATURE:
<221> NAME/KEY: misc_feature
<222> LOCATION: (2)..(2)
<223> OTHER INFORMATION: Xaa is Ala or Thr

<400> SEQUENCE: 124

```
Gln Xaa Val Val Thr Gln Glu Pro Ser Leu Thr Val Ser Pro Gly Gly
1               5                   10                  15

Thr Val Thr Leu Thr Cys
            20
```

<210> SEQ ID NO 125
<211> LENGTH: 22
<212> TYPE: PRT
<213> ORGANISM: Artificial Sequence
<220> FEATURE:
<223> OTHER INFORMATION: Human consensus sequence: VL8

<400> SEQUENCE: 125

```
Gln Thr Val Val Thr Gln Glu Pro Ser Phe Ser Val Ser Pro Gly Gly
1               5                   10                  15

Thr Val Thr Leu Thr Cys
            20
```

<210> SEQ ID NO 126
<211> LENGTH: 22
<212> TYPE: PRT
<213> ORGANISM: Artificial Sequence
<220> FEATURE:
<223> OTHER INFORMATION: Lama glama consensus sequence: VL2-18

<400> SEQUENCE: 126

```
Gln Ser Val Leu Thr Gln Pro Pro Ser Val Ser Gly Thr Leu Gly Lys
1               5                   10                  15

Thr Val Thr Ile Ser Cys
            20
```

<210> SEQ ID NO 127
<211> LENGTH: 15
<212> TYPE: PRT
<213> ORGANISM: Artificial Sequence
<220> FEATURE:
<223> OTHER INFORMATION: Lama glama consensus sequence: VL2-11

<400> SEQUENCE: 127

```
Trp Tyr Gln Gln Leu Pro Gly Met Ala Pro Lys Leu Leu Ile Tyr
1               5                   10                  15
```

<210> SEQ ID NO 128
<211> LENGTH: 15
<212> TYPE: PRT
<213> ORGANISM: Artificial Sequence
<220> FEATURE:
<223> OTHER INFORMATION: Lama glama consensus sequence: VL2-18

```
<400> SEQUENCE: 128

Trp Tyr Gln Gln Leu Pro Gly Thr Ala Pro Lys Leu Leu Ile Tyr
1               5                   10                  15

<210> SEQ ID NO 129
<211> LENGTH: 32
<212> TYPE: PRT
<213> ORGANISM: Artificial Sequence
<220> FEATURE:
<223> OTHER INFORMATION: Lama glama consensus sequence: VL2-11

<400> SEQUENCE: 129

Gly Ile Ala Asp Arg Phe Ser Gly Ser Lys Ser Gly Asn Thr Ala Ser
1               5                   10                  15

Leu Thr Ile Ser Gly Leu Gln Ser Glu Asp Glu Ala Asp Tyr Tyr Cys
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Human consensus sequence: VL1

<400> SEQUENCE: 130

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Human consensus sequence: VL2

<400> SEQUENCE: 131

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Human consensus sequence: VL3
<220> FEATURE:
<221> NAME/KEY: misc_feature
<222> LOCATION: (22)..(22)
<223> OTHER INFORMATION: Xaa is Ala or Val

<400> SEQUENCE: 132

Gly Ile Pro Glu Arg Phe Ser Gly Ser Ser Ser Gly Asn Thr Ala Thr
1               5                   10                  15

Leu Thr Ile Ser Gly Xaa Gln Ala Glu Asp Glu Ala Asp Tyr Tyr Cys
            20                  25                  30

<210> SEQ ID NO 133
<211> LENGTH: 32
<212> TYPE: PRT
<213> ORGANISM: Artificial Sequence
<220> FEATURE:
```

<223> OTHER INFORMATION: Human consensus sequence: VL4

<400> SEQUENCE: 133

Gly Ile Pro Asp Arg Phe Ser Gly Ser Ser Gly Ala Asp Arg Tyr
1               5                   10                  15

Leu Thr Ile Ser Asn Leu Gln Ser Glu Asp Glu Ala Asp Tyr Tyr Cys
            20                  25                  30

<210> SEQ ID NO 134
<211> LENGTH: 34
<212> TYPE: PRT
<213> ORGANISM: Artificial Sequence
<220> FEATURE:
<223> OTHER INFORMATION: Human consensus sequence: VL5

<400> SEQUENCE: 134

Gly Val Pro Ser Arg Phe Ser Gly Ser Lys Asp Ala Ser Ala Asn Ala
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 135
<211> LENGTH: 34
<212> TYPE: PRT
<213> ORGANISM: Artificial Sequence
<220> FEATURE:
<223> OTHER INFORMATION: Human consensus sequence: VL6

<400> SEQUENCE: 135

Gly Val Pro Asp Arg Phe Ser Gly Ser Ile Asp Ser Ser Ser Asn Ser
1               5                   10                  15

Ala Ser Leu Thr Ile Ser Gly Leu Lys Thr Glu Asp Glu Ala Asp Tyr
            20                  25                  30

Tyr Cys

<210> SEQ ID NO 136
<211> LENGTH: 32
<212> TYPE: PRT
<213> ORGANISM: Artificial Sequence
<220> FEATURE:
<223> OTHER INFORMATION: Human consensus sequence: VL7
<220> FEATURE:
<221> NAME/KEY: misc_feature
<222> LOCATION: (22)..(22)
<223> OTHER INFORMATION: Xaa is Ala or Val

<400> SEQUENCE: 136

Trp Thr Pro Ala Arg Phe Ser Gly Ser Leu Leu Gly Gly Lys Ala Ala
1               5                   10                  15

Leu Thr Leu Ser Gly Xaa Gln Pro Glu Asp Glu Ala Glu Tyr Tyr Cys
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Human consensus sequence: VL8

<400> SEQUENCE: 137

Gly Val Pro Asp Arg Phe Ser Gly Ser Ile Leu Gly Asn Lys Ala Ala
1               5                   10                  15

Leu Thr Ile Thr Gly Ala Gln Ala Asp Asp Glu Ser Asp Tyr Tyr Cys
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Human consensus sequence: VL9

<400> SEQUENCE: 138

Gly Ile Pro Asp Arg Phe Ser Val Leu Gly Ser Gly Leu Asn Arg Tyr
1               5                   10                  15

Leu Thr Ile Lys Asn Ile Gln Glu Glu Asp Ser Asp Tyr His Cys
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: Human consensus sequence: VL10

<400> SEQUENCE: 139

Gly Ile Ser Glu Arg Leu Ser Ala Ser Arg Ser Gly Asn Thr Ala Ser
1               5                   10                  15

Leu Thr Ile Thr Gly Leu Gln Pro Glu Asp Glu Ala Asp Tyr Tyr Cys
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Lama glama consensus sequence: VL2-18

<400> SEQUENCE: 140

Gly Ile Pro Asp Arg Phe Ser Gly Ser Lys Ser Gly Asn Thr Ala Ser
1               5                   10                  15

Leu Thr Ile Ser Gly Leu Gln Ser Glu Asp Glu Ala Asp Tyr Tyr Cys
            20                  25                  30

<210> SEQ ID NO 141
<211> LENGTH: 22
<212> TYPE: PRT
<213> ORGANISM: Artificial Sequence
<220> FEATURE:
<223> OTHER INFORMATION: Lama glama consensus sequence: VL3-19

<400> SEQUENCE: 141

Gln Ser Ala Leu Thr Gln Pro Ser Ala Leu Ser Val Thr Leu Gly Gln
1               5                   10                  15

Thr Ala Lys Ile Thr Cys
            20

<210> SEQ ID NO 142
<211> LENGTH: 22
<212> TYPE: PRT
<213> ORGANISM: Artificial Sequence
<220> FEATURE:
<223> OTHER INFORMATION: Lama glama consensus sequence: VL3-25

<400> SEQUENCE: 142

Gln Ala Gly Leu Thr Gln Pro Ser Ala Val Ser Val Ser Leu Gly Gln
1               5                   10                  15

```
Thr Ala Arg Ile Thr Cys
         20

<210> SEQ ID NO 143
<211> LENGTH: 15
<212> TYPE: PRT
<213> ORGANISM: Artificial Sequence
<220> FEATURE:
<223> OTHER INFORMATION: Lama glama consensus sequence: VL3-19

<400> SEQUENCE: 143

Trp Tyr Gln Gln Lys Pro Gly Gln Ala Pro Val Leu Val Ile Tyr
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Lama glama consensus sequence: VL3-25
<220> FEATURE:
<221> NAME/KEY: misc_feature
<222> LOCATION: (10)..(10)
<223> OTHER INFORMATION: Xaa is Pro or Arg
<220> FEATURE:
<221> NAME/KEY: misc_feature
<222> LOCATION: (12)..(12)
<223> OTHER INFORMATION: Xaa is Leu or Gln

<400> SEQUENCE: 144

Trp Tyr Gln Gln Lys Pro Gly Gln Ala Xaa Val Xaa Val Ile Tyr
1               5                   10                  15

<210> SEQ ID NO 145
<211> LENGTH: 32
<212> TYPE: PRT
<213> ORGANISM: Artificial Sequence
<220> FEATURE:
<223> OTHER INFORMATION: Lama glama consensus sequence: VL3-19

<400> SEQUENCE: 145

Gly Ile Pro Glu Arg Phe Ser Gly Ser Ser Gly Gly Arg Ala Thr
1               5                   10                  15

Leu Thr Ile Ser Gly Ala Gln Ala Glu Asp Glu Gly Asp Tyr Tyr Cys
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Lama glama consensus sequence: VL3-25
<220> FEATURE:
<221> NAME/KEY: misc_feature
<222> LOCATION: (11)..(11)
<223> OTHER INFORMATION: Xaa is Leu or Ser

<400> SEQUENCE: 146

Gly Ile Pro Glu Arg Phe Ser Gly Ser Arg Xaa Gly Gly Thr Ala Thr
1               5                   10                  15

Leu Thr Ile Ser Gly Ala Gln Ala Glu Asp Glu Ala Asp Tyr Tyr Cys
            20                  25                  30

<210> SEQ ID NO 147
<211> LENGTH: 22
<212> TYPE: PRT
<213> ORGANISM: Artificial Sequence
```

```
<220> FEATURE:
<223> OTHER INFORMATION: Lama glama consensus sequence: VL5

<400> SEQUENCE: 147

Gln Ala Val Leu Thr Gln Pro Pro Ser Leu Ser Ala Ser Pro Gly Ser
1               5                   10                  15

Ser Val Arg Leu Thr Cys
            20

<210> SEQ ID NO 148
<211> LENGTH: 15
<212> TYPE: PRT
<213> ORGANISM: Artificial Sequence
<220> FEATURE:
<223> OTHER INFORMATION: Lama glama consensus sequence: VL5

<400> SEQUENCE: 148

Trp Tyr Gln Gln Lys Ala Gly Ser Pro Pro Arg Tyr Leu Leu Tyr
1               5                   10                  15

<210> SEQ ID NO 149
<211> LENGTH: 32
<212> TYPE: PRT
<213> ORGANISM: Artificial Sequence
<220> FEATURE:
<223> OTHER INFORMATION: Lama glama consensus sequence: VL5

<400> SEQUENCE: 149

Val Pro Ser Arg Phe Ser Gly Ser Lys Asp Ala Ser Ala Asn Ala Gly
1               5                   10                  15

Leu Leu Leu Ile Ser Gly Leu Gln Pro Glu Asp Glu Ala Asp Tyr Tyr
            20                  25                  30

<210> SEQ ID NO 150
<211> LENGTH: 30
<212> TYPE: PRT
<213> ORGANISM: Artificial Sequence
<220> FEATURE:
<223> OTHER INFORMATION: Human consensus sequence: VL1

<400> SEQUENCE: 150

Val Pro Asp Arg Phe Ser Gly Ser Lys Ser Gly Thr Ser Ala Ser Leu
1               5                   10                  15

Ala Ile Ser Gly Leu Gln Ser Glu Asp Glu Ala Asp Tyr Tyr
            20                  25                  30

<210> SEQ ID NO 151
<211> LENGTH: 30
<212> TYPE: PRT
<213> ORGANISM: Artificial Sequence
<220> FEATURE:
<223> OTHER INFORMATION: Human consensus sequence: VL2

<400> SEQUENCE: 151

Val Pro Asp Arg Phe Ser Gly Ser Lys Ser Gly Asn Thr Ala Ser Leu
1               5                   10                  15

Thr Ile Ser Gly Leu Gln Ala Glu Asp Glu Ala Asp Tyr Tyr
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: Human consensus sequence: VL3
```

```
<220> FEATURE:
<221> NAME/KEY: misc_feature
<222> LOCATION: (21)..(21)
<223> OTHER INFORMATION: Xaa is Ala or Val

<400> SEQUENCE: 152

Ile Pro Glu Arg Phe Ser Gly Ser Ser Ser Gly Asn Thr Ala Thr Leu
1               5                   10                  15

Thr Ile Ser Gly Xaa Gln Ala Glu Asp Glu Ala Asp Tyr Tyr
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Human consensus sequence: VL4

<400> SEQUENCE: 153

Ile Pro Asp Arg Phe Ser Gly Ser Ser Ser Gly Ala Asp Arg Tyr Leu
1               5                   10                  15

Thr Ile Ser Asn Leu Gln Ser Glu Asp Glu Ala Asp Tyr Tyr
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: Human consensus sequence: VL5

<400> SEQUENCE: 154

Val Pro Ser Arg Phe Ser Gly Ser Lys Asp Ala Ser Ala Asn Ala Gly
1               5                   10                  15

Ile Leu Leu Ile Ser Gly Leu Gln Ser Glu Asp Glu Ala Asp Tyr Tyr
                20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Human consensus sequence: VL6

<400> SEQUENCE: 155

Val Pro Asp Arg Phe Ser Gly Ser Ile Asp Ser Ser Ser Asn Ser Ala
1               5                   10                  15

Ser Leu Thr Ile Ser Gly Leu Lys Thr Glu Asp Glu Ala Asp Tyr Tyr
                20                  25                  30

<210> SEQ ID NO 156
<211> LENGTH: 30
<212> TYPE: PRT
<213> ORGANISM: Artificial Sequence
<220> FEATURE:
<223> OTHER INFORMATION: Human consensus sequence: VL7
<220> FEATURE:
<221> NAME/KEY: misc_feature
<222> LOCATION: (21)..(21)
<223> OTHER INFORMATION: Xaa is Ala or Val

<400> SEQUENCE: 156

Thr Pro Ala Arg Phe Ser Gly Ser Leu Leu Gly Gly Lys Ala Ala Leu
1               5                   10                  15

Thr Leu Ser Gly Xaa Gln Pro Glu Asp Glu Ala Glu Tyr Tyr
            20                  25                  30
```

<210> SEQ ID NO 157
<211> LENGTH: 30
<212> TYPE: PRT
<213> ORGANISM: Artificial Sequence
<220> FEATURE:
<223> OTHER INFORMATION: Human consensus sequence: VL8

<400> SEQUENCE: 157

Val Pro Asp Arg Phe Ser Gly Ser Ile Leu Gly Asn Lys Ala Ala Leu
1               5                   10                  15
Thr Ile Thr Gly Ala Gln Ala Asp Asp Glu Ser Asp Tyr Tyr
            20                  25                  30

<210> SEQ ID NO 158
<211> LENGTH: 30
<212> TYPE: PRT
<213> ORGANISM: Artificial Sequence
<220> FEATURE:
<223> OTHER INFORMATION: Human consensus sequence: VL9

<400> SEQUENCE: 158

Ile Pro Asp Arg Phe Ser Val Leu Gly Ser Gly Leu Asn Arg Tyr Leu
1               5                   10                  15
Thr Ile Lys Asn Ile Gln Glu Glu Asp Glu Ser Asp Tyr His
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Human consensus sequence: VL10

<400> SEQUENCE: 159

Ile Ser Glu Arg Leu Ser Ala Ser Arg Ser Gly Asn Thr Ala Ser Leu
1               5                   10                  15
Thr Ile Thr Gly Leu Gln Pro Glu Asp Glu Ala Asp Tyr Tyr
            20                  25                  30

<210> SEQ ID NO 160
<211> LENGTH: 22
<212> TYPE: PRT
<213> ORGANISM: Artificial Sequence
<220> FEATURE:
<223> OTHER INFORMATION: Lama glama consensus sequence: VL8-61

<400> SEQUENCE: 160

Gln Ala Val Val Thr Gln Glu Pro Ser Leu Ser Val Ser Pro Gly Gly
1               5                   10                  15
Thr Val Thr Leu Thr Cys
            20

<210> SEQ ID NO 161
<211> LENGTH: 15
<212> TYPE: PRT
<213> ORGANISM: Artificial Sequence
<220> FEATURE:
<223> OTHER INFORMATION: Lama glama consensus sequence: VL8-61

<400> SEQUENCE: 161

Trp Tyr Gln Gln Thr Pro Gly Gln Ala Pro Arg Thr Leu Ile Tyr
1               5                   10                  15

<210> SEQ ID NO 162
<211> LENGTH: 30
<212> TYPE: PRT
<213> ORGANISM: Artificial Sequence
<220> FEATURE:
<223> OTHER INFORMATION: Lama consensus sequence: VL8-61

<400> SEQUENCE: 162

Pro Ser Arg Phe Ser Gly Ser Ile Ser Gly Asn Lys Ala Ala Leu Thr
1               5                   10                  15

Ile Thr Gly Ala Gln Pro Glu Asp Glu Ala Asp Tyr Tyr Cys
            20                  25                  30

<210> SEQ ID NO 163
<211> LENGTH: 23
<212> TYPE: PRT
<213> ORGANISM: Artificial Sequence
<220> FEATURE:
<223> OTHER INFORMATION: Lama glama consensus sequence: VK1

<400> SEQUENCE: 163

Asp Ile Val Met Thr Gln Ser Pro Ser Ser Leu Ser Ala Ser Leu Gly
1               5                   10                  15

Asp Arg Val Thr Ile Thr Cys
            20

<210> SEQ ID NO 164
<211> LENGTH: 23
<212> TYPE: PRT
<213> ORGANISM: Artificial Sequence
<220> FEATURE:
<223> OTHER INFORMATION: Human consensus sequence: VK1

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 165
<211> LENGTH: 23
<212> TYPE: PRT
<213> ORGANISM: Artificial Sequence
<220> FEATURE:
<223> OTHER INFORMATION: Human consensus sequence: VK2
<220> FEATURE:
<221> NAME/KEY: misc_feature
<222> LOCATION: (17)..(17)
<223> OTHER INFORMATION: Xaa is Gln or Glu

<400> SEQUENCE: 165

Asp Ile Val Met Thr Gln Thr Pro Leu Ser Leu Pro Val Thr Pro Gly
1               5                   10                  15

Xaa Pro Ala Ser Ile Ser Cys
            20

<210> SEQ ID NO 166
<211> LENGTH: 23
<212> TYPE: PRT
<213> ORGANISM: Artificial Sequence
<220> FEATURE:
<223> OTHER INFORMATION: Human consensus sequence: VK3

<400> SEQUENCE: 166

Glu Ile Val Leu Thr Gln Ser Pro Ala Thr Leu Ser Leu Ser Pro Gly

```
                1               5                  10                 15
Glu Arg Ala Thr Leu Ser Cys
            20

<210> SEQ ID NO 167
<211> LENGTH: 23
<212> TYPE: PRT
<213> ORGANISM: Artificial Sequence
<220> FEATURE:
<223> OTHER INFORMATION: Human consensus sequence: VK4

<400> SEQUENCE: 167

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 168
<211> LENGTH: 23
<212> TYPE: PRT
<213> ORGANISM: Artificial Sequence
<220> FEATURE:
<223> OTHER INFORMATION: Human consensus sequence: VK5

<400> SEQUENCE: 168

Glu Thr Thr Leu Thr Gln Ser Pro Ala Phe Met Ser Ala Thr Pro Gly
1               5                   10                  15

Asp Lys Val Asn Ile Ser Cys
            20

<210> SEQ ID NO 169
<211> LENGTH: 23
<212> TYPE: PRT
<213> ORGANISM: Artificial Sequence
<220> FEATURE:
<223> OTHER INFORMATION: Lama glama consensus sequence: VK2

<400> SEQUENCE: 169

Asp Ile Val Met Thr Gln Thr Pro Gly Ser Leu Ser Val Val Pro Gly
1               5                   10                  15

Glu Ser Ala Ser Ile Ser Cys
            20

<210> SEQ ID NO 170
<211> LENGTH: 23
<212> TYPE: PRT
<213> ORGANISM: Artificial Sequence
<220> FEATURE:
<223> OTHER INFORMATION: Lama glama consensus sequence: VK4

<400> SEQUENCE: 170

Asp Ile Val Met Thr Gln Ser Pro Ser Ser Val Thr Ala Ser Val Gly
1               5                   10                  15

Glu Lys Val Thr Ile Asn Cys
            20

<210> SEQ ID NO 171
<211> LENGTH: 15
<212> TYPE: PRT
<213> ORGANISM: Artificial Sequence
<220> FEATURE:
<223> OTHER INFORMATION: Lama glama consensus sequence: VK1

<400> SEQUENCE: 171
```

Trp Tyr Gln Gln Lys Pro Gly Gln Thr Pro Lys Leu Leu Ile Tyr
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Human consensus sequence: VK1

<400> SEQUENCE: 172

Trp Tyr Gln Gln Lys Pro Gly Lys Ala Pro Lys Leu Leu Ile Tyr
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Human consensus sequence: VK2

<400> SEQUENCE: 173

Trp Tyr Leu Gln Lys Pro Gly Gln Ser Pro Gln Leu Leu Ile Tyr
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Human consensus sequence: VK3

<400> SEQUENCE: 174

Trp Tyr Gln Gln Lys Pro Gly Gln Ala Pro Arg Leu Leu Ile Tyr
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Human consensus sequence: VK4

<400> SEQUENCE: 175

Trp Tyr Gln Gln Lys Pro Gly Gln Pro Pro Lys Leu Leu Ile Tyr
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Human consensus sequence: VK5

<400> SEQUENCE: 176

Trp Tyr Gln Gln Lys Pro Gly Glu Ala Ala Ile Phe Ile Ile Gln
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Lama glama consensus sequence: VK2

<400> SEQUENCE: 177

Trp Leu Leu Gln Lys Pro Gly Gln Ser Pro Gln Arg Leu Ile Tyr

```
<210> SEQ ID NO 178
<211> LENGTH: 15
<212> TYPE: PRT
<213> ORGANISM: Artificial Sequence
<220> FEATURE:
<223> OTHER INFORMATION: Lama glama consensus sequence: VK4

<400> SEQUENCE: 178

Trp Tyr Gln Gln Arg Pro Gly Gln Ser Pro Arg Leu Leu Ile Tyr
1               5                   10                  15

<210> SEQ ID NO 179
<211> LENGTH: 32
<212> TYPE: PRT
<213> ORGANISM: Artificial Sequence
<220> FEATURE:
<223> OTHER INFORMATION: Lama glama consensus sequence: VK1

<400> SEQUENCE: 179

Gly Val Pro Ser Arg Phe Ser Gly Ser Gly Ser Gly Thr Ser Phe Thr
1               5                   10                  15

Leu Thr Ile Ser Gly Leu Glu Ala Glu Asp Leu Ala Thr Tyr Tyr Cys
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Human consensus sequence: VK1

<400> SEQUENCE: 180

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 181
<211> LENGTH: 32
<212> TYPE: PRT
<213> ORGANISM: Artificial Sequence
<220> FEATURE:
<223> OTHER INFORMATION: Human consensus sequence: VK2

<400> SEQUENCE: 181

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 182
<211> LENGTH: 32
<212> TYPE: PRT
<213> ORGANISM: Artificial Sequence
<220> FEATURE:
<223> OTHER INFORMATION: Human consensus sequence: VK3

<400> SEQUENCE: 182

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 183
<211> LENGTH: 32
<212> TYPE: PRT
<213> ORGANISM: Artificial Sequence
<220> FEATURE:
<223> OTHER INFORMATION: Human consensus sequence: VK4

<400> SEQUENCE: 183

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Human consensus sequence: VK5

<400> SEQUENCE: 184

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 185
<211> LENGTH: 32
<212> TYPE: PRT
<213> ORGANISM: Artificial Sequence
<220> FEATURE:
<223> OTHER INFORMATION: Lama glama consensus sequence: VK2

<400> SEQUENCE: 185

Gly Val Pro Asp Arg Phe Thr Gly Ser Gly Ser Gly Thr Asp Phe Thr
1               5                   10                  15

Leu Lys Ile Ser Gly Val Lys Ala Glu Asp Ala Gly Val Tyr Tyr Cys
            20                  25                  30

<210> SEQ ID NO 186
<211> LENGTH: 32
<212> TYPE: PRT
<213> ORGANISM: Artificial Sequence
<220> FEATURE:
<223> OTHER INFORMATION: Lama glama consensus sequence: VK4

<400> SEQUENCE: 186

Gly Ile Pro Asp Arg Phe Ser Gly Ser Gly Ser Thr Thr Asp Phe Thr
1               5                   10                  15

Leu Thr Ile Ser Ser Val Gln Pro Glu Asp Ala Ala Val Tyr Tyr Cys
            20                  25                  30

<210> SEQ ID NO 187
<211> LENGTH: 35
<212> TYPE: DNA
<213> ORGANISM: Artificial Sequence
<220> FEATURE:
<223> OTHER INFORMATION: Synthetic primer: HuVl1A-BACK-ApaLI

<400> SEQUENCE: 187
gcctccacca gtgcacagtc tgtgytgack cagcc                              35

<210> SEQ ID NO 188
<211> LENGTH: 35

<212> TYPE: DNA
<213> ORGANISM: Artificial Sequence
<220> FEATURE:
<223> OTHER INFORMATION: Synthetic primer: HuVl1B-BACK-ApaLI

<400> SEQUENCE: 188
gcctccacca gtgcacagtc tgtgytgacg cagcc                             35

<210> SEQ ID NO 189
<211> LENGTH: 35
<212> TYPE: DNA
<213> ORGANISM: Artificial Sequence
<220> FEATURE:
<223> OTHER INFORMATION: Synthetic primer: HuVl1C-BACK-ApaLI

<400> SEQUENCE: 189
gcctccacca gtgcacagtc tgtcgtgacg cagcc                             35

<210> SEQ ID NO 190
<211> LENGTH: 35
<212> TYPE: DNA
<213> ORGANISM: Artificial Sequence
<220> FEATURE:
<223> OTHER INFORMATION: Synthetic primer: HuVl2-BACK-ApaLI

<400> SEQUENCE: 190
gcctccacca gtgcacagtc tgccctgact cagcc                             35

<210> SEQ ID NO 191
<211> LENGTH: 38
<212> TYPE: DNA
<213> ORGANISM: Artificial Sequence
<220> FEATURE:
<223> OTHER INFORMATION: Synthetic primer: HuVl3A-BACK-ApaLI

<400> SEQUENCE: 191
gcctccacca gtgcactttc ctatgagctg acwcagcc                          38

<210> SEQ ID NO 192
<211> LENGTH: 38
<212> TYPE: DNA
<213> ORGANISM: Artificial Sequence
<220> FEATURE:
<223> OTHER INFORMATION: Synthetic primer: HuVl3B-BACK-ApaLI

<400> SEQUENCE: 192
gcctccacca gtgcactttc ttctgagctg actcagga                          38

<210> SEQ ID NO 193
<211> LENGTH: 35
<212> TYPE: DNA
<213> ORGANISM: Artificial Sequence
<220> FEATURE:
<223> OTHER INFORMATION: Synthetic primer: HuVl4-BACK-ApaLI

<400> SEQUENCE: 193
gcctccacca gtgcacagcy tgtgctgact caatc                             35

<210> SEQ ID NO 194
<211> LENGTH: 35
<212> TYPE: DNA
<213> ORGANISM: Artificial Sequence
<220> FEATURE:
<223> OTHER INFORMATION: Synthetic primer: HuVl5-BACK-ApaLI

<400> SEQUENCE: 194
gcctccacca gtgcacaggc tgtgctgact cagcc        35

<210> SEQ ID NO 195
<211> LENGTH: 38
<212> TYPE: DNA
<213> ORGANISM: Artificial Sequence
<220> FEATURE:
<223> OTHER INFORMATION: Synthetic primer: HuVl6-BACK-ApaLI

<400> SEQUENCE: 195
gcctccacca gtgcacttaa ttttatgctg actcagcc     38

<210> SEQ ID NO 196
<211> LENGTH: 35
<212> TYPE: DNA
<213> ORGANISM: Artificial Sequence
<220> FEATURE:
<223> OTHER INFORMATION: Synthetic primer: HuVl7/8-BACK-ApaLI

<400> SEQUENCE: 196
gcctccacca gtgcacagrc tgtggtgacy cagga        35

<210> SEQ ID NO 197
<211> LENGTH: 35
<212> TYPE: DNA
<213> ORGANISM: Artificial Sequence
<220> FEATURE:
<223> OTHER INFORMATION: Synthetic primer: HuVl9-BACK-ApaLI

<400> SEQUENCE: 197
gcctccacca gtgcacwgcc tgtgctgact cagcc        35

<210> SEQ ID NO 198
<211> LENGTH: 35
<212> TYPE: DNA
<213> ORGANISM: Artificial Sequence
<220> FEATURE:
<223> OTHER INFORMATION: Synthetic primer: HuVl10-BACK-ApaLI

<400> SEQUENCE: 198
gcctccacca gtgcacaggc agggctgact cagcc        35

<210> SEQ ID NO 199
<211> LENGTH: 30
<212> TYPE: DNA
<213> ORGANISM: Artificial Sequence
<220> FEATURE:
<223> OTHER INFORMATION: Synthetic primer: caClambda1-FOR

<400> SEQUENCE: 199
ctaacactgg gagggggaca ccgtcttctc              30

<210> SEQ ID NO 200
<211> LENGTH: 30
<212> TYPE: DNA
<213> ORGANISM: Artificial Sequence
<220> FEATURE:
<223> OTHER INFORMATION: Synthetic primer: caClambda2-FOR
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 200

```
ctaacactgg gagggnctca cngtcttctc                                       30
```

<210> SEQ ID NO 201
<211> LENGTH: 41
<212> TYPE: DNA
<213> ORGANISM: Artificial Sequence
<220> FEATURE:
<223> OTHER INFORMATION: Synthetic primer: HuVk1B-BACK-ApaLI

<400> SEQUENCE: 201

```
gcctccacca gtgcacttga catccagwtg acccagtctc c                          41
```

<210> SEQ ID NO 202
<211> LENGTH: 41
<212> TYPE: DNA
<213> ORGANISM: Artificial Sequence
<220> FEATURE:
<223> OTHER INFORMATION: Synthetic primer: HuVk2-BACK-ApaLI

<400> SEQUENCE: 202

```
gcctccacca gtgcacttga tgttgtgatg actcagtctc c                          41
```

<210> SEQ ID NO 203
<211> LENGTH: 41
<212> TYPE: DNA
<213> ORGANISM: Artificial Sequence
<220> FEATURE:
<223> OTHER INFORMATION: Synthetic primer: HuVk3B-BACK-ApaLI

<400> SEQUENCE: 203

```
gcctccacca gtgcacttga aattgtgwtg acrcagtctc c                          41
```

<210> SEQ ID NO 204
<211> LENGTH: 41
<212> TYPE: DNA
<213> ORGANISM: Artificial Sequence
<220> FEATURE:
<223> OTHER INFORMATION: Synthetic primer: HuVk2/4-BACK-ApaLI

<400> SEQUENCE: 204

```
gcctccacca gtgcacttga yatygtgatg acccagwctc c                          41
```

<210> SEQ ID NO 205
<211> LENGTH: 41
<212> TYPE: DNA
<213> ORGANISM: Artificial Sequence
<220> FEATURE:
<223> OTHER INFORMATION: Synthetic primer: HuVk5-BACK-ApaLI

<400> SEQUENCE: 205

```
gcctccacca gtgcacttga aacgacactc acgcagtctc c                          41
```

<210> SEQ ID NO 206
<211> LENGTH: 41
<212> TYPE: DNA
<213> ORGANISM: Artificial Sequence
<220> FEATURE:
<223> OTHER INFORMATION: Synthetic primer: HuVk6-BACK-ApaLI

<400> SEQUENCE: 206

```
gcctccacca gtgcacttga aattgtgctg actcagtctc c                          41
```

<210> SEQ ID NO 207
<211> LENGTH: 41
<212> TYPE: DNA

```
<213> ORGANISM: Artificial Sequence
<220> FEATURE:
<223> OTHER INFORMATION: Synthetic primer: HuVk4B-BACK-ApaLI

<400> SEQUENCE: 207
gcctccacca gtgcacttga tattgtgatg acccagactc c                    41

<210> SEQ ID NO 208
<211> LENGTH: 48
<212> TYPE: DNA
<213> ORGANISM: Artificial Sequence
<220> FEATURE:
<223> OTHER INFORMATION: Synthetic primer: caCHkapFOR-AscI

<400> SEQUENCE: 208
gcctccaccg ggcgcgcctt attagcagtg tctccggtcg aagctcct            48

<210> SEQ ID NO 209
<211> LENGTH: 42
<212> TYPE: DNA
<213> ORGANISM: Artificial Sequence
<220> FEATURE:
<223> OTHER INFORMATION: Synthetic primer: caCHkap2FOR-AscI
<220> FEATURE:
<221> NAME/KEY: misc_feature
<222> LOCATION: (34)..(34)
<223> OTHER INFORMATION: n is a, c, g, or t

<400> SEQUENCE: 209
gcctccaccg ggcgcgcctt attarcartg yctncgrtcr aa                  42

<210> SEQ ID NO 210
<211> LENGTH: 23
<212> TYPE: DNA
<213> ORGANISM: Artificial Sequence
<220> FEATURE:
<223> OTHER INFORMATION: Synthetic primer: VH1a-BACK

<400> SEQUENCE: 210
caggtkcagc tggtgcagtc tgg                                       23

<210> SEQ ID NO 211
<211> LENGTH: 23
<212> TYPE: DNA
<213> ORGANISM: Artificial Sequence
<220> FEATURE:
<223> OTHER INFORMATION: Synthetic primer: VH5a-BACK

<400> SEQUENCE: 211
gargtgcagc tggtgcagtc tgg                                       23

<210> SEQ ID NO 212
<211> LENGTH: 23
<212> TYPE: DNA
<213> ORGANISM: Artificial Sequence
<220> FEATURE:
<223> OTHER INFORMATION: Synthetic primer: VH4a-BACK

<400> SEQUENCE: 212
cagstgcagc tgcaggagtc tgg                                       23

<210> SEQ ID NO 213
<211> LENGTH: 23
<212> TYPE: DNA
<213> ORGANISM: Artificial Sequence
<220> FEATURE:
<223> OTHER INFORMATION: Synthetic primer: VH4b-BACK
```

```
<400> SEQUENCE: 213
caggtgcagc tacagcagtc tgg                                              23

<210> SEQ ID NO 214
<211> LENGTH: 23
<212> TYPE: DNA
<213> ORGANISM: Artificial Sequence
<220> FEATURE:
<223> OTHER INFORMATION: Synthetic primer: VH2b-BACK

<400> SEQUENCE: 214
caggtcacct tgarggagtc tgg                                              23

<210> SEQ ID NO 215
<211> LENGTH: 53
<212> TYPE: DNA
<213> ORGANISM: Artificial Sequence
<220> FEATURE:
<223> OTHER INFORMATION: Synthetic primer: VH1a-BACK-SfiI

<400> SEQUENCE: 215
ctcgcaactg cggcccagcc ggccatggcc caggtkcagc tggtgcagtc tgg             53

<210> SEQ ID NO 216
<211> LENGTH: 53
<212> TYPE: DNA
<213> ORGANISM: Artificial Sequence
<220> FEATURE:
<223> OTHER INFORMATION: Synthetic primer: VH5a-BACK-SfiI

<400> SEQUENCE: 216
ctcgcaactg cggcccagcc ggccatggcc gargtgcagc tggtgcagtc tgg             53

<210> SEQ ID NO 217
<211> LENGTH: 53
<212> TYPE: DNA
<213> ORGANISM: Artificial Sequence
<220> FEATURE:
<223> OTHER INFORMATION: Synthetic primer: VH4a-BACK-SfiI

<400> SEQUENCE: 217
ctcgcaactg cggcccagcc ggccatggcc cagstgcagc tgcaggagtc tgg             53

<210> SEQ ID NO 218
<211> LENGTH: 53
<212> TYPE: DNA
<213> ORGANISM: Artificial Sequence
<220> FEATURE:
<223> OTHER INFORMATION: Synthetic primer: VH4b-BACK-SfiI

<400> SEQUENCE: 218
ctcgcaactg cggcccagcc ggccatggcc caggtgcagc tacagcagtc tgg             53

<210> SEQ ID NO 219
<211> LENGTH: 53
<212> TYPE: DNA
<213> ORGANISM: Artificial Sequence
<220> FEATURE:
<223> OTHER INFORMATION: Synthetic primer: VH2b-BACK-SfiI

<400> SEQUENCE: 219
ctcgcaactg cggcccagcc ggccatggcc caggtcacct tgarggagtc tgg             53
```

```
<210> SEQ ID NO 220
<211> LENGTH: 122
<212> TYPE: PRT
<213> ORGANISM: Artificial Sequence
<220> FEATURE:
<223> OTHER INFORMATION: Synthetic peptide: VH-1A1, EB8, 3D9

<400> SEQUENCE: 220

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Thr Ile Ser Trp Asn Gly Gly Ala Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Pro Tyr Tyr Ser Asp Tyr Val Gly Val Glu Tyr Asp Tyr Trp
            100                 105                 110

Gly Gln Gly Thr Gln Val Thr Val Ser Ser
        115                 120

<210> SEQ ID NO 221
<211> LENGTH: 6
<212> TYPE: PRT
<213> ORGANISM: Artificial Sequence
<220> FEATURE:
<223> OTHER INFORMATION: Synthetic peptide

<400> SEQUENCE: 221

Ser Tyr Thr Asn Asp Arg
1               5

<210> SEQ ID NO 222
<211> LENGTH: 127
<212> TYPE: PRT
<213> ORGANISM: Artificial Sequence
<220> FEATURE:
<223> OTHER INFORMATION: Synthetic peptide: VH-1C3, 1e3, 2a7

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ser Ala Ile Asn Thr Gly Gly Gly Arg Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Gly Thr Ser Ala Asp Gly Ser Ser Trp Tyr Val Pro Ala Asp
            100                 105                 110

Pro Tyr Asp Tyr Trp Gly Gln Gly Thr Gln Val Thr Val Ser Ser
        115                 120                 125
```

-continued

```
<210> SEQ ID NO 223
<211> LENGTH: 98
<212> TYPE: PRT
<213> ORGANISM: Artificial Sequence
<220> FEATURE:
<223> OTHER INFORMATION: Synthetic peptide: X07448, IGHV1-2

<400> SEQUENCE: 223

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Tyr Tyr Cys
                85                  90                  95

Ala Arg

<210> SEQ ID NO 224
<211> LENGTH: 117
<212> TYPE: PRT
<213> ORGANISM: Artificial Sequence
<220> FEATURE:
<223> OTHER INFORMATION: Synthetic peptide: VH-1B3, 1G2, 2D8

<400> SEQUENCE: 224

Glu Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
    50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Ser Gly Arg Tyr Glu Leu Asp Tyr Trp Gly Gln Gly Thr Gln
            100                 105                 110

Val Thr Val Ser Ser
        115

<210> SEQ ID NO 225
<211> LENGTH: 117
<212> TYPE: PRT
<213> ORGANISM: Artificial Sequence
<220> FEATURE:
<223> OTHER INFORMATION: Synthetic peptide: VH-1G1, 2B7

<400> SEQUENCE: 225

Glu Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
            20                  25                  30
```

```
Tyr Thr Asp Trp Val Arg Gln Ala Pro Gly Gln Gly Leu Glu Trp Met
        35                  40                  45
Gly Arg Ile Asp Pro Glu Asp Gly Asp Thr Lys Tyr Ala Gln Lys Phe
 50                  55                  60
Gln Gly Arg Val Thr Phe Thr Ala Asp Thr Ser Thr Ser Thr Ala Tyr
 65              70                  75                  80
Val Glu Leu Thr Ser Leu Arg Ser Glu Asp Thr Ala Val Tyr Tyr Cys
                85                  90                  95
Leu Arg Ser Gly Ala Tyr Glu Leu Asp Tyr Trp Gly Gln Gly Thr Gln
            100                 105                 110
Val Thr Val Ser Ser
        115

<210> SEQ ID NO 226
<211> LENGTH: 7
<212> TYPE: PRT
<213> ORGANISM: Artificial Sequence
<220> FEATURE:
<223> OTHER INFORMATION: Synthetic peptide

<400> SEQUENCE: 226

His Glu Asn Gln Ser Tyr Thr
 1               5

<210> SEQ ID NO 227
<211> LENGTH: 7
<212> TYPE: PRT
<213> ORGANISM: Artificial Sequence
<220> FEATURE:
<223> OTHER INFORMATION: Synthetic peptide

<400> SEQUENCE: 227

Ala Gly Tyr Ser Lys Thr Asn
 1               5
```

HUMANIZED ANTIBODIES

RELATED APPLICATIONS

This application claims the benefit of priority to U.S. Provisional Patent Application No. 61/292,028, filed Jan. 4, 2010. This application also claims the benefit of priority to British Patent Application No. GB1000064.4, filed Jan. 4, 2010. The contents of each of these related applications are hereby incorporated by reference in their entireties.

FIELD OF THE INVENTION

The invention relates to novel humanized antibodies derived from the conventional antibody repertoire of species in the family Camelidae.

BACKGROUND TO THE INVENTION

Monoclonal antibodies have many applications as research tools and, increasingly, as therapeutic or diagnostic agents. Currently more than 20 different monoclonal antibodies have received regulatory approval to treat a variety of different diseases, including cancer, inflammation, auto-immune disorders, infectious disease, asthma, cardiovascular diseases and transplant rejection and the number of monoclonal antibody drugs in the development pipeline is increasing year-on-year.

The utility of rodent (specifically murine) monoclonal antibodies in human therapy is limited because of problems associated with their non-human origin, in particular their immunogenicity in a human host. In order to minimize the human immune response against therapeutic antibody drugs, monoclonal antibody technology has evolved from full mouse antibodies to chimeric antibodies (mouse variable domains grafted on a human IgG backbone), to humanized antibodies (mouse CDRs grafted on a human IgG backbone), to "fully human" antibodies derived from synthetic and non-immune libraries or immunized transgenic mice expressing part of the human IgG repertoire.

A number of technology platforms have been developed which allow production of fully human or "humanized" monoclonal antibodies against target antigens of therapeutic interest. Each of these platforms has its own particular characteristics and potential shortcomings.

Humanisation of mouse monoclonal antibodies was initially achieved by combining mouse variable domains with human constant domains, creating so called chimeric antibodies having about 70% of human content. A further degree of humanization was subsequently achieved by grafting the complementarity-determining regions (CDRs) of mouse monoclonal antibodies onto human framework regions of the variable antibody domains of human antibodies. In addition, several amino acid residues present in those framework regions were identified as interacting with the CDRs or antigen and were back mutated in the humanized antibody to improve binding. (Almagro et al. Frontiers in Bioscience. 13: 1619-1633 (2008)). Monoclonal antibodies engineered using this approach have a relatively high degree of primary sequence homology to human VH and VL domain sequences after humanisation, but a drawback is the possibility of ending up with hypervariable loops not having human-like structure, because not all mouse-encoded CDRs use canonical folds, and canonical fold combinations, which are not found in human antibodies (Almagro et al., Mol. Immunol. 34:1199-1214 (1997); Almagro et al., Immunogen. 47:355-63 (1998)). A further drawback is the large number of mutations typically required to humanise such antibodies (the procedure for which is complex and time-consuming), with the consequent risk of losing affinity and potency as a result of the number of changes needed for humanisation and, the fact that VKappa domains are mainly used in the murine repertoire, whereas approximately half of all human antibodies possess VLambda domains. Alternative humanization procedures include resurfacing or veneering, in which only solvent exposed framework residue deviating from human are substituted, while buried or partly buried residues and residues involved in interdomain contacts are maintained (Padlan E. (1991) Mol. Immunol.). A more stringent method is SDR grafting, in which CDR grafting onto human FRs is applied, but on top of this residues within the CDRs are mutated to the human counterpart maintaining only the Specificity Determining Residues (SDRs) which are contacting the antigen (Kashmiri S. V. S. et al. (2005) Methods).

As a potential improvement on humanised mouse monoclonal antibodies, "fully human" monoclonal antibodies can be produced by two very different approaches. The first approach is selection from a fully synthetic human combinatorial antibody library (for example HuCAL®, MorphoSys) or from a non-immune antibody library (Vaughan T. J. et al (1996) Nat. Biotechnol., Cambridge Antibody Technology; de Haard H. J. et al (1999) J Biol. Chem., DYAX). The potential drawback of this approach is that the such libraries only approximates the functional diversity naturally present in the human germline, thus the diversity is somewhat limited. Also, antibodies generated using this approach do not contain in vivo selected CDRs as these occur in antibodies obtained via active immunisation, and typically affinity maturation has to be done in order to improve affinity for the target antigen. Affinity maturation is a lengthy process which may add considerable time to the antibody discovery process. Also, in the process of affinity maturation certain amino acid residues may be changed which may negatively affect the binding specificity or stability and production of the resulting antibody (Wu et al., J. Mol. Biol. 368: 652-65 (2007)).

Alternative "fully human" platforms are based on transgenic mice which have been engineered to replace the murine immunoglobulin encoding region with antibody-encoding sequences from the human germline (for example HuMab, Medarex). These systems have the advantage that antibodies are raised by active immunisation, with the target antigen, i.e. they have a high starting affinity for the antigen, and that no or only minimal antibody engineering of the original antibodies is required in order to make them more human-like. However, the transgenic mouse strains are by definition highly inbred and this has adverse consequences for the strength and diversity of the antibody response. Another drawback with this platform may be impaired B cell maturation due to human Fc/mouse Fc receptor interaction in some transgenic mouse systems.

A further platform is based on immunisation of non-human primates, specifically cynomologous monkeys. Due to the high degree of amino acid sequence identity between monkey and human immunoglobulins it is postulated that antibodies raised in monkeys will require little or no additional "humanisation" in the variable domains in order to render them useful as human therapeutics (see WO 93/02108). However, quite often non-human canonical fold combinations for CDR1 and CDR2 in the VH are observed in these primatized antibodies.

SUMMARY OF THE INVENTION

The present invention provides a "humanised" monoclonal antibody (antigen binding polypeptide) platform which avoids some or all of the shortcomings they have observed with prior art humanised or fully human antibody platforms and which enables the production of antibodies of high specificity and affinity against a broad range of target antigens of therapeutic importance whilst minimising immunogenicity in a human host.

It has been observed that both the VH and the VL domains of conventional antibodies from the family Camelidae exhibit a high degree of amino acid sequence identity with the VH and VL domains of human antibodies over the framework regions. In fact, the degree of sequence identity between camelid conventional VH domains and human VH domains, and between camelid conventional VL domains and human VL domains can approach that observed between humans and other primate species, e.g. cynomologous monkeys, and is much higher than might be expected given the phylogenetic distance between humans and camelids. This finding is surprising given that the variable domains of heavy-chain camelid antibodies (VHH) do not show this high degree of sequence homology with human variable domains.

In addition, it has been observed that the hypervariable loops (H1, H2, L1, L2 and L3) of camelid VH and VL domains often exhibit a high degree of structural homology with the hypervariable loops of human VH and VL domains, which is again unexpected given the evolutionary distance between humans and camelids. The high degree of structural homology between camelid conventional antibodies (or rather the hypervariable loops of such antibodies) and human antibodies is also surprising since the hypervariable loops of heavy-chain camelid antibodies have been reported to vary substantially in conformation and length from the corresponding loops in human and mouse VH (see review De Genst et al., Develop Comp. Immunol. 30:187-98 (2006)).

The high degree of primary amino acid sequence homology with the framework regions of human antibodies, coupled with the high degree of structural homology of the antigen binding sites comprising the hypervariable loops with the binding sites of human antibodies, plus the fact that Camelidae conventional antibodies can be raised by active immunisation of an outbred animal population, which are phylogenetically quite distant from humans, has led to the identification of conventional antibodies from the family Camelidae as an attractive starting point for engineering monoclonal antibodies having potential utility as human therapeutics.

Furthermore, a large number of novel conventional camelid antibodies have been sequenced and the amino acid sequences of the camelid VH and VL domains analysed in comparison to human VH and VL sequences. From these analyses, several key amino acid positions have identified in the camelid VH or VL sequences where the amino acid residues differ significantly between camelid and human VH and VL. This knowledge has facilitated a novel humanization strategy in which one or more specified positions in a camelid VH and/or VL domain are substituted with an amino acid from the corresponding position in a human VH or VL sequence.

Accordingly, in a first aspect, the invention provides antibody comprising a camelid VH domain and a camelid VL domain of either the lambda light chain class (Vλ) or the kappa light chain class (Vκ), characterised in that at least one amino acid substitution is present in said VH domain and/or said VL domain, said amino acid substitution(s) being selected from the following:

(a) amino acid substitution(s) in said camelid VH domain, wherein an amino acid at one or more positions selected from the group consisting of H1, H5, H7, H11, H12, H13, H14, H29, H30, H37, H40, H48, H67, H68, H69, H71, H74, H77, H78, H80, H81, H82b, H83, H84, H85, H86, H89, H93, H94 and H108 of the camelid VH domain, according to Kabat, is replaced with an amino acid found at the corresponding position in a human VH domain sequence; and (b) amino acid substitutions in said camelid VL domain, wherein for a camelid VL domain of the lambda light chain class (Vλ) an amino acid at one or more positions selected from the group consisting of L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 and L103 of the camelid Vλ domain, according to Kabat, is replaced with an amino acid found at the corresponding position in a human Vλ domain sequence; and for a camelid VL domain of the kappa light chain class (Vκ) an amino acid at one or more positions selected from the group consisting of K1, K3, K4, K7, K9, K11, K12, K13, K14, K15, K18, K19, K36, K42, K43, K45, K46, K58, K63, K70, K77, K78, K79, K80, K83, K100, K103, K104 and K106 of the camelid Vκ domain, according to Kabat, is replaced with an amino acid found at the corresponding position in a human Vκ domain sequence.

In a second aspect the invention provides an antibody comprising a camelid VH domain, wherein the amino acid at one or more of positions H1, H5, H7, H11, H12, H13, H14, H29, H30, H37, H40, H48, H67, H68, H69, H71, H74, H77, H78, H80, H81, H82b, H83, H84, H85, H86, H89, H93, H94 or H108 of said camelid VH domain, numbering according to Kabat, is replaced with an amino acid found at the corresponding position in a human VH domain sequence, and/or comprising a camelid VL domain belonging to the lambda light chain class (Vλ), wherein the amino acid at one or more of positions L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 or L103 of said camelid Vλ domain, numbering according to Kabat, is replaced with an amino acid found at the corresponding position in a human Vλ domain sequence, and/or comprising a camelid VL domain belonging to the kappa light chain class (Vκ), wherein the amino acid at one or more of positions K1, K3, K4, K7, K9, K11, K12, K13, K14, K15, K18, K19, K36, K42, K43, K45, K46, K58, K63, K70, K77, K78, K79, K80, K83, K100, K103, K104 or K106 of said camelid Vκ domain, numbering according to Kabat, is replaced with an amino acid found at the corresponding position in a human Vκ domain sequence.

In another embodiment, an amino acid at one or more positions in the framework residues present in camelid germline domains (i.e. observed in all or most of analyzed somatically mutated domains) deviating from the corresponding residues occurring in the best matching human germline family member or less preferred to the residues occurring in the corresponding consensus human germline family is/are replaced with an amino acid found at the corresponding position(s) in the human germline and/or consensus sequence. Less preferred are mutations of residues introduced by somatic mutations deviating from human germline domains (i.e. occurring at lower frequencies in somatically mutated Camelid domains), when these residues in Camelid germline domains are identical to the residues present in the best matching human germlines when aligned.

In various embodiments, mutations in VH domains converting the Camelid germline encoded residues into the residues present in the best matching human germline family member or residues of the consensus human germline family therefore are as follows:

In one embodiment the amino acid at H1 is replaced. In non-limiting embodiments the amino acid at H1 is replaced with Q or E.

In one embodiment the amino acid at H7 is replaced. In non-limiting embodiments the amino acid at H7 is replaced with S.

In one embodiment the amino acid at H11 is replaced. In a non-limiting embodiment the amino acid at H11 is replaced with V.

In one embodiment the amino acid at H12 is replaced with K.

In one embodiment the amino acid at H13 is replaced with K, or less preferred with R or Q.

In one embodiment the amino acid at H14 is replaced with P.

In one embodiment the amino acid at H29 is replaced with V, or less preferred with F.

In one embodiment the amino acid at H30 is replaced with S.

In one embodiment the amino acid at H37 is replaced with V or I, or less preferred with F.

In one embodiment the amino acid at H40 is replaced with A.

In one embodiment the amino acid at H48 is replaced with I.

In one embodiment the amino acid at H67 is replaced with V.

In one embodiment the amino acid at H68 is replaced with T.

In one embodiment the amino acid at H69 is replaced with M, or less preferred with I or S.

In one embodiment the amino acid at H71 is replaced with R or V, or less preferred with A, E or T.

In one embodiment the amino acid at H74 is replaced. In non-limiting embodiments the amino acid at H74 may be replaced with S or less preferred with A.

In one embodiment the amino acid at H77 is replaced with S or less preferred with T.

In one embodiment the amino acid at H78 is replaced with V or L, or less preferred by A.

In one embodiment the amino acid at H80 is replaced with M.

In one embodiment the amino acid at H81 is replaced with K.

In one embodiment the amino acid at H83 is replaced with R or less preferred with K.

In one embodiment the amino acid at H84 is replaced with A or less preferred with T.

In one embodiment the amino acid at H85 is replaced with A.

In one embodiment the amino acid at H86 is replaced with D.

In one embodiment the amino acid at H94 is replaced with R, or less preferred with K or T.

In one embodiment the amino acid at H108 is replaced with M or less preferred with L or T.

Listed below are other mutations in the VH domains, converting somatically mutated residues deviating from human germline domains, whereas these residues in Camelid germline domains are identical to the residues present in the best matching human germlines:

In one embodiment the amino acid at H5 is replaced with L or less preferred with V.

In one embodiment the amino acid at H82b is replaced with S.

In one embodiment the amino acid at H89 is replaced with V or less preferred with L.

In one embodiment the amino acid at H93 is replaced with A or less preferred with T.

Most preferred mutations in light chains of the Vλ class, converting the Camelid germline encoded residues into the best matching human germline family member or less preferred to the consensus human germline family are:

In one embodiment the amino acid at L1 is replaced with S.

In one embodiment the amino acid at L2 is replaced with Y.

In one embodiment the amino acid at L3 is replaced with E.

In one embodiment the amino acid at L7 is replaced with D or less preferred with P or L.

In one embodiment the amino acid at L8 is replaced with R or P or less preferred with A, S, L or H.

In one embodiment the amino acid at L9 is replaced with P or less preferred with A.

In one embodiment the amino acid at L11 is replaced with A, V, S or F or less preferred with L or H.

In one embodiment the amino acid at L14 is replaced with T, S or A.

In one embodiment the amino acid at L15 is replaced with P or less preferred with L or T.

In one embodiment the amino acid at L17 is replaced with Q or E or less preferred with A.

In one embodiment the amino acid at L18 is replaced with R or S or less preferred with K.

In one embodiment the amino acid at L19 is replaced with V or P or A.

In one embodiment the amino acid at L20 is replaced with R or less preferred with S.

In one embodiment the amino acid at L39 is replaced with H or less preferred with P.

In one embodiment the amino acid at L40 is replaced with P.

In one embodiment the amino acid at L42 is replaced with K or less preferred with T.

In one embodiment the amino acid at L47 is replaced with M.

In one embodiment the amino acid at L58 is replaced with V.

In one embodiment the amino acid at L59 is replaced with P or less preferred with S.

In one embodiment the amino acid at L60 is replaced with D or less preferred with E.

In one embodiment the amino acid at L66 is replaced with S or less preferred with N, T.

In one embodiment the amino acid at L67 is replaced with S or L or less preferred with P.

In one embodiment the amino acid at L69 is replaced with T or N.

In one embodiment the amino acid at L70 is replaced with T or less preferred with M, I or A.

In one embodiment the amino acid at L71 is replaced with V or less preferred with A or T.

In one embodiment the amino acid at L72 is replaced with S or I or less preferred with T or L.

In one embodiment the amino acid at L74 is replaced with A or less preferred with G.

In one embodiment the amino acid at L76 is replaced with S or T.

In one embodiment the amino acid at L78 is replaced with V or less preferred with A, T or I.

In one embodiment the amino acid at L80 is replaced with S or A or less preferred with T or P.

In one embodiment the amino acid at L84 is replaced with A or S.

In one embodiment the amino acid at L103 is replaced with K.

Listed below are other mutations in light chains of the Vλ class, converting somatically mutated residues deviating from human germline domains, whereas these residues in Camelid germline domains are identical to the residues present in the best matching human germlines:

In one embodiment the amino acid at L38 is replaced with Q.

In one embodiment the amino acid at L44 is replaced with P.

In one embodiment the amino acid at L46 is replaced with L.

In one embodiment the amino acid at L49 is replaced with Y.

Listed below are the most preferred mutations in light chains of the Vκ class, converting the Camelid germline encoded residues into the best matching human germline family member or less preferred to the consensus human germline family are:

In one embodiment the amino acid at K1 is replaced with A or less preferred with D or N.

In one embodiment the amino acid at K4 is replaced with L or less preferred with M.

In one embodiment the amino acid at K7 is replaced with S or less preferred with T.

In one embodiment the amino acid at K9 is replaced with L or D.

In one embodiment the amino acid at K11 is replaced with V or L.

In one embodiment the amino acid at K12 is replaced with K, P or A or less preferred with S.

In one embodiment the amino acid at K13 is replaced with K or V.

In one embodiment the amino acid at K14 is replaced with T.

In one embodiment the amino acid at K15 is replaced with V or L or less preferred with T.

In one embodiment the amino acid at K18 is replaced with P or R or less preferred with Q.

In one embodiment the amino acid at K19 is replaced with A.

In one embodiment the amino acid at K36 is replaced with Y or less preferred with F or L.

In one embodiment the amino acid at K39 is replaced with K.

In one embodiment the amino acid at K42 is replaced with K.

In one embodiment the amino acid at K43 is replaced with A or P or less preferred with V.

In one embodiment the amino acid at K45 is replaced with K.

In one embodiment the amino acid at K46 is replaced with L or less preferred with R.

In one embodiment the amino acid at K58 is replaced with V.

In one embodiment the amino acid at K63 is replaced with S.

In one embodiment the amino acid at K68 is replaced with G.

In one embodiment the amino acid at K70 is replaced with D or less preferred with E.

In one embodiment the amino acid at K77 is replaced with S or less preferred with C.

In one embodiment the amino acid at K78 is replaced with L.

In one embodiment the amino acid at K79 is replaced with Q or E.

In one embodiment the amino acid at K80 is replaced with P or A or less preferred with S.

In one embodiment the amino acid at K83 is replaced with F or V or less preferred with I.

In one embodiment the amino acid at K100 is replaced with Q.

In one embodiment the amino acid at K103 is replaced with K.

In one embodiment the amino acid at K104 is replaced with V.

In one embodiment the amino acid at K106 is replaced with I.

Listed below are the less preferred mutations in light chains of the Vκ class, converting somatically mutated residues deviating from human germline domains, whereas these residues in Camelid germline domains are identical to the residues present in the best matching human germlines:

In one embodiment the amino acid at K3 is replaced with Q or less preferred with R.

In another aspect, the invention provides an antibody comprising a camelid VH domain and a camelid VL domain, wherein an amino acid at one or more positions selected from the group consisting of H1, H5, H7, H11, H12, H13, H14, H29, H30, H37, H40, H48, H67, H68, H69, H71, H74, H77, H78, H80, H81, H82b, H83, H84, H85, H86, H89, H93, H94 and H108 of the camelid VH domain, according to Kabat, is replaced with an amino acid found at the corresponding position in a human VH domain sequence.

In one embodiment, the camelid VH domain has homology to a human VH3 domain, wherein the one or more positions are selected from the group consisting of H1, H13, H14, H29, H30, H37, H40, H74, H77, H78, H82b, H83, H84, H86, H89, H93 and H94 of the camelid VH domain, according to Kabat, and wherein the amino acid is replaced with an amino acid found at the corresponding position in the human VH3 domain sequence. In certain embodiments, the antibody comprises one or more amino acid replacements selected from the group consisting of: (a) amino acid at H74 replaced with S or A; (b) amino acid at H83 replaced with R or K; (c) amino acid at H84 replaced with A or T; and (d) amino acid at H94 replaced with R. In other embodiments, the antibody comprises one or more amino acid replacements selected from the group consisting of: (a) amino acid at H1 replaced with Q or E; (b) amino acid at H13 replaced with Q, K or R; (c) amino acid at H14 replaced with P, (d) amino acid at H29 replaced with F or V; (e) amino acid at H30 replaced with S, D or G; (f) amino acid at H37 replaced with V, F or I; (g) amino acid at H40 replaced with A; (h) amino acid at H77 replaced with T or S; (i) amino acid at H78 replaced with L or A; (j) amino acid at H82b replaced with S; (k) amino acid at H86 replaced with D; (l) amino acid at H89 replaced with V or L; and (m) amino acid at H93 replaced with A or T.

In another embodiment, the camelid VH domain has homology to a human VH1 domain, wherein the one or more positions are selected from the group consisting of H1, H7, H11, H12, H13, H69, H71, H78, H80 and H86 of the camelid VH domain, according to Kabat, and wherein the amino acid is replaced with an amino acid found at the corresponding position in the human VH1 domain sequence. In certain embodiments, one or more amino acid replacements selected from the group consisting of: (a) amino acid at H1 replaced with Q or E; (b) amino acid at H7 replaced with S; (c) amino acid at H11 replaced, with V; (d) amino acid at H12 replaced with K; (e) amino acid at H13 replaced with K; (f) amino acid at H69 replaced with I, M or S; (g) amino acid at H71 replaced with R, A, E or T; (h) amino acid at H78 replaced with V or A; (i) amino acid at H80 replaced with M; and (j) amino acid at H86 replaced with D.

In another embodiment, wherein the camelid VH domain has homology to a human VH4 domain, wherein the one or more positions are selected from the group consisting of H1, H16, H23, H30, H48, H49, H67, H68, H71, H81, H84, H85, and H86 of the camelid VH domain, according to Kabat, and wherein the amino acid is replaced with an amino acid found at the corresponding position in the human VH4 domain sequence. In certain embodiments, the antibody comprises one or more amino acid replacements selected from the group consisting of: (a) amino acid at H1 replaced with Q or E; (b) amino acid at H16 replaced with E; (c) amino acid at H23 replaced with A or T; (d) amino acid at H30 replaced with S; (e) amino acid at H48 replaced with I; (f) amino acid at H67 replaced with V; (g) amino acid at H68 replaced with T; (h) amino acid at H71 replaced with V; (i) amino acid at H81 replaced with K; (j) amino acid at H84 replaced with A; (k) amino acid at H85 replaced with A; (l) amino acid at H86 replaced with D; and (m) amino acid at H108 replaced with L.

In another aspect, the invention provides an antibody comprising a camelid VH domain and a camelid VL domain, wherein the camelid VL domain is a camelid Vλ domain with homology to a human Vλ domain, and wherein an amino acid at one or more positions selected from the group consisting of L1, L2, L3, L5, L7, L8, L9, L11, L14, L15, L18, L17, L19, L20, L38, L39, L40, L42, L44, L46, L47, L49, L58, L59, L60, L66, L67, L69, L70, L71, L72, L74, L76, L78, L80, L81, L84, L103, L104 and L108 of the camelid Vλ domain, according to Kabat, is replaced with an amino acid found at the corresponding position in the human Vλ domain sequence.

In one embodiment, the human Vλ domain is a human Vλ1 domain, wherein the one or more positions are selected from the group consisting of L11, L14, L18, L19, L38, L69, L74, L76 and L80 of the camelid Vλ domain, according to Kabat, and wherein the amino acid is replaced with an amino acid found at the corresponding position in the human Vλ1 domain sequence. In certain embodiment, the antibody comprises one or more amino acid replacements selected from the group consisting of: (a) amino acid at L11 replaced with A or V; (b) amino acid at L14 replaced with A or T; (c) amino acid at L18 replaced with R or K; (d) amino acid at L19 replaced with V; (e) amino acid at L38 replaced with Q; (f) amino acid at L69 replaced with T; (g) amino acid at L74 replaced with A or G; (h) amino acid at L76 replaced with S or T; and (i) amino acid at L80 replaced with S, T or A.

In another embodiment, the human Vλ domain is a human Vλ2 domain, wherein the one or more positions are selected from the group consisting of L3, L8, L14, L15, L17, L18, L39, L42, L47, L58, L59 and L80 of the camelid Vλ domain, according to Kabat, and wherein the amino acid is replaced with an amino acid found at the corresponding position in the human Vλ2 domain sequence. In certain embodiments, the antibody comprises one or more amino acid replacements selected from the group consisting of: (a) amino acid at L3 replaced with A; (b) amino acid at L8 replaced with A, P or R; (c) amino acid at L14 replaced with S; (d) amino acid at L15 replaced with P; (e) amino acid at L17 replaced with Q; (f) amino acid at L18 replaced with S; (g) amino acid at L39 replaced with H or P; (h) amino acid at L42 replaced with K or T; (i) amino acid at L47 replaced with M; (j) amino acid at L58 replaced with V; (k) amino acid at L59 replaced with P or S; and (l) amino acid at L80 replaced with A.

In another embodiment, the human Vλ domain is a human Vλ3 domain, wherein the one or more positions are selected from the group consisting of L1, L2, L3, L5, L7, L8, L9, L11, L14, L15, L19, L20, L44, L46, L49, L60, L66, L67, L69, L70, L71, L72, L76, L78 and L84 of the camelid Vλ domain, according to Kabat, and wherein the amino acid is replaced with an amino acid found at the corresponding position in the human Vλ3 domain sequence. In certain embodiments, the antibody comprises one or more o amino acid replacements selected from the group consisting of: (a) amino acid at L1 replaced with S; (b) amino acid at L2 replaced with Y; (c) amino acid at L3 replaced with E; (d) amino acid at L5 replaced with M; (e) amino acid at L7 replaced with D, L or P; (f) amino acid at L8 replaced with P, S, L or H; (g) amino acid at L9 replaced with S or A; (h) amino acid at L11 replaced with V; (i) amino acid at L14 replaced with A or S; (j) amino acid at L15 replaced with P, L or T; (k) amino acid at L19 replaced with A or V; (l) amino acid at L20 replaced with R or S; (m) amino acid at L44 replaced with P; (n) amino acid at L46 replaced with L; (o) amino acid at L49 replaced with Y; (p) amino acid at L60 replaced with E or D; (q) amino acid at L66 replaced with S, N or T; (r) amino acid at L67 replaced with S or P; (s) amino acid at L69 replaced with T or N; (t) amino acid at L70 replaced with T, M or I; (u) amino acid at L71 replaced with A, V or T; (v) amino acid at L72 replaced with T or S; (w) amino acid at L76 replaced with S or T; (x) amino acid at L78 replaced with V, A, T or I; and (y) amino acid at L84 replaced with A.

In another embodiment, the human Vλ domain is a human Vλ5 domain, wherein the one or more positions are selected from the group consisting of L2, L11, L17, L19, L40, L70, L72 and L80 of the camelid Vλ domain, according to Kabat, and wherein the amino acid is replaced with an amino acid found at the corresponding position in the human Vλ5 domain sequence. In certain embodiments, the antibody comprises one or more amino acid replacements selected from the group consisting of: (a) amino acid at L2 with P; (b) amino acid at L11 replaced with L, S or H; (c) amino acid at L17 replaced with A or E; (d) amino acid at L19 replaced with A or V; (e) amino acid at L40 replaced with P; (f) amino acid at L70 replaced with A or T; (g) amino acid at L72 replaced with I or L; and (h) amino acid at L80 replaced with S or P.

In another embodiment, the human Vλ domain is a human Vλ8 domain, wherein the one or more positions are selected from the group consisting of L2, L11, L60, L67, L80, L81 and L84 of the camelid Vλ domain, according to Kabat, and wherein the amino acid is replaced with an amino acid found at the corresponding position in a human Vλ8 domain sequence. In certain embodiments, the antibody comprises one or more amino acid replacements selected from the group consisting of: (a) amino acid at L2 replaced with T; (b) amino acid at L11 replaced with F; (c) amino acid at L60 replaced with D; (d) amino acid at L67 replaced with L; (e) amino acid at L80 replaced with A; (f) amino acid at L81 replaced with D; and (g) amino acid at L84 replaced with S.

In another embodiment, wherein the amino acid at L103 is replaced with K.

In another aspect the invention provides antibody comprising a camelid VH domain and a camelid VL domain, wherein the camelid VL domain is a camelid Vκ domain with homology to a human Vκ domain, and wherein an amino acid at one or more positions selected from the group consisting of K1, K2, K3, K4, K7, K9, K11, K12, K13, K14, K15, K18, K19, K36, K39, K42, K43, K45, K46, K58, K63, K68, K70, K77, K78, K79, K80, K83, K100, K103, K104 and K106 of the camelid Vκ domain, according to Kabat, is replaced with an amino acid found at the corresponding position in the human Vκ domain sequence.

In one embodiment, the human Vκ domain is a human Vk1 domain, wherein the one or more of positions are selected from the group consisting of K1, K2, K4, K11, K12, K13, K15, K42, K43, K70, K77, K79, K80 and K83 of the camelid Vκ domain, according to Kabat, and wherein the amino acid is replaced with an amino acid found at the corresponding position in the human Vk1 domain sequence. In certain embodiment, the antibody comprises one or more amino acid replacements selected from the group consisting of: (a) amino acid at K2 replaced with D, A or N; (b) amino acid at K4 replaced with M or L; (c) amino acid at K11 replaced with V; (d) amino acid at K12 replaced with K; (e) amino acid at K13 replaced with K; (f) amino acid at K15 replaced with V or T; (g) amino acid at K42 replaced with K; (h) amino acid at K43 replaced with A or V; (i) amino acid at K70 replaced with D or E; (j) amino acid at K77 replaced with S or C; (k) amino acid at K79 replaced with Q; (l) amino acid at K80 replaced with P or S; and (m) amino acid at K83 replaced with F, I or V.

In another embodiment, the human Vκ domain is a human Vk2 domain, wherein the one or more positions are selected from the group consisting of K7, K9, K12, K14, K18, K36, K46, K63, K77, K79 and K83 of the camelid Vκ domain, according to Kabat, and wherein the amino acid is replaced with an amino acid found at the corresponding position in the human Vk2 domain sequence. In certain embodiments, the antibody comprises one or more amino acid replacements selected from the group consisting of: (a) amino acid at K7 replaced with T or S; (b) amino acid at K9 replaced with L; (c) amino acid at K12 replaced with P or S; (d) amino acid at K14 replaced with T; (e) amino acid at K18 replaced with P or Q; (f) amino acid at K36 replaced with Y, F or L; (g) amino acid at K46 replaced with L or R; (h) amino acid at K63 replaced with S; (i) amino acid at K77 replaced with R; (j) amino acid at K79 replaced with E; and (k) amino acid at K83 replaced with V or F.

In another embodiment, the human Vκ domain is a human Vk4 domain, wherein the one or more positions are selected from the group consisting of K9, K11, K12, K13, K15, K18, K19, K39, K43, K45, K58, K68, K78, K80 and K83 of the camelid Vκ domain, according to Kabat, and wherein the amino acid is replaced with an amino acid found at the corresponding position in the human Vk4 domain sequence. In certain embodiments, the antibody comprises one or more amino acid replacements selected from the group consisting of: (a) amino acid at K9 replaced with D; (b) amino acid at K11 replaced with L; (c) amino acid at K12 replaced with A; (d) amino acid at K13 replaced with V; (e) amino acid at K15 replaced with L; (f) amino acid at K18 replaced with R; (g) amino acid at K19 replaced with A; (h) amino acid at K39 replaced with K; (i) amino acid at K43 replaced with P; (j) amino acid at K45 replaced with K; (k) amino acid at K58 replaced with V; (l) amino acid at K68 replaced with G; (j) amino acid at K78 replaced with L; (k) amino acid at K80 replaced with A; and (l) amino acid at K83 replaced with V.

In another embodiment, the antibody further comprises amino acid replacements selected from the group consisting of (a) amino acid at K103 replaced with K; (b) amino acid at K104 replaced with V; and (c) amino acid At K106 replaced with I.

In another aspect the invention provides a polynucleotide molecule encoding an antibody of the invention.

In a further aspect the invention provides an expression vector comprising the polynucleotide molecule operably linked to regulatory sequences that permit expression of the antibody in a host cell or transcription and translation in a cell-free expression system, and also a host cell or cell free expression system containing the expression vector.

In a still further aspect the invention provides a method of producing a recombinant antibody comprising culturing the host cell or cell free expression system under conditions which permit expression of the antibody and recovering the expressed antibody.

BRIEF DESCRIPTION OF THE DRAWINGS

FIG. 2 (SEQ ID NOS: 1-23)—illustrates the amino acid sequences of "humanized" variants of two Fabs immunoreactive with IL-1Beta, coded 1E2 and 1F2. Based on the alignment against the closest human germlines, mutations in the VH and Vλ framework regions of 1E2 and 1F2 were proposed. Besides the fully humanized (hum) and the wild type (wt) V regions, also a "safe variant" with only three wild type residues remaining was proposed (safe).

Figure 6A:
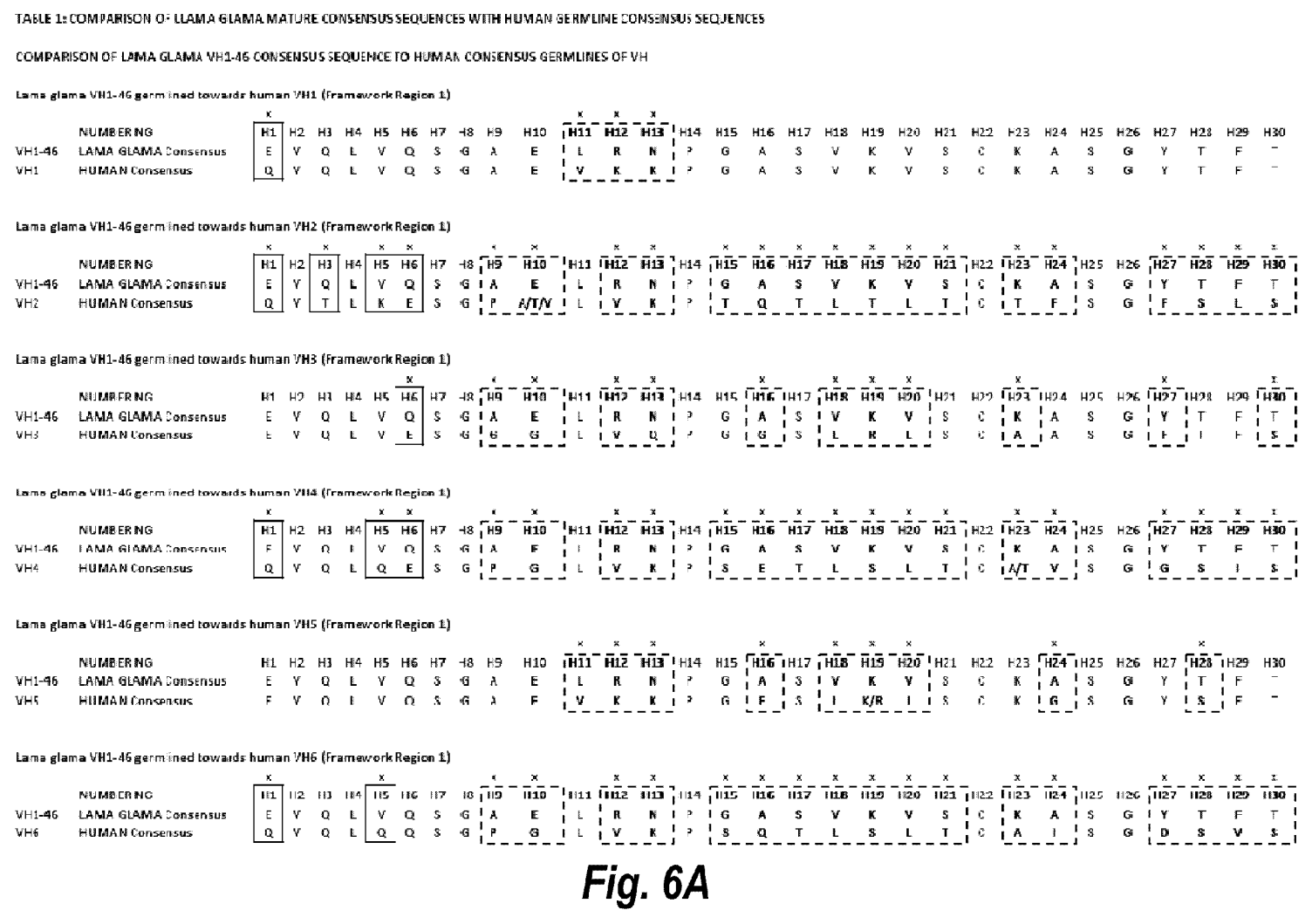
Figure 6B:
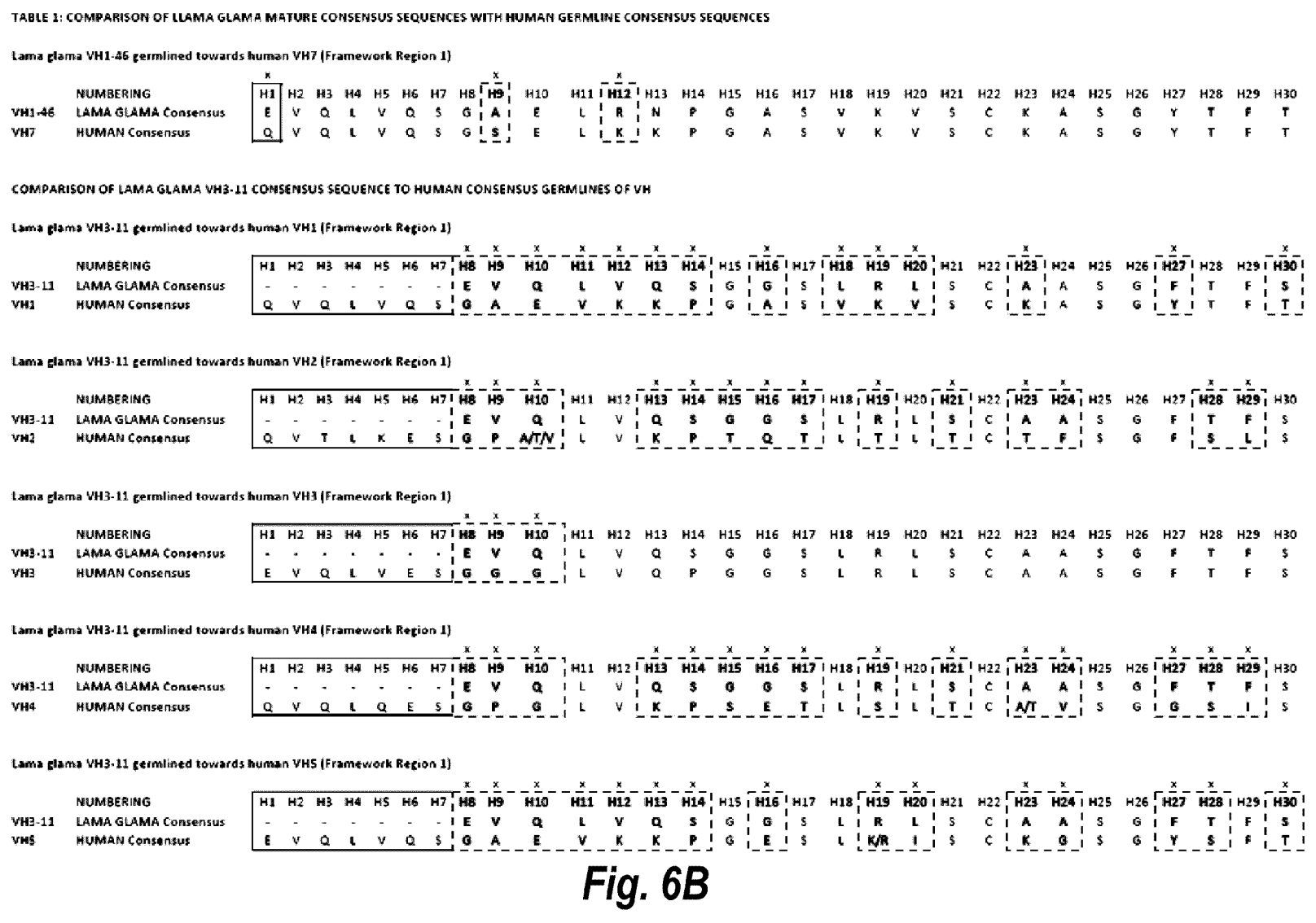
Figure 6C:
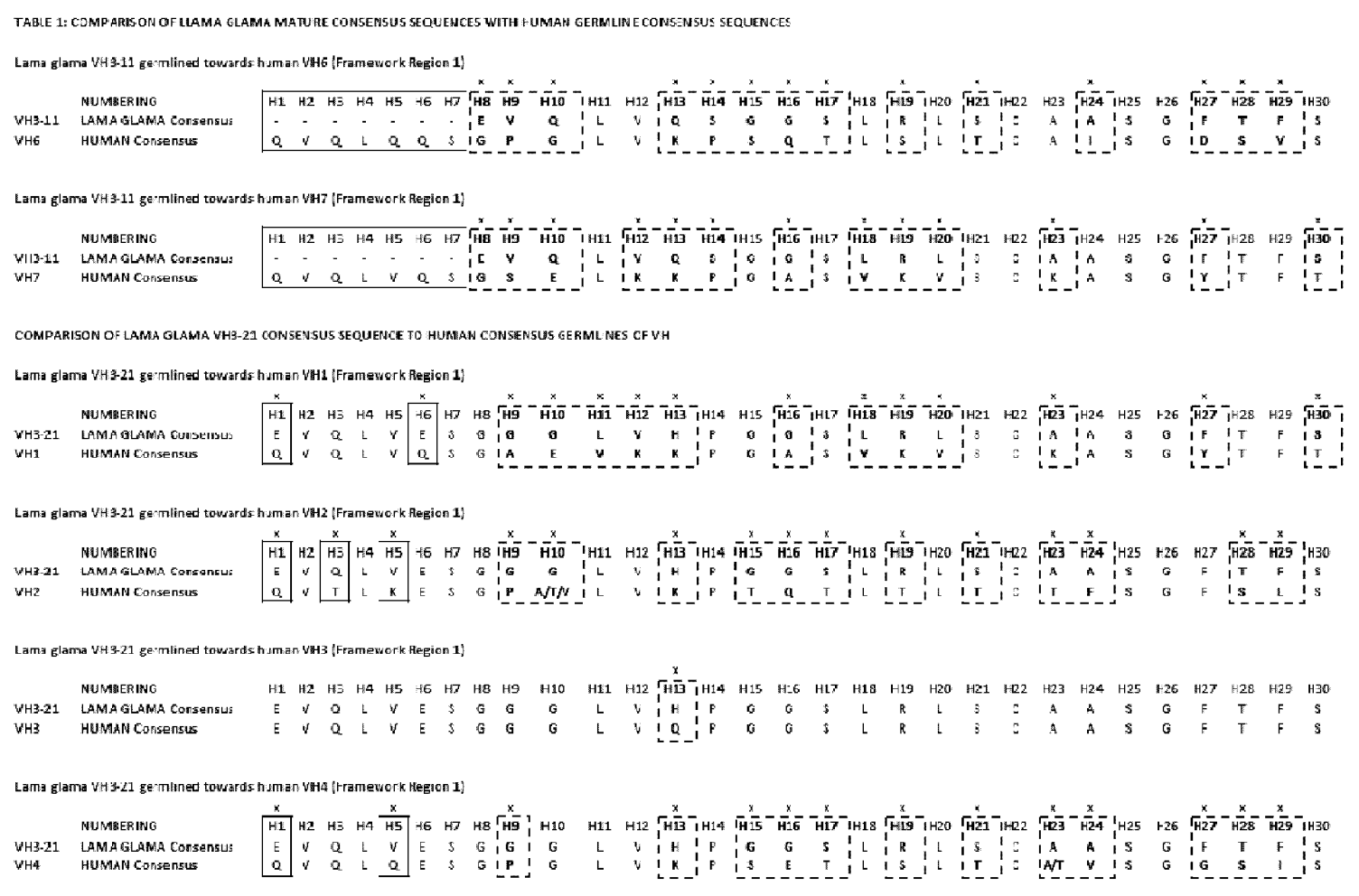
Figure 6D:
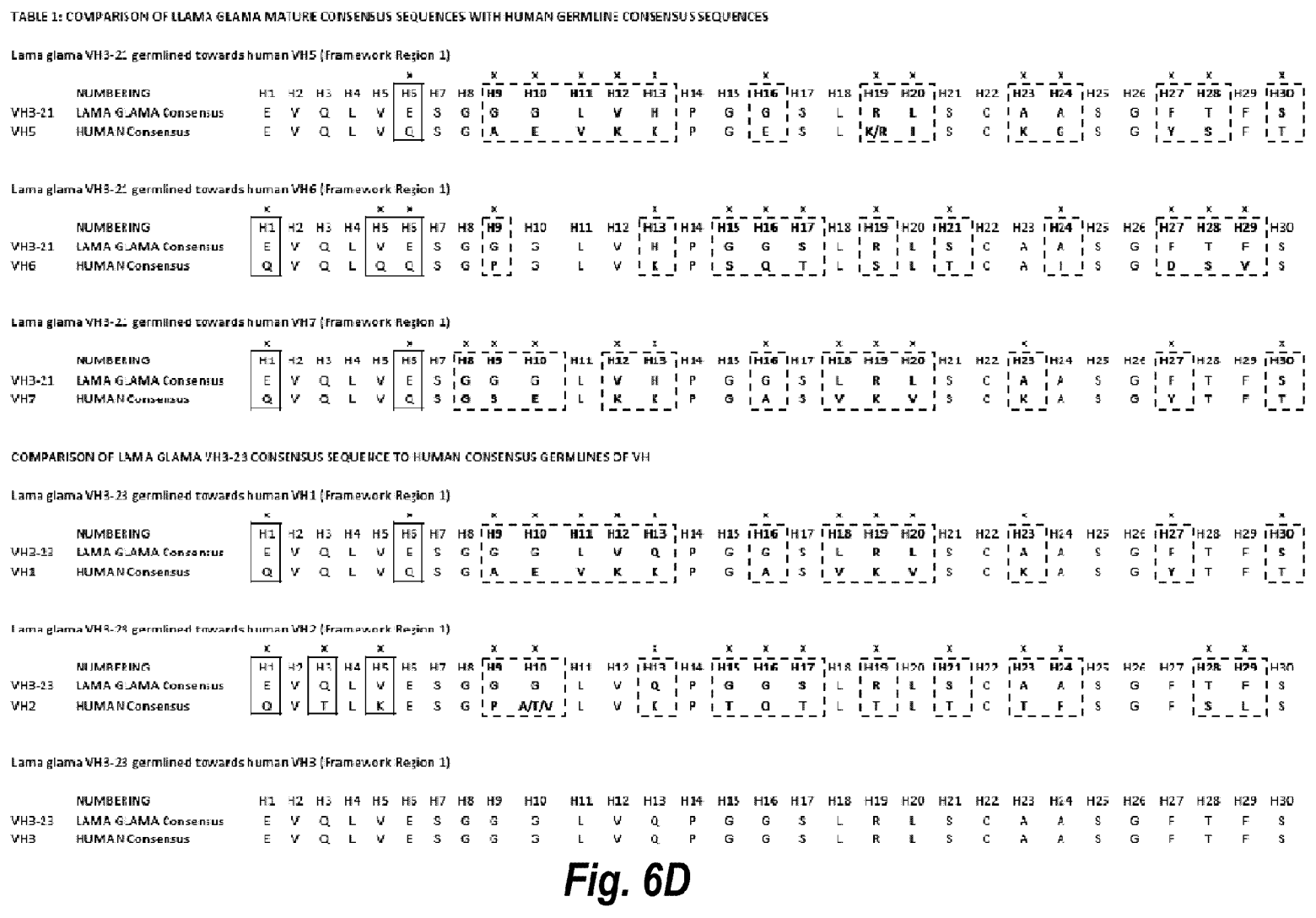
Figure 6E:
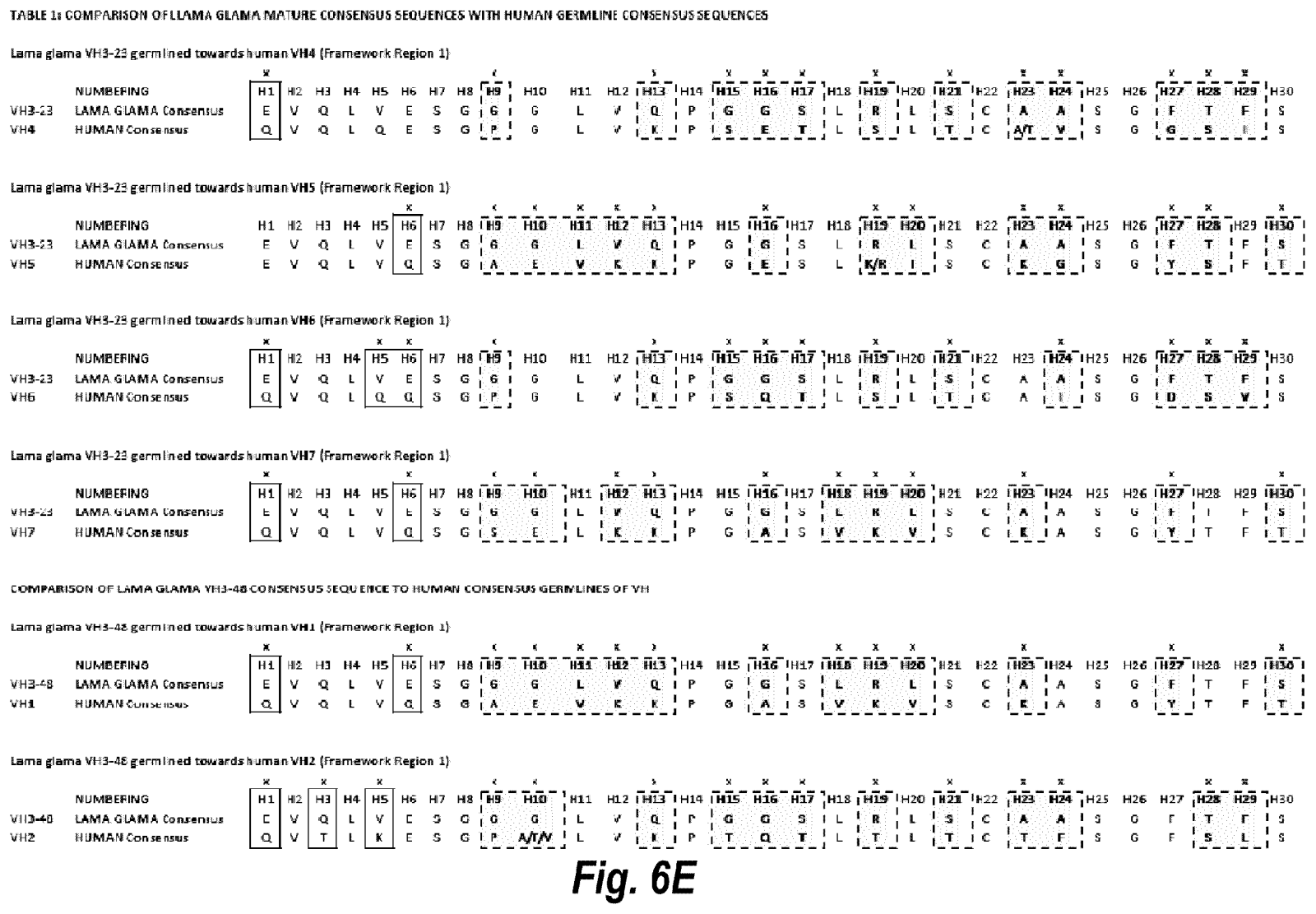
Figure 6F:
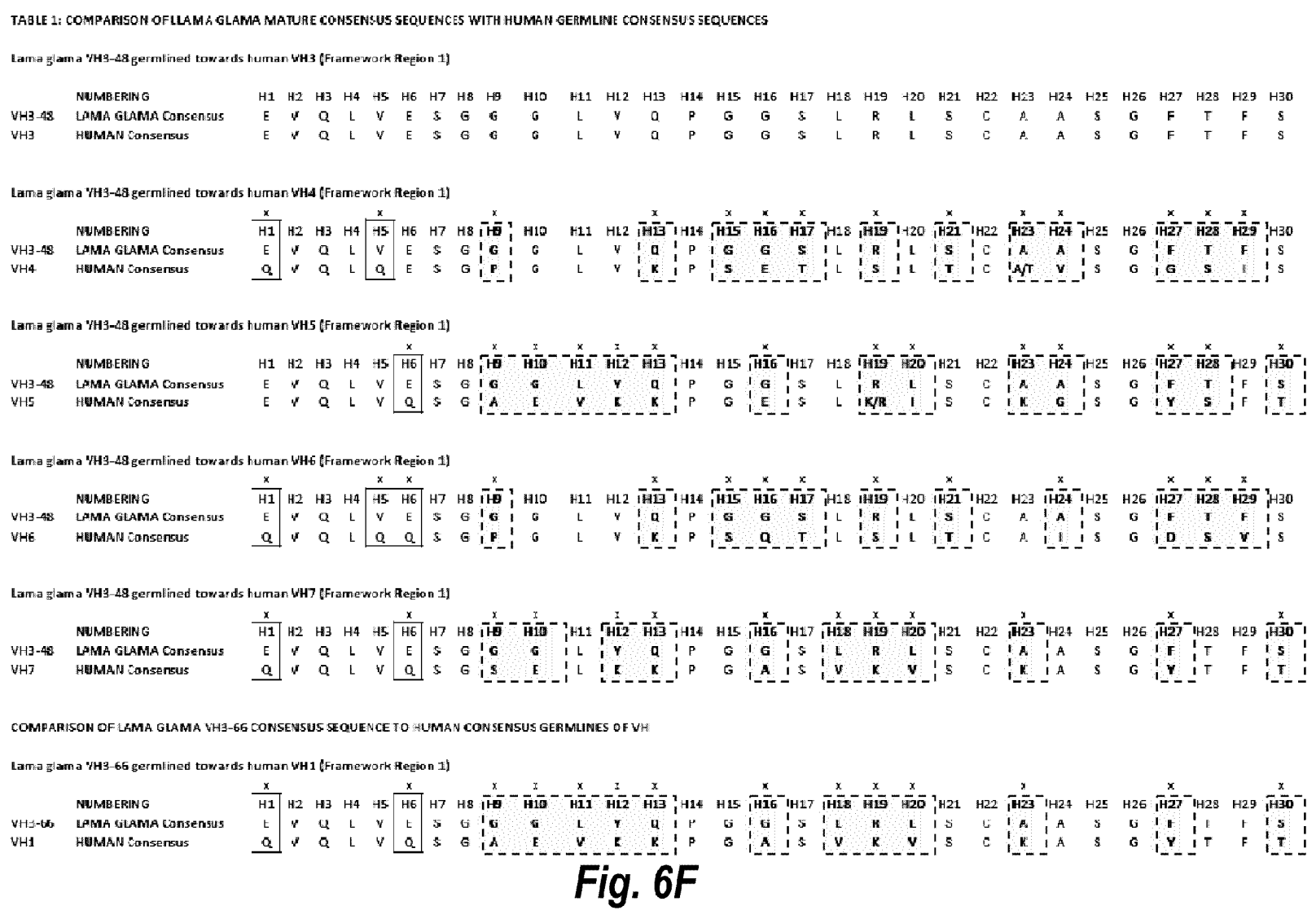
Figure 6H:
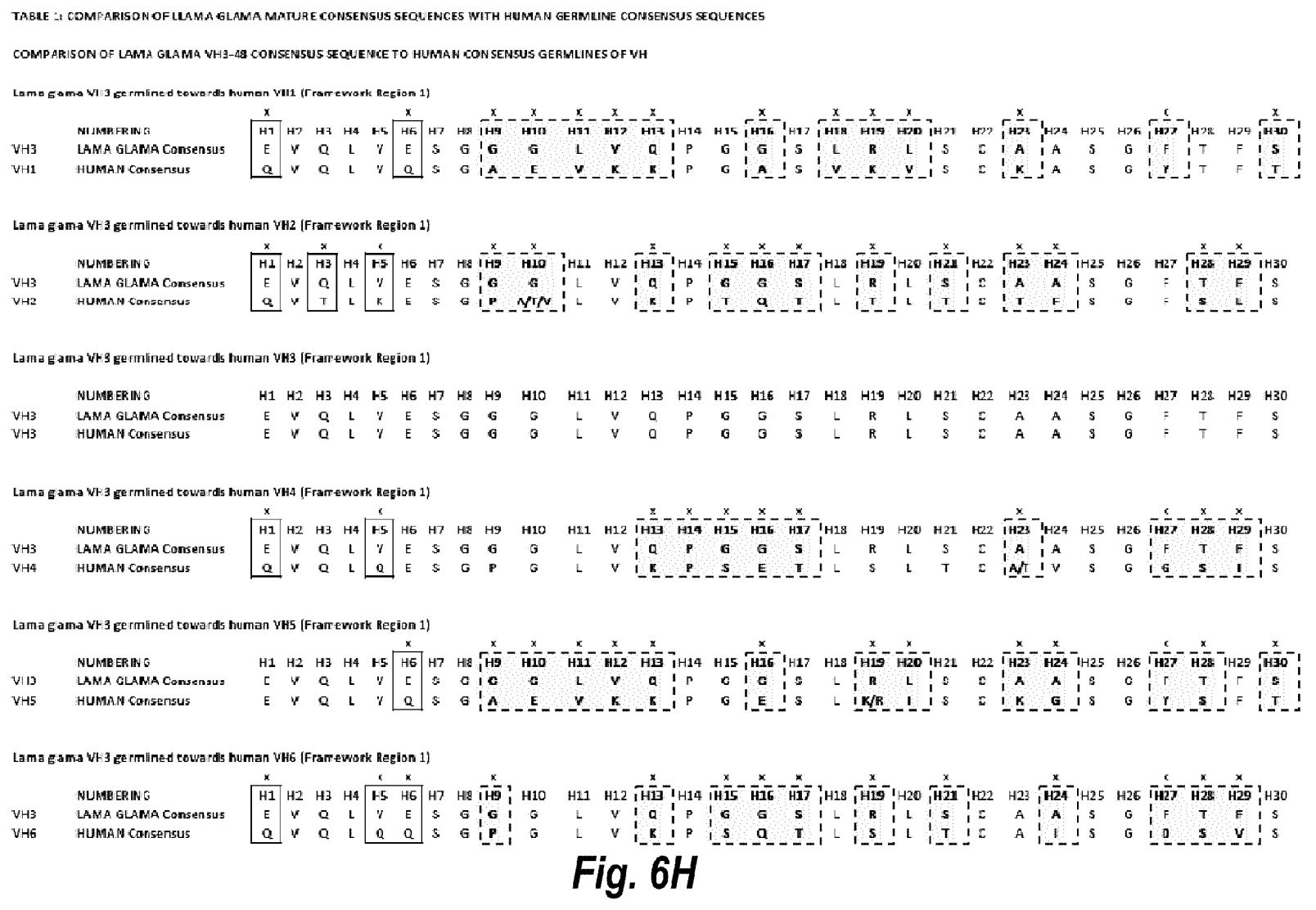
Figure 6I:
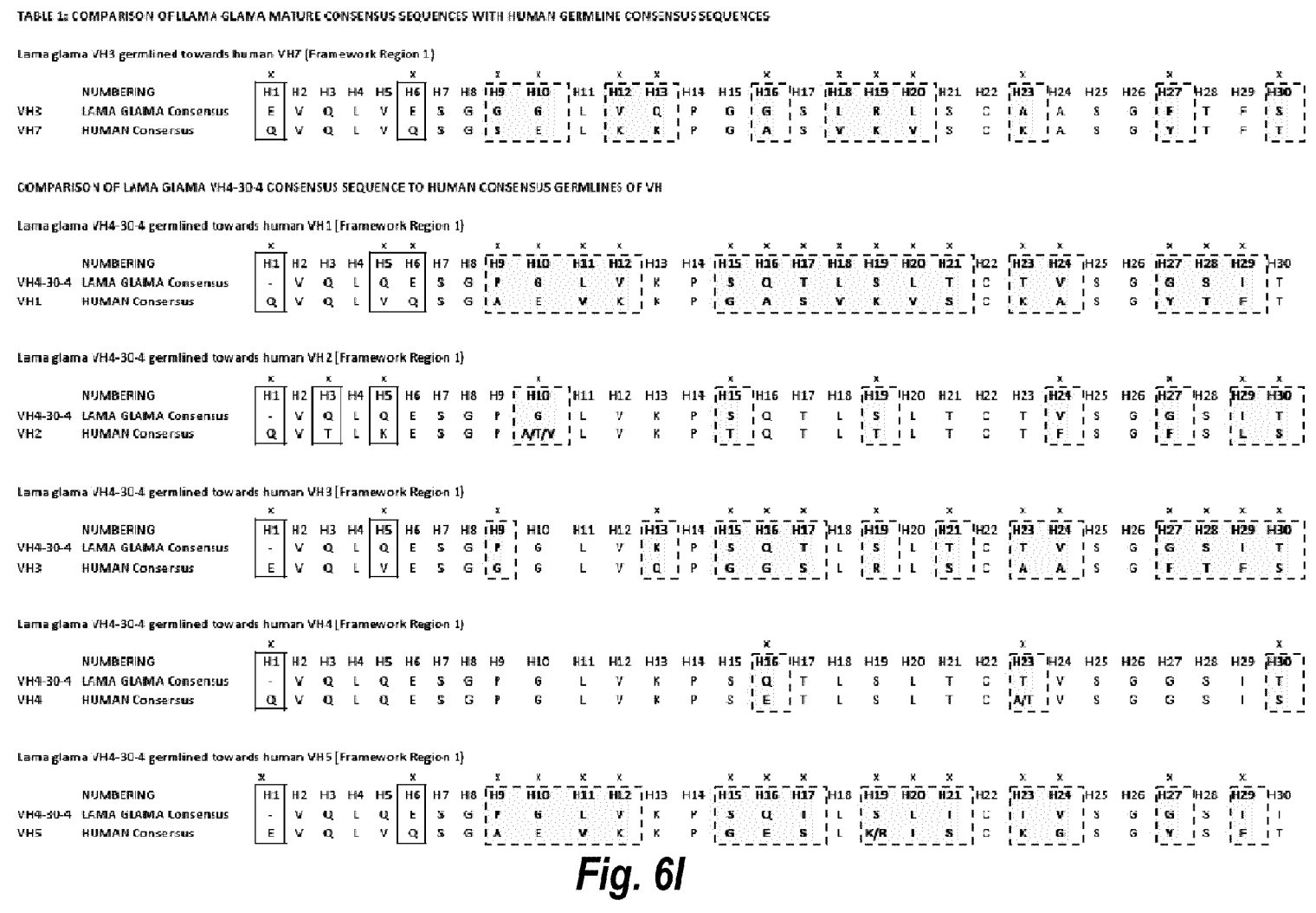

FIG. 6—shows a comparison of mature *Llama glama* consensus sequences of VH framework region 1 (FR1) with human germline consensus sequences of VH FR1 (VH1-VH7; SEQ ID NOS: 25-31). (A) VH1-46 *Llama glama* FR1 consensus sequence (SEQ ID NO:24). (B) VH3-11 *Llama glama* FR1 consensus sequence (SEQ ID NO:32). (C) VH3-21 *Llama glama* FR1 consensus sequence (SEQ ID NO:33). (D) VH3-23 *Llama glama* FR1 consensus sequence (SEQ ID NO:34). (E) VH3-48 *Llama glama* FR1 consensus sequence (SEQ ID NO:35). (F)-(G) VH3-66 *Llama glama* FR1 consensus sequence (SEQ ID NO:36). (H) VH3 *Llama glama* FR1 consensus sequence (SEQ ID NO:37). (I)-(J) VH4-30-4 *Llama glama* FR1 consensus sequence (SEQ ID NO:38).

FIG. 7—shows a comparison of mature *Llama glama* consensus sequences of VH framework region 2 (FR2) with human germline consensus sequences of VH FR2 (VH1-VH7; SEQ ID NOS: 40-46). (A) VH1-46 *Llama glama* FR2 consensus sequence (SEQ ID NO:39). (B) VH3-11 *Llama glama* FR2 consensus sequence (SEQ ID NO:47). (C) VH3-21 *Llama glama* FR2 consensus sequence (SEQ ID NO:48). (D) VH3-23 *Llama glama* FR2 consensus sequence (SEQ ID NO:49). (E) VH3-48 *Llama glama* FR2 consensus sequence (SEQ ID NO:50). (F)-(G) VH3-66 *Llama glama* FR2 consensus sequence (SEQ ID NO:51). (H) VH3 *Llama glama* FR2 consensus sequence (SEQ ID NO:52). (I)-(J) VH4-30-4 *Llama glama* FR2 consensus sequence (SEQ ID NO:53).

Figure 8C:
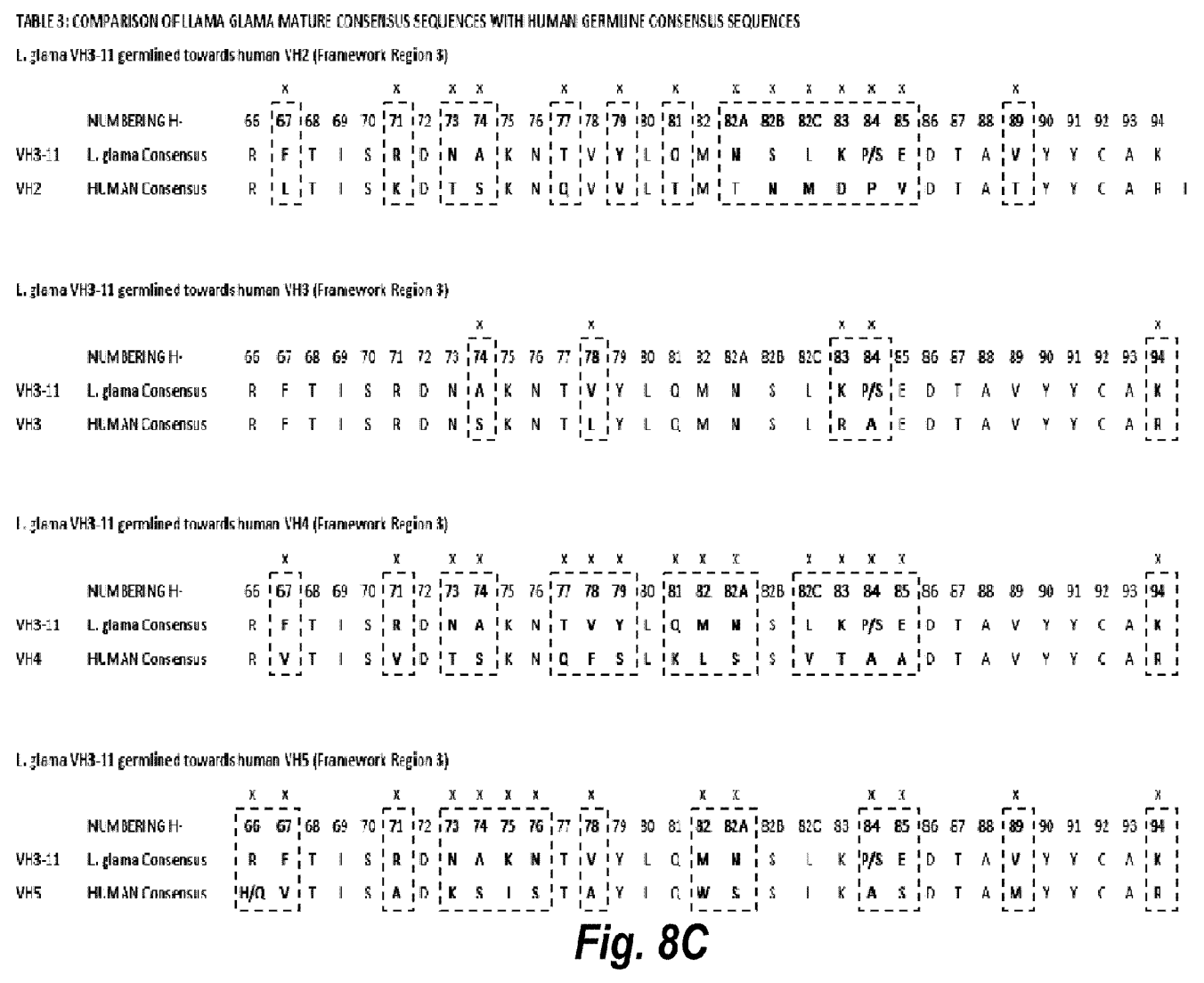
Figure 8D:
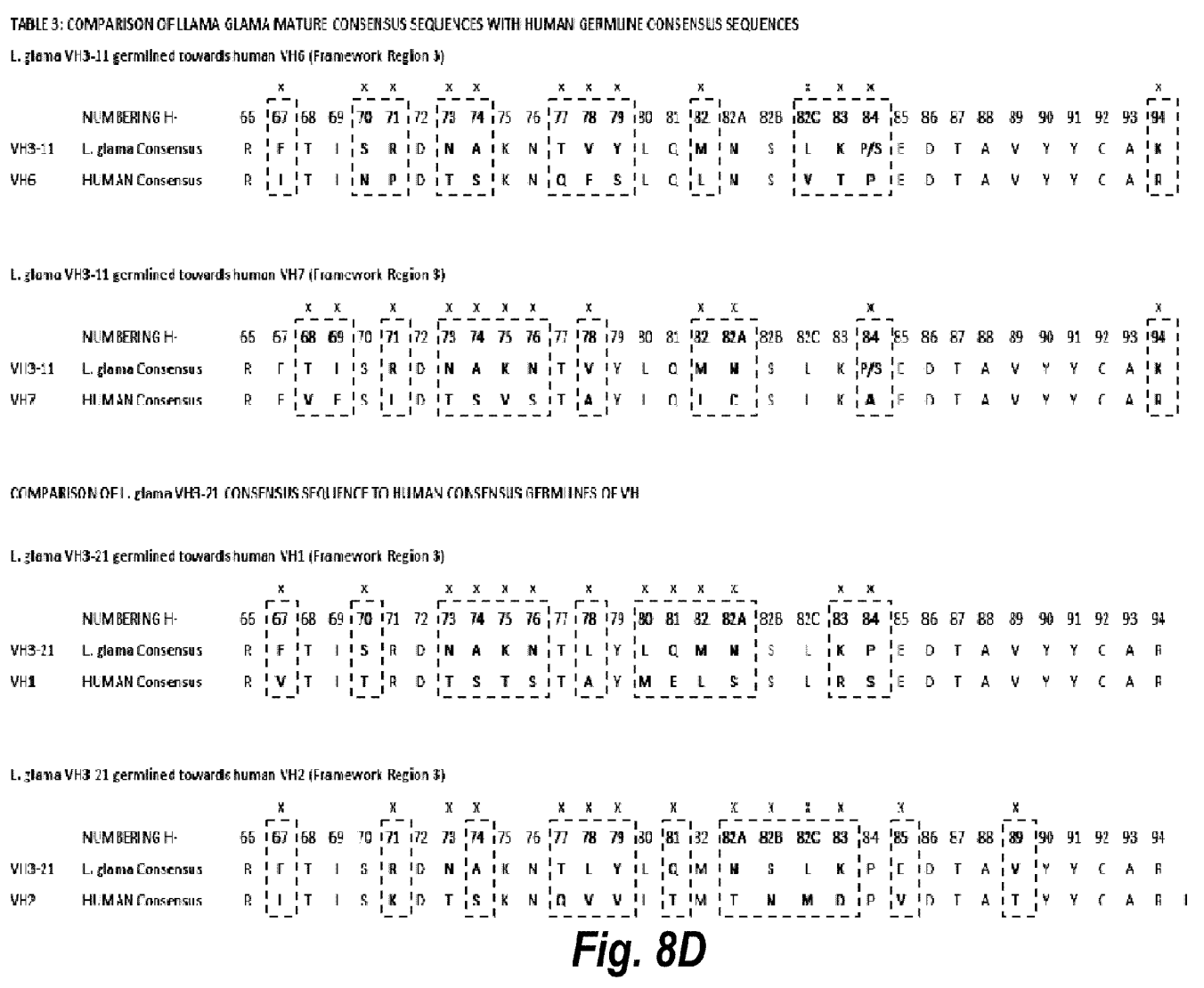
Figure 8G:
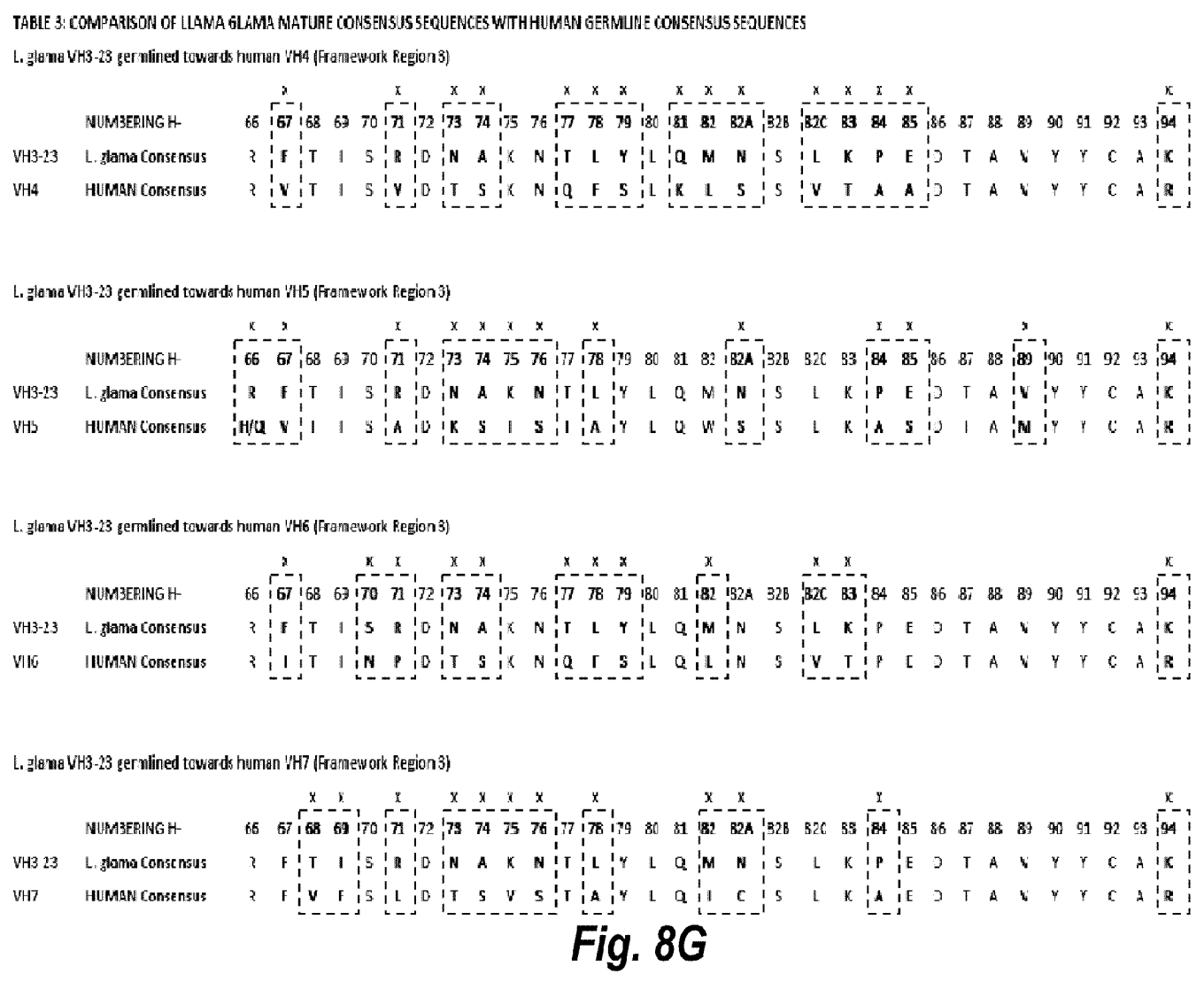
Figure 8J:
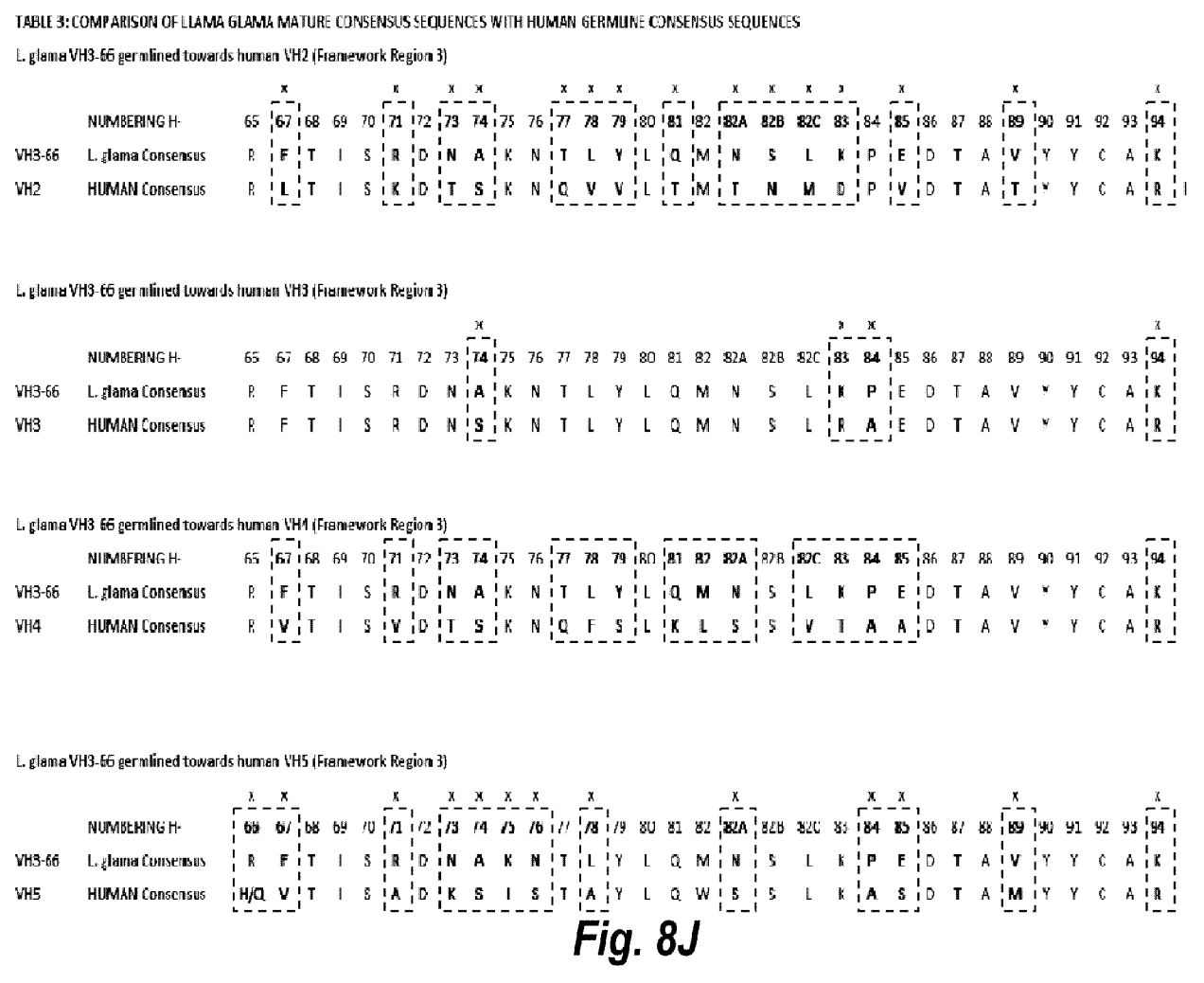
Figure 8K:
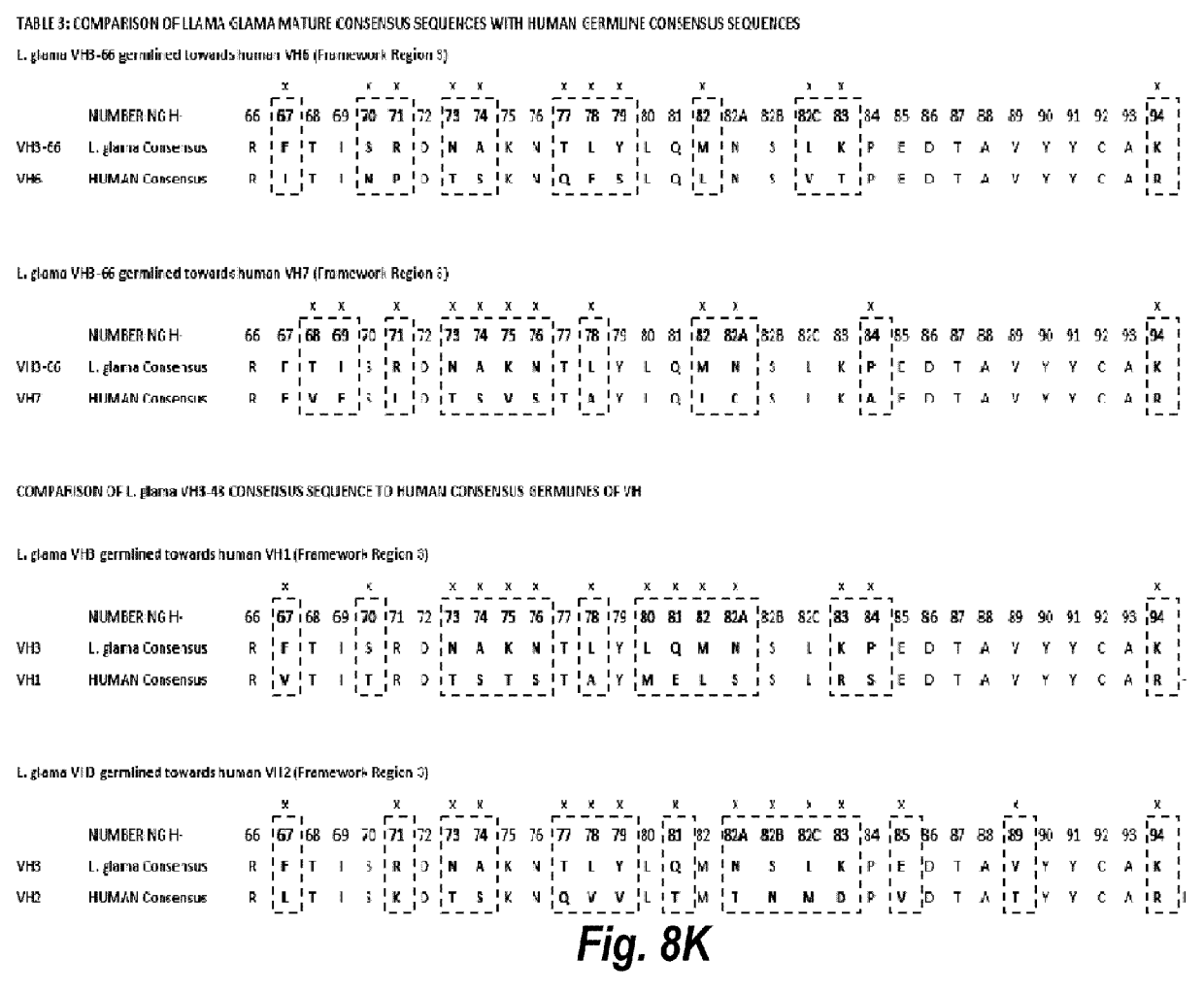
Figure 8N:
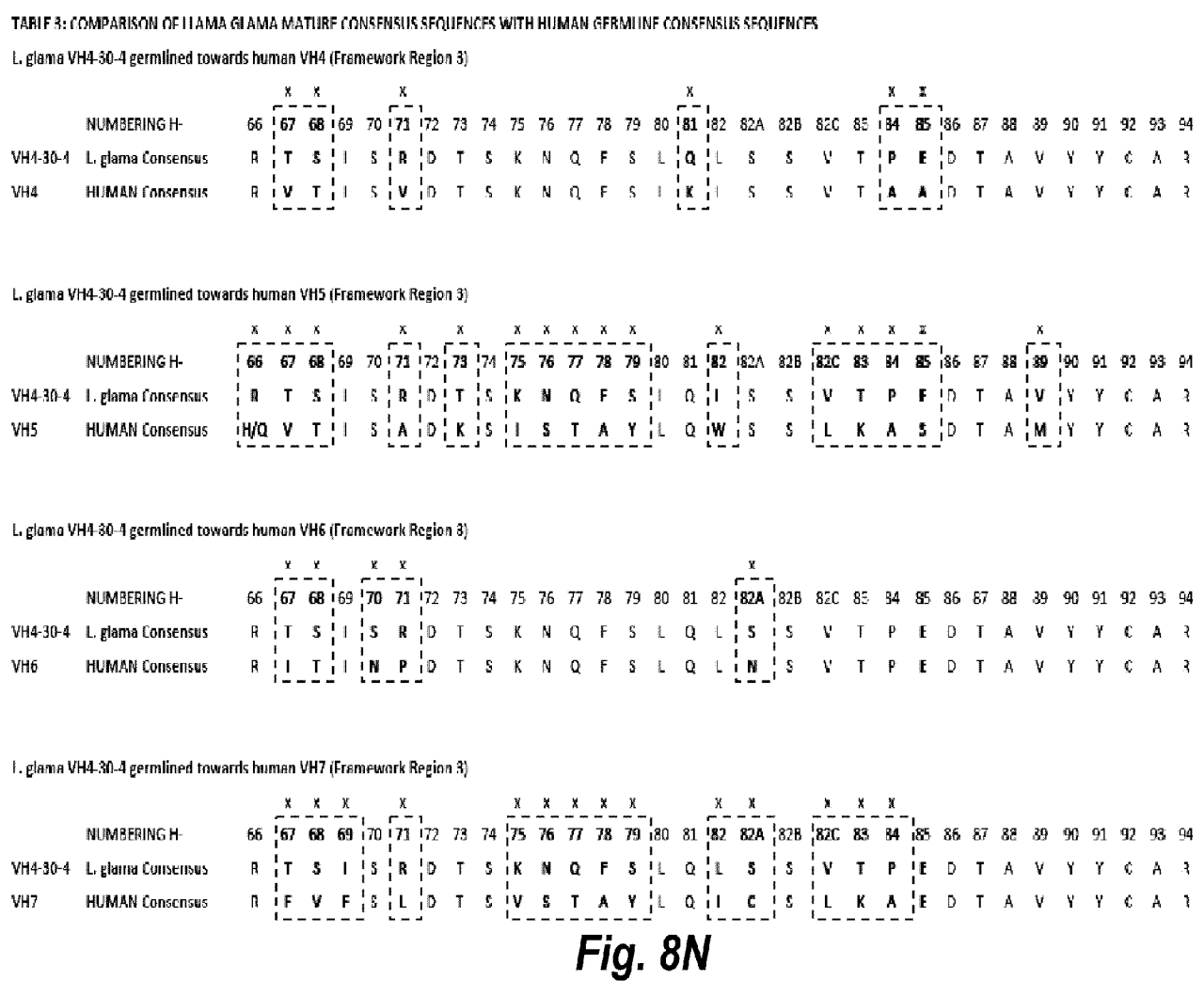

FIG. 8—shows a comparison of mature *Llama glama* consensus sequences of VH framework region 3 (FR3) with human germline consensus sequences of VH FR3 (VH1-VH7; SEQ ID NOS: 55-61). (A) VH1-46 *Llama glama* FR3 consensus sequence (SEQ ID NO:54). (B)-(C) VH3-11 *Llama glama* FR3 consensus sequence (SEQ ID NO:62). (D)-(E) VH3-21 *Llama glama* FR3 consensus sequence (SEQ ID NO:63). (F)-(G) VH3-23 *Llama glama* FR3 consensus sequence (SEQ ID NO:64). (H) VH3-48 *Llama glama* FR3 consensus sequence (SEQ ID NO:65). (I)-(J) VH3-66 *Llama glama* FR3 consensus sequence (SEQ ID NO:66). (K)-(L) VH3 *Llama glama* FR3 consensus sequence (SEQ ID NO:67). (M)-(N) VH4-30-4 *Llama glama* FR3 consensus sequence (SEQ ID NO:68).

Figure 9C:
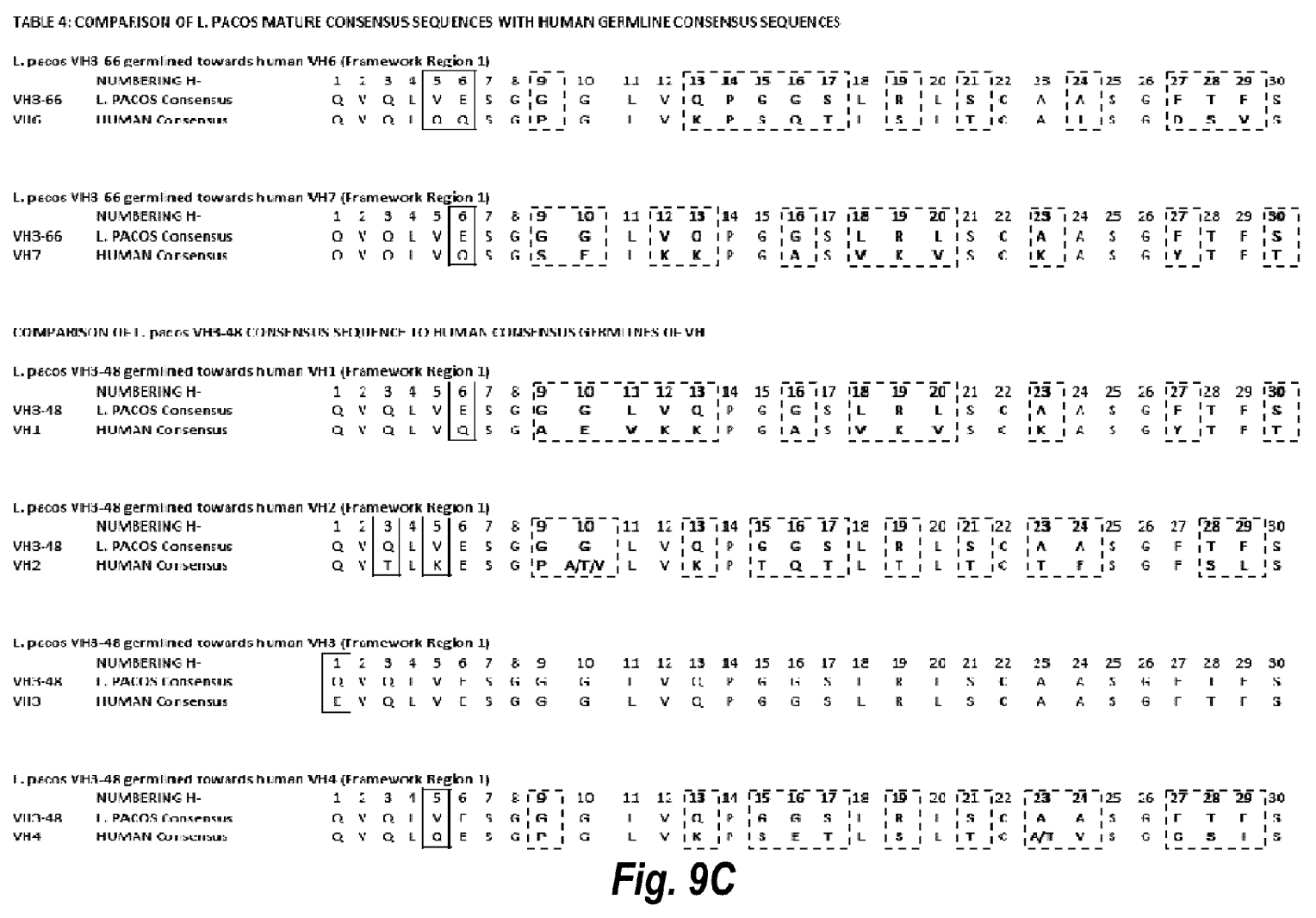
Figure 9E:
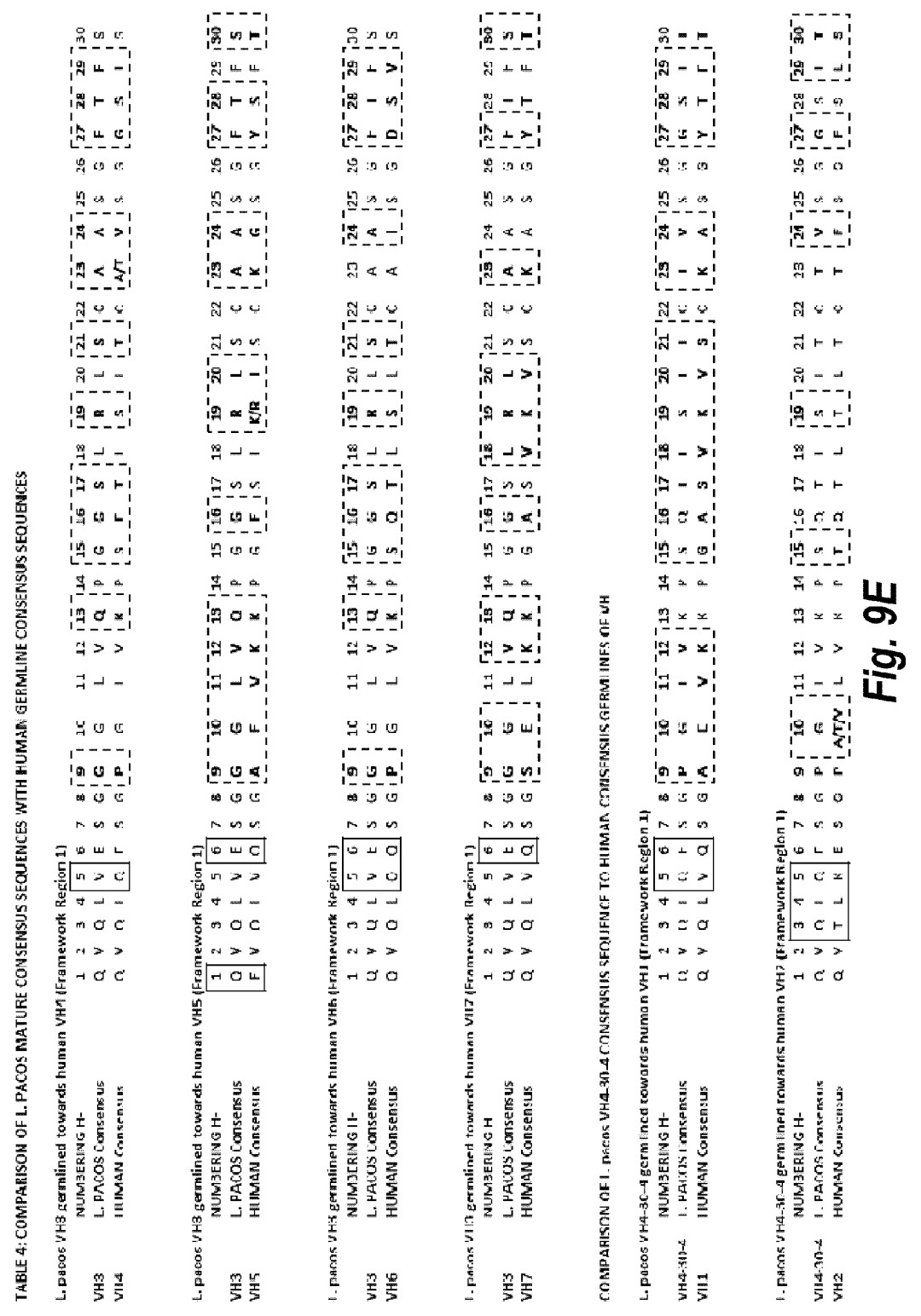

FIG. 9—shows a comparison of mature *Llama pacos* consensus sequences of VH framework region 1 (FR1) with human germline consensus sequences of VH FR1 (VH1-VH7; SEQ ID NOS: 25-31). (A) VH1-46 *Llama pacos* FR1 consensus sequence (SEQ ID NO:69). (B) VH3-66 *Llama pacos* FR1 consensus sequence (SEQ ID NO:70). (C) VH3-48 *Llama pacos* FR1 consensus sequence (SEQ ID NO:71). (D) VH3 *Llama pacos* FR1 consensus sequence (SEQ ID NO:72). (E)-(F) VH4-30-4 *Llama pacos* FR1 consensus sequence (SEQ ID NO:73).

FIG. 10—shows a comparison of mature *Llama pacos* consensus sequences of VH framework region 2 (FR2) with human germline consensus sequences of VH FR2 (VH1-VH7; SEQ ID NOS: 40-46). (A) VH1-46 *Llama pacos* FR2 consensus sequence (SEQ ID NO:74). (B)-(C) VH3-66 *Llama pacos* FR2 consensus sequence (SEQ ID NO:75). (D) VH3-48 *Llama pacos* FR2 consensus sequence (SEQ ID NO:76). (E)-(F) VH3 *Llama pacos* FR2 consensus sequence (SEQ ID NO:77). (G)-(H) VH4-30-4 *Llama pacos* FR2 consensus sequence (SEQ ID NO:78).

Figure 11A:
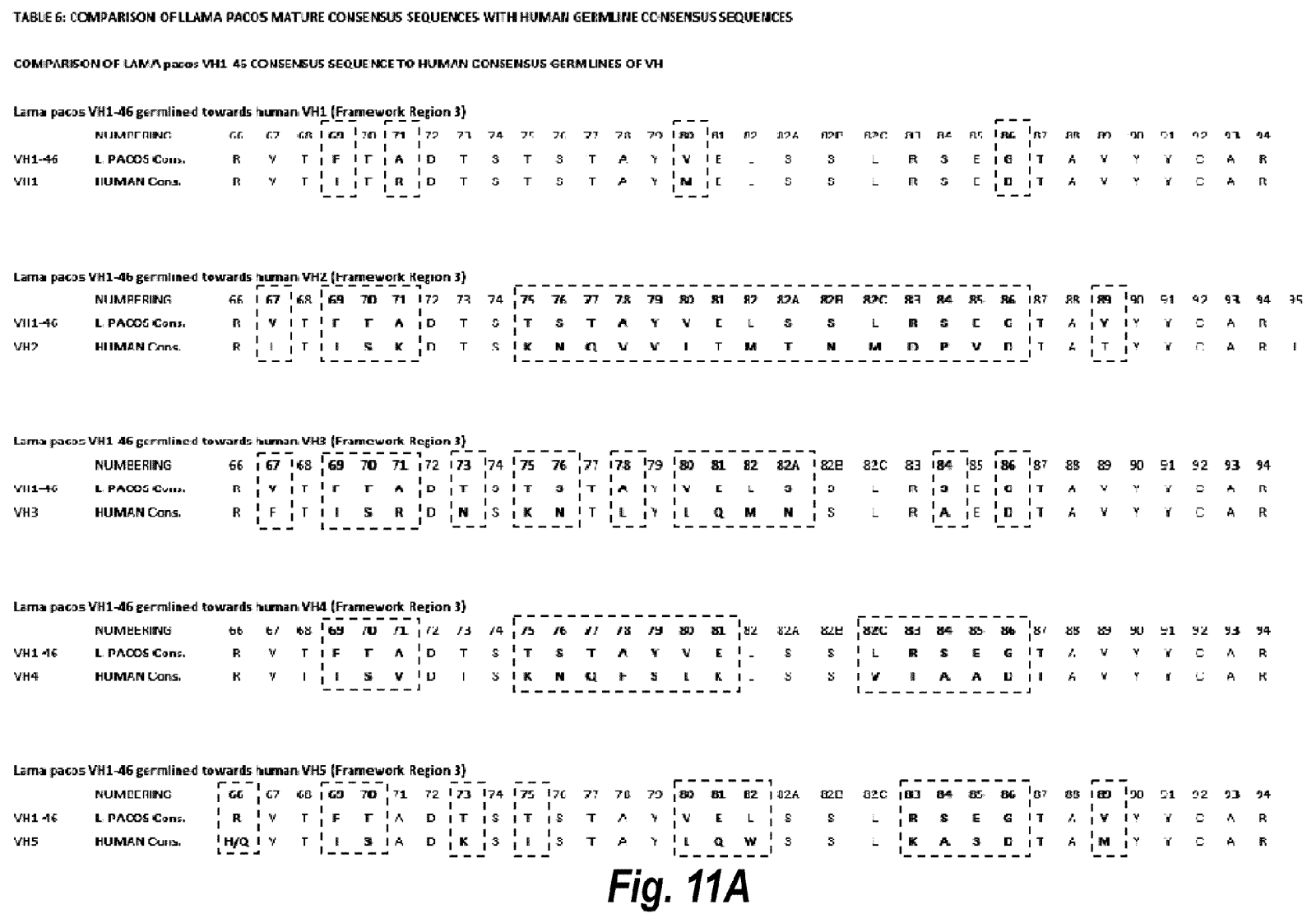
Figure 11C:
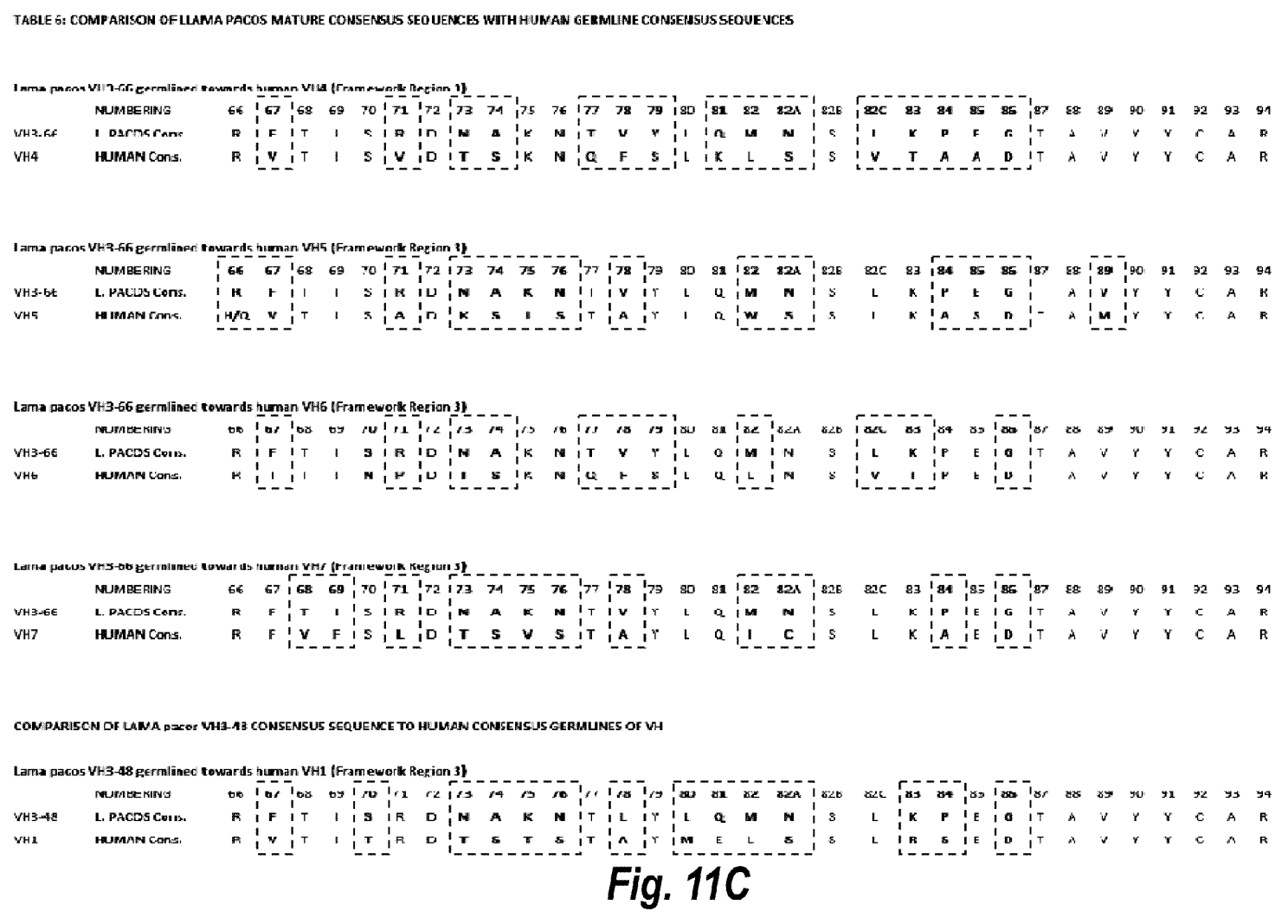
Figure 11E:
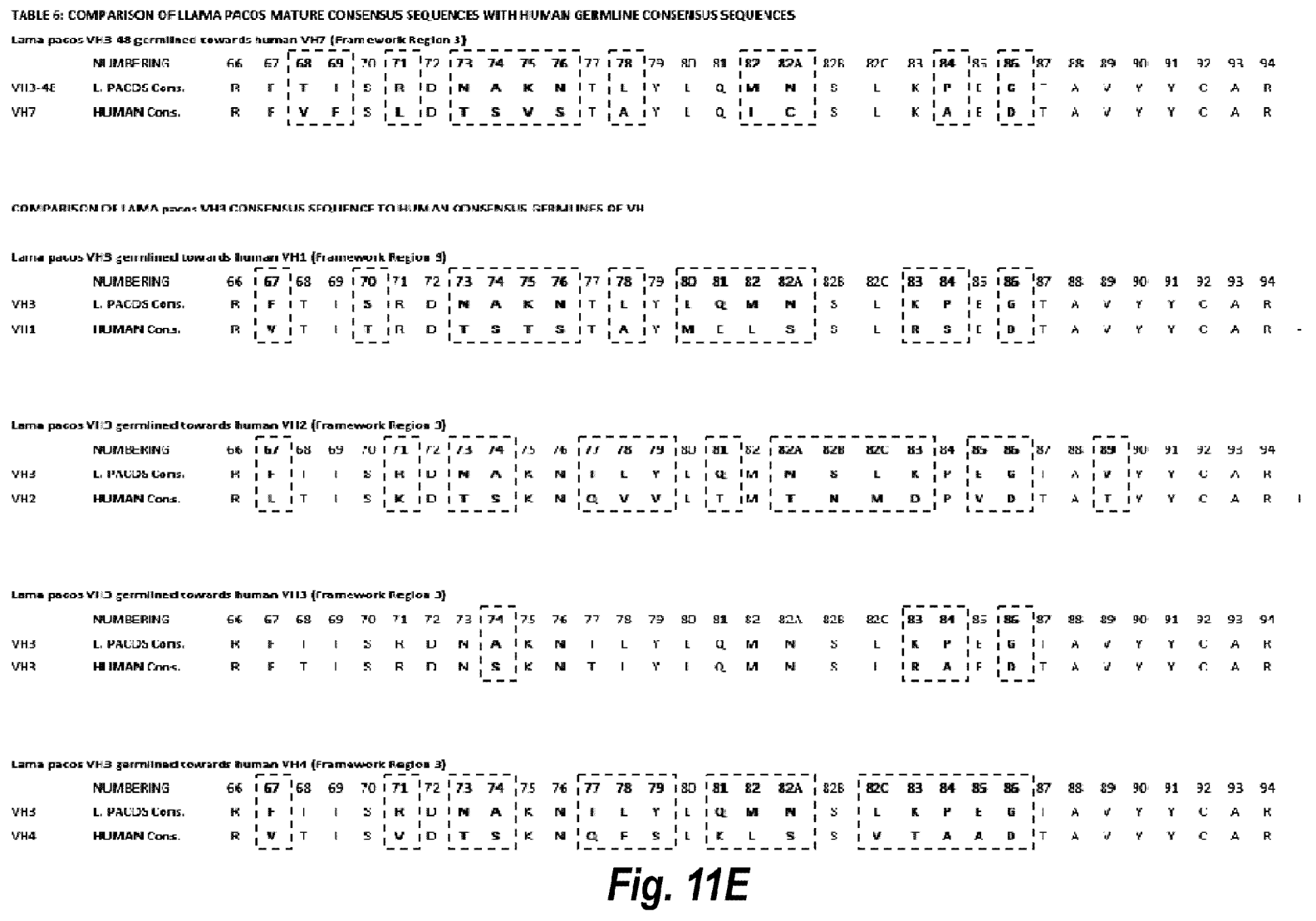

FIG. 11—shows a comparison of mature *Llama pacos* consensus sequences of VH framework region 3 (FR3) with human germline consensus sequences of VH FR3 (VH1-VH7; SEQ ID NOS: 55-61). (A) VH1-46 *Llama pacos* FR3 consensus sequence (SEQ ID NO:79). (B) VH3-66 *Llama pacos* FR3 consensus sequence (SEQ ID NO:80). (C)-(D) VH3-48 *Llama pacos* FR3 consensus sequence (SEQ ID NO:81). (E) VH3 *Llama pacos* FR3 consensus sequence (SEQ ID NO:82). (F)-(G) VH4-30-4 *Llama pacos* FR3 consensus sequence (SEQ ID NO:83).

FIG. 12—shows a comparison of the framework region 1 (FR1) sequence of the mature *Llama glama* consensus sequence VL1-44 (SEQ ID NO:84) with human germline consensus sequences of VL (Lambda) FR1. (A) alignment with Human VL1-VL6 FR1 sequences (SEQ ID NOS:85-90). (B) alignment with Human VL7-VL10 FR1 sequences (SEQ ID NOS:91-94).

FIG. 13—shows a comparison of the framework region 2 (FR2) sequence of the mature *Llama glama* consensus sequence VL1-44 (SEQ ID NO:95) with human germline consensus sequences of VL (Lambda) FR2. (A) alignment with Human VL1-VL6 FR2 sequences (SEQ ID NOS:96-101). (B) alignment with Human VL7-VL10 FR2 sequences (SEQ ID NOS:102-105).

Figure 14A:
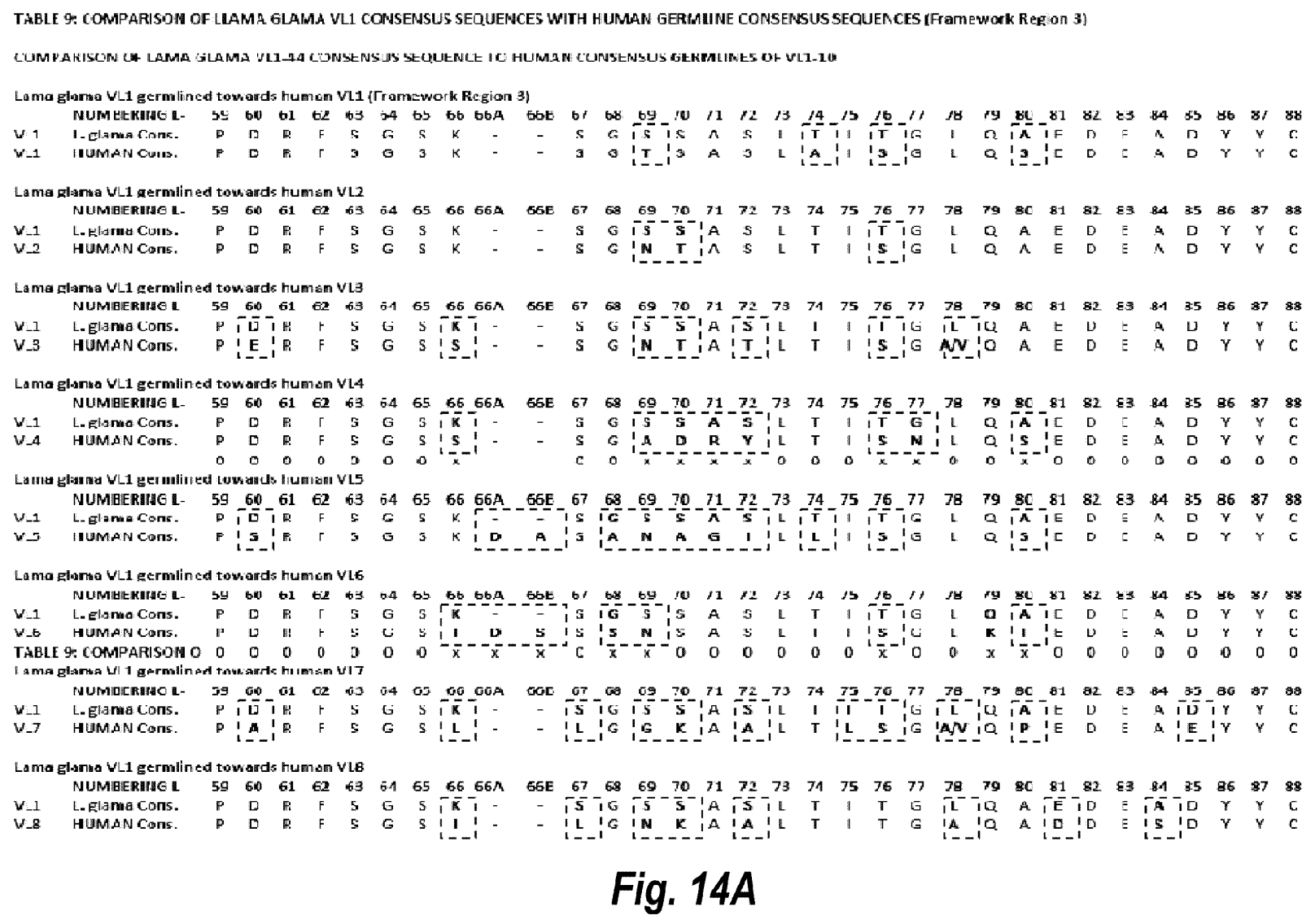

FIG. 14—shows a comparison of the framework region 3 (FR3) sequence of the mature *Llama glama* consensus sequence VL1-44 (SEQ ID NO:106) with human germline consensus sequences of VL (Lambda) FR3. (A) alignment with Human VL1-VL8 FR3 sequences (SEQ ID NOS:107-114). (B) alignment with Human VL9-VL10 FR3 sequences (SEQ ID NOS:115-116).

FIG. 15—shows a comparison of mature *Llama glama* consensus sequences of VL2 framework region 1 (FR1) with human germline consensus sequences of VL FR1 (VK1-VK10; SEQ ID NOS: 118-125). (A) VL2-11 *Llama glama* FR1 consensus sequence (SEQ ID NO:117) alignments. (B)-(C) VL2-18 *Llama glama* FR1 consensus sequence (SEQ ID NO:126) alignments.

FIG. 16—shows a comparison of mature *Llama glama* consensus sequences of VL2 framework region 2 (FR2) with human germline consensus sequences of VL FR2 (VK1-VK10). (A) VL2-11 *Llama glama* FR2 consensus sequence (SEQ ID NO:127) alignments. (B)-(C) VL2-18 *Llama glama* FR2 consensus sequence (SEQ ID NO:128) alignments.

Figure 17A:
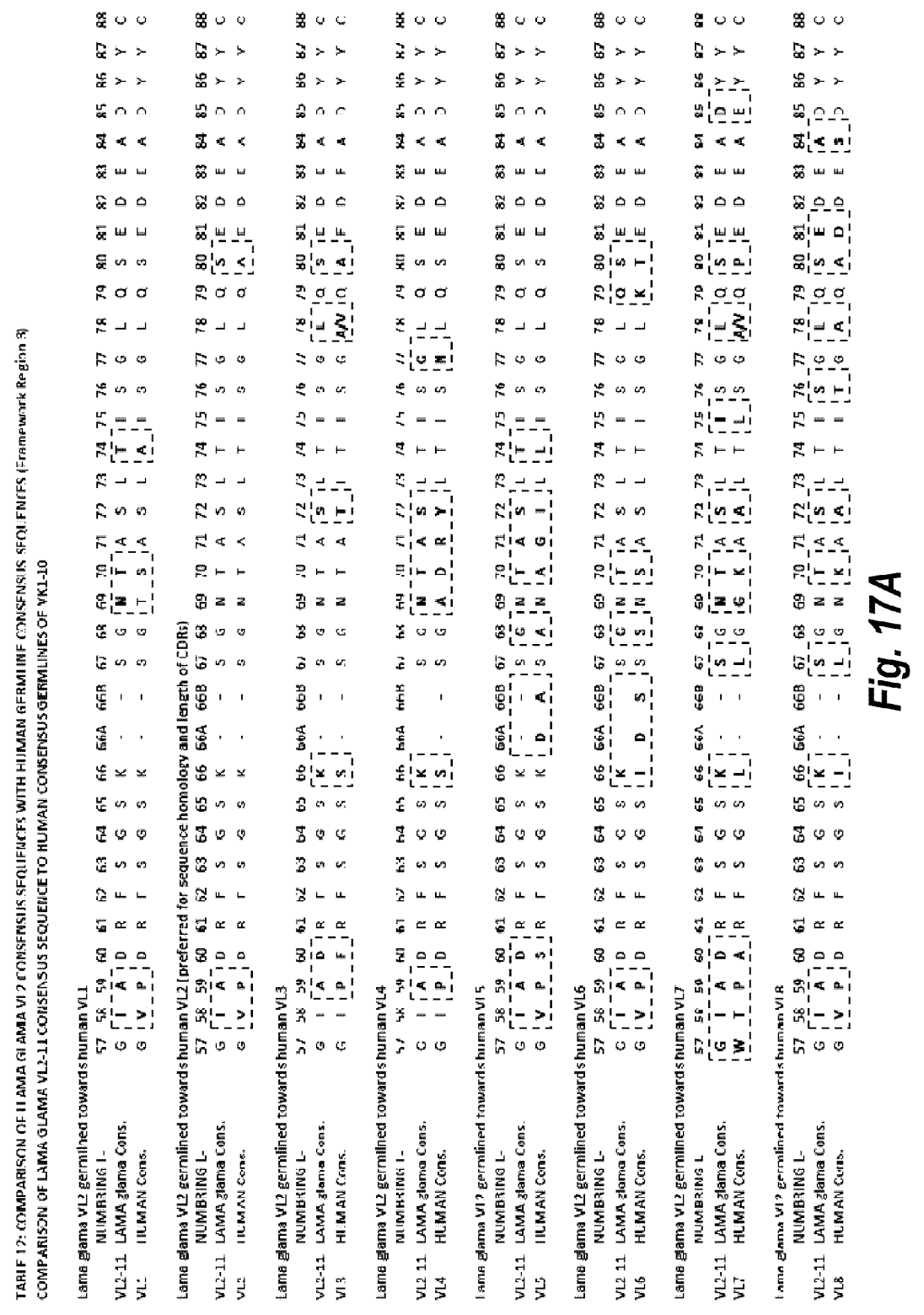
Figure 17B:
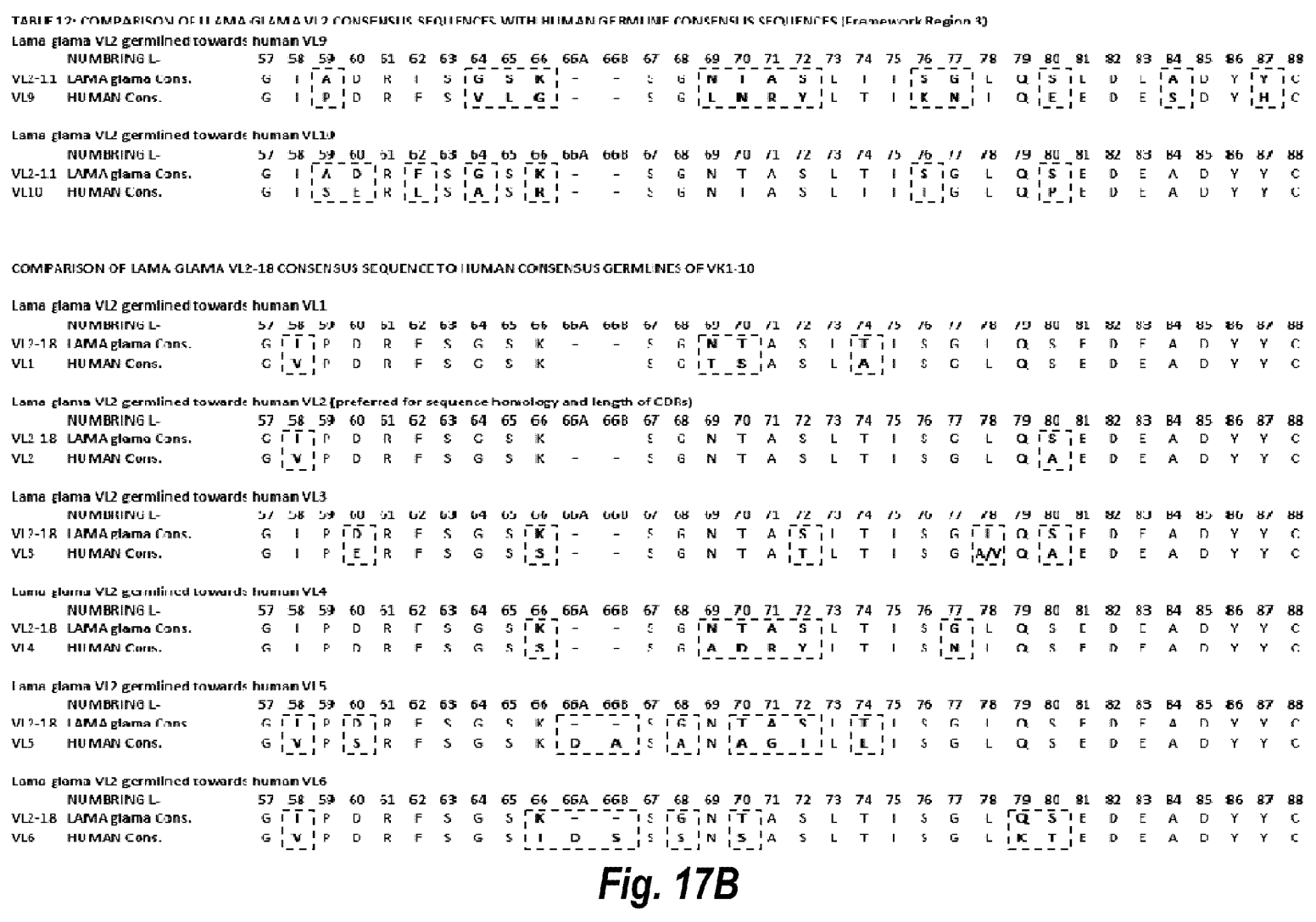

FIG. 17—shows a comparison of mature *Llama glama* consensus sequences of VL2 framework region 3 (FR3) with human germline consensus sequences of VL FR3 (VK1-VK10; SEQ ID NOS:130-139). (A) VL2-11 *Llama glama* FR3 consensus sequence (SEQ ID NO:129) alignments. (B)-(C) VL2-18 *Llama glama* FR3 consensus sequence (SEQ ID NO:140) alignments.

Figure 18B:
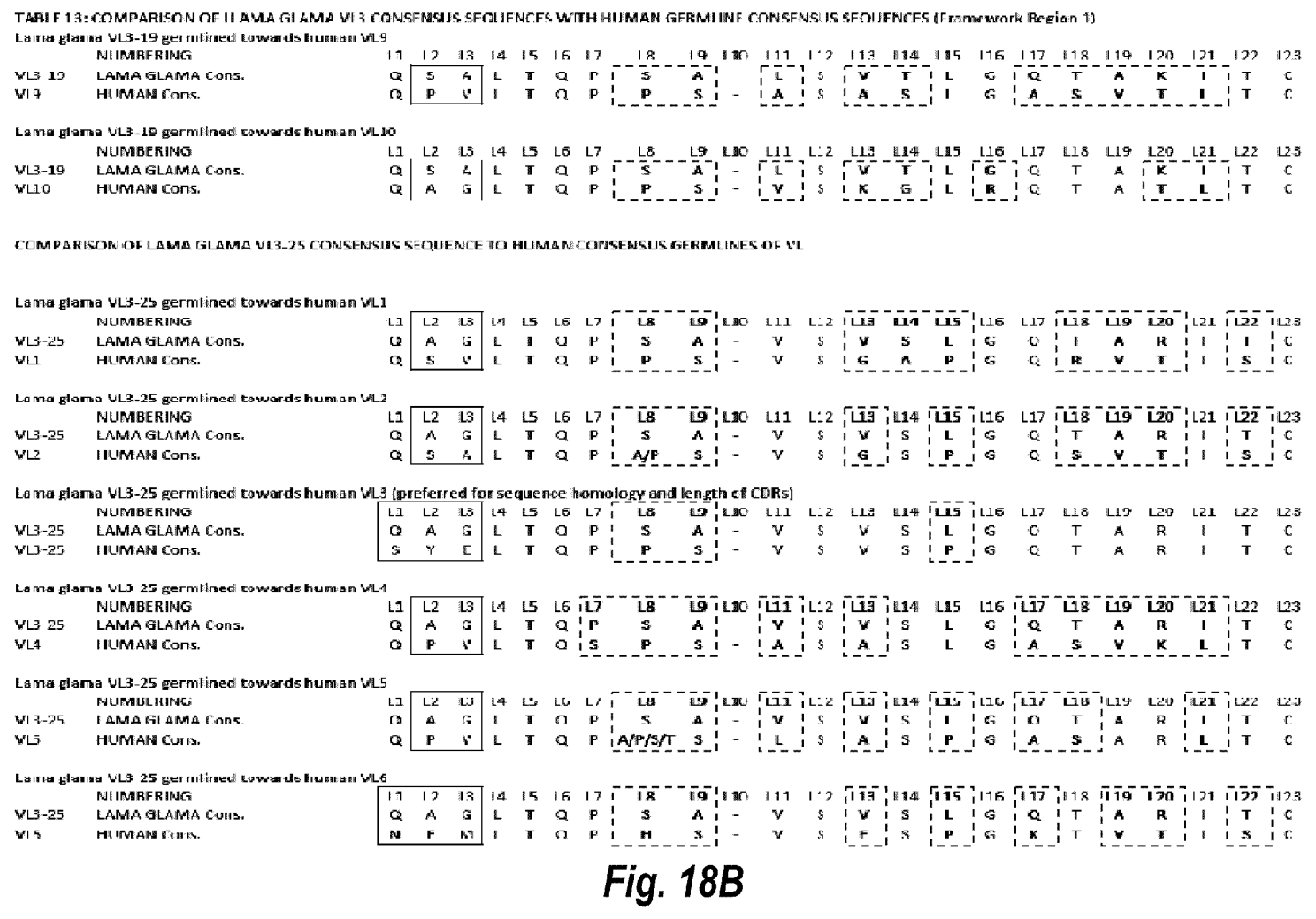

FIG. 18—shows a comparison of mature *Llama glama* consensus sequences of VL3 framework region 1 (FR1) with human germline consensus sequences of VL FR1 (VL1-VL10; SEQ ID NOS:85-94). (A) VL3-19 *Llama glama* FR1 consensus sequence (SEQ ID NO:141) alignments. (B)-(C) VL3-25 *Llama glama* FR1 consensus sequence (SEQ ID NO:142) alignments.

FIG. 19—shows a comparison of mature *Llama glama* consensus sequences of VL3 framework region 2 (FR2) with human germline consensus sequences of VL FR2 (VL1-VL10; SEQ ID NOS:96-105). (A) VL3-19 *Llama glama* FR2 consensus sequence (SEQ ID NO:143) alignments. (B)-(C) VL3-25 *Llama glama* FR2 consensus sequence (SEQ ID NO:144) alignments.

Figure 20A:
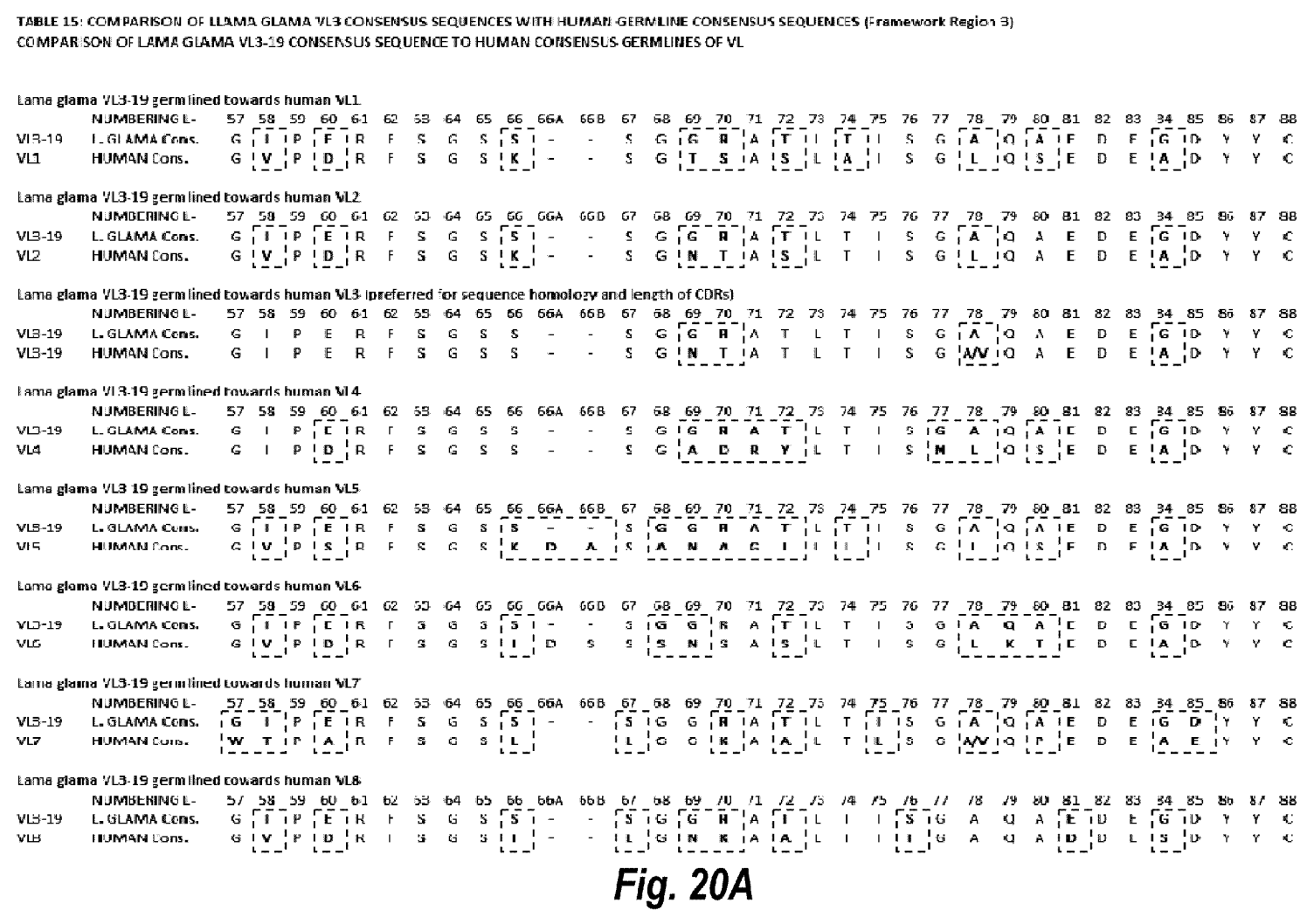
Figure 20B:
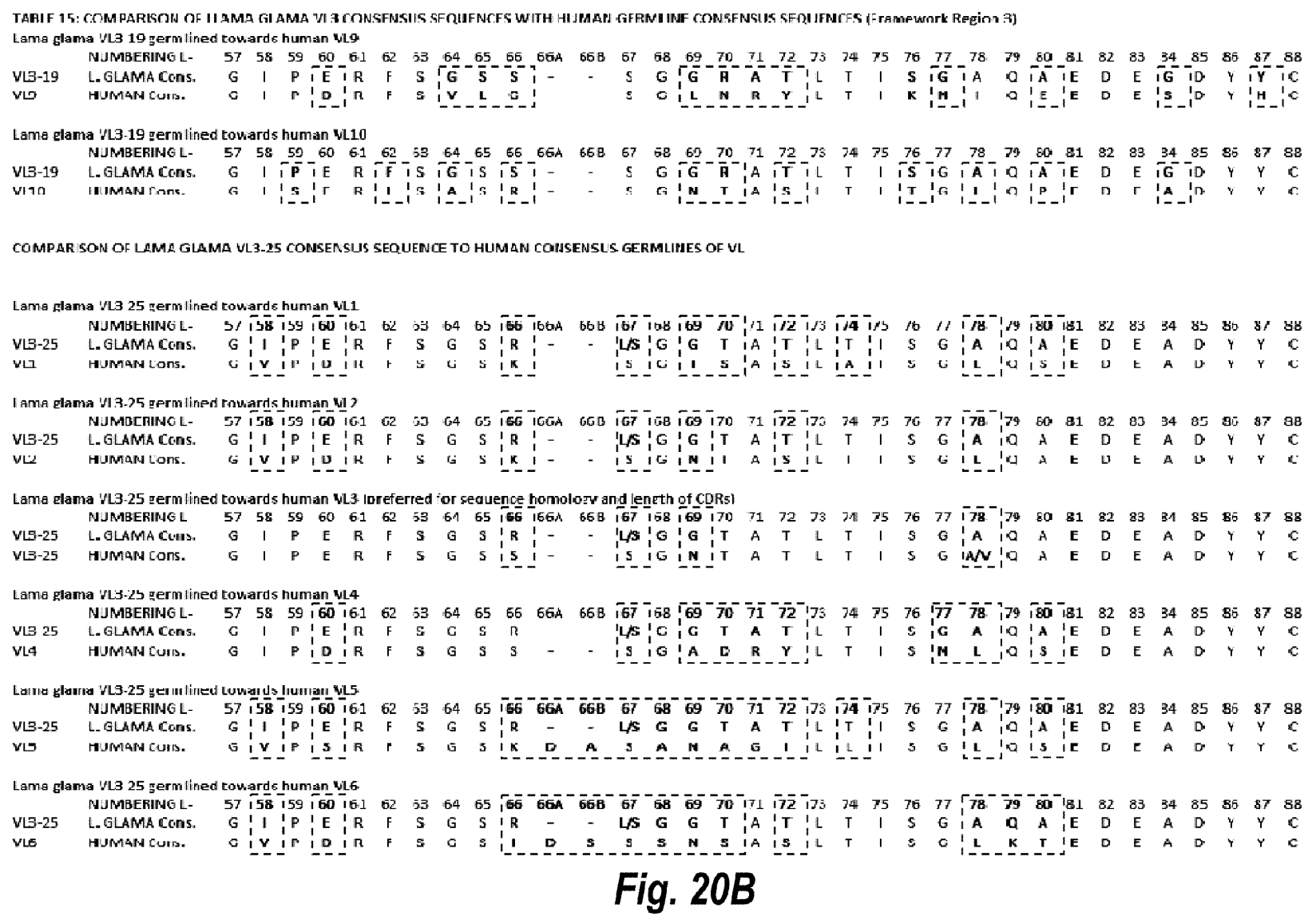

FIG. 20—shows a comparison of mature *Llama glama* consensus sequences of VL3 framework region 3 (FR3) with human germline consensus sequences of VL (lambda) FR3 (VL1-VL10; SEQ ID NOS:130-139). (A) VL3-19 *Llama glama* FR3 consensus sequence (SEQ ID NO:145) alignments. (B)-(C) VL3-25 *Llama glama* FR3 consensus sequence (SEQ ID NO:146) alignments.

FIG. 21—shows a comparison of the mature *Llama glama* consensus sequence framework region 1 (FR1) sequence of VL5 (SEQ ID NO:147) with human germline consensus sequences of VL FR1. (A) alignments with FR1 sequences of human germlines VL1-VL6 (SEQ ID NOS:85-90). (B) alignments with FR1 sequences of human germlines VL7-VL10 (SEQ ID NOS:91-94).

FIG. 22—shows a comparison of the mature *Llama glama* consensus sequence framework region 2 (FR2) sequence of VL5 (SEQ ID NO:148) with human germline consensus sequences of VL FR2. (A) alignments with FR2 sequences of human germlines VL1-VL6 (SEQ ID NOS:96-101). (B) alignments with FR2 sequences of human germlines VL7-VL10 (SEQ ID NOS:102-105).

FIG. 23—shows a comparison of the mature *Llama glama* consensus sequence framework region 3 (FR3) sequence of VL5 (SEQ ID NO:149) with human germline consensus sequences of VL FR3. (A) alignments with FR3 sequences of human germlines VL1-VL6 (SEQ ID NOS:150-155). (B) alignments with FR3 sequences of human germlines VL7-VL10 (SEQ ID NOS:156-159).

FIG. 24—shows a comparison of the mature *Llama glama* consensus sequence framework region 1 (FR1) sequence of VL8-61 (SEQ ID NO:160) with human germline consensus sequences of VL FR1. (A) alignments with FR1 sequences of human germlines VL1-VL6 (SEQ ID NOS:85-90). (B) alignments with FR1 sequences of human germlines VL7-VL10 (SEQ ID NOS: 91-94).

FIG. 25—shows a comparison of the mature *Llama glama* consensus sequence framework region 2 (FR2) sequence of VL8-61 (SEQ ID NO:161) with human germline consensus sequences of VL FR2. (A) alignments with FR2 sequences of human germlines VL1-VL6 (SEQ ID NOS:96-101). (B) alignments with FR2 sequences of human germlines VL7-VL10 (SEQ ID NOS:102-105).

FIG. 26—shows a comparison of the mature *Llama glama* consensus sequence framework region 3 (FR3) sequence of VL8-61 (SEQ ID NO:162) with human germline consensus sequences of VL FR3. (A) alignments with FR3 sequences of human germlines VL1-VL6 (SEQ ID NOS:107-112). (B) alignments with FR3 sequences of human germlines VL7-VL10 (SEQ ID NOS:113-116).

FIG. 27—shows a comparison of mature *Llama glama* consensus sequences of V Kappa framework region 1 (FR1) with human germline consensus sequences of VL (kappa) FR1 (VK1-VK5; (SEQ ID NOS:164-168). (A) VK1 *Llama glama* FR1 consensus sequence (SEQ ID NO:163) alignments. (B) VK2 *Llama glama* FR1 consensus sequence (SEQ ID NO:169) alignments. (C) VK4 *Llama glama* FR1 consensus sequence (SEQ ID NO:170) alignments.

FIG. 28—shows a comparison of mature *Llama glama* consensus sequences of V Kappa framework region 2 (FR2) with human germline consensus sequences of VL (kappa) FR2 (VK1-VK5; (SEQ ID NOS:172-176). (A) VK1 *Llama glama* FR2 consensus sequence (SEQ ID NO:171) alignments. (B) VK2 *Llama glama* FR2 consensus sequence (SEQ ID NO:177) alignments. (C) VK4 *Llama glama* FR2 consensus sequence (SEQ ID NO:178) alignments.

Figure 29B:
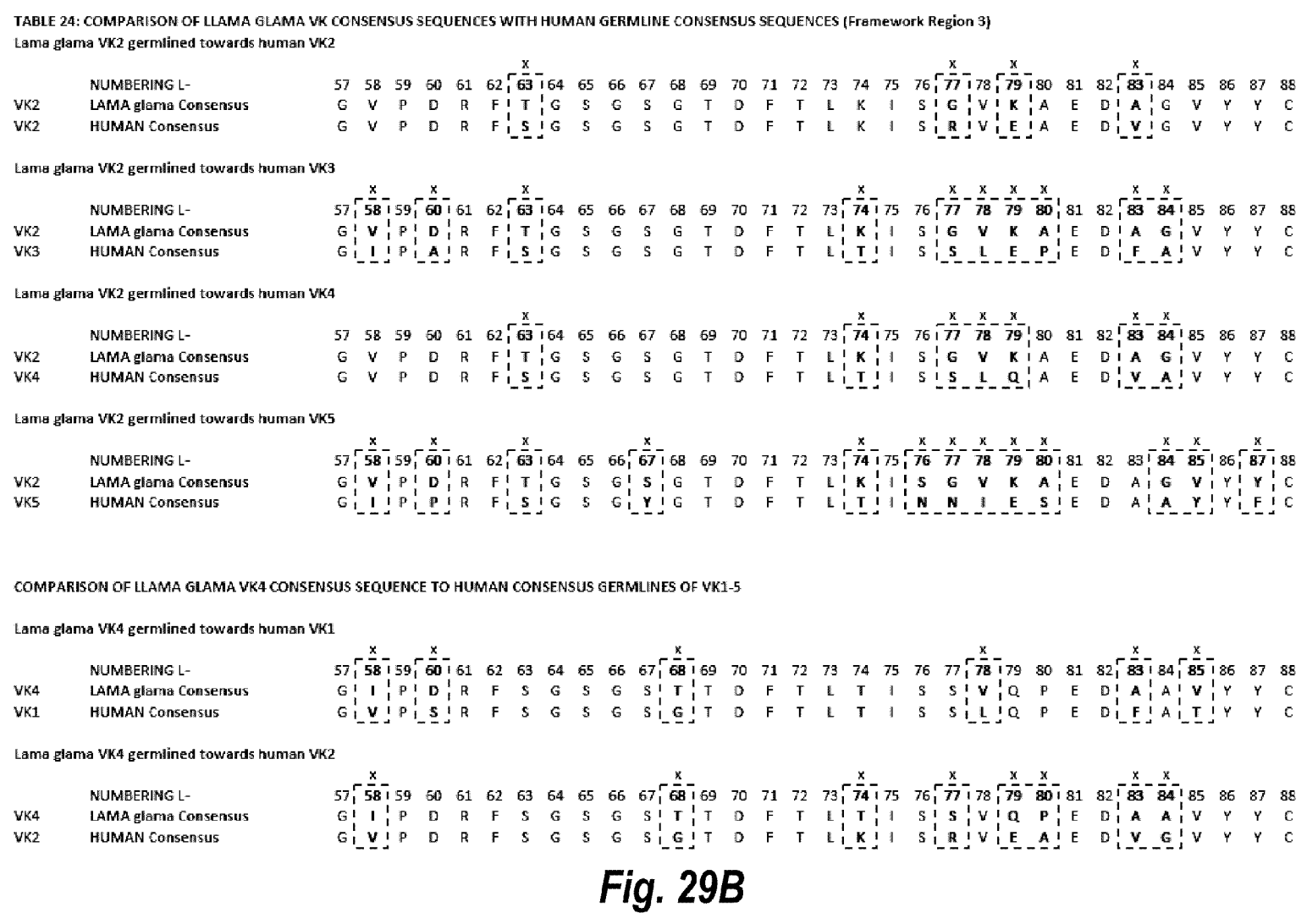

FIG. 29—shows a comparison of mature *Llama glama* consensus sequences of V Kappa framework region 3 (FR3) with human germline consensus sequences of VL (kappa) FR3 (VK1-VK5; (SEQ ID NOS:180-184). (A) VK1 *Llama glama* FR3 consensus sequence (SEQ ID NO:179) alignments. (B) VK2 *Llama glama* FR3 consensus sequence (SEQ ID NO:185) alignments. (C) VK4 *Llama glama* FR3 consensus sequence (SEQ ID NO:186) alignments.

FIG. 30—shows % utilisation of different amino acid residues at particular positions within human VKappa sequences (VK1-13, VK2-28, VK4-1) and at corresponding positions in the camelid (*L. glama*) sequence with closest homology to each human Vkappa sequence. (A) % amino acid utilisation at particular Kabat positions in FR1 and CDR1 (dashed section). (B) % amino acid utilisation at particular Kabat positions in FR2, CDR2, FR3 and CDR3.

FIG. 31—shows % utilisation of different amino acid residues at particular positions within a human VL1 sequence (VL1-44) and at corresponding positions in the camelid (*L. glama*) sequence with closest homology to the human sequence.

FIG. 32—shows % utilisation of different amino acid residues at particular positions within particular human VL2 sequences (VL2-11 and VL2-18) and at corresponding positions in the camelid (*L. glama*) sequence with closest homology to each human sequence. (A) selected positions in CDR1, FR1, CDR2 and FR2. (B) selected positions in FR2 and CDR3.

FIG. 33—shows % utilisation of different amino acid residues at particular positions within particular human VL3 sequences (VL3-19 and VL3-25) and at corresponding positions in the camelid (*L. glama*) sequence with closest homology to each human sequence. (A) selected positions in CDR1, FR1, and CDR2. (B) selected positions in FR2, CDR3 and FR3.

FIG. 34—shows % utilisation of different amino acid residues at particular positions within a human VL5 sequence (VL5-37) and at corresponding positions in the camelid (*L. glama*) sequence with closest homology to the human sequence.

FIG. 35—shows % utilisation of different amino acid residues at particular positions within a human VL8 sequence (VL8-61) and at corresponding positions in the camelid (*L. glama*) sequence with closest homology to the human sequence.

FIG. 36—shows % utilisation of different amino acid residues at particular positions within a human VH1 sequence (VH1-46) and at corresponding positions in the camelid (*L. glama*) sequence with closest homology to the human sequence.

FIG. 37—shows % utilisation of different amino acid residues at particular positions within selected human VH3 sequences (VH3-21, VH3-48, VH3-23, VH3-66, VH3-11) and at corresponding positions in the camelid (*L. glama*) sequence with closest homology to the human sequence. (A). Selected positions with FR1, CDR1 and FR2. (B) Selected positions with CDR2. (C) Selected positions within FR3.

FIG. 38—shows % utilisation of different amino acid residues at particular positions within a human VH4 sequence (VH4-30-4) and at corresponding positions in the camelid (*L. glama*) sequence with closest homology to the human sequence.

FIG. 39—shows % utilisation of different amino acid residues at particular positions within a human germline sequence (HJ3) and at corresponding positions in the camelid (*L. glama*) sequence with closest homology to the human sequence.

FIG. 40—shows % utilisation of different amino acid residues at particular positions within a human VH1 sequence (VH1-46) and at corresponding positions in the camelid (*L. pacos*) sequence with closest homology to the human sequence.

FIG. 41—shows % utilisation of different amino acid residues at particular positions within a human VH3 sequence (VH3-48 and VH3-66) and at corresponding positions in the camelid (*L. pacos*) sequence with closest homology to the human sequence. (A) selected positions within FR1, CDR1, FR2 and CDR2. (B) Selected positions within CDR2 and FR3.

FIG. 42—shows % utilisation of different amino acid residues at particular positions within a human VH4 sequence (VH4-30-4) and at corresponding positions in the camelid (*L. pacos*) sequence with closest homology to the human sequence.

DETAILED DESCRIPTION OF THE INVENTION

Figure 1:
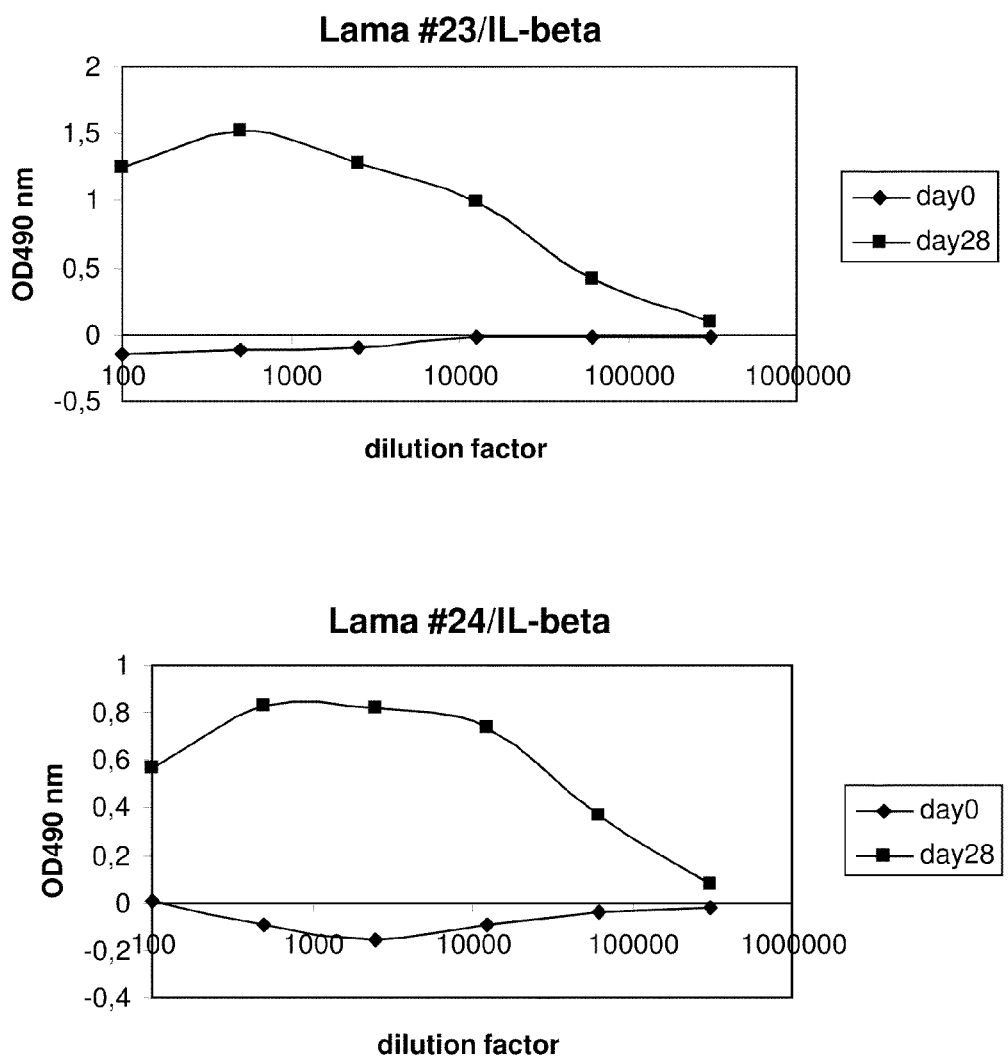
FIG. 1—shows the results of an ELISA in which sera from llamas immunised with IL1-Beta were tested for the presence of antibodies against IL1-Beta, on day 0 and day 28 following immunisation.

The invention relates to humanized antibodies, having specificity for a desired target antigen, derived from the conventional antibody repertoire of species in the family Camelidae.

Thus, in a first aspect the invention provides an antibody, and more particularly a humanized variant of a camelid-derived antibody, comprising a camelid VH domain and a camelid VL domain of either the lambda light chain class (Vλ) or the kappa light chain class (Vκ), characterised in that at least one amino acid substitution is present in said VH domain and/or said VL domain, said amino acid substitution(s) being selected from the following:

(a) amino acid substitution(s) in said camelid VH domain, wherein an amino acid at one or more positions selected from the group consisting of H1, H5, H7, H11, H12, H13, H14, H29, H30, H37, H40, H48, H67, H68, H69, H71, H74, H77, H78, H80, H81, H82b, H83, H84, H85, H86, H89, H93, H94 and H108 of the camelid VH domain, according to Kabat, is replaced with an amino acid found at the corresponding position in a human VH domain sequence; and (b) amino acid substitutions in said camelid VL domain, wherein for a camelid VL domain of the lambda light chain class (Vλ) an amino acid at one or more positions selected from the group consisting of L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 and L103 of the camelid Vλ domain, according to Kabat, is replaced with an amino acid found at the corresponding position in a human Vλ domain sequence; and for a camelid VL domain of the kappa light chain class (Vκ) an amino acid at one or more positions selected from the group consisting of K1, K3, K4, K7, K9, K11, K12, K13, K14, K15, K18, K19, K36, K42, K43, K45, K46, K58, K63, K70, K77, K78, K79, K80, K83, K100, K103, K104 and K106 of the camelid Vκ domain, according to Kabat, is replaced with an amino acid found at the corresponding position in a human Vκ domain sequence.

In the following passages different aspects of the invention are defined in more detail. Each aspect so-defined may be combined with any other aspect or aspects unless clearly indicated to the contrary. In particular, any feature indicated as being preferred or advantageous may be combined with any other feature or features indicated as being preferred or advantageous.

Definitions

The term "antibody" is used in the broadest sense to cover monoclonal antibodies (including full length monoclonal antibodies), polyclonal antibodies, multispecific antibodies (e.g., bispecific antibodies), antibody fragments, immunoadhesins and antibody-immunoadhesin chimeras, that specifically recognizes a target antigen. Non-limiting examples of antibody fragments include single variable domains (VH, VL or Vκ) (Skerra A. and Pluckthun, A. (1988) Science 240: 1038-41), single chain antibodies (e,g, scFv) (Bird, R. E. et al. (1988) Science 242:423-26; Huston, J. S. et al. (1988) Proc. Natl. Acad. Sci. USA 85:5879-83), Fab, (Fab')2 or other fragments well known to a person skilled in the art.

The VL domains in the antibodies of the invention may be of the VLambda type or the Vkappa type. Unless otherwise stated, term "VL domain" is used herein in a generic sense and refers to both variable domains of immunoglobulin light chains of the kappa type (Vκ) and variable domains of immunoglobulin light chains of the lambda type (Vλ). The terms "camelid VL domain" and "camelid-derived VL domain" refer to VL domains (or either the Vκ type or the Vλ type, unless otherwise stated) isolated from camelid species, and engineered variants thereof which contain one or more amino acid substitutions, insertions or deletions relative to a native camelid VL domain.

The term "camelid VH domain" refers to the VH domain of any known heavy chain isotype of camelids, including γ, ε, δ, α or μ isotypes, as well as engineered variants thereof which contain one or more amino acid substitutions, insertions or deletions relative to a native camelid VH domain. The term "camelid VH domain" refers only to VH domains of camelid conventional antibodies and does not encompass camelid VHH domains.

The terms "camelid VH domain" or "camelid VL domain" refer to a VH or VL domain, respectively comprising an amino acid sequence encoded by a conventional Camelidae immunoglobulin variable region gene sequence. The conventional Camelidae immunoglobulin gene sequences encoding the camelid VH and/or VL domains (lambda or kappa light chain) can be obtained from naturally occurring immunoglobulin genes (including, without limitation, germline, rearranged or somatically mutated immunoglobulin genes obtained from camelids, e.g., a camelid immunized with a desired antigen), or from synthetic genes derived from naturally occurring conventional Camelidae immunoglobulin gene sequences (including, without limitation, naturally occurring Camelidae immunoglobulin genes that have been altered to contain "heterologous CDR or framework region sequences", or ab initio generated immunoglobulin genes that comprise consensus sequences or chimeras of naturally occurring conventional Camelidae immunoglobulin gene sequences). The term "camelid VH domain" does not encompass a Camelidae VHH domain.

The term "heterologous CDR or framework region sequences" encompasses any CDR or framework region amino acid sequence alteration that is made in a camelid VH or VL (Vλ/Vκ) domain.

The term "corresponding position" refers to the amino acid at the same numbered position in a human VH or VL (Vλ or Vκ) domain sequence according to the numbering system set forth in Kabat et al., Sequences of Proteins of Immunological Interest, 5th Ed. Public Health Service, National Institutes of Health, Bethesda, Md., 1983, which is hereby incorporated by reference in its entirety.

The term "human VH domain sequence" broadly encompasses any antibody heavy chain variable region sequence, or portion thereof, encoded by a human germline, plus derivatives thereof. Suitable, non-limiting examples of human VH domain sequences include human heavy-chain germline V, D and/or J region sequences, mature human VH domain sequences, including somatically mutated VH domains, and consensus human germline or mature human VH domain sequences, or portions thereof. The term "human VL domain sequence" is similarly defined. Suitable, non-limiting examples of consensus sequences, and methods of making the same, are described in US648213.

The term "derived from" refers to the degree of homology between mature variable region amino acid sequences from an organism and the germline-encoded V, D and/or J region amino acid sequences from that same organism. A variable region with the highest degree of homology to a particular germline-encoded V, D and/or J region amino acid sequence is considered to be "derived from" that germline sequence.

The term "germline sequence" refers to an amino acid sequence encoded by unrearranged immunoglobulin V, D and/or J regions, or portions thereof, present in the genomic DNA of an organism.

References may be made herein to a camelid VH or VL (Vλ or Vκ) domain belonging to a certain family or matching to a certain family member. Unless otherwise stated, camelid VH and VL (Vλ or Vκ) domains are "assigned" to a particular family or family member based on alignment to human VH or VL (Vλ or Vκ) domain sequences of a defined family or a specific family member. Therefore, a camelid VH domain which aligns most closely to VH domains of the human VH3 family (as opposed to VH1, VH2 or VH4, etc.) may be identified herein as a "camelid VH3 domain". A camelid VH domain which aligns most closely to VH domains of the human VH1 family would be referred to herein as a "camelid VH1 domain". A camelid VH domain which aligns most closely to VH domains of the human VH4 family would be referred to herein as a "camelid VH4 domain". Similarly, unless otherwise stated, camelid VL (Vλ or Vκ) domains are assigned to a particular class based on alignment to human VL (Vλ or Vκ) domains of known family or a family member. Therefore, camelid VL domains which align most closely to human VL domains of the Kappa class may be referred to herein as "camelid Vκ domains", abbreviated as "Vκ", whereas camelid VL domains which align most closely to human VL domains of the Lambda class may be referred to herein as "camelid VLambda domains", abbreviated "Vλ".

Within the classification of VKappa domains, camelid Vκ domains may be assigned to a particular subclass on the basis of alignment to the closest human subclass. Accordingly, camelid Vκ domains which align most closely to human Vκ1, Vκ2 and Vκ4 may respectively be referred to herein as "camelid Vκ1, camelid Vκ2 and camelid Vκ4" domains.

Camelid VH and VL (Vλ or Vκ) domains may also be classified on the basis of the closest matching human germline sequence. Hence, by way of example, a camelid VH domain which aligns most closely to the human VH3-23 germline may be referred to herein as a camelid VH3-23 domain, etc. Similarly, a camelid Vκ domain which aligns most closely to the human Vκ1-46 germline may be identified herein as a camelid W1-46 domain.

In addition FR4 regions encoded by the J segment of heavy or kappa/lambda light chain domains may also be classified on the basis of the closest matching human germline. Hence, by way of example, a FR4 of a Camelid heavy chain variable domain which aligns most closely to human JH3 germline may be referred to herein as a Camelid JH3 region and the C-terminal part encoding the FR4 is in particular of interest for humanization or germlining.

The camelid species are known to possess two different types of antibodies; the classical or "conventional" antibodies and also the heavy-chain antibodies.

As used herein, the term "conventional antibody" refers to antibodies of any isotype, including IgA, IgG, IgD, IgE or IgM. Native or naturally occurring "conventional" camelid antibodies are usually heterotetrameric glycoproteins, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end (N-terminal) a variable domain (VH) followed by a number of constant domains. Each light chain has a variable domain (VL) at one end (N-terminal) and a constant domain (CL) at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "heavy-chain antibody" refers to the second type of antibodies known to occur naturally in camelid species, such antibodies being naturally devoid of light chains (Hamers-Casterman, et al. Nature. 1993; 363; 446-8). The heavy-chain antibodies (abbreviated to HCAb) are composed of two heavy chains linked by a covalent disulphide bond. Each heavy chain in the HCAb has a variable domain at one end. The variable domains of HCAbs are referred to as "VHH" in order to distinguish them from the variable domains of the heavy chains of "conventional" camelid antibodies (VH). The VHH domains and VH domains are entirely distinct and are encoded by different gene segments in the camelid genome.

The first, second and third hypervariable loops of the VLambda light chain domain are referred to herein as L1(λ), L2(λ) and L3(λ) and may be defined as comprising residues 24-34 (L1(λ), 50-56 (L2(λ),and 89-97 (L3(λ) in the VL domain (numbering residues according to Kabat; definitions CDRs according to Chothia (see world wide web dot bioinf dot org dot uk/abs/#cdrdef). The first, second and third hypervariable loops of the VKappa light chain domain are referred to herein as L1(κ), 2(κ) and L3(κ) and may be defined as comprising residues 24-34 (L1(κ), 50-56 (L2(κ) and 89-97 (L3(κ) in the VKappa domain (numbering residues according to Kabat; definitions CDRs according to Chothia (see world wide web dot bioinf dot org dot uk/abs/#cdrdef). The first, second and third hypervariable loops of the VH domain are referred to herein as H1, H2and H3 and may be defined as comprising residues 26-32.34 (H1), 52-56 (H2) and 95-102 (H3, highly variable in length) in the VH domain (numbering residues according to Kabat; CDR definitions according to Kabat (see world wide web dot bioinf dot org dot uk/abs/#cdrdef)

Unless otherwise indicated, the terms L1, L2 and L3 respectively refer to the first, second and third hypervariable loops of a VL domain, and encompass hypervariable loops obtained from both VKappa and VLambda isotypes from Camelida. The terms H1, H2 and H3 respectively refer to the first, second and third hypervariable loops of the VH domain, and encompass hypervariable loops obtained from any of the known heavy chain isotypes from Camelida, including γ, ε, Y, α or μ.

The hypervariable loops L1, L2, L3, H1, H2 and H3 may each comprise part of a "complementarity determining region" or "CDR". The terms "hypervariable loop" and "complementarity determining region" are not strictly synonymous, since the hypervariable loops (HVs) are defined on the basis of structure (referred to as Chothia definition in the webpage world wide web dot bioinf dot org dot uk/abs/#cdrdef, whereas complementarity determining regions (CDRs) are defined based on sequence variability (referred to as Kabat definition on previously mentioned webpage; Kabat et al., Sequences of Proteins of Immunological Interest, 5th Ed. Public Health Service, National Institutes of Health, Bethesda, Md., 1983) and the limits of the HVs and the CDRs may be different in some VH and VL domains. The definitions of the CDRs according to Kabat (sequence variability), Chothia (structure), AbM or on the basis of contacts can be found on the earlier mentioned website of Andrew C. R. Martin's Bioinformatics Group at UCL (world wide web dot bioinf dot org dot uk/abs/#cdrdef.

The CDRs of the VLambda domains can typically be defined as comprising the following amino acids: residues 24-34 (L1(λ), consisting of 11, 12, 13 or 14 amino acid residues in human VLambda germlines), residues 50-56 (L2 (λ), consisting of 7, 11 or 12 residues in human VLambda germlines) and residues 89-97 (L3(λ), consisting of between 9 and 11 residues in the majority of somatically mutated human antibodies (Knappik et al., J. Mol. Biol. 296:57-86 (1999))); numbering according to Kabat.

The CDRs of the VKappa domains can typically be defined as comprising the following amino acids: residues 24-34 (L1(κ), consisting of 11, 12, 16 or 17 residues in human VKappa germlines), 50-56 (L2(κ), consisting of 7 residues in human VKappa germlines) and 89-97 (L3(κ), consisting of 10 residues in the majority of somatically mutated human antibodies (Knappik et al., J. Mol. Biol. 296:57-86 (1999))); numbering according to Kabat. The CDRs of the VH domains can typically be defined as comprising the following amino acids: residues 31-35B (H1, consisting of 5, 6 or 7 residues as present in human germline VH), 50-65 (H2, consisting of 16, 17, 18 or 19 residues as present in human germline VH) and 95-102 (H3, highly variable in length) in the VH domain; numbering according to Kabat. Thus, the HVs may be comprised within the corresponding CDRs and references herein to the "hypervariable loops" of VH and VL domains should be interpreted as also encompassing the corresponding CDRs, and vice versa, unless otherwise indicated. During the analysis of the somatically mutated and germline VH, as well as somatically mutated VKappa and VLambda sequences (Tables 1 to 37) the definitions of CDRs according to Kabat (based on variability) were applied.

The more highly conserved portions of variable domains are called the framework region (FR). The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

The constant domains are not involved directly in binding of an antibody to an antigen, but exhibit various effector functions, such as participation of the antibody in antibody-dependent cellular toxicity (ADCC), complement-dependent cytotoxicity (CDC), antibody dependent cellular phagocytosis (ADCP) or FcRn binding.

In all aspects and embodiments of the invention, the Camelidae (or camelid) species (from which the hypervariable loops or CDRs of the antigen binding polypeptide of the invention are obtained) can be camel, llama, dromedary, vicunia, guanaco or alpaca and any crossings thereof. Llama (*Lama glama*), alpaca (*Lama pacos*) and dromedary (*Camelus dromedarius*) are the preferred Camelidae species for all aspects of the invention.

By "hypervariable loop or complementarity determining region obtained from a VH domain or a VL domain of a species in the family Camelida" is meant that that hypervariable loop (HV) or CDR has an amino acid sequence which is identical, or substantially identical, to the amino acid sequence of a hypervariable loop or CDR which is encoded by a Camelidae immunoglobulin gene. In this context "immunoglobulin gene" includes germline genes, immunoglobulin genes which have undergone rearrangement, and also somatically mutated genes. Thus, the amino acid sequence of the HV or CDR obtained from a VH or VL domain of a Camelidae species may be identical to the amino acid sequence of a HV or CDR present in a mature Camelidae conventional antibody. The term "obtained from" in this context implies a structural relationship, in the sense that the HVs or CDRs of the humanised antibodies of the invention embody an amino acid sequence (or minor variants thereof) which was originally encoded by a Camelidae immunoglobulin gene. However, this does not necessarily imply a particular relationship in terms of the production process used to prepare the antigen binding polypeptide of the invention. As will be discussed below, there are several processes which may be used to prepare humanised antibodies comprising HVs or CDRs with amino acid sequences identical to (or substantially identical to) sequences originally encoded by a Camelidae immunoglobulin gene.

For the avoidance of doubt, the terms "VH domain of a conventional antibody of a camelid" and "VH domain obtained from a species of Camelida" are used synonymously and encompass VH domains which are the products of synthetic or engineered recombinant genes (including codon-optimised synthetic genes), which VH domains have an amino acid sequence identical to (or substantially identical to) the amino acid sequence of a VH domain encoded by a Camelidae immunoglobulin gene (germline, rearranged or somatically mutated). Similarly, the terms "VL domain of a conventional antibody of a camelid" and "VL domain obtained from a species of Camelida" are used synonymously and encompass VL domains which are the products of synthetic or engineered recombinant genes (including codon-optimised synthetic genes), which VL domains have an amino acid sequence identical to (or substantially identical to) the amino acid sequence of a VL domain encoded by a Camelidae immunoglobulin gene (germline, rearranged or somatically mutated).

The humanised antibodies of the invention are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

The humanised antibodies of the invention are not naturally occurring human antibodies, specifically human autoantibodies, due to the presence of at least a camelid VH domain and/or a camelid VL domain. The term "naturally occurring human antibody" refers to an antibody which is naturally expressed within a human subject. Antibodies having an amino acid sequence which is 100% identical to the amino acid sequence of a naturally occurring human antibody, or a fragment thereof, which natural antibody or fragment is not chimeric and has not been subject to any engineered changes in amino acid sequence (excluding somatic mutations) are excluded from the scope of the invention.

Humanisation of Camelid VH and VL Domains

Is has been recognised that the conventional antibody repertoire of camelids provide an advantageous starting point for the preparation of antibodies with utility as human therapeutic agents due to the following factors, discussed in U.S. Ser. No. 12/497,239 which is incorporated herein by reference:
1) High % sequence homology between camelid VH and VL domains and their human counterparts;
2) High degree of structural homology between CDRs of camelid VH and VL domains and their human counterparts (i.e. human-like canonical fold structures and human-like combinations of canonical folds).

The utility of antibodies comprising camelid VH and/or camelid VL domains for human therapy can be improved still further by "humanisation" of natural camelid VH and VL domains, for example to render them less immunogenic in a human host. The overall aim of humanisation is to produce a molecule in which the VH and VL domains exhibit minimal immunogenicity when introduced into a human subject, whilst retaining the specificity and affinity of the antigen binding site formed by the parental VH and VL domains.

One approach to humanisation, so-called "germlining", involves engineering changes in the amino acid sequence of a camelid VH or VL domain to bring it closer to the sequence of a human VH or VL domain.

Determination of homology between a camelid VH (or VL) domain and human VH (or VL) domains is a critical step in the humanisation process, both for selection of camelid amino acid residues to be changed (in a given VH or VL domain) and for selecting the appropriate replacement amino acid residue(s).

An approach to humanisation was developed based on alignment of a large number of novel camelid VH (and VL) domain sequences, typically somatically mutated VH (or VL) domains which are known to bind a target antigen, with human germline VH (or VL) sequences, human VH (and VL) consensus sequences, as well as germline sequence information available for *llama pacos*. This approach allowed the identification of certain residues within camelid VH (or VL) domains which typically show mismatches with human germline VH (or VL) domains as candidate residues for substitution. Large numbers of V domains of somatically mutated antibodies generated in *Lama glama* were aligned with germline encoded framework residues (and complementarity determining residues) deviating from the human germline, to which these most optimally align, were identified and preferred mutations for humanization or germlining were identified. Additionally deviations introduced by somatic mutations, which in the majority of the other camelid family members were identical to the human germline, were recognized and these were classified as less preferred mutations.

The following passages outline the principles applied to (i) select "camelid" amino acid residues for replacement and (ii) select replacement "human" amino acid residues to substitute in, when humanising any given camelid VH (or VL) domain.

Outline of Humanisation Approach

Step 1. Select human (germline) family and member of this family that shows highest homology/identity to the mature camelid sequence to be humanised. A general procedure for identifying the closest matching human germline for any given camelid VH (or VL) domain is outlined below.

Step 2. Select specific human germline family member used to germline against. Preferably this is the germline with the highest homology or another germline family member from the same family.

Step 3. Identify the preferred positions considered for germlining on the basis of the table of amino acid utilisation for the camelid sequence that is closest to the selected human germline.

Step 4. Try to change amino acids in the camelid sequence that deviate from the closest human germline; germlining of FR residues is preferred over CDR residues.

a. Preferred are positions that are deviating from the selected human germline used to germline against, for which the amino acid found in the camelid sequence does not match with the selected germline and is not found in other germlines of the same subclass (both for V as well as for J encoded FR amino acids).

b. Positions that are deviating from the selected human germline family member but which are used in other germlines of the same family may also be addressed in the germlining process.

c. Additional mismatches (e.g. due to additional somatic mutations) towards the selected human germline may also be addressed.

The following approach may be used to determine the closest matching human germline for a given camelid VH (or VL) domain:

Before analyzing the percentage sequence identity between Camelidae and human germline VH and VL, the canonical folds may first be determined, which allows the identification of the family of human germline segments with the identical combination of canonical folds for H1 and H2 or L1 and L2 (and L3). Subsequently the human germline family member that has the highest degree of sequence homology with the Camelidae variable region of interest may be chosen for scoring sequence homology. The determination of Chothia canonical classes of hypervariable loops L1, L2, L3, H1 and H2 can be performed with the bioinformatics tools publicly available on webpage world wide web dot bioinf dot org dot uk/abs/chothia dot html dot page www.bioinf.org.uk/abs/chothia.html.page. The output of the program shows the key residue re-quirements in a datafile. In these datafiles, the key residue positions are shown with the allowed amino acids at each position. The sequence of the variable region of the antibody is given as in-put and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815(1996)). The boundaries of the individual framework regions may be assigned using the IMGT numbering scheme, which is an adaptation of the numbering scheme of Chothia (Lefranc et al., NAR 27: 209-212 (1999); world wide web dot imgt dot cines dot fr).

With the particular human germline V segment known, which uses the same combination of canonical folds for H1 and H2 or L1 and L2 (and L3), the best matching family member in terms of sequence homology can be determined. The percentage sequence identity between Camelidae VH and VL domain framework amino acid sequences and corresponding sequences encoded by the human germline can be determined using bioinformatic tools, but manual alignment of the sequences could also be used. Human immunoglobulin sequences can be identified from several protein data bases, such as VBase (world wide web dot vbase.mrc-cpe.ca-m.ac.uk/ or the Pluckthun/Honegger database (world wide web dot unizh dot ch/antibody/Sequences/Germlines. To compare the human sequences to the V regions of Camelidae VH or VL domains a sequence alignment algorithm such as available via websites like world wide web dot expasy dot ch/tools#align can be used, but also manual alignment can also be performed with a limited set of sequences. Human germline light and heavy chain sequences of the families with the same combinations of canonical folds and with the highest degree of homology with the framework regions 1, 2, and 3 of each chain may be selected and compared with the Camelidae variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences in FR1). However, for the purposes of humanization, residues in framework regions identical to members of other human germline families, which do not have the same combination of canonical folds, can be considered for humanization, despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)).

Core Lists of Amino Acid Positions for Humanisation

Based on sequence alignment of mature camelid VH and VL domains to consensus human germline VH/VL sequences, and also alignments to the closest aligning human germline sequences, the following residues in camelid VH domains and VL domains have been identified as candidates for substitution:

H1, H5, H7, H11, H12, H13, H14, H29, H30, H37, H40, H48, H67, H68, H69, H71, H74, H77, H78, H80, H81, H82b, H83, H84, H85, H86, H89, H93, H94 or H108 of the camelid VH domain, numbering according to Kabat;

L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 or L103 of the camelid VLambda domain, numbering according to Kabat.

K1, K3, K4, K7, K9, K11, K12, K13, K14, K15, K18, K19, K36, K42, K43, K45, K46, K58, K63, K70, K77, K78, K79, K80, K83, K100, K103, K104 or K106 of the camelid VKappa domain, numbering according to Kabat.

These lists should be viewed as a core set of camelid VH framework amino acid positions and a core set of camelid VLambda and VKappa framework amino acid positions which can be considered for change when germlining towards a specific human germline which is the closest aligning human germline for the camelid VH or VLambda or VKappa domain one intends to humanise. The amino acid positions within each core set all occur in framework regions, FR1, FR2, FR3, or FR4.

Accordingly, the present invention provides an antibody comprising a camelid VH domain in which the natural amino acid at one or more of positions H1, H5, H7, H11, H12, H13, H14, H29, H30, H37, H40, H48, H67, H68, H69, H71, H74, H77, H78, H80, H81, H82b, H83, H84, H85, H86, H89, H93, H94 or H108, according to Kabat, is substituted for an amino acid other than that which is naturally found at that position in the camelid VH domain. In particular, the amino acid(s) at one or more of H1, H5, H7, H11, H12, H13, H14, H29, H30, H37, H40, H48, H67, H68, H69, H71, H74, H77, H78, H80, H81, H82b, H83, H84, H85, H86, H89, H93, H94 or H108 may be substituted for an amino acid found at the corresponding position in a human VH domain sequence.

The invention also provides antibodies comprising a camelid VLambda domain (Vλ in which the natural amino acid at one or more of positions L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 or L103, according to Kabat, is substituted for an amino acid other than that which is naturally found at that position in the camelid VLambda domain. In particular, the amino acid(s) at one or more of L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 or L103 may be substituted for an amino acid found at the corresponding position in a human VLambda domain sequence.

The invention also provides antibodies comprising a camelid VKappa domain (Vκ) in which the natural amino acid at one or more of positions K1, K3, K4, K7, K9, K11, K12, K13, K14, K15, K18, K19, K36, K42, K43, K45, K46, K58, K63, K70, K77, K78, K79, K80, K83, K100, K103, K104 or K106, according to Kabat, is substituted for an amino acid other than that which is naturally found at that position in the camelid VKappa domain.

In particular, the amino acid(s) at one or more of K1, K3, K4, K7, K9, K11, K12, K13, K14, K15, K18, K19, K36, K42, K43, K45, K46, K58, K63, K70, K77, K78, K79, K80, K83, K100, K103, K104 or K106 may be substituted for an amino acid found at the corresponding position in a human VKappa domain sequence.

Antibodies according to the invention may comprise a camelid VH domain containing amino acid substitution(s) at any one or more of the VH amino acid positions in the core list set out above, in combination with a camelid VLambda or VKappa domain containing amino acid substitution(s) at any one or more of the VLambda or VKappa amino acid positions in the core list set out above.

The amino acid to be substituted in at each of positions H1, H5, H7, H11, H12, H13, H14, H29, H30, H37, H40, H48, H67, H68, H69, H71, H74, H77, H78, H80, H81, H82b, H83, H84, H85, H86, H89, H93, H94 or H108 in the core list can be any amino acid which is a) not the natural amino acid at that position in the starting camelid VH domain and b) is found at the corresponding position in one or more human VH domain sequences.

Similarly, the amino acid to be substituted in at each of positions L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 or L103 in the core list can be any amino acid which is a) not the natural amino acid at that position in the starting camelid VLambda domain and b) is found at the corresponding position in one or more human VLambda domain sequences.

Similarly, the amino acid to be substituted in at each of positions K1, K3, K4, K7, K9, K11, K12, K13, K14, K15, K18, K19, K36, K42, K43, K45, K46, K58, K63, K70, K77, K78, K79, K80, K83, K100, K103, K104 or K106 in the core list can be any amino acid which is a) not the natural amino acid at that position in the starting camelid VKappa domain and b) is found at the corresponding position in one or more human VKappa domain sequences.

Germlining of Camelid VH or VL Towards Particular VH or VL Classes or Subclasses Further sets of amino acid residues have been identified which are particularly relevant for germlining camelid VH or VL domains towards a particular human germline class or subclass. Accordingly, in particular embodiments the invention provides the following:

An antibody comprising a camelid VH domain with homology to a human VH3 domain, wherein the amino acid at one or more of positions H1, H5, H13, H14, H29, H37, H40, H74, H77, H78, H83, H84, H86 or H94 of the camelid VH domain, according to Kabat, is replaced with an amino acid found at the corresponding position in a human VH3 domain sequence.

An antibody comprising a camelid VH domain with homology to a human VH1 domain, wherein the amino acid at one or more of positions H1, H7, H11, H12, H13, H69, H71, H78, H80 or H86 of the camelid VH domain, according to Kabat, is replaced with an amino acid found at the corresponding position in a human VH1 domain sequence.

An antibody comprising a camelid VH domain with homology to a human VH4 domain, wherein the amino acid at one or more of positions H1, H30, H48, H67, H68, H71, H81, H84, H85 or H86 of the camelid VH domain, according to Kabat, is replaced with an amino acid found at the corresponding position in a human VH4 domain sequence.

An antibody comprising a camelid VLambda domain with homology to a human Vλ1 domain, wherein the amino acid at one or more of positions L11, L14, L18, L19, L69, L74, L76 or L80 of the camelid VLambda domain, according to Kabat, is replaced with an amino acid found at the corresponding position in a human VL1 domain sequence.

An antibody comprising a camelid VLambda domain with homology to a human Vλ2 domain, wherein the amino acid at one or more of positions L8, L14, L15, L17, L18, L39, L42, L47, L58, L59 or L80 of the camelid VLambda domain, according to Kabat, is replaced with an amino acid found at the corresponding position in a human Vλ2 domain sequence.

An antibody comprising a camelid VLambda domain with homology to a human Vλ3 domain, wherein the amino acid at one or more of positions L1, L2, L3, L5, L7, L8, L9, L11, L14, L15 L19, L20, L60, L66, L69, L70, L71, L72, L76, L78 or L84 of the camelid VLambda domain, according to Kabat, is replaced with an amino acid found at the corresponding position in a human Vλ3 domain sequence.

An antibody comprising a camelid VLambda domain with homology to a human Vλ5 domain, wherein the amino acid at one or more of positions L2, L11, L17, L19, L40, L70, L72 or L80 of the camelid VLambda domain, according to Kabat, is replaced with an amino acid found at the corresponding position in a human Vλ5 domain sequence.

An antibody comprising a camelid VLambda domain with homology to a human Vλ8 domain, wherein the amino acid at one or more of positions L2, L11, L60, L67, L80, L81 or L84 of the camelid VLambda domain, according to Kabat, is replaced with an amino acid found at the corresponding position in a human Vλ8 domain sequence.

An antibody comprising a camelid VKappa domain with homology to a human Vκ1 domain, wherein the amino acid at one or more of positions K1, K4, K11, K12, K13, K15, K42, K43, K70, K77, K79, K80 or K83 of the camelid VKappa domain, according to Kabat, is replaced with an amino acid found at the corresponding position in a human Vκ1 domain sequence.

An antibody comprising a camelid VKappa domain with homology to a human Vκ2 domain, wherein the amino acid at one or more of positions K7, K9, K12, K14, K18, K36, K46, K63, K77, K79 or K83 of the camelid VKappa domain, according to Kabat, is replaced with an amino acid found at the corresponding position in a human Vκ2 domain sequence.

An antibody comprising a camelid VKappa domain with homology to a human Vκ4 domain, wherein the amino acid at one or more of positions K9, K11, K12, K13, K15, K18, K19, K39, K43, K45, K58, K68, K78, K80 or K83 of the camelid VKappa domain, according to Kabat, is replaced with an amino acid found at the corresponding position in a human Vκ4 domain sequence.

Rationale for Selection of Replacement Amino Acids

In order to select appropriate replacement amino acids to be substituted in to the camelid VH (or Vλ or Vκ) domain at an amino acid position selected for replacement, one can again refer to alignments of the camelid VH (or Vλ or Vκ) domain amino acid sequence with amino acid sequences of human VH (or Vλ or Vκ) domains, typically human germline VH (or Vλ or Vκ) sequences as well germline JH (or Jλ or Jκ) sequences, or consensus sequences for a particular VH (or Vλ or Vκ) family or member of that family.

Several different approaches can be taken to select "human" residues to replace the natural camelid amino acid residues at one or more of the positions identified herein. First, one can select replacement human amino acid residues which are found at the corresponding position in the closest matching/aligning human germline VH or Vλ or Vκ domain, or at least a human germline which is a very close match for the starting camelid VH or Vλ or Vκ, this preferably being a member of the same family or member of that family as the closest matching human germline sequence. An algorithm for selection of the closest matching human germline sequence for any given camelid VH or Vλ or Vκ domain is set out above.

Second, one can select replacement human residues from the most frequently used human germlines for the VH or Vλ or Vκ family or family member to which the camelid VH/Vλ/Vκ domain is assigned. For example, if a camelid VH domain is identified as belonging to the VH3 family, then the most commonly used human VH3 germline family member, V3-23, can be used as a source of replacement amino acid residues. Sequence alignment is used to identify the human residue equivalent to the amino acid residue to be replaced in the camelid VH/Vλ/Vκ domain sequence. Tables 1 to 3 below list preferred human VH, VLambda and VKappa germlines as a source of replacement human amino acid residues for camelid VH/Vλ/Vκ domains belonging to particular families or family members.

TABLE 1

| Preferred VH germlines: | |
|---|---|
| Camelid sequence Homology to human | preferred human VH germline |
| VH3 family | 3-23, 3-66, 3-74, 3-48, 3-53, 3-21, 3-11, 3-20, 3-7, 3-15, 3-13 |
| VH4 family | 4-30, 4-31, 4-59, 4-61, 4-39, 4-b, 4-28, 4-34, 4-4 |
| VH1 family | 1-46, 1-18, 1-3, 1-49, 1-15, 3-73, 3-15, 3-49 |

TABLE 2

| Preferred VKappa germlines | |
|---|---|
| Camelid sequence homology to human | preferred human Vκ germline |
| Vκ2 family | 2D-29, 2-28, 2-29, 2-40, 2-30, 2-D40, 4-1, 3-20 |
| Vκ1 family | 1-13, 1-27, 1-39, 1-6, 1-5, 1-33, 1-8, 1-9, 1-17, 1-12, 4-1, 3-20 |
| Vκ4 family | 4-1, 2-40, 2-D40, 1-12, 1-13, 1-D12, 1-27, 3-20, 3D-7, 2D-29, 1D-39, 3-15 |

TABLE 3

| Preferred VLambda germlines | |
|---|---|
| Camelid sequence homology to human | preferred human Vλ germline |
| Vλ1 family | 1-44, 1-47, 1-51, 1-36, 1-40, 2-18 |
| Vλ2 family | 2-18, 2-11, 2-8,, 2-14, 2-23, 1-44, 1-47, 1-51, 1-40 |
| Vλ3 family | 3-19, 3-25, 3-27, 3-9, 3-10, 3-16, 3-21, 3-1, 3-11, 2-29, 4-1 |
| Vλ5 family | 5-37, 5-39, 5-45, 5-52, 4-60, 1-13, 1-17, 1-39 |
| Vλ8 family | 8-61, 7-46, 7-43, 2-16, 1-13, 1-5, 3-10, 3-19 |

Finally, in a third approach one can select replacement human amino acid residues from any other human germline VH or Vλ or Vκ domain sequence, including VH or Vλ or Vκ domains from another germline family. In this case, overall sequence homology between the starting camelid VH domain and the selected human VH germline may be less of a consideration; it may be sufficient merely that the replacement residue is one which is found in a human germline, possibly in a similar local sequence context.

A combination of the above-listed approaches can be used within single camelid VH or Vλ or Vκ domain; it is permitted to mix and match replacement residues taken from two or more different human germlines. For any given camelid VH or Vλ or Vκ domain, the decision whether or not to replace the native camelid residues at one or more of the positions identified herein, particularly amino acid positions on the core lists (H1, H5, H7, H11, H12, H13, H14, H29, H30, H37, H40, H48, H67, H68, H69, H71, H74, H77, H78, H80, H81, H82b, H83, H84, H85, H86, H89, H93, H94 or H108 of the camelid VH domain; L1, L2, L3, L7, L8, L9, L11, L14, L15, L17, L18, L19, L20, L38, L39, L40, L42, L44, L46, L47, L49, L58, L59, L60, L66, L67, L69, L70, L71, L72, L74, L76, L78, L80, L84 or L103 of the camelid VLambda domain; K1, K3, K4, K7, K9, K11, K12, K13, K14, K15, K18, K19, K36, K42, K43, K45, K46, K58, K63, K70, K77, K78, K79, K80, K83, K100, K103, K104 or K106 of the camelid Vκ domain) may be determined on a case-by-case basis.

When humanising given VH or Vλ or Vκ domain, as a first step one would typically identify potential residues to be changed by alignment of the camelid sequence with a benchmark human sequence (which may be a specific germline sequence or a consensus sequence). Camelid residues which are mismatched (i.e. do not align with the human sequence) at positions identified as being on the core list (for VH or Vλ or Vκ, as appropriate) may be selected for replacement with a corresponding human residue, selected according to the criteria set out above.

In some cases a decision may be taken to replace all mismatched camelid residues with a corresponding human residue. In other cases, a decision may be made not to change one or more residues at specific positions, for example because of their importance for the structure of the antibody (e.g. the conformation of the antigen binding site). Other residues may be excluded (i.e. not changed) because they appear in the same sequence context in other human germlines (not necessarily the closest match over the entire VH/Vλ/Vκ domain) and hence could be considered human. In addition, one may take into account of the position of the "mismatched" residues, i.e. it is generally preferred to change mismatched residues in FR1, FR2 and FR3, whilst mismatches in the CDRs may be tolerated to a greater extent. One may also consider whether the mismatched residue(s) are solvent exposed. Mismatched residues which are internal and not solvent exposed may be tolerated to a greater extent than solvent exposed residues.

In addition to the germlining approach described herein, humanisation can also be achieved by "veneering", in which only those mismatched residues which are solvent-exposed on the surface of the folded molecule are considered for replacement.

VL residues 1, 2*, 3, 5, 7, 8, 10, 11, 12, 13*, 14, 15, 16, 17, 18, 20, 22, 37* 39, 40, 41, 42, 43*, 45, 46*, 49*, 57, 59, 60, 63, 65, 66, 67, 68, 69, 70, 72, 74, 76, 77, 79, 80, 81, 83, 85*, 99*, 100, 101*, 103, 105 and 106 are exposed, mostly exposed or partly buried and could be considered for mutation during humanization (asterisk indicates inconsistency for two different VLs). VH residues 1, 3, 5, 7, 8, 10, 11, 13, 14, 15, 16, 17, 19, 21, 23, 25, 26, 28, 30, 40, 41, 42, 43, 44, 46, 66*, 68, 70, 72, 73, 74, 75, 76, 77*, 79*, 81, 82a*, 82b, 83, 84, 85, 87, 88*, 89, 104*, 105, 108, 110, 112 and 113 are exposed, mostly exposed or partly buried and again can be mutagenized during humanization (Padlan, Mol. Immunol. 31:169-217 (1994)). By using these lists solvent exposed camelid VL and VH candidate residues can be selected from the core list for mutagenesis, thereby following the process of veneering.

As explained below, the humanisation process can be carried out iteratively, or one can pursue a library approach. For example, one may prepare a set of "humanised" variants of a give starting camelid VH or Vλ or Vκ domain in which different combinations of amino acid residues are substituted. These variants may then be tested for binding affinity for the target antigen, and other parameters/indicators of function, including potential or actual immunogenicity in a human host.

The choice of a particular replacement human residue from the pool of possible replacement residues at each of the positions selected to be changed [in a starting camelid VH or Vλ or Vκ domain] may be governed by local sequence context, or by the need to minimise the presence of human T cell epitopes within the camelid VH domain sequence.

When selecting appropriate residues for humanisation of a given camelid VH or Vλ or Vκ domain, one may therefore look first at the closest matching human germlines, i.e. the highest sequence homology with appropriate canonical fold structures in the CDRs, but also at germlines which exhibit high sequence homology with non-matching canonical folds (e.g. CDRs of different length), also other human germline family members within the same family which are not necessarily the closest match, and even human germlines of different families.

Preferred Substitutions—VH

Taking account of the criteria set out above, the amino acid substitutions listed in Table 4 have been identified as suitable for humanisation of a camelid VH domain. The subject-matter of the invention therefore includes, but is not limited to, antibodies comprising camelid VH domains including one or more, or any combination, of the amino acid substitution listed in Table 4. In each case, the amino acid which is encoded by the camelid VH sequence at the position identified in the left-hand column may be replaced by one of the preferred human residues for that position, as listed in the right-hand column. Table 4 also provides an indication of which changes are considered most relevant for particular human VH families or family members, however this should not be taken as limiting. Residues, which in the camelid germline deviate from human germline (as concluded from high frequency occurrence of deviating residue) are described in Table 4 and preferred changes are those converting the camelid residue into the residue present in the best human germline with the identical canonical fold combination for CDR1 and CDR2. These conclusion were derived from FIGS. 36, 37 and 38, which show the residues in somatically mutated *Lama glama* VH deviating from the best matching human germline family member as well as the residues present in the entire human germline family. The mentioned figures also indicate that quite often the human germline residue occurs in somatically mutated VH regions, although at lower frequencies, hence giving confidence that back mutation into the residue present in the human germline should be feasible. In addition FIGS. 40, 41 and 42 show the same type of analysis, but for *Lama pacos* germline VH.

TABLE 4

Preferred camelid VH substitutions

| Position in camelid VH (Kabat numbering) | Preferred human residue |
|---|---|
| Changes appropriate for germlining camelid VH aligning to human VH3 | |
| H1 | Q or E |
| H13 | Q, K, R with K preferred |
| H14 | P |
| H29 | F or V with F preferred |
| H37 | V, F or I with I preferred |
| H40 | A |
| H74 | S or A with S preferred |
| H77 | T or S with S preferred |
| H78 | L or A with L preferred |
| H83 | R or K with R preferred |
| H84 | A or T with A preferred |
| H86 | D |
| H94 | R, T or K with R preferred |
| Changes appropriate for germlining camelid VH aligning to human VH1 | |
| H1 | Q or E |
| H7 | S |
| H11 | V |
| H12 | K |
| H13 | K |

TABLE 4-continued

Preferred camelid VH substitutions

| Position in camelid VH (Kabat numbering) | Preferred human residue |
|---|---|
| H69 | I, M or S with M preferred |
| H71 | R, A, E or T wth R preferred |
| H80 | M |
| H78 | V, A |
| H86 | D |
| Changes appropriate for germlining camelid VH aligning to human VH4 | |
| H1 | Q |
| H30 | S |
| H48 | I |
| H67 | V |
| H68 | T |
| H71 | V |
| H81 | K |
| H84 | A |
| H85 | A |
| H86 | D |

In particular embodiments, the invention encompasses a humanised antibody comprising a camelid VH domain containing at least one of the amino acid changes listed in Table 4, wherein said camelid VH domain is derived from Llama (*Lama glama*) or alpaca (*Lama pacos*).

Humanised antibodies according to the invention may also comprise a camelid VH domain containing any combination of two or more of the specific amino acid substitutions listed in Table 4. Again, said camelid VH domains may be derived from Llama (*Lama glama*) or alpaca (*Lama pacos*).

Germlining Towards a Specific Human VH Sequence

Based on alignment of mature (functional antigen-binding) camelid VH (and VL or Vκ) domain sequences to their closest aligning human germline sets of amino acid substitutions have been derived which are particularly useful when germlining a given camelid VH (and VL or Vκ) domain towards a specific human germline sequence. This human sequence may be (but is not necessarily) the closest matching human germline for the particular camelid sequence selected for humanisation.

Preferred sets of substitutions for humanisation towards specific human germline VH subclasses are as follows (in each case the natural camelid-encoded residue at the position(s) listed can be replaced with the specific amino acid given below):
Hu VH3-21: H1 E, H13 K, H77 S, H83 R, H84 A In a particular embodiment the invention provides an antibody comprising a camelid VH domain (preferably derived from *Lama glama* or *Lama pacos*) which aligns to a human VH3-21 sequence and which includes one or more or all of the amino acids listed above at the stated position(s).
Hu VH3-48: H1 E, H77 S, H83 R, H84 A In a particular embodiment the invention provides an antibody comprising a camelid VH domain (preferably derived from *Lama glama* or *Lama pacos*) which aligns to a human VH3-48 sequence and which includes one or more or all of the amino acids listed above at the stated position(s).
Hu VH3-23: H1 E, H74 S, H83 R, H84 A In a particular embodiment the invention provides an antibody comprising a humanised camelid VH domain (preferably derived from *Lama glama* or *Lama pacos*) which aligns to a human VH3-23 sequence and which includes one or more or all of the amino acids listed above at the stated position(s).
Hu VH3-66: H1 E, H29 V, H37 V, H40 A, H74 S, H83 R, H84 A, H94 R In a particular embodiment the invention provides an antibody comprising a humanised camelid VH domain (preferably derived from *Lama glama* or *Lama pacos*) which aligns to a human VH3-66 sequence and which includes one or more or all of the amino acids listed above at the stated position(s).
Hu VH3-11: H1 Q, H13 K, H14 P, H37 I, H77 S, H78 L, H83 R, H84 A, H94 R In a particular embodiment the invention provides an antibody comprising a humanised camelid VH domain (preferably derived from *Lama glama* or *Lama pacos*) which aligns to a human VH3-11 sequence and which includes one or more or all of the amino acids listed above at the stated position(s).
Hu VH3-66: H1 E, H29 V, H37 V, H40 A, H74 S, H78 L, H83 R, H84 A, H86 D, H94 R In a particular embodiment the invention provides an antibody comprising a camelid VH domain (preferably derived from *Lama glama* or *Lama pacos*) which aligns to a human VH3-66 sequence and which includes one or more or all of the amino acids listed above at the stated position(s).
Hu VH3-48: H1 E, H77 S, H83 R, H84 A, H86 D In a particular embodiment the invention provides an antibody comprising a camelid VH domain (preferably derived from *Lama glama* or *Lama pacos*) which aligns to a human VH3-48 sequence and which includes one or more or all of the amino acids listed above at the stated position(s).
Hu VH1-46: H1 Q, H11 V, H12 K, H13 K, H69 M, H71 R, H78 V, H80 M In a particular embodiment the invention provides an antibody comprising a camelid VH domain (preferably derived from *Lama glama*) which aligns to a human VH1-46 sequence and which includes one or more or all of the amino acids listed above at the stated position(s).
Hu VH1-46: H1 Q, H7 S, H11 V, H12 K, H69 M, H71 R, H78 V, H80 M, H86 D In a particular embodiment the invention provides an antibody comprising a camelid VH domain (preferably derived from *Lama pacos*) which aligns to a human VH1-46 sequence and which includes one or more or all of the amino acids listed above at the stated position(s).
Hu VH4-30-4: H1Q, H30 S, H48 I, H67 V, H68 T, H71 V, H81 K, H84 A, H85 A In a particular embodiment the invention provides an antibody comprising a camelid VH domain (preferably derived from *Lama glama*) which aligns to a human VH4-30-4 sequence and which includes one or more or all of the amino acids listed above at the stated position(s).
Hu VH4-30-4: H1 Q, H30 S, H48 I, H67 V, H68 T, H71 V, H81 K, H84 A, H85 A, H86 D In a particular embodiment the invention provides an antibody comprising a camelid VH domain (preferably derived from *Lama pacos*) which aligns to a human VH4-30-4 sequence and which includes one or more or all of the amino acids listed above at the stated position(s).

Each of the above-listed embodiments may additionally include amino acid L at position 108.

Preferred Substitutions—VKappa (Vκ) and VLamba (Vλ)

Figure 30B:
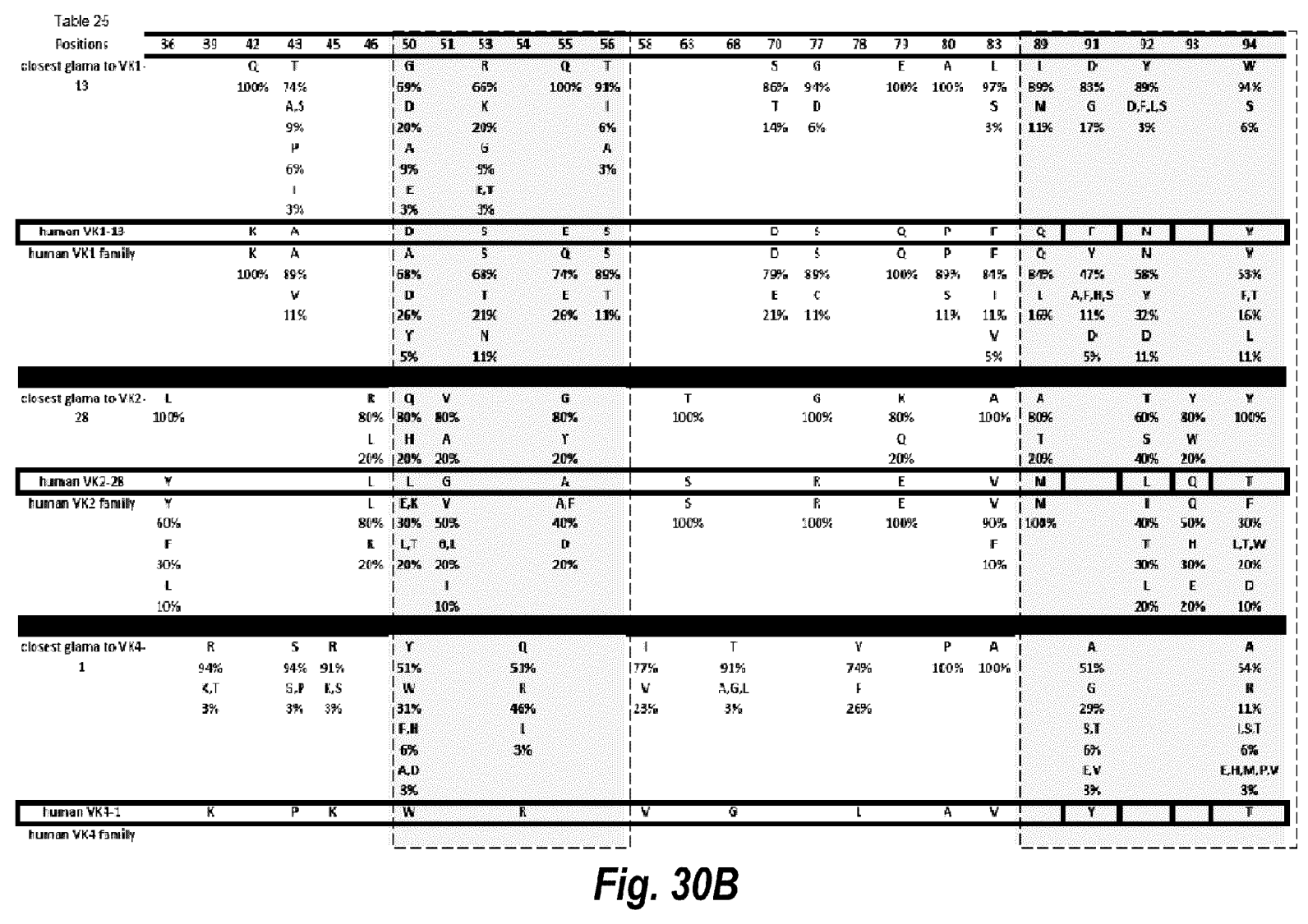
Figure 32A:
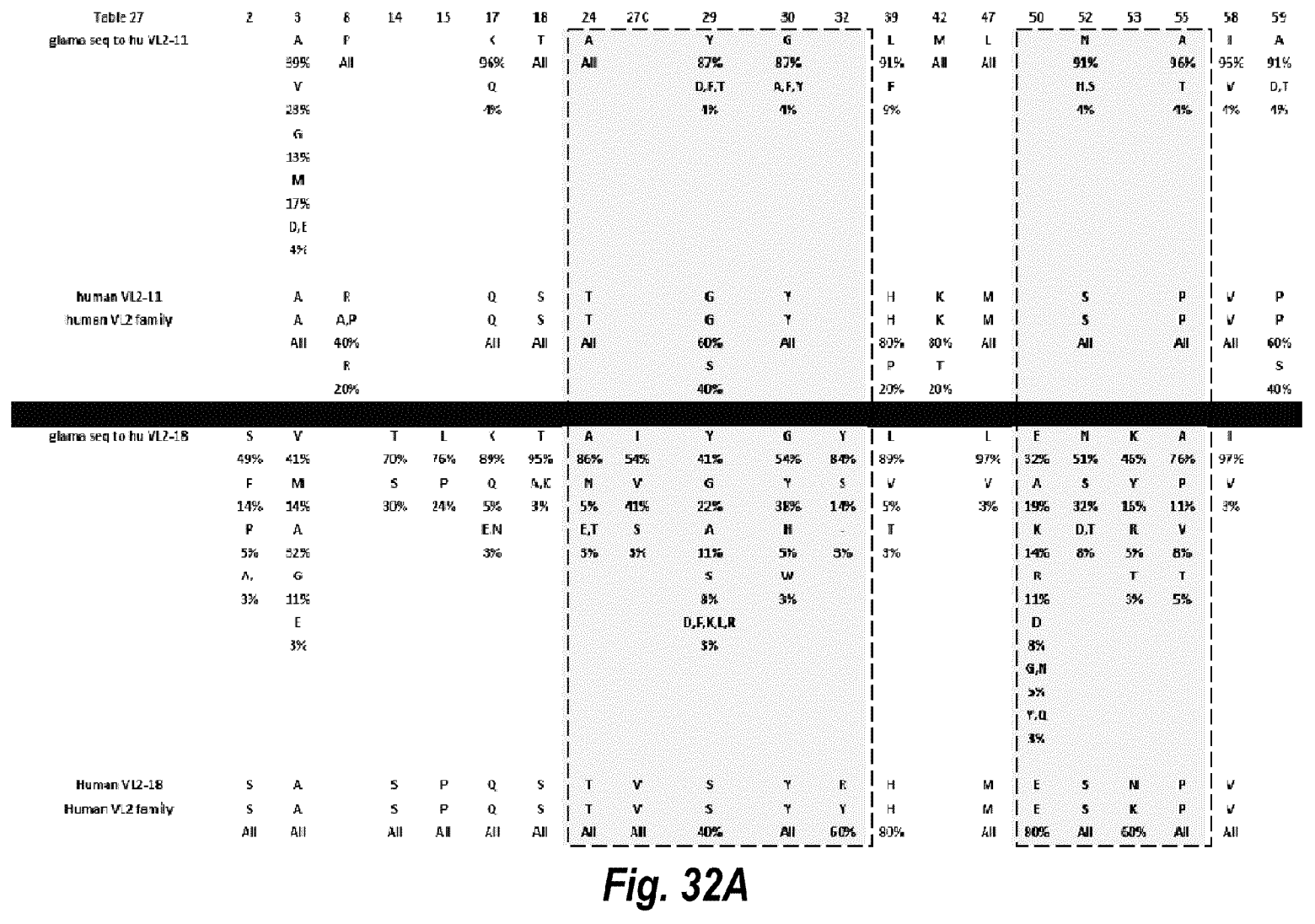
Figure 33B:
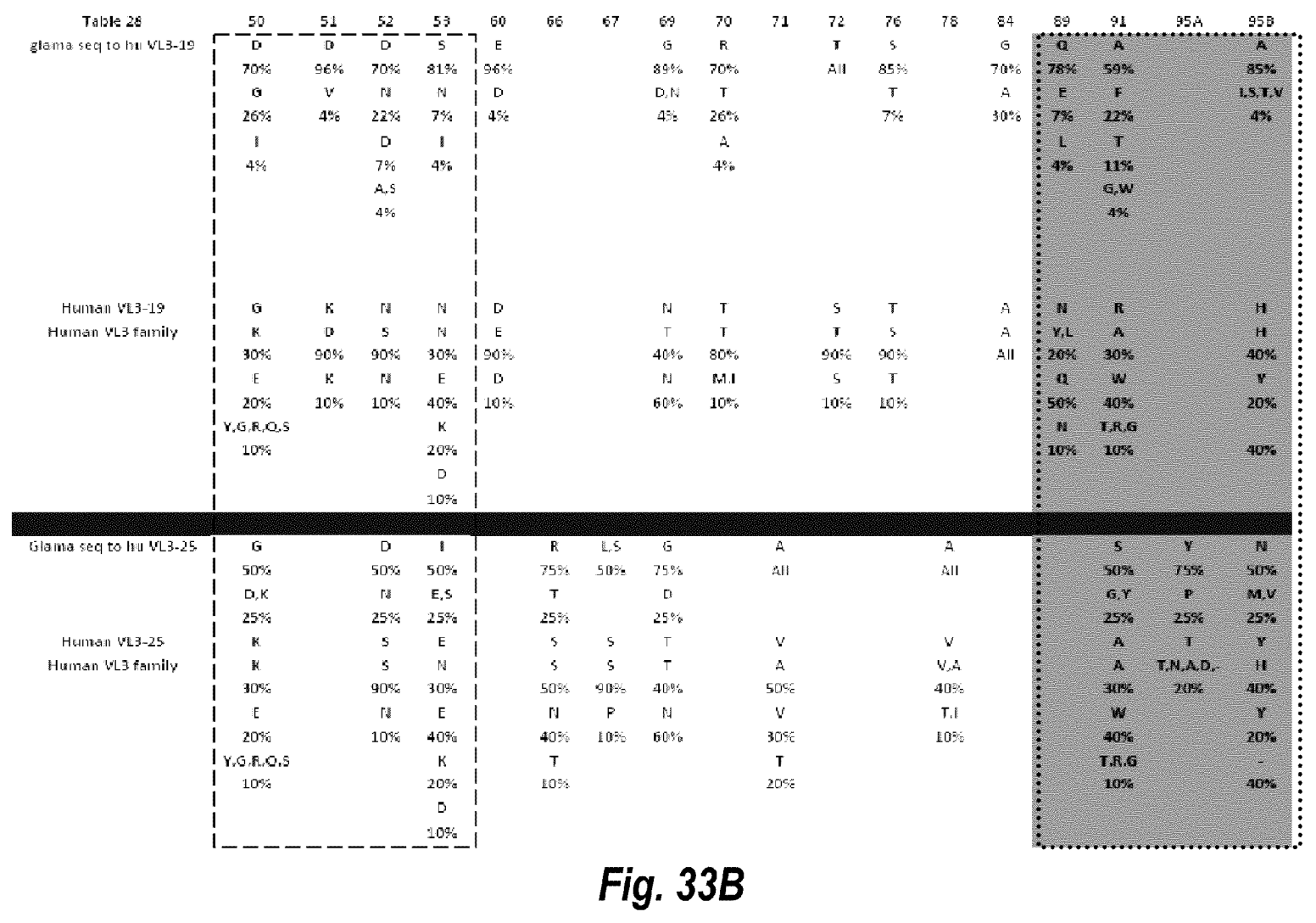
Figure 34:
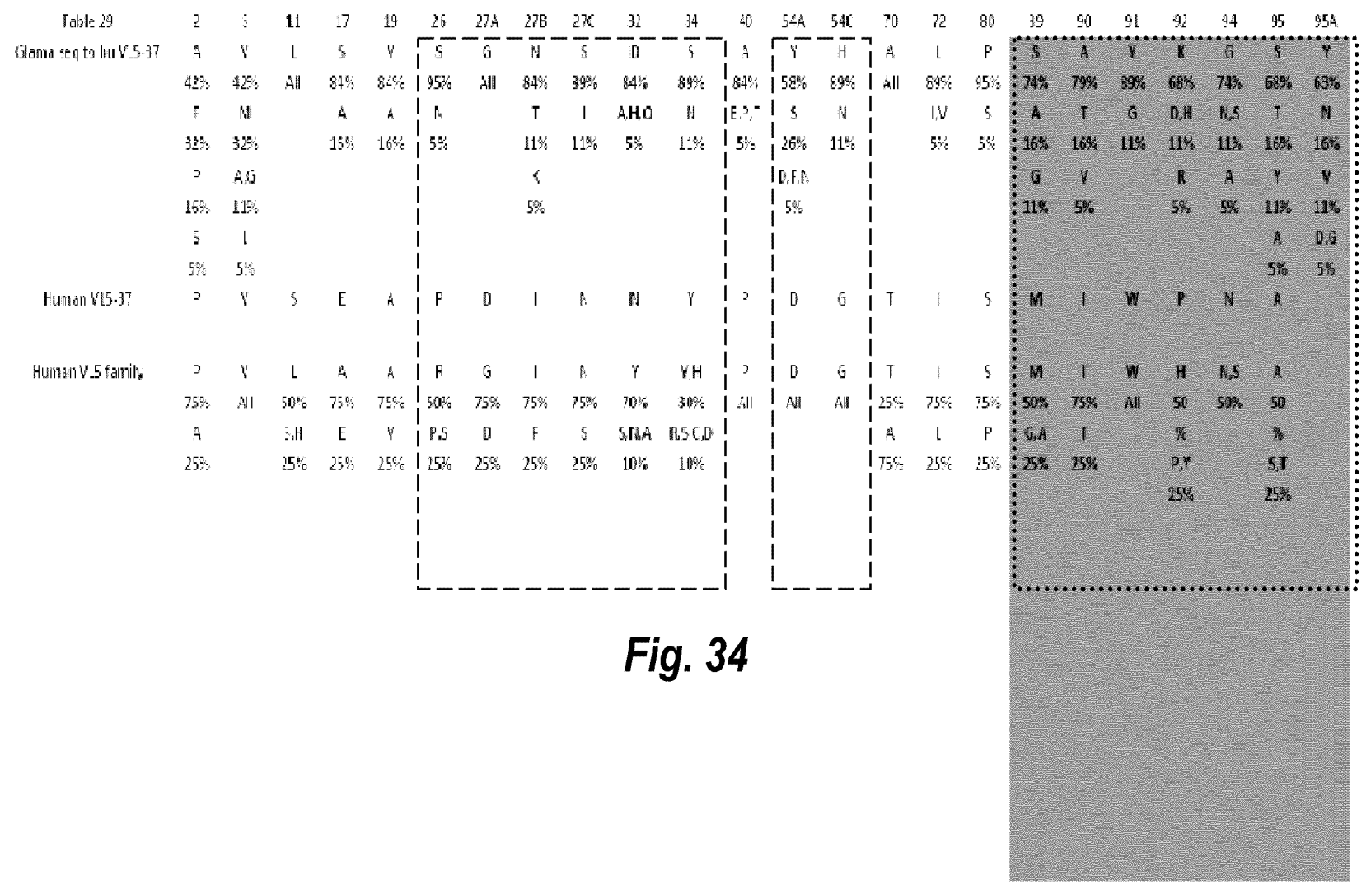
Figure 35:
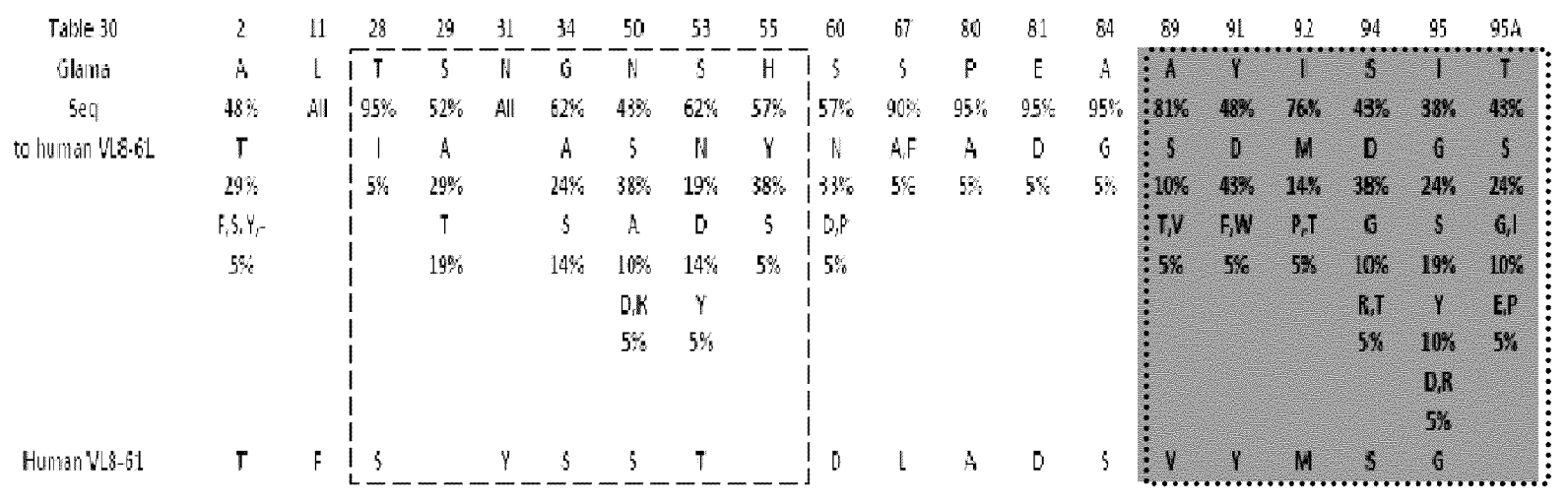

The amino acid substitutions listed in Table 5 have been identified as suitable for humanisation of a camelid VL domain. The subject-matter of the invention therefore includes, but is not limited to, antibodies comprising camelid VL domains including one or more, or any combination, of the amino acid substitution listed in Table 5. In each case, the amino acid which is encoded by the camelid VL sequence at the position identified in the left-hand column may be replaced by one of the preferred human residues for that position, as listed in the right-hand column of Table 5. Residues, which in the camelid germline deviate from human germline (as concluded from high frequency occurrence of deviating residue) are described in Table 5 and preferred changes are those converting the camelid residue into the residue present in the best human germline with the identical canonical fold combination for CDR1 and CDR2. These conclusions were derived from FIG. 30 for VKappa and from FIGS. 31 to 35 for VLambda, which show the residues in somatically mutated *Lama glama* Vκ/Vλ deviating from the best matching human germline family member as well as the residues present in the entire human germline family. The mentioned tables also indicate that quite often the human germline residue occurs in somatically mutated VKappa/VLambda regions, although at lower frequencies, thus indicating that back mutation into the residue present in the human germline is permissible.

TABLE 5

| Preferred camelid Vκ and Vλ substitutions | |
| --- | --- |
| Position in camelid Vκ (Kabat numbering) | Preferred human residue |
| Changes appropriate for germlining camelid Vκ aligning to human Vκ1 | |
| K2 | D, A or N with D preferred |
| K4 | M or L with L preferred |
| K11 | V |
| K12 | K |
| K13 | K |
| K15 | V or T with V preferred |
| K42 | K |
| K43 | A or V with A preferred |
| K70 | D or E with D preferred |
| K77 | S or C with S preferred |
| K79 | Q |
| K80 | P or S with P preferred |
| K83 | F, I or V with F preferred |
| Changes appropriate for germlining camelid Vκ aligning to human Vκ2 | |
| K7 | T, S with S preferred |
| K9 | L |
| K12 | P, S with P preferred |
| K14 | T |
| K18 | P or Q with P preferred |
| K36 | Y, F or L with Y preferred |
| K46 | L or R with L preferred |
| K63 | S |
| K77 | R |
| K79 | E |
| K83 | V or F with V preferred |
| Changes appropriate for germlining camelid Vκ aligning to human Vκ4 | |
| K9 | D |
| K11 | L |
| K12 | A |
| K13 | V |
| K15 | L |
| K18 | R |
| K19 | A |
| K39 | K |
| K43 | P |
| K45 | K |
| K58 | V |
| K68 | G |
| K78 | L |
| K80 | A |
| K83 | V |
| Changes appropriate for germlining camelid Vλ aligning to human Vλ1 | |
| L11 | A or V with A preferred |
| L14 | A or T with T preferred |
| L18 | R or K with R preferred |
| L19 | V |
| L38 | Q |
| L69 | T |
| L74 | A or G with A preferred |
| L76 | S or T with S preferred |
| L80 | S, T or A with S preferred |

TABLE 5-continued

| Preferred camelid Vκ and Vλ substitutions | |
| --- | --- |
| Position in camelid Vκ (Kabat numbering) | Preferred human residue |
| Changes appropriate for germlining camelid Vλ aligning to human Vλ2 | |
| L3 | A |
| L8 | A, P or R with P preferred |
| L14 | S |
| L15 | P |
| L17 | Q |
| L18 | S |
| L39 | H or P with H preferred |
| L42 | K, T; K preferred |
| L47 | M |
| L58 | V |
| L59 | P or S with P preferred |
| L80 | A |
| Changes appropriate for germlining camelid Vλ aligning to human Vλ3 | |
| L1 | S |
| L2 | Y |
| L3 | E |
| L5 | M |
| L7 | D, L or P with D preferred |
| L8 | P, S, L or H with P preferred |
| L9 | S or A with S preferred |
| L11 | V |
| L14 | A or S with A preferred |
| L15 | P, L or T with P preferred |
| L19 | A or V with A preferred |
| L20 | R or S with R preferred |
| L44 | P |
| L46 | L |
| L60 | E or D with D preferred |
| L66 | S, N or T with S preferred |
| L67 | S or P |
| L69 | T or N |
| L70 | T, M or I with T preferred |
| L71 | A, V or T with V preferred |
| L72 | T or S with S preferred |
| L76 | S or T with T preferred |
| L78 | V, A, T or I with V preferred |
| L84 | A |
| Changes appropriate for germlining camelid Vλ aligning to human Vλ5 | |
| L2 | P |
| L11 | L, S or H with S preferred |
| L17 | A or E with E preferred |
| L19 | A or V with A preferred |
| L40 | P |
| L70 | A or T with T preferred |
| L72 | I or L with I preferred |
| L80 | S or, P with S preferred |
| Changes appropriate for germlining camelid Vλ aligning to human Vλ8 | |
| L2 | T |
| L11 | F |
| L60 | D |
| L67 | L |
| L80 | A |
| L81 | D |
| L84 | S |

In particular embodiments, the invention encompasses a humanised antibody comprising a camelid Vκ or Vλ domain containing at least one of the amino acid changes listed in Table 5, wherein said camelid Vκ or Vλ domain is derived from Llama (*Lama glama*) or alpaca (*Lama pacos*).

Humanised antibodies according to the invention may also comprise a camelid Vκ or Vλ domain containing any combination of two or more of the specific amino acid substitutions listed in Table 5, again wherein the camelid Vκ or Vλ domain is derived from Llama (*Lama glama*) or alpaca (*Lama pacos*).

Germlining Towards a Specific Human Vκ or Vλ Sequence

Based on alignment of mature (functional antigen-binding) camelid Vκ or Vλ domain sequences to their closest aligning human germline sets of amino acid substitutions have been derived which are particularly useful when germlining a given camelid VL domain towards a specific human germline sequence. This human sequence may be (but is not necessarily) the closest matching human germline for the particular camelid sequence selected for humanisation.

Preferred sets of substitutions for humanisation towards specific human germline VLambda family members are as follows (in each case the natural camelid-encoded residue at the position(s) listed can be replaced with the specific amino acid given below):
Vλ1-44: L11 A, L14 T, L18 R, L19 V, L38 Q, L69 T, L74 A, L76 S, L80 S In a particular embodiment the invention provides an antibody comprising a camelid VLambda domain (preferably derived from *Lama glama*) which aligns to a human Vλ1-44 sequence and which includes one or more or all of the amino acids listed above at the stated position(s).
Vλ2-11: L8 R, L17 Q, L18 S, L39 H, L42 K, L47 M, L58 V, L59 P, L80 A In a particular embodiment the invention provides an antibody comprising a camelid VLambda domain (preferably derived from *Lama glama*) which aligns to a human Vλ2-11 sequence and which includes one or more or all of the amino acids listed above at the stated position(s).
Vλ2-18: L3 A, L14 S, L15 P, L17 Q, L18 S, L39 H, L47 M, L58 V, L80 A In a particular embodiment the invention provides an antibody comprising a camelid VLambda domain (preferably derived from *Lama glama*) which aligns to a human Vλ2-18 sequence and which includes one or more or all of the amino acids listed above at the stated position(s).
Vλ3-19: L1 S, L3 E, L7 D, L8 P, L11 V, L14 A, L19 V, L20 R, L60 D, L69 N, L70 T, L72 S, L76 T, L84 A In a particular embodiment the invention provides an antibody comprising a camelid VLambda domain (preferably derived from *Lama glama*) which aligns to a human Vλ3-19 sequence and which includes one or more or all of the amino acids listed above at the stated position(s).
Vλ3-25: L1 S, L2 Y, L3 E, L5 M, L8 P, L9 S, L15 P, L66 S, L69T, L71 V, L78 V In a particular embodiment the invention provides an antibody comprising a camelid VLambda domain (preferably derived from *Lama glama*) which aligns to a human Vλ3-25 sequence and which includes one or more or all of the amino acids listed above at the stated position(s).
Vλ5-37: L2 P, L11 S, L17 E, L19 A, L 40 P, L70 T, L72 I, L80 S In a particular embodiment the invention provides an antibody comprising a camelid VLambda domain (preferably derived from *Lama glama*) which aligns to a human Vλ5-37 sequence and which includes one or more or all of the amino acids listed above at the stated position(s).
Vλ8-61: L2 T, L11 F, L60 D, L67 L, L80 A, L81 D, L84 S In a particular embodiment the invention provides an antibody comprising a camelid VLambda domain (preferably derived from *Lama glama*) which aligns to a human Vλ8-61 sequence and which includes one or more or all of the amino acids listed above at the stated position(s).

Preferred sets of substitutions for humanisation towards specific human germline VKappa family members are as follows (in each case the natural camelid-encoded residue at the position(s) listed can be replaced with the specific amino acid given below):
Vκ1-13: K11 V, K12 K, K13 K, K15 V, K42 K, K43 A, K70 D, K77 S, K79 Q, K80 P, K83 F In a particular embodiment the invention provides an antibody comprising a camelid VKappa domain (preferably derived from *Lama glama*) which aligns to a human Vκ1-13 sequence and which includes one or more or all of the amino acids listed above at the stated position(s).
Vκ2-28: K7 S, K9 L, K12 P, K14 T, K18 P, K36 Y, K46 L, K63 S, K77 R, K79 E, K83 V In a particular embodiment the invention provides an antibody comprising a camelid VKappa domain (preferably derived from *Lama glama*) which aligns to a human Vκ2-28 sequence and which includes one or more or all of the amino acids listed above at the stated position(s).
Vκ4-1: K9 D, K11 L, K12 A, K13 V, K15 L, K18 R, K19 A, K39 K, K43 P, K45 K, K58 V, K68 G, K78 L, K80 A, K83 V In a particular embodiment the invention provides an antibody comprising a camelid VKappa domain (preferably derived from *Lama glama*) which aligns to a human Vκ4-1 sequence and which includes one or more or all of the amino acids listed above at the stated position(s).

Each of the above-listed embodiments may also include an amino acid replacement at the FR4 residue 103, preferably having K at this position for both VKappa and VLambda. In addition, amino acid replacements in VKappa might be introduced in FR4 residue 100, preferably having Q at this position, or in FR4 residue 104, preferably with V.

The camelid VH and/or Vλ and/or Vκ domains in the antibodies of the invention may be engineered to include additional amino acid sequence changes compared to a natural camelid VH, VL or Vκ domain (e.g. VH, Vλ or Vκ domain of a conventional camelid antibody obtained by active immunisation of *camelidae* with a target antigen), in additional to the amino acid substitution(s) at one or more of the amino acid positions identified on the "core" VH, Vλ and Vκ lists provided herein. In certain embodiments, the VH, Vλ and Vκ domains of said antibodies may have been (independently) engineered to introduce up to 10, and possibly even more, amino acid substitutions across the framework regions FR1, FR2, FR3 and FR4 in either one or both of the VH domain and the Vλ/Vκ domain.

Lists of amino acid substitutions which may be made in FR4 residues encoded by the camelid germline J segment for the purposes of humanisation are provided below:
Amino Acid Replacements in FR4 Residues Encoded by J Segments In a further embodiment the invention provides an antibody comprising a camelid VH domain wherein the FR4 encoded amino acid at position H108 of the camelid VH domain, according to Kabat, is replaced with an amino acid found at the corresponding position in a human VH domain sequence.

The replacement residues at H108 may be selected according to the general principles for humanisation of camelid VH domains, discussed above. In particular, replacement "human" residues may be selected on the basis of alignment to the closest human germline sequence, or to a human consensus sequence, or from a human germline sequence of the same class or subclass as the closest aligning human germline, or even from a human germline of a different class or subclass.

In one embodiment the amino acid at H108 is replaced, preferably with L or less preferred with M.

Amino acid changes in JKappa or JLambda may be selected following similar principles.

Accordingly, the invention provides an antibody comprising a camelid Vλ or Vκ domain wherein the amino acid at one or more of positions of the camelid Vλ or Vκ domain, according to Kabat, is replaced with an amino acid found at the corresponding position in a human Vλ or Vκ domain sequence.

In one embodiment the VLambda domain has homology to a human VLambda domain and the amino acid at L103 is replaced, preferably with K or less preferred with E or Q.

In one embodiment the VKappa domain has homology to a human VKappa domain and the amino acid at K103 is replaced, preferably with K or less preferred with R.

In one embodiment the VKappa domain has homology to a human VKappa domain and the amino acid at K104 is replaced, preferably with V.

In one embodiment the VKappa domain has homology to a human VKappa domain and the amino acid at K104 is replaced, preferably with L.

Amino Acid Changes in CDRs

In addition to amino acid substitutions which result in "humanisation", by replacing mis-matched amino acid residues in a starting Camelidae VH, Vλ or Vκ domain with the equivalent residue found in a human VH, Vλ or Vκ domain, it is also possible to independently make amino acid substitutions in the hypervariable loops (CDRs) of said camelid-derived VH, Vλ and Vκ domains, particularly in CDR1 and/or CDR2, but also in CDR3, also for the purposes of humanisation. Of interest are residues positioned at the borders with the FRs, since these might determine T cell epitopes consisting of FR and CDR encoded residues.

The following tables summarise possible amino acid substitutions for humanisation of camelid-derived CDRs.

TABLE 6 amino acid replacements in CDRs

| CDR amino acid position (Kabat) | Preferred human amino acids |
|---|---|
| Changes relevant to humanisation of camelid VH aligning to human VH1 domains | |
| H34 CDR1 | M, I, V, L with M preferred |
| H35 CDR1 | H, S, Q, N with H preferred |
| H50 CDR2 | W, G, I, L, R with I preferred |
| H52 CDR2 | N, D, I, T, S with N preferred |
| H53 CDR2 | E, G, N, I, S, F, Y with S preferred |
| H54 CDR2 | N, S, D, G, F with G preferred |
| H56 CDR2 | N, E, G, T, S with S preferred |
| H58 CDR2 | N, I, G, S with S preferred |
| Changes relevant to humanisation of camelid VH aligning to human VH3 domains | |
| H31 CDR1 | S, D, N with S or D preferred |
| H32 CDR1 | Y, N with N preferred |
| H33 CDR1 | S, A, W, Y with S or A or Y preferred |
| H35 CDR1 | S, H, N with S or N preferred |
| H50 CDR2 | R, V, A, Y, G, S with S or Y or V preferred |
| H52 CDR2 | S, K, R, Y with S or Y preferred |
| H52a CDR2 | S, W, G with G or S preferred |
| H53 CDR2 | D, S, N with S preferred |
| H54 CDR2 | G, S |
| H55 CDR2 | G, S, Y with S preferred |
| H56 CDR2 | S, T, N, Y with S, T or Y preferred |
| H57 CDR2 | T, I, K with I preferred |
| H58 CDR2 | Y, G, D, E, S, A, N with Y or N preferred |
| H60 CDR2 | A, T, V, P with A preferred |
| Changes relevant to humanisation of camelid VH aligning to human VH4 domains | |
| H31 CDR1 | S, G with S preferred |
| H32 CDR1 | G, S, Y with G preferred |
| H33 CDR1 | Y, G, N, D with D preferred |
| H35 CDR1 | Y, W, S with Y preferred |
| H50 CDR2 | Y, E, S with Y preferred |
| H52 CDR2 | Y, N with Y preferred |
| H54 CDR2 | S |
| H60 CDR2 | N |

TABLE 6-continued amino acid replacements in CDRs

| CDR amino acid position (Kabat) | Preferred human amino acids |
|---|---|
| Changes relevant to humanisation of camelid VLambda aligning to human Vλ1 domains | |
| L24 CDR1 | S, T with S preferred |
| L30 CDR1 | S, N, G with S preferred |
| L32 CDR1 | T, D, A, Y with T preferred |
| L52 CDR2 | N, S, D with N preferred |
| L53 CDR2 | Q, K, N, L with Q preferred |
| L55 CDR2 | P |
| L89 CDR3 | A, G, Q with A preferred |
| L90 CDR3 | A, T, S with A preferred |
| L94 CDR3 | S |
| L95a CDR3 | N, S with N preferred |
| Changes relevant to humanisation of camelid VLambda aligning to human Vλ2 domains | |
| L24 CDR1 | T |
| L27c CDR1 | V |
| L29 CDR1 | S, G |
| L30 CDR1 | Y |
| L32 CDR1 | Y, R, L with R preferred |
| L50 CDR2 | E, D with E preferred |
| L52 CDR2 | S |
| L53 CDR2 | K, N with N preferred |
| L55 CDR2 | P |
| L89 CDR3 | S, C |
| L90 CDR3 | S, L with L preferred |
| L92 CDR3 | A, T with A preferred |
| L93 CDR3 | G, S with G preferred |
| L94 CDR3 | S |
| L95 CDR3 | S, Y, N with Y preferred |
| L95a CDR3 | T, N with T preferred |
| L95b CDR3 | F, L with F preferred |
| Changes relevant to humanisation of camelid VLambda aligning to human Vλ3 domains | |
| L24 CDR1 | S, G, Q with S preferred |
| L26 CDR1 | D, N, E with D preferred |
| L27 CDR1 | A, N, V, S, K with A preferred |
| L29 CDR1 | R, P, G, A with R or P preferred |
| L30 CDR1 | K, S, D, E with K preferred |
| L31 CDR1 | Y, N, Q, K with Y or Q preferred |
| L32 CDR1 | Y, S, N, A with Y preferred |
| L34 CDR1 | Y, H, R, S, C, D with S or Y preferred |
| L50 CDR2 | K, E, Y, G, R, Q, S with G or K preferred |
| L51 CDR2 | D, K with K preferred |
| L52 CDR2 | S, N |
| L53 CDR2 | N, E, K, D with N or E preferred |
| L89 CDR3 | Y, L, Q, N with N preferred |
| L91 CDR3 | A, W, T, R, G with R or A preferred |
| L95a CDR3 | T, N, A, D with T preferred |
| L95b CDR3 | H, Y |
| Changes relevant to humanisation of camelid VLambda aligning to human Vλ5 domains | |
| L26 CDR1 | R, P, S with P preferred |
| L27a CDR1 | G, D with D preferred |
| L27b CDR1 | I, F with I preferred |
| L27c CDR1 | N, S with N preferred |
| L32 CDR1 | Y, S, N, A with N preferred |
| L34 CDR1 | Y, H, R, S, C, D with Y preferred |
| L54a CDR2 | D |
| L54c CDR2 | G |
| L89 CDR3 | M, G, A with M preferred |
| L90 CDR3 | I, T with I preferred |
| L91 CDR3 | W |
| L92 CDR3 | H, P, Y with P preferred |
| L94 CDR3 | N, S with N preferred |
| L95 CDR3 | A, S, T with A preferred |
| L95a CDR3 | S, K with S preferred |
| Changes relevant to humanisation of camelid VLambda aligning to human Vλ8 domains | |
| L28 CDR1 | S |
| L29 CDR1 | T |

TABLE 6-continued amino acid replacements in CDRs

| CDR amino acid position (Kabat) | Preferred human amino acids |
|---|---|
| L31 CDR1 | Y |
| L34 CDR1 | S |
| L50 CDR2 | S |
| L53 CDR2 | T |
| L55 CDR2 | S |
| L89 CDR3 | V |
| L91 CDR3 | Y |
| L92 CDR3 | M |
| L94 CDR3 | S |
| L95 CDR3 | G |
| L95a CDR3 | I |
| Changes relevant to humanisation of camelid VKappa aligning to human Vκ1 domains | |
| L24 CDR1 | R, Q, W with R preferred |
| L28 CDR1 | G, S, D with G preferred |
| L31 CDR1 | S, N with S preferred |
| L32 CDR1 | Y, W, A, D with A preferred |
| L34 CDR1 | A, N, G with A preferred |
| L50 CDR2 | A, D, Y with D preferred |
| L53 CDR2 | S, T, N with S preferred |
| L55 CDR2 | Q, E with E preferred |
| L56 CDR2 | S, T with S preferred |
| L89 CDR3 | Q, L with Q preferred |
| L91 CDR3 | Y, A, F, H, S, D with F preferred |
| L92 CDR3 | N, Y, D with N preferred |
| L94 CDR3 | Y, F, T, L with Y preferred |
| Changes relevant to humanisation of camelid VKappa aligning to human Vκ2 domains | |
| L24 CDR1 | R, K with R preferred |
| L25 CDR1 | S |
| L27c CDR1 | L, V with L preferred |
| L28 CDR1 | D, N with N preferred |
| L30 CDR1 | N, Y, K with Y preferred |
| L31 CDR1 | T, N with N preferred |
| L34 CDR1 | D, Y, N with D preferred |
| L50 CDR2 | E, K, L, T with L preferred |
| L51 CDR2 | V, G, L, I with G preferred |
| L55 CDR2 | A, F, D with A preferred |
| L89 CDR3 | M |
| L92 CDR3 | I, T, L with L preferred |
| L93 CDR3 | Q, H, E with Q preferred |
| L94 CDR3 | F, L, T, W, D with T preferred |
| Changes relevant to humanisation of camelid VKappa aligning to human Vκ4 domains | |
| L27c CDR1 | L |
| L27d CDR1 | Y |
| L27e CDR1 | S |
| L29 CDR1 | N |
| L31 CDR1 | N |
| L34 CDR1 | A |
| L50 CDR2 | W |
| L54 CDR2 | R |
| L91 CDR3 | Y |
| L94 CDR3 | T |

Accordingly, the scope of the invention extends to antibody comprising a camelid VH domain, wherein one or more amino acids in CDR1 and/or CDR2 and/or CDR3 is/are replaced with an amino acid found at the corresponding position in a human VH domain sequence. Permitted amino acid replacements include those summarised in Table 6, one or more of which may be present in any combination.

The invention also encompasses an antibody comprising a camelid Vλ or Vκ domain, wherein one or more amino acids in CDR1 and/or CDR2 and/or CDR3 is/are replaced with an amino acid found at the corresponding position in a human Vλ or Vκ domain sequence. Permitted amino acid replacements include those summarised in Table 6, one or more of which may be present in any combination.

For any given "humanised" camelid VH, Vλ or Vκ domain, amino acid replacements in the CDRs may be included with or without amino acid replacements in the framework regions.

Where framework amino acid replacements are also present, preferred changes include all of those summarised in Table 4 (VH) and Table 5 (Vλ and Vκ).

When humanising within the CDRs of camelid VH, Vλ and Vκ domains the general principles of the germlining approach outlined above for framework regions may be followed. Therefore, one can chose to germline towards a particular human germline sequence of the same family or family member, which may or may not be the closest aligning human germline for the starting camelid VH/Vλ/Vκ domain, or one could chose to germline towards a human germline sequence of a different family or family member.

Germlining Across Families

Alignment of mature camelid VH (and Vλ/Vκ) sequences (and consensus sequences derived therefrom) to consensus sequences for human VH (and Vλ/Vκ) domains which are not of the same family (or family member) as the human VH (or Vλ/Vκ) domain sequence with which the camelid VH (Vλ/Vκ) domain aligns most closely has allowed the derivation of sets of amino acid substitutions which may enable humanisation of a camelid VH (or Vλ/Vκ) domains towards human VH (or Vλ/Vκ) domain sequences of a different germline family or family member. These sets of amino acid substitutions are listed in the accompanying Figures.

FIGS. 6 to 11 show all permutations to germline camelid VH sequences that best align with human germline sequences of family VH 1, 3, and 4 towards human germlines or mature VH sequences of the families 1, 3, 4, 5, 6, and 7. FIGS. 12 to 26 show all permutations to germline camelid Vλ sequences (denoted VL) that best align with human germline sequences of Vλ family 1, 3, 5, and 8 towards human germlines or mature Vλ sequences of the human Vλ families 1, 3, 4, 5, 6, 7, 8, 9, and 10 and FIGS. 27 to 29 show all permutations to germline camelid Vκ sequences that best align with human germline sequences of Vκ family 1, and 4 towards human germlines or mature Vκ sequences of the human Vκ families 1, 3, 4, and 5.

The amino acid positions which may be considered for replacement in order to enable humanization are highlighted in the respective tables that compare the starting consensus sequence of a camelid VH, Vλ or Vκ family with consensus sequences for multiple different human germline families. These tables can therefore be used firstly to select which human germline family or subfamily to germline towards, and secondly to select appropriate amino acid replacements for consideration during the humanisation process. As outlined elsewhere herein, humanisation may be carried out as an iterative process, or using a library approach which allows one to test multiple replacements, or combinations of replacements, in parallel.

The following table 7 lists the amino acid substitutions derived from the alignments shown in FIGS. 6 to 11 which could be considered for germlining a camelid sequence best aligning with the human VH1 family towards a family member of human VH3. The preferred human amino acid is the most commonly found amino acid in that family which may be used for germlining. However, in certain positions the amino acid present in certain family members may deviate from the amino acid found in the consensus sequence of the respective human germline family.

TABLE 7 examples replacements for germlining camelid VH1 to human VH3

| Camelid VH1 Position | Human VH3 Preferred human amino acid |
|---|---|
| H9 | G |
| H10 | G |
| H12 | V |
| H13 | Q |
| H16 | G |
| H18 | L |
| H19 | R |
| H20 | L |
| H23 | A |
| H27 | F |
| H30 | S |
| H43 | K |
| H48 | V |
| H49 | S |
| H67 | F |
| H69 | I |
| H70 | S |
| H71 | R |
| H73 | N |
| H75 | K |
| H76 | N |
| H78 | L |
| H80 | L |
| H81 | Q |
| H82 | M |
| H84 | N |

Although all of the above-listed replacements may be useful to enable germlining from camelid VH1 towards human VH3, it does not necessarily mean that ALL of these replacements must, or indeed will, be made when germlining any one specific mature camelid VH1 domain towards human VH3. Rather, the skilled reader will be able to select appropriate replacements from this table by following the general principles for the germlining approach, outlined elsewhere herein.

The following example lists the amino acid substitutions derived from FIGS. 27 to 29 which could be considered for germlining a camelid sequence best aligning with the human Vκ1 family towards a family member of human Vκ3. The preferred human amino acid is the most commonly found amino acid in that family which may be used for germlining. However, in certain positions the amino acid present in certain family members may deviate from the amino acid found in the consensus sequence of the respective human germline family.

TABLE 8 example replacements for germlining camelid Vκ1 to human Vκ3

| Camelid Vκ1 Position | Human Vκ3 Preferred human amino acid |
|---|---|
| L9 | A |
| L10 | T |
| L13 | L |
| L15 | P |
| L17 | E |
| L19 | A |
| L21 | L |
| L22 | S |
| L43 | A |
| L45 | R |
| L58 | I |
| L60 | A |
| L70 | D |
| L77 | S |
| L80 | P |

TABLE 8-continued example replacements for germlining camelid Vκ1 to human Vκ3

| Camelid Vκ1 Position | Human Vκ3 Preferred human amino acid |
|---|---|
| L83 | F |
| L85 | V |

Figure 24A:
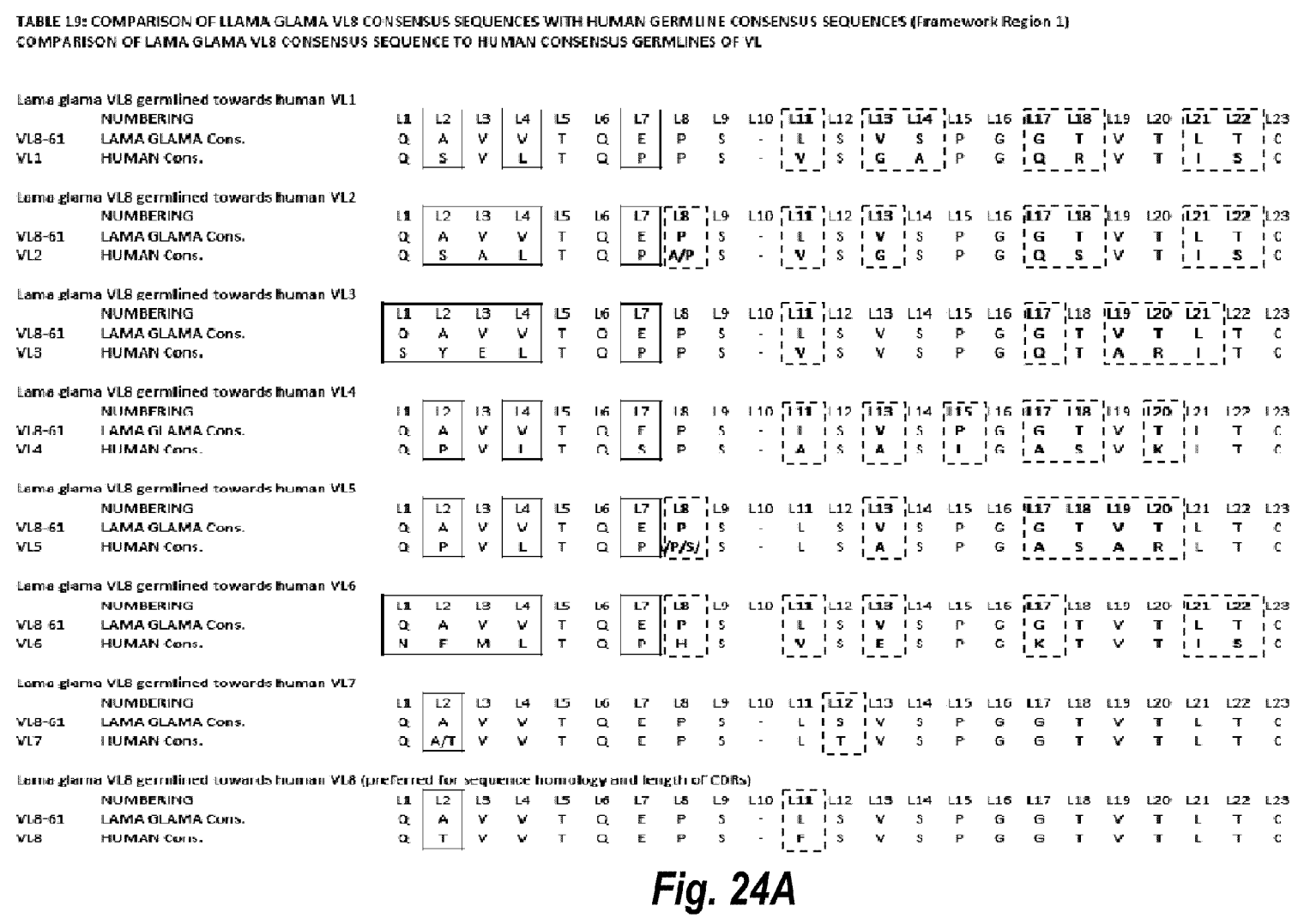
Figure 26A:
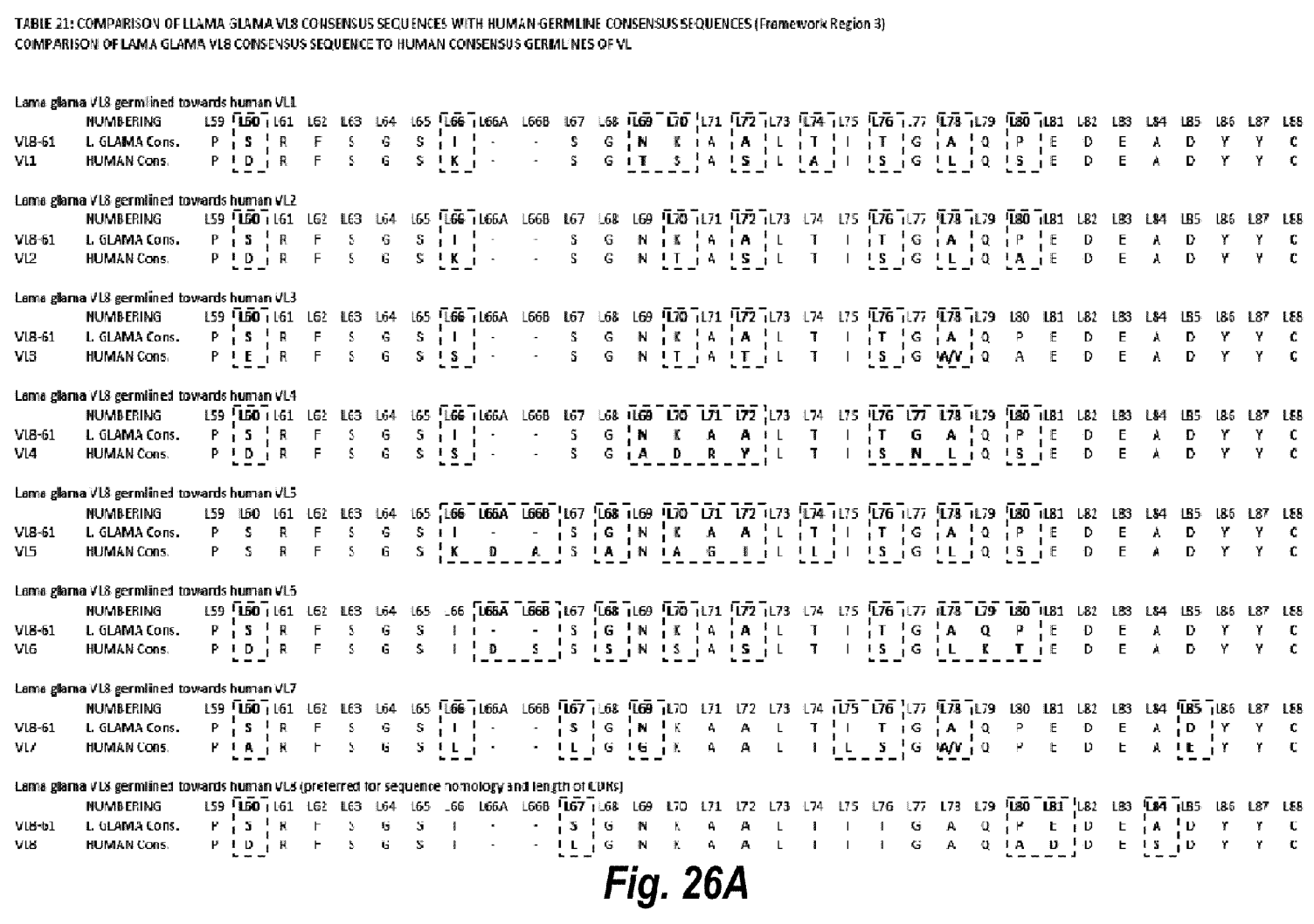

The following example lists the amino acid substitutions derived from FIGS. 24 to 26 which could be considered for germlining a camelid sequence best aligning with the human Vλ8 family towards a family member of human Vλ2. The preferred human amino acid is the most commonly found amino acid in that family which may be used for germlining. However, in certain positions the amino acid present in certain family members may deviate from the amino acid found in the consensus sequence of the respective human germline family.

TABLE 9 example replacements for germlining camelid Vλ8 to human Vλ2

| Camelid Vλ8 Position | Human Vλ2 Preferred human amino acid |
|---|---|
| L11 | V |
| L13 | G |
| L17 | Q |
| L18 | S |
| L21 | I |
| L22 | S |
| L39 | H |
| L42 | K |
| L45 | K |
| L46 | L |
| L47 | M |
| L60 | D |
| L66 | K |
| L70 | T |
| L72 | S |
| L76 | S |
| L78 | L |
| L80 | A |

The above examples for germlining VH1 to VH3, Vκ1 to Vκ3 and Vλ8 to Vλ2 are listed to illustrate how the sequence alignment information presented in FIGS. 6 to 29 can be utilised to enable germlining of a mature camelid VH (or VL) domain of one particular family towards a human germline of a different family or subfamily. In this context, the term "different family or subfamily" refers to any family or subfamily which is not the family or subfamily to which the closest aligning human germline (for the mature camelid VH or VL one desires to humanise) belongs.

The invention also provides for the ability to germline across families to end up with an antibody containing a VH and Vλ/Vκ, which are used most dominantly in the human immune system to avoid the risk of immunogenicity. Preferred are VH3 family and family member DP-47 (or 3-23), Vκ3 family and family member DPK22 (or A27) and Vλ2 family with family member DPL11 (or 2a2) (or Vλ1 family with family member DPL5 or Vλ3 family with family member DPL23). Techniques disclosed by Genentech in US2003190317 and Morphosys (Knappik et al., J. Mol. Biol. 296:57-86 (2000)) can be employed.

The skilled reader will appreciate that the sequence alignment information presented in FIGS. 6 to 29 enables a large number of germlining possibilities across families or subfamilies for camelid VH, VLambda and VKappa domains.

The number of possibilities is increased still further when one considers that a "mix and match" approach can be used, in which for any given mature camelid VH or VL domain each of FR1, FR2, FR3 and FR4 can be germlined towards the same or a different human germline. It is intended that all of the germlining possibilities enabled by the sequence alignment information presented in FIGS. 6 to 29 form part of the subject-matter of this invention. Therefore, the scope of the invention extends to any humanised camelid antibody comprising a camelid VH domain and/or a camelid VL domain which includes one or more of the amino acid replacements summarised in FIGS. 6 to 29.

Scope of the Invention

Humanised VHH domains containing amino acid substitutions analogous to the VH substitutions listed in Table 4 are preferably not encompassed within the scope of the present invention.

In one embodiment the entire VH domain and/or the entire Vλ/Vκ domain of the antibody of the invention may be obtained from a species in the family Camelida. The Camelidae VH domain and/or the Camelidae Vλ/Vκ domain is then be subject to protein engineering, in which amino acid substitutions are introduced into the Camelidae sequence, at one or more of the specific positions identified herein.

In certain embodiments, Camelidae hypervariable loops (or CDRs) may be obtained by active immunisation of a species in the family Camelidae with a desired target antigen. As discussed and exemplified in detail herein, following immunisation of Camelidae (either the native animal or a transgenic animal engineered to express the immunoglobulin repertoire of a camelid species) with the target antigen, B cells producing (conventional Camelida) antibodies having specificity for the desired antigen can be identified and polynucleotide encoding the VH and Vλ/Vκ domains of such antibodies can be isolated using known techniques.

Isolated Camelidae VH and Vλ/Vκ domains obtained by active immunisation can be used as a basis for engineering humanised antibodies according to the invention. Starting from intact Camelidae VH and Vλ/Vκ domains, it is possible to engineer one or more amino acid substitutions, insertions or deletions in the framework regions of the VH domain and/or the Vλ/Vκ domain which depart from the starting Camelidae sequence, including substitutions at the specific amino acid positions identified herein. The purpose of such changes in primary amino acid sequence may be to reduce presumably unfavourable properties (e.g. immunogenicity in a human host), sites of potential product heterogeneity and or instability (glycosylation, deamidation, isomerisation, etc.) or to enhance some other favourable property of the molecule (e.g. solubility, stability, bioavailability, etc.). In other embodiments, changes in primary amino acid sequence can be engineered in one or more of the hypervariable loops (or CDRs) of a Camelidae VH and/or Vλ/Vκ domain obtained by active immunisation. Such changes may be introduced in order to enhance antigen binding affinity and/or specificity, or to reduce presumably unfavourable properties, e.g. immunogenicity in a human host (so-called humanization), sites of potential product heterogeneity and or instability, glycosylation, deamidation, isomerisation, etc., or to enhance some other favourable property of the molecule, e.g. solubility, stability, bioavailability, etc.

As an alternative to "active immunisation" with a target antigen (or a composition comprising the target antigen or a polynucleotide encoding it) it is also possible to make use of immune responses in diseased Camelidae animals or naturally occurring immune responses within Camelidae species as a source of VH and/or Vλ/Vκ domains which can be used as components of humanised antibodies with the desired antigen-binding properties. Such VH/Vλ/Vκ domains may also be used as the starting point for engineering humanised antibodies in an analogous manner to VH/Vλ/Vκ domains obtained by active immunisation. The invention still further encompasses the use of non-immune libraries, and to humanised antibodies obtained/derived therefrom.

In other embodiments, the invention encompasses "chimeric" antibody molecules comprising humanised VH and Vλ/Vκ domains from Camelidae and one or more constant domains from a non-camelid antibody, for example human-encoded constant domains (or engineered variants thereof). The invention also extends to chimeric antigen binding polypeptides (e.g. antibody molecules) wherein one of the VH or the Vλ/Vκ domain is camelid-encoded but humanised according to the invention, and the other variable domain is non-camelid (e.g. from human, rodent, lagomorph, non-human primate or cartilaginous fish). In such embodiments it is preferred that both the VH domain and the Vλ/Vκ domain are obtained from the same species of camelid, for example both VH and Vλ/Vκ may be from *Lama glama* or both VH and Vλ/Vκ may be from *Lama pacos* (prior to introduction of engineered amino acid sequence variation). In such embodiments both the VH and the Vλ/Vκ domain may be derived from a single animal, particularly a single animal which has been actively immunised.

Structure of the Humanised Antibody

In non-limiting embodiments, humanised antibodies according to the invention may comprise CH1 domains and/or CL domains, the amino acid sequence of which is fully or substantially human. Where the antibody of the invention is an antibody intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) in the antibody of the invention may be fully or substantially human with respect to it's amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates antibodies comprising constant domains of "human" sequence which have been altered, by one or more amino acid additions, deletions or substitutions with respect to the human sequence.

As discussed elsewhere herein, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp. Med. 176:1191-1195 (1992) and Shopes, B. J. Immunol. 148:2918-2922 (1992). Alternatively, an antibody can be engineered which has dual Fc regions and may thereby have enhanced complement lysis and ADCC capabilities. See Stevenson et al., Anti-Cancer Drug Design 3:219-230 (1989). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension.

The invention can, in certain embodiments, encompass chimeric Camelida/human antibodies, and in particular chimeric antibodies in which the VH and Vλ/Vκ domains are of fully camelid sequence (e.g. Llama or alpaca) and the remainder of the antibody is of fully human sequence. In preferred embodiments the invention also encompasses "humanised" or "germlined" Camelidae antibodies, and Camelida/human chimeric antibodies, in which the VH and Vλ/Vκ domains contain one or more amino acid substitutions in the framework regions in comparison to Camelidae VH and Vλ/Vκ domains obtained by active immunisation. Such "humanisation" increases the % sequence identity with human germline VH or Vλ/Vκ domains by replacing mis-matched amino acid residues in a starting Camelidae VH or Vλ/Vκ domain with the equivalent residue found in a human germline-encoded VH or Vλ/Vκ domain.

The invention still further encompasses CDR-grafted antibodies in which CDRs (or hypervariable loops) derived from a heterologous antibody, which could be derived from a species other than a camelid (e.g. rodent, primate, lagomorph, or cartilaginous fish), or a different camelid species, are grafted onto a humanised camelid VH and Vλ/Vκ framework, with the remainder of the antibody also being of fully human origin.

The invention also encompasses antigen binding polypeptides wherein either one or other of the VH or Vλ/Vκ domain is a humanised camelid VH or Vλ/Vκ domain, containing at amino acid substitution at one or more of the specific positions identified herein, and the "other" variable domain has non-camelid, e.g. human, amino acid sequence. Thus, it is contemplated to pair a humanised camelid VH domain with a human Vλ/Vκ domain, or to pair a human VH domain with a humanised camelid Vλ/Vκ domain. Such pairings may increase the available antigen-binding repertoire from which to select high affinity binders with the desired antigen binding properties.

The invention still further extends to antigen binding polypeptides wherein the hypervariable loop(s) or CDR(s) of the VH domain and/or the Vλ/Vκ domain are obtained from Camelidae, but wherein at least one of said (camelid-derived) hypervariable loops or CDRS has been engineered to include one or more amino acid substitutions, additions or deletions relative to the camelid-encoded sequence. Such changes include "humanisation" of the hypervariable loops/CDRs. Camelid-derived HVs/CDRs which have been engineered in this manner may still exhibit an amino acid sequence which is "substantially identical" to the amino acid sequence of a camelid-encoded HV/CDR. In this context, "substantial identity" may permit no more than one, or no more than two amino acid sequence mis-matches with the camelid-encoded HV/CDR.

Antibodies according to the invention may be of any isotype. Antibodies intended for human therapeutic use will typically be of the IgA, IgD, IgE IgG, IgM type, often of the IgG type, in which case they can belong to any of the four sub-classes IgG1, IgG2a and IgG2b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

Humanised antibodies according to the invention may be useful in a wide range of applications, both in research and in the diagnosis and/or treatment of diseases, but find particular utility as human therapeutic agents, particularly in the form of monoclonal antibodies.

The invention provides a platform for production of humanised antibodies, and specifically monoclonal antibodies, against a wide range of antigens and in its broadest aspect the invention is not intended to be limited with respect to the exact identity of the target antigen, nor indeed the specificity or affinity of binding to the target antigen. However, in particular, non-limiting, embodiments the target antigen may be a non-camelid antigen, a bacterial antigen, a viral antigen or a human antigen. In a preferred embodiment the target antigen may be an antigen of particular therapeutic importance. The term "target of therapeutic importance" refers to a target involved in formation, onset, progression, mediation of human or animal diseases or of the effects related to the respective disease. Included within this definition are targets wherein the expression levels and/or activity of the target are modulated by antibody binding (e.g. receptors whose activity may be modulated by binding of agonist or antagonist antibodies), and targets wherein the activity and/or expression of the target has a direct or indirect impact on a disease.

By way of example, "human antigens" may include naturally occurring human polypeptides (proteins) which function as receptors, receptor ligands, cell-signalling molecules, hormones, cytokines or cytokine receptors, neurotransmitters, etc. By "naturally occurring" is meant that the polypeptide is expressed within the human body, at any stage if its development, including polypeptides expressed by the human body during the course of a disease.

Polynucleotides, Vectors and Recombinant Expression

The invention also provides a polynucleotide molecule encoding the humanised antibody of the invention, an expression vector containing a nucleotide sequence encoding the humanised antibody of the invention operably linked to regulatory sequences which permit expression of the antibody in a host cell or cell-free expression system, and a host cell or cell-free expression system containing this expression vector.

Polynucleotide molecules encoding the humanised antibody of the invention include, for example, recombinant DNA molecules.

The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of a humanised antibody according to the invention, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the scope of the invention.

In an important aspect, the invention also provides a method of producing a recombinant humanised antibody which comprises culturing a host cell (or cell free expression system) containing polynucleotide (e.g. an expression vector) encoding the recombinant antigen binding polypeptide under conditions which permit expression of the antigen binding polypeptide, and recovering the expressed antibody. This recombinant expression process can be used for large scale production of antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

Further aspects of the invention relate to test kits, including diagnostic kits etc. comprising an antibody according to the invention, and also pharmaceutical formulations comprising an antibody according to the invention.

Where the humanised antibody is intended for diagnostic use, for example where the antibody is specific for an antigen which is a biomarker of a disease state or a disease susceptibility, then it may be convenient to supply the antigen binding polypeptide as a component of a test kit. Diagnostic tests typically take the form of standard immunoassays, such as ELISA, radioimmunoassay, Elispot, etc. The components of such a test kit may vary depending on the nature of the test or assay it is intended to carry out using the antigen binding polypeptide of the invention, but will typically include additional reagents required to carry out an immunoassay using the antigen binding polypeptide of the invention. Antibodies, or antigen binding fragments thereof, for use as diagnostic reagents may carry a revealing label, such as for example a fluorescent moiety, enzymatic label, or radiolabel.

Humanised antibodies intended for in vivo therapeutic use are typically formulated into pharmaceutical dosage forms, together with one or more pharmaceutically acceptable diluents, carriers or excipients (Remington's Pharmaceutical Sciences, 16th edition., Osol, A. Ed. 1980). Antibodies according to the invention are typically formulated as sterile aqueous solutions, to be administered intravenously, or by intramuscular, intraperitoneal, intra-cerebrospinal, intratumoral, oral, peritumoral, subcutaneous, intra-synovial, intrathecal, topical, sublingual or inhalation routes, to a mammalian subject, typically a human patient, in need thereof. For the prevention or treatment of disease, the appropriate dosage of antibody will depend on the type of disease to be treated, the severity and clinical course of the disease, plus the patient's age, weight and clinical history, and will be determined by the judgement of the attending physician.

Processes for the Production of Humanised Antibodies

Processes for the production of humanised antibodies according to the invention may involve first isolating a conventional camelid antibody with the desired antigen binding properties, and then subjecting the antibody to humanisation by engineering one or more amino acid substitutions in either the VH or VL domain, as described herein.

The first step of the process may involve active immunisation of a species in the family Camelidae in order to elicit an immune response against the target antigen, thereby raising camelid conventional antibodies immunoreactive with the target antigen. Protocols for immunisation of camelids are described in the accompanying examples. The antigen preparation used for immunisation may be a purified form of the target antigen, for example recombinantly expressed polypeptide, or an immunogenic fragment thereof. However, it is also possible to immunise with crude preparations of the antigen, such as like isolated cells or tissue preparations expressing or encoding the target antigen, cell lysates, cell supernatants or fractions such as cell membranes, etc., or with a polynucleotide encoding said target antigen (a DNA immunisation).

The process will typically involve immunisation of animals of a Camelidae species (including, but limited to, llamas and alpacas), and advantageously these animals will belong to an outbred population. However, it is also contemplated to use transgenic animals (e.g. transgenic mice) containing the Camelid conventional Ig locus, or at least a portion thereof.

A topic of increasing interest seems to be the difference between the complementarity determining regions (CDRs) of in vivo and in vitro generated antibodies. It is surmised that the in vivo selection has a favourable impact on the immunogenicity, functionality, stability and therefore improved manufacturability of the resulting antibodies, whilst synthetic CDRs generated and selected in vitro may have a disadvantage from this point of view. This is important since a given therapeutic antibody risks to be neutralized by the so called anti-idiotypic antibody response from the patient (Lonberg, Nature Biotechnology, 23: 1117-1125, (2005)).

A key advantage of processes based on active immunisation of camelids stems from the fact that all species of Camelidae can be maintained in large outbred populations where the individual animals have a different genetic background. It is therefore possible to use active immunisation to elicit a strong and diverse immune response against the antigen of interest from which a diverse pool of potential antigen binding molecules can be obtained. As illustrated in the accompanying examples, it has been observed that active immunisation of camelids can generate Fab fragments binding to a target antigen with a high degree of immunodiversity. Without wishing to be bound by theory, it is surmised that the phylogenetic distance between humans and camelids may be important for production of a diverse immune response against a given target antigen. In contrast, the non-human primates are phylogenetically close to humans, thus targets with high homology between non-human primates and humans may elicit only a limited immune response in terms of strength and diversity in non-human primates.

The ability to use active immunisation in an outbred population which is phylogenetically distant from human would not be particularly advantageous if the antibodies so-produced were to exhibit a low sequence and structural homology with human antibodies such that substantial "protein engineering" would be required to create a candidate antibody with therapeutic potential. It is therefore extremely important that it has been shown that the Camelidae germline (and somatically mutated sequences) encodes both VH and VL domains with a very high degree of sequence and structural homology with human VH and VL domains. This high degree of homology in combination with the availability of large outbred populations results in a very powerful platform for development of monoclonal antibodies for use as human therapeutics.

Following active immunisation with the target antigen, peripheral blood lymphocytes or biopsies such as lymph nodes or spleen biopsies may be isolated from the immunised animal and screened for production of conventional camelid antibodies against the target antigen. Techniques such as enrichment using panning or FACS sorting may be used at this stage to reduce the complexity of the B cell repertoire to be screened, as illustrated in the examples. Antigen-specific B cells are then selected and used for total RNA extraction and subsequent cDNA synthesis. Nucleic acid encoding the native camelid VH and VL domains (specific for the target antigen) can be isolated by PCR.

It is not essential to use active immunisation in order to identify camelid conventional antibodies immunoreactive with a target of interest. It may also be possible to make use of the camelid's own immune response, either the immunodiversity naturally present in the animal, or for example a diseased animal or animal which has been naturally exposed to a particular pathogen, e.g. by normal infection routes. In this regard, use can be made of non-immune camelid libraries. If "natural" immune responses within the camelid already give rise to antibodies which bind the target antigen of interest, then it is possible to make use of the genetic engineering techniques described herein, and other standard techniques known in the art, in order to culture and isolate B cells producing such antibodies, or produce monoclonal cultures of such antibodies, and/or to determine the nucleotide sequence of the camelid gene segments encoding the VH and/or VL domains of such antibodies. Armed with this sequence information, it is then possible to engineer recombinant DNA constructs encoding antibodies which embody the camelid derived VH and/or VL, or the hypervariable loops (or CDRs) thereof.

Nucleic acid encoding camelid VH and VL domains (whether obtained by active immunisation or by other means) may be cloned directly into an expression vector for the production of an antigen binding polypeptide according to the invention. In particular, these sequences could be cloned into an expression vector which also encodes a human antibody constant region, or a portion thereof, in order to produce a chimeric antibody. However, it is typical to carry out further manipulations on the isolated camelid VH and VL sequences before cloning and expression with human constant region sequences.

As a first step, candidate camelid VH and VL sequences (including sequences isolated following the active immunisation) may be used to prepare a camelid libraries (e.g. Fab libraries, as described in the accompanying examples). The library may then be screened (e.g. using phage display) for binding to the target antigen. Promising lead candidates can be further tested for target antigen binding, for example using Biacore or a suitable bioassay. Finally, the sequences encoding the VH and VL domains of the most promising leads can be cloned as an in-frame fusion with sequences encoding a human antibody constant region.

It is possible to introduce changes in the polynucleotide sequences used to encode camelid-derived sequences in the VH/VL domains, or humanised variants thereof, for the purposes of codon optimisation, and make other changes in polynucleotide sequence related to cloning and/or expression, which do not alter the encoded amino acid sequence.

In certain processes, "chain shuffling" may be performed in which a particular variable domain known to bind the antigen of interest is paired with each of a set of variable domains of the opposite type (i.e. VH paired with VL library or vice versa), to create libraries, and the resulting "promiscuous" combinations of VH/VL tested for antigen binding affinity and/or specificity. Alternatively, a library of VH domains could be paired with a library of VL domains, either randomly or in a hierarchical manner, and the resulting combinations tested (see Clackson et al., Nature, Vol. 352. pp 624-638, 1991). In this process, the libraries may be libraries of rearranged VH and VL (Vκ or Vλ) from camelids which display immunity to the antigen of interest (including animals which have been actively immunised). The chain shuffling process can increase immunodiversity and produce pairings with significantly enhanced affinity.

Camelid VH/VL domain pairings with useful antigen-binding properties can also be isolated using a reverse "chain shuffling" process, starting with non-camelid (preferably human)-encoded VH/VL domain combination which binds to an antigen of interest. This could be, for example, a fully human therapeutic antibody against a validated disease target. Starting from this VH/VL combination, it is possible to carry out a first round of selection in which the VH domain is "shuffled" with a library of camelid-encoded VL domains (or vice versa), and the pairings tested for antigen binding. Selected non-camelid (e.g. human) VH/camelid VL pairings may then be subjected to a second round of selection in which the camelid-encoded VL is shuffled against a library of camelid-encoded VH, and the resulting pairings tested for antigen binding. As a result, it may be possible to produce a camelid VH/camelid VL combination which carries the epitope imprint of the starting VH/VL combination. This camelid VH/VL combination could be further engineered/modified and combined with human-encoded constant domains as required, using any of the processes described herein.

Cloned polynucleotide sequences encoding the camelid-derived VH domains and/or the camelid VL domains are then engineered to introduce amino acid substitutions at one or more of the specific amino acid positions disclosed herein. The preferred substitutions include, but are not limited to, those listed in Table 4 for VH and those listed in Table 5 for VL, optionally in combination with any of the J segment substitutions disclosed herein and/or any of the CDR substitutions disclosed herein.

The overall aim of humanisation is to produce a molecule in which the VH and VL domains exhibit minimal immunogenicity when introduced into a human subject, whilst retaining the specificity and affinity of the antigen binding site formed by the parental VH and VL domains encoded by Camelidae (e.g. camelid VH/VL obtained by active immunisation). The humanisation protocol may be carried out as an iterative process, in which amino acid changes from camelid to human are introduced sequentially and tested at each stage until a significant drop in affinity (e.g. 5-10 fold) is observed. It is also possible to use a "library" approach in order to test multiple amino acid changes in parallel.

Methods of Library Construction

A method of producing a library of expression vectors encoding VH and/or VL domains of camelid conventional antibodies, may comprise the steps:
a) amplifying regions of nucleic acid molecules encoding VH and/or VL domains of camelid conventional antibodies to obtain amplified gene segments, each gene segment containing a sequence of nucleotides encoding a VH domain or a sequence of nucleotides encoding a VL domain of a camelid conventional antibody, and
b) cloning the gene segments obtained in a) into expression vectors, such that each expression vector contains at least a gene segment encoding a VH domain and/or a gene segment encoding a VL domain, whereby a library of expression vectors is obtained.

The nucleic acid amplified in step a) may comprise cDNA or genomic DNA prepared from lymphoid tissue of a camelid, said lymphoid tissue comprising one or more B cells, lymph nodes, spleen cells, bone marrow cells, or a combination thereof. Circulating B cells are particularly preferred. It has been surprisingly found that peripheral blood lymphocytes (PBLs) can be used as a source of nucleic acid encoding VH and VL domains of conventional camelid antibodies, i.e. there is sufficient quantity of plasma cells (expressing antibodies) present in a sample of PBLs to enable direct amplification. This is advantageous because PBLs can be prepared from a whole blood sample taken from the animal (camelid). This avoids the need to use invasive procedures to obtain tissue biopsies (e.g. from spleen or lymph node), and means that the sampling procedure can be repeated as often as necessary, with minimal impact on the animal. For example, it is possible to actively immunise the camelid, remove a first blood sample from the animal and prepare PBLs, then immunise the same animal a second time, either with a "boosting" dose of the same antigen or with a different antigen, then remove a second blood sample and prepare PBLs.

Lymphoid tissue (e.g. circulating B cells) may be obtained from a camelid which has been actively immunised. It is also contemplated to prepare non-immune libraries and libraries derived from lymphoid tissue of diseased camelids.

Conveniently, total RNA (or mRNA) can be prepared from the lymphoid tissue sample (e.g. peripheral blood cells or tissue biopsy) and converted to cDNA by standard techniques. It is also possible to use genomic DNA as a starting material.

One can use either a diverse library approach, or a B cell selection approach for construction of the library. In a diverse library approach, repertoires of VH and VL-encoding gene segments may be amplified from nucleic acid prepared from lymphoid tissue without any prior selection of B cells. In a B cell selection approach, B cells displaying antibodies with desired antigen-binding characteristics may be selected, prior to nucleic acid extraction and amplification of VH and VL-encoding gene segments.

Various conventional methods may be used to select camelid B cells expressing antibodies with desired antigen-binding characteristics. For example, B cells can be stained for cell surface display of conventional IgG with fluorescently labelled monoclonal antibody (mAb, specifically recognizing conventional antibodies from llama or other camelids) and with target antigen labelled with another fluorescent dye. Individual double positive B cells may then be isolated by FACS, and total RNA (or genomic DNA) extracted from individual cells. Alternatively cells can be subjected to in vitro proliferation and culture supernatants with secreted IgG can be screened, and total RNA (or genomic DNA) extracted from positive cells. In a still further approach, individual B cells may be transformed with specific genes or fused with tumor cell lines to generate cell lines, which can be grown "at will", and total RNA (or genomic DNA) subsequently prepared from these cells.

Instead of sorting by FACS, target specific B cells expressing conventional IgG can be "panned" on immobilized monoclonal antibodies (directed against camelid conventional antibodies) and subsequently on immobilized target antigen. RNA (or genomic DNA) can be extracted from pools of antigen specific B cells or these pools can be transformed and individual cells cloned out by limited dilution or FACS.

B cell selection methods may involve positive selection, or negative selection.

Whether using a diverse library approach without any B cell selection, or a B cell selection approach, nucleic acid (cDNA or genomic DNA) prepared from the lymphoid tissue is subject to an amplification step in order to amplify gene segments encoding individual VH domains or VL domains.

Total RNA extracted from the lymphoid tissue (e.g. peripheral B cells or tissue biopsy) may be converted into random primed cDNA or oligo dT primer can be used for cDNA synthesis, alternatively Ig specific oligonucleotide primers can be applied for cDNA synthesis, or mRNA (i.e. poly A RNA) can be purified from total RNA with oligo dT cellulose prior to cDNA synthesis. Genomic DNA isolated from B cells can be used for PCR.

PCR amplification of heavy chain and light chain (kappa and lambda) gene segments encoding at least VH or VL can be performed with FR1 primers annealing to the 5' end of the variable region in combination with primers annealing to the 3' end of CH1 or Ckappa/Clambda region with the advantage that for these constant region primers only one primer is needed for each type. This approach enables camelid Fabs to be cloned. Alternatively sets of FR4 primers annealing to the 3' end of the variable regions can be used, again for cloning as Fabs (fused to vector encoded constant regions) or as scFv (single chain Fv, in which the heavy and light chain variable regions are linked via a flexible linker sequence); alternatively the variable regions can be cloned in expression vectors allowing the production of full length IgG molecules displayed on mammalian cells.

In general the amplification is performed in two steps; in the first step with non-tagged primers using a large amount of cDNA (to maintain diversity) and in the second step the amplicons are re-amplified in only a few cycles with tagged primers, which are extended primers with restriction sites introduced at the 5' for cloning. Amplicons produced in the first amplification step (non-tagged primers) may be gel-purified to remove excess primers, prior to the second amplification step. Alternatively, promoter sequences may be introduced, which allow transcription into RNA for ribosome display. Instead of restriction sites recombination sites can be introduced, like the Cre-Lox or TOPO sites, that permit the site directed insertion into appropriate vectors.

Amplified gene segments encoding camelid conventional VH and VL domains may then be cloned into vectors suitable for expression of VH/VL combinations as functional antigen binding polypeptides. By way of example, amplified VHCH1/VκCκ/VλCλ gene segments from pools of B cells (or other lymphoid tissue not subject to any B cell selection) may be first cloned separately as individual libraries (primary libraries), then in a second step Fab or scFV libraries may be assembled by cutting out the light chain fragments and ligating these into vectors encoding the heavy chain fragments. The two step procedure supports the generation of large libraries, because the cloning of PCR products is relatively inefficient (due to suboptimal digestion with restriction enzymes). scFv encoding DNA fragments can be generated by splicing-by-overlap extension PCR (SOE) based on a small overlap in sequence in amplicons; by mixing VH and VL encoding amplicons with a small DNA fragment encoding the linker in a PCR a single DNA fragment is formed due to the overlapping sequences.

Amplicons comprising VH and VL-encoding gene segments can be cloned in phage or phagemid vectors, allowing selection of target specific antibody fragments by using phage display based selection methods. Alternatively amplicons can be cloned into expression vectors which permit display on yeast cells (as Fab, scFv or full length IgG) or mammalian cells (as IgG).

In other embodiments, cloning can be avoided by using the amplicons for ribosome display, in which a T7 (or other) promoter sequence and ribosome binding site is included in the primers for amplification. After selection for binding to target antigen, pools are cloned and individual clones are analyzed. In theory, larger immune repertoires can be sampled using this approach as opposed to a phage display library approach, because cloning of libraries and selection with phage is limited to $10^{10}$ to $10^{12}$ clones.

When applying B cell sorting, amplicons contain VH or VL-encoding gene segments of individual target specific B cells can be cloned directly into bacterial or mammalian expression vectors for the production of antibody fragments (scFVs or Fabs) or even full length IgG.

Screening and Selection of Clones Immunoreactive with Target Antigen

Screening/selection typically involves contacting expression products encoded by clones in the library (ie. VH/VL pairings in the form of antigen binding polypeptides, e.g. Fabs, scFVs or antibodies) with a target antigen, and selecting one or more clones which encode a VH/VL pairings exhibiting the desired antigen binding characteristics.

Phage display libraries may be selected on immobilized target antigen or on soluble (often biotinylated) target antigen. The Fab format allows affinity driven selection due to its monomeric appearance and its monovalent display on phage, which is not possible for scFv (as a consequence of aggregation and multivalent display on phage) and IgG (bivalent format). Two to three rounds of selections are typically needed to get sufficient enrichment of target specific binders.

Affinity driven selections can be performed by lowering the amount of target antigen in subsequent rounds of selection, whereas extended washes with non-biotinylated target enables the identification of binders with extremely good affinities.

The selection procedure allows the user to home in on certain epitopes; whereas the classical method for elution of phage clones from the immobilized target is based on a pH shock, which denatures the antibody fragment and/or target, competition with a reference mAb against the target antigen or soluble receptor or cytokine leads to the elution of phage displaying antibody fragments binding to the relevant epitope of the target (this is of course applicable to other display systems as well, including the B cells selection method).

Individual clones taken from the selection outputs may be used for small scale production of antigen-binding polypeptides (e.g. antibody fragments) using periplasmic fractions prepared from the cells or the culture supernatants, into which the fragments "leaked" from the cells. Expression may be driven by an inducible promoter (e.g. the lac promoter), meaning that upon addition of the inducer (IPTG) production of the fragment is initiated. A leader sequence ensures the transport of the fragment into the periplasm, where it is properly folded and the intramolecular disulphide bridges are formed.

The resulting crude protein fractions may be used in target binding assays, such as ELISA. For binding studies, phage prepared from individual clones can be used to circumvent the low expression yields of Fabs, which in general give very low binding signals. These protein fractions can also be screened using in vitro receptor—ligand binding assays to identify antagonistic antibodies; ELISA based receptor—ligand binding assays can be used, also high throughput assays like Alphascreen are possible. Screening may be performed in radiolabelled ligand binding assays, in which membrane fractions of receptor overexpressing cell lines are immobilized; the latter assay is extremely sensitive, since only picomolar amounts of radioactive cytokine are needed, meaning that minute amounts of antagonistic Fabs present in the crude protein fraction will give a positive read-out. Alternatively, FACS can be applied to screen for antibodies, which inhibit binding of a fluorescently labelled cytokine to its receptor as expressed on cells, while FMAT is the high throughput variant of this.

Fabs present in periplasmic fractions or partially purified by IMAC on its hexahistidine tag or by protein G (known to bind to the CH1 domain of Fabs) can be directly used in bioassays using cells, which are not sensitive to bacterial impurities; alternatively, Fabs from individual *E. coli* cells can be recloned in mammalian systems for the expression of Fabs or IgG and subsequently screened in bioassays.

Following identification of positive expression vector clones, i.e. clones encoding a functional VH/VL combination which binds to the desired target antigen, it is a matter of routine to determine the nucleotide sequences of the variable regions, and hence deduce the amino acid sequences of the encoded VH and VL domains.

If desired, the Fab (or scFV) encoding region may be recloned into an alternative expression platform, e.g. a bacterial expression vector (identical to the phagemid vector, but without the gene 3 necessary for display on phage), which allows larger amounts of the encoded fragment to be produced and purified.

The affinity of target binding may be determined for the purified Fab (or scFV) by surface plasmon resonance (e.g. Biacore) or via other methods, and the neutralizing potency tested using in vitro receptor—ligand binding assays and cell based assays.

Families of antigen-binding, and especially antagonistic Fabs (or scFVs) may be identified on the basis of sequence analysis (mainly of VH, in particular the length and amino acid sequence of CDR3 of the VH domain).

Potency Optimisation

Clones identified by screening/selection as encoding a VH/VL combination with affinity for the desired target antigen may, if desired, be subject to downstream steps in which the affinity and/or neutralising potency is optimised.

Potency optimization of the best performing member of each VH family can be achieved via light chain shuffling, heavy chain shuffling or a combination thereof, thereby selecting the affinity variants naturally occurring in the animal. This is particularly advantageous in embodiments where the original camelid VH/VL domains were selected from an actively immunised camelid, since it is possible to perform chain shuffling using the original library prepared from the same immunised animal, thereby screening affinity variants arising in the same immunised animal.

For light chain shuffling the gene segment encoding the VH region (or VHCH1) of VH/VL pairing with desirable antigen binding characteristics (e.g. an antagonistic Fab) may be used to construct a library in which this single VH-encoding gene segment is combined with the light chain repertoire of the library from which the clone was originally selected. For example, if the VH-encoding segment was selected from a library (e.g. Fab library) prepared from a camelid animal actively immunised to elicit an immune response against a target antigen, then the "chain shuffling" library may be constructed by combining this VH-encoding segment with the light chain (VL) repertoire of the same immunised camelid. The resulting library may then be subject to selection of the target antigen, but under stringent conditions (low concentrations of target, extensive washing with non-biotinylated target in solution) to ensure the isolation of the best affinity variant. Off-rate screening of periplasmic fractions may also assist in the identification of improved clones. After sequence analysis and recloning into a bacterial production vector, purified selected Fabs may be tested for affinity (e.g. by surface plasmon resonance) and potency (e.g. by bioassay).

Heavy chain shuffling can be performed by cloning back the gene segment encoding the light chain (VL) of a clone selected after light-chain shuffling into the original heavy chain library from the same animal (from which the original VH/VL-encoding clone was selected). Alternatively a CDR3 specific oligonucleotide primer can be used for the amplification of the family of VH regions, which can be cloned as a repertoire in combination with the light chain of the antagonistic Fab. Affinity driven selections and off-rate screening then allow the identification of the best performing VH within the family.

It will be appreciated that the light chain shuffling and heavy chain shuffling steps may, in practice, be performed in either order, i.e. light chain shuffling may be performed first and followed by heavy chain shuffling, or heavy chain shuffling may be performed first and followed by light chain shuffling. Both possibilities are encompassed within the scope of the invention.

From light chains or heavy chains of VH/VL pairings (e.g. Fabs) with improved affinity and potency the sequences of, in particular, the CDRs can be used to generate engineered variants in which mutations of the individual Fabs are combined. It is known that often mutations can be additive, meaning that combining these mutations may lead to an even more increased affinity.

Germlining and Formatting for Human Therapeutic Use

The VH and VL-encoding gene segments of selected expression clones encoding VH/VL pairings exhibiting desirable antigen-binding characteristics (e.g. phage clones encoding scFVs or Fabs) may be subjected to downstream processing steps and recloned into alternative expression platforms, such as vectors encoding antigen binding polypeptide formats suitable for human therapeutic use (e.g. full length antibodies with fully human constant domains).

Promising "lead" selected clones may be engineered to introduce one or more changes in the nucleotide sequence encoding the VH domain and/or the VL domain, which changes may or may not alter the encoded amino acid sequence of the VH domain and/or the VL domain. Such changes in sequence of the VH or VL domain include the substitutions of the specific VH and VL amino acid residues identified herein. In particular, camelid VH domains may be engineered to introduce one or more of the specific amino acid substitutions listed in Table 4, whereas camelid VL domains may be engineered to introduce one or more of the specific amino acid substitutions listed in Table 5.

The germlining of a VH domain having an amino acid sequence homologous to a member of the human VH3 family will often involve replacement/substitution of a number of residues, which already deviate in publically known *Lama glama*, *Lama pacos* or *Camelus dromedarius* derived germline sequences. Permitted amino acid substitutions for germlining/humanisation of a VH3 domain of *Lama glama*, *Lama pacos* or *Camelus dromedarius*, and in particular *Lama glama* include, but are not limited to, amino acid replacements at any one or any combination of positions 74, 83 and 84 in the framework region (using Kabat numbering). Such replacement(s) will involve substitution of the camelid-encoded residue(s) at these positions with a different amino acid, which may be a natural or non-natural amino acid, and is preferably an amino acid known to occur at the corresponding position in a human-encoded VH3 domain. For example, Alanine at position 74 might be replaced with serine, or alanine retained at this position, Lysine at position 83 might be replaced with Arginine and Proline at position 84 might be replaced with Alanine. Accordingly, particular non-limiting embodiments of the antigen binding polypeptide of the invention include variants comprising a camelid (and more specifically llama, alpaca or dromedary) VH domain exhibiting sequence homology to a human VH3 domain, which VH domain includes amino acid substitutions (versus the camelid-encoded sequence) at one or more or all of positions 74, 83 and 84 (using Kabat numbering). In particular, variants with one or more or any combination of the following substitutions are permitted: A changed to S at position 74, K changed to R at position 83 or P changed to A at position 84.

Once the amino acid sequences of the lead VH and VL domains (following potency optimisation, as appropriate) are known, synthetic genes of VH and VL can be designed, in which residues deviating from the human germline are replaced with the preferred human residue (from the closest matching human germline, or with residues occurring in other human germlines, or even the camelid wild type residue). At this stage the gene segments encoding the variable domains may be re-cloned into expression vectors in which they are fused to human constant regions of the Fab, either during gene synthesis or by cloning in an appropriate display vector.

The resulting VH and VL synthetic genes can be recombined into a Fab library or the germlined VH can be recombined with the wild type VL (and vice versa, referred to as "hybrid" libraries). Affinity-driven selections will allow the isolation of the best performing germlined version, in case of the "hybrid" libraries, the best performing germlined VH can be recombined with the best performing germlined VL.

Amino acid and nucleotide sequence information for the germlined Fabs can be used to generate codon-optimized synthetic genes for the production of full length human IgG of the preferred isotype (IgG1 for ADCC and CDC, IgG2 for limited effector functions, IgG4 as for IgG2, but when monovalent binding is required). For non-chronic applications and acute indications bacterially or mammalian cell produced human Fab can produced as well.

The invention will be further understood with reference to the following non-limiting experimental examples.

Examples 1 to 9 illustrate the process of raising an antibody against an example antigen denoted "cytokine x", starting from immunization of llamas. The same general protocol can be adapted for any target antigen in any camelid species, hence the precise identity of "cytokine x" is not material. The process is also illustrated for preparation of Fabs binding IL-1 Beta.

Various publications are cited in the foregoing description and throughout the following examples, each of which is incorporated by reference herein in its entirety.

General Protocol

Example 1

Immunization of Llamas.

Immunizations of llamas (Lama glama) and harvesting of peripheral blood lymphocytes as well as the subsequent extraction of RNA and amplification of antibody gene fragments were performed as described by De Haard and colleagues (De Haard et al., J. Bact. 187: 4531-4541(2005)). One llama was immunized intramuscularly with recombinant human Cytokine x using Freund's complete adjuvant or an appropriate animal-friendly adjuvant Stimune[198](Cedi Diagnostics BV, The Netherlands). Cytokine x (recombinantly expressed in engineered human cell line) was purchased. Prior to immunization the lyophilized cytokine x was reconstituted in PBS (Dulbecco) at a concentration of 250 µgml. The llama received 6 injections at weekly intervals, the first two injections with 100 µof cytokine per injection, the four last injections with 50 µg for each boost. Four days after the last immunization a blood sample (PBL1) of 150 ml was collected from the animal and serum was prepared. Ten days after the last immunization a second blood sample (PBL2) of 150 ml was taken and serum was prepared. Peripheral blood lymphocytes (PBLs), as the genetic source of the llama immunoglobulins, were isolated from the blood sample using a FICOLL-PAQUE® gradient (Amersham Biosciences) yielding between 1 and $5 \times 10^8$ PBLs. The maximal diversity of antibodies is expected to be equal to the number of sampled B-lymphocytes, which is about 10% (between 9.2 -23.2% (De Genst et al., Dev. Comp. Immunol. 30:187-98(2006)) of the number of PBLs (1 - $5 \times 10^7$). The fraction of conventional antibodies in llama serum is up to 80% of the amount of total immunoglobulin, which might be extrapolated to a similar fraction of B-lymphocytes that produce the conventional antibodies. Therefore, the maximal diversity of conventional antibodies in the 150ml blood sample is calculated as 0.8 - $4 \times 10^7$ different molecules. Total RNA was isolated from PBLs according to the method of Chomczynski et al. Anal. Biochem.162:1569-159 (1987)).

Example 2

Enrichment of Antigen Reactive B Cells by Panning or FACS Sorting (Optional).

In order to reduce the complexity of the sampled B cell repertoire enabling the efficient cloning of the recombinatorial Fab phage display library, antigen reactive B cells were enriched by a FACS sorting (Weitkamp et al., J. Immunol. Meth. (2003) 275: 223-237) using fluorescently labelled antigen and a mAb recognizing camelid conventional antibody specifically (as B cell marker) or by a panning procedure on immobilized antigen (Lightwood et al., J. Immunol. Meth. 316:133-143 (2006)).

PBLs from immunized animals were isolated via a density centrifugation on FICOLL-PAQUE® as described above. Optionally co-purified red blood cells were lysed by resuspending the PBL pellet in 20 ml of lysis buffer (8.29 g/L NH4Cl, 1.09 g/L KHCO3 and 37mg/L EDTA) at room temperature followed by centrifugation for 10 minutes at 200xg. Optional was also the depletion of monocytes by adhering these to the plastic surface of TI50 culture flask. To achieve this cells were resuspended in 70 ml RPMI (Invitrogen) supplemented with 10% foetal calf serum, GLUTAMAX® , 25 mM Hepes, penicillin-streptomycin (Invitrogen) and 0.38% sodium citrate and incubated for 2 hours at 37 ° C. and 5% CO2 in the flasks. The supernatant fraction containing the B selected was recovered and cells were counted.

Bulk sorting in FACS of (living) B cells displaying target specific conventional antibodies was performed by simultaneous staining with the fluorescently labelled mAb specifically recognizing camelid conventional antibodies and target antigen, labelled with yet another fluorescent dye. Between 1,000 and 100,000 antigen specific cells were sorted and used for RNA extraction by applying the protocol of Gough and colleagues (Gough, Anal. Biochem. 173:93-95 (1988)) or by using the TRIZOL® kit (Invitrogen). Total RNA was converted into random primed cDNA as template for the amplification of the antibody heavy and light chain variable genes (see Example 3 and further).

Example 3

Amplification and Cloning of Variable Region Genes.

Random primed cDNA was prepared from 80 µg of PBL RNA using the SUPERSCRIPT® III First-Strand Synthesis System for RT-PCR (Invitrogen). RNA was heat-denatured for 5 min at 65 ° C. in the presence of 2.5 µM of random hexanucleotide primer and 500 µM dNTPs in 8 independent reaction of 20u1 reaction. Subsequently, buffer and dithiothreitol were added according to the supplier's instructions, as well as 640 units of RNasOUT (40units/µl, Invitrogen), and 3200 units of SUPERSCRIPT® III reverse transcriptase (200 units/µl; Invitrogen) in a total final volume of 8×40 µl. After 50min at 50° C., 5min at 85° C. and 1min at 1° C. RNAse H was added (~4U) and incubated for 20min at 37° C. The pooled cDNA was cleanup using QIAquick[198] PCR Purification Kit according to supplier's recommendation and used for PCR.

Primers annealing to the 3' end of CH1 and 5' and 3' end of VH were designed on the basis of germline sequences from llama and dromedary, for which the deposited sequences could be retrieved from IMGT and other databases following the citations from De Genst and colleagues (De Genst et al, Dev. Comp. Immunol. 30:187-198 (2006)). For design of oligonucleotides for amplification of the light chain the rearranged and somatically mutated dromedary sequences were used that were published in a thesis study (I. Legssyer, Free University Brussels).

All primary PCRs were carried out with separate BACK primers annealing to the 5' end of the variable region and combined with FOR primers annealing to the 3' end of CH1, on relatively large amounts of random primed cDNA as template (up to 2.5 µl corresponding to 6 µg of total RNA) to maintain maximal diversity. The heavy chain derived amplicons can be reamplified with a combination of JHFOR primers, annealing to the 3' end of VH and containing a naturally occurring BstEII site, and SfiI-tagged VHBACK primers annealing to the 5' end of the VH gene, and subsequently cloned as VH fragments. The light chain V-genes were obtained by PCR with a set of CKFOR or CLFOR primer annealing to the 3' end of the constant domain and BACK primers priming at the 5' end of the V-regions. The amplicons from the first PCR reactions were reamplified with extended CH1FOR (containing a NotI site) or CKFOR and CLFOR primers (containing an AscI site) and subsequently cloned as llama Fab fragments.

Alternatively, the DNA segments can be reamplified with primers tagged with restriction sites (FOR primers with AscI site and FR4 based BACK primers with XhoI site) and cloned as VL fragments thus creating chimeric Fab's containing llama derived V regions combined with human C regions.

PCR was performed in a volume of 50 µA reactions using Phusion™ polymerase (Finnzymes) and 500 pM of each primer for 28 cycles (1 min at 96° C., 1 min at 60° C., and 1 min at 72° C. All products were purified from agarose gel with the QIAex-II extraction kit (Qiagen). As input for reamplification to introduce restriction sites, 100-200 ng of purified DNA fragment was used as template in a 100-µl reaction volume. The large amount of input, ensuring the maintenance of variability, was checked by analysis of 4 µl of the "unamplified" PCR mixture on agarose gel.

Example 4

Construction of the Primary and Secondary Camelid Fab Repertoires.

For the construction of the primary heavy chain and the two primary light chain repertoires, the PCR products, appended with restriction sites, were gel-purified prior to digestion and the different VH, Vκ, and Vλ families combined into three groups. The VHCH1 fragments were digested with SfiI and NotI and the VκCκ and VλCλ fragments were digested with ApaLI and AscI, and cloned into the phagemid vector pCB3 (similar to vector pCES1 with adapted multiple cloning site). The digested fragment (1 to 2 µg) were ligated to digested and purified pCB3 (2 to 4 µg) using T4-DNA ligase (Fermentas) at room temperature for several hours and then at 37° C. for 1-2 hours. The desalted ligation mixture for light or heavy chain pools was used for electroporation of the E. coli strain TG1, to create the one-chain libraries.

Alternatively, the VH fragments, 1.5 µg in total, may be digested with SfiI and BstEII (present in the VH) and ligated in a 100-200-µl reaction mixture with 9 units of T4-DNA ligase at room temperature to 4 µg, gel-purified vector pCB4 (similar to vector pCB3, but with the pIII gene deleted). In addition, the VH gene segments may be cloned via SfiI and BstEII and the Vκ/Vλ gene segments via ApaLI and XhoI, yielding the chimeric Fd and VκCκ and VλCλ.

The Fab library was obtained by cloning of light chain fragments, digested from plasmid DNA prepared from the light chain repertoires, into the plasmid collection containing the heavy chain repertoires. Plasmid DNA, isolated from at least $3 \times 10^9$ bacteria of the VL library (the donor vector), was digested with ApaLI and AscI for cloning of the gel purified DNA fragments in the acceptor vector that already contained the heavy chain libraries, thus creating a separate Fab library with kappa light chains and another library consisting of Fabs with a lambda light chain with a size of $1-10 \times 10^9$ clones. Similarly, the VλCλ or VκCκ from the single chain library can be extracted from agarose gel using ApaLI/AscI and cloned into the VHCH library vector using the same restriction site.

Example 5

Selection of the Library.

The rescue of phagemid particles with helper phage M13-KO7 or VCSM-13 was performed on 2-liter scale, using representative numbers of bacteria from the library for inoculation, to ensure the presence of at least 10 bacteria from each clone in the start inoculum. For selections, $10^{13}$ colony-forming units were used with antigens immobilized in immunotubes (Maxisorp™ tubes, Nunc) or in 96 wells microtiterplates (Maxisorp™, Nunc) or with soluble biotinylated antigens. The amount of the immobilized antigens was reduced 10-100 fold during subsequent selection rounds, starting at 10 µg/ml at round 1. Antigens were biotinylated at a ratio of 3 to 10 molecules of NHS-Biotin (Pierce) per molecule of antigen according to the supplier's recommendations and tested for their bioactivity in a bioassay. Unless stated otherwise, the antigens were used for selection at concentrations of 1 to 10 nM during round1 and 10 pM to 1 nM during subsequent rounds.

Example 6

Screening for Antagonistic Cytokine x Specific Fab's.

Soluble Fab was produced from individual clones as described in Marks et al. (Marks et al., J. Mol. Biol. 222:581-597 (1991)), but preferably as monoclonal phage (Lee et al., Blood 108:3103-3111 (2006)) to boost the sensitivity. Culture supernatants containing soluble Fab or Fab displaying phage were tested in ELISA with directly coated antigen or captured via immobilized streptavidin. Recombinant human cytokine x and streptavidin were coated at 10 µg/ml in 0.1 M NaHCO$_3$, pH 9.6, for 16 h at 4° C. Following 3 washes with PBS, 0.1% (v/v) Tween 20, biotinylated antigen was added for 30 to 60 minutes at room temperature at a concentration of 0.5 µg/ml. The plates were blocked during 30 min at room temperature with 2% (w/v) semi-skim milk powder (Marvel) in PBS or with 1% casein solution (in PBS). The culture supernatant was diluted 1- or 5-fold in 2% (w/v) Marvel/PBS and incubated 2 h; bound Fab was detected with anti-myc antibody 9E10 (5 µg/ml) recognizing the myc-peptide tag at the carboxyl terminus of the heavy Fd chain, and rabbit anti-mouse-HRP conjugate (Dako). Following the last incubation, staining was performed with tetramethylbenzidine and H$_2$O$_2$ as substrate and stopped by adding 0.5 volume of 1M H$_2$SO$_4$; the optical density was measured at 450 nm. Clones giving a positive signal in ELISA (over 2 times background), were analyzed by BstNI or HinfI fingerprinting of the PCR products obtained by amplification with the oligonucleotide primers M13-reverse and geneIII-forward (4) or of the separate F$_d$ and VκCκ or VλCλ amplicons.

Screening for the Fab's capacity to interfere with binding of cytokine x to its receptor was performed in an appropriate receptor—ligand binding ELISA. For this, low amounts of biotinylated cytokine x were incubated with Fab in culture supernatant on cytokine x—Receptor coated plates and bound cytokine x was subsequently detected with streptavidin-HRP conjugate. Positive hits were sequenced and Fab purified for determining their potency (IC50) in the in vitro receptor—ligand assay and to assess their affinity in BIAcore on immobilized cytokine x.

Large scale induction of soluble Fab fragments from individual clones was performed on a 50-ml or 250-ml scale in 2×TY containing 100 μg/ml carbenicillin and 2% glucose. After growth at 37° C. to an OD600 of 0.9, the cells were pelleted (10 min at 2,934×g) and resuspended in 2×TY with carbenicillin and 1 mM isopropyl-1-thio-D-galactopyranoside (IPTG). Alternative the De Bellis procedure (De Bellis and Schwartz, NAR (1990) 18(5): 1311) was followed using 0.2% in stead of 2% glucose, thus permitting the direct addition of IPTG to the medium of the late log phase cells. Bacteria were harvested after 3.5 h of growth at 30° C. by centrifugation (as before); periplasmic fractions were prepared by resuspending the cell pellet in 1 ml of ice-cold PBS. After 2-16 h of rotating head-over-head at 4° C., the spheroplasts were removed by two centrifugation steps; after spinning during 10 min at 3,400×g, the supernatant was clarified by an additional centrifugation step during 10 min at 13,000×g in an Eppendorf centrifuge. The periplasmic fraction obtained was directly used in the different functional assays (target binding ELISA, in vitro receptor—ligand binding assays and Biacore).

For sequencing, plasmid DNA was prepared from 5-ml cultures grown at 30° C. in LB-medium, containing 100 μg/ml carbenicillin and 2% glucose, using the Qiagen Minikit (Qiagen) or on amplicons with vector primers M13-reverse and geneIII-forward, which anneal at the borders of the Fab insert.

Example 7

Large Scale Production and Purification of Lead Fab's.

Fab inserts from 3 to 6 different leads were recloned via ApaLI-NotI in an expression vector (coded pCBS) identical to pCB3 including the hexahistidine and C-MYC tags fused to the carboxyterminus of the Fd, but lacking the bacteriophage M13 gene3. In parallel the V regions were recloned with the appropriate combination of restriction enzymes and sequentially cloned in gene3 deleted vectors containing human CH1 and Cκ or Cλ for the expression of chimeric Fabs. After fingerprint analysis, individual clones obtained after recloning were grown on 50-ml or 250-ml scale and periplasmic fractions were prepared as described above. Fab fragment was IMAC purified and the correctly formed Fab was further purified via Size Exclusion Chromatography using a Superdex™ 75HR column (Amersham Pharmacia Biotech). Depending on the cell based assay endotoxin was removed by passage over an anion exchange column (Source30Q, GE Healthcare), which was sensitized overnight in 1 M NaOH and subsequently equilibrated in D-PBS. The yield was determined by measuring the optical density at 280 nm using a molar extinction coefficient of 13 for Fabs.

The purified Fab's were tested in the in vitro receptor—ligand binding assay and Biacore to confirm the observations made with the Fab fragment as produced by the gene3 containing pCB3 vector. Finally the potency of the Fab was determined in the bioassay.

Example 8

In this example the llama derived lead Fabs against cytokine x were humanized by using a soft randomization procedure targeting a small set of framework residues and by monovalent display of the resulting Fab library on the surface of filamentous phage in order to identify high affinity framework sequences via affinity based selection (US2003/0190317A1, incorporated herein by reference). For instance, for dromedary derived germline VH (IGHV1S20) a small library was generated for positions 5 (Val, Leu), 55 (Gly, Ala), 83 (Ala, Ser), 95 (Lys, Arg), 96 (Ser, Ala) and 101 (Met, Val) maintaining 70% of the wild type residues (IMGT numbering). Amino acids in the hypervariable loops could be addressed in a similar way.

Site-directed mutagenesis to correct PCR errors or to introduce additional specific single codon changes was performed essentially as described by Kunkel et al. Curr. Protoc. Mol. Biol. CH8U8.1 (2001) or alternatively Synthetic genes encoding the variants ordered from GeneArt. The template for site-directed experiments was single-stranded DNA from a humanized Fab clone.

Site directed mutagenesis was also used to directly change a limited number of amino acid codons for humanization or modification purposes in the DNA encoding the wild type or humanized Fabs.

After selection the individual leads were tested on affinity and potency and the best leads were chosen for reformatting into human Fab/IgGs.

Example 9

Expression of Human Fab Fragments and Human Monoclonal Antibodies.

Starting from the humanized VH and VL regions expression of humanized Fabs was performed as described in Rauchenberger et al. J. Biol. Chem. 278:38194-204 (2003). For the expression of human monoclonal antibodies two separate expressions vectors, one for the light chain and one for the heavy chain construct were constructed based on the pcDNA 3.1 vector. The expression vector for the light chain contained either the human C kappa or human C lambda sequence downstream of a CMV promoter as well as restriction sites allowing the cloning of the light chain construct as KPN1 BsmB1 fragments downstream of the CMV promoter and in frame with the light chain constant domain. The expression vector for the heavy chain contained then human CH1-hinge-CH2-CH3 sequence downstream of a CMV promoter as well as restriction sites allowing the cloning of the VH construct as KPN1 BsmB1 fragments downstream of the CMV promoter and in frame with the heavy chain constant domains.

The VL and VH fragments were cloned into the appropriate expression vectors as KPN1 BsmB1 fragments containing the Kozak sequence followed by the mouse IgG kappa leader sequences in frame with the respective VL or VH sequence. These sequences were obtained by gene synthesis and optimized for expression in mammalian cells (Geneart).

For full length IgG production VH and VL expression vectors constructs were co-transfected into mammalian cells (HEK-293 (transient) or CHO (stable)). Supernatant from transiently transfected cells or from stably transfected cells was purified via protein A chromatography.

Monoclonal antibodies or Fabs were tested in receptor binding assays and in bioassays and the best leads were selected for further development.

Example 10

Generating Fabs Against IL-1 Beta

Unless otherwise indicated, the materials and protocols used in the following study were analogous to those used in examples 1-9.

Llamas were Successfully Immunized with IL-1 Beta

Two llamas (*Lama glama*) were immunized with human IL-1Beta according to a standard protocol (as described in Example 1).

Sera from both llamas were tested for the presence of antibodies against IL-1Beta by ELISA prior (day 0) and after immunization (day 28). As shown in FIG. 1, a specific signal against IL-1Beta was observed in ELISA after immunization, even after 10,000 fold dilution of the serum. This high antibody titer indicates a specific and appropriate immune response.

Fab Libraries with Good Diversity were Constructed

PBLs isolated from both immunized llamas were used for RNA extraction, RT-PCR and PCR-cloning of Fab in a phagemid using the strategy described by de Haard et al (JBC 1999), to obtain a diverse library of good diversity ($2-5\times10^8$).

The following primers were used:

| SEQ ID NO | Name | Sequence |
|---|---|---|
| colspan=3 | Primers for cloning of lambda light chain | |
| 187 | HuVl1A-BACK-ApaLl | GCC TCC ACC AGT GCA CAGTCTGTGYTGACKCAGCC |
| 188 | HuVl1B-BACK-ApaLl | GCC TCC ACC AGT GCA CAGTCTGTGYTGACGCAGCC |
| 189 | HuVl1C-BACK-ApaLl | GCC TCC ACC AGT GCA CAGTCTGTCGTGACGCAGCC |
| 190 | HuVl2-BACK-ApaLl | GCC TCC ACC AGT GCA CAGTCTGCCCTGACTCAGCC |
| 191 | HuVl3A-BACK-ApaLl | GCC TCC ACC AGT GCA CTT TCCTATGAGCTGACWCAGCC |
| 192 | HuVl3B-BACK-ApaLl | GCC TCC ACC AGT GCA CTT TCTTCTGAGCTGACTCAGGA |
| 193 | HuVl4-BACK-ApaLl | GCC TCC ACC AGT GCA CAGCYTGTGCTGACTCAATC |
| 194 | HuVl5-BACK-ApaLl | GCC TCC ACC AGT GCA CAGGCTGTGCTGACTCAGCC |
| 195 | HuVl6-BACK-ApaLl | GCC TCC ACC AGT GCA CTT AATTTTATGCTGACTCAGCC |
| 196 | HuVl7/8-BACK-ApaLl | GCC TCC ACC AGT GCA CAGRCTGTGGTGACYCAGGA |
| 197 | HuVl9-BACK-ApaLl | GCC TCC ACC AGT GCA CWGCCTGTGCTGACTCAGCC |
| 198 | HuVl10-BACK-ApaLl | GCC TCC ACC AGT GCA CAGGCAGGGCTGACTCAGCC |
| 199 | caClambda1-FOR | CTAACACTGGGAGGGGGACACCGTCTTCTC |
| 200 | caClambda2-FOR | CTAACACTGGGAGGGNCTCACNGTCTTCTC |
| colspan=3 | Primers for cloning of kappa light chain | |
| 201 | HuVk1B-BACK-ApaLl | GCC TCC ACC AGT GCA CTT GACATCCAGWTGACCCAGTCTCC |
| 202 | HuVk2-BACK-ApaLl | GCC TCC ACC AGT GCA CTT GATGTTGTGATGACTCAGTCTCC |
| 203 | HuVk3B-BACK-ApaLl | GCC TCC ACC AGT GCA CTT GAAATTGTGWTGACRCAGTCTCC |
| 204 | HuVk2/4-BACK-ApaLl | GCC TCC ACC AGT GCA CTT GAYATYGTGATGACCCAGWCTCC |
| 205 | HuVk5-BACK-ApaLl | GCC TCC ACC AGT GCA CTT GAAACGACACTCACGCAGTCTCC |
| 206 | HuVk6-BACK-ApaLl | GCC TCC ACC AGT GCA CTT GAAATTGTGCTGACTCAGTCTCC |
| 207 | HuVk4B-BACK-ApaLl | GCC TCC ACC AGT GCA CTT GATATTGTGATGACCCAGACTCC |
| 208 | caCHkapFOR-Ascl | GCC TCC ACC GGG CGC GCC TTA TTAGCAGTGTCTCCGGTCGAAGCTCCT |
| 209 | caCHkap2FOR-Ascl | GCC TCC ACC GGG CGC GCC TTA TTARCARTGYCTNCGRTCRAA |
| colspan=3 | Non-tagged primers for cloning of Heavy chain (step 1) | |
| 210 | VH1a-BACK | CAGGTKCAGCTGGTGCAGTCTGG |
| 211 | VH5a-BACK | GARGTGCAGCTGGTGCAGTCTGG |
| 212 | VH4a-BACK | CAGSTGCAGCTGCAGGAGTCTGG |
| 213 | VH4b-BACK | CAGGTGCAGCTACAGCAGTCTGG |
| 214 | VH2b-BACK | CAGGTCACCTTGARGGAGTCTGG |
| colspan=3 | Tagged primers for cloning of Heavy chain (step 2) | |
| 215 | VH1a-BACK-Sfil | CTC GCA ACT GCG GCC CAG CCG GCC ATG GCCCAGGTKCAGC TGGTGCAGTCTGG |
| 216 | VH5a-BACK-Sfil | CTC GCA ACT GCG GCC CAG CCG GCC ATG GCCGARGTGCAGC TGGTGCAGTCTGG |

-continued

| SEQ ID NO | Name | Sequence |
|---|---|---|
| 217 | VH4a-BACK-Sfi1 | CTC GCA ACT GCG GCC CAG CCG GCC ATG GCCCAGSTGCAGC TGCAGGAGTCTGG |
| 218 | VH4b-BACK-Sfi1 | CTC GCA ACT GCG GCC CAG CCG GCC ATG GCCCAGGTGCAGC TACAGCAGTCTGG |
| 219 | VH2b-BACK-Sfi1 | CTC GCA ACT GCG GCC CAG CCG GCC ATG GCCCAGGTCACCT TGARGGAGTCTGG |

Independent VλCλ and VκCκ libraries were constructed using a single (tagged) -PCR step (30 cycles) to conserve a greater clonal diversity.

The VHCH1 libraries were built in parallel using a two step PCR (25 cycles with non tagged primers (step 1) followed by 10 cycles of tagged primers (step 2)).

Next, the light chain from the VλCλ and VκCκ libraries are re-cloned separately in the VHCH1-expressing vector to create the "Lambda" and "Kappa" llama Fab-library respectively (two for each immunized llama). Quality control of the libraries was routinely performed using PCR.

Up to 93% of the clones tested randomly contained full length Fab sequences, indicating a high quality of the libraries.

Human IL-1Beta Specific Fabs were Selected

Phage display was used to identify a large diversity of llama Fabs binding to biotinylated IL-1Beta. Biotinylated IL-1Beta was used for capturing to conserve the active conformation of the protein. After two rounds of selection, a good enrichment compared to control was observed. Phage ELISA revealed presence of clones expressing cytokine specific Fabs (data not shown).

The phage binding to biotinylated IL-1Beta were eluted by pH shock. Sequential dilutions of the output ($10^{-1}$ to $10^{-5}$) were used to infect fresh *E. coli* TG1 cells. The number of colonies obtained indicate the number of phage bound during the selection. In the example above, 5 µl of output gave around $10^5$ phage when selection was done with 100 nM and 10 nM of biot-IL-1Beta. Compared to the $10^2$ phages obtained by non-specific binding, this gives a 1000 fold enrichment.

94 Single clones were grown and used to produce monoclonal phage. These phage were used in a phage ELISA. Many phage showed good binding to biot-IL-1Beta after two rounds of selection on biotinylated IL-1Beta.

Human IL-1Beta Specific Fabs have High Starting Homology to Human Germline

Target specific VH and Vλ domains were matched with those common human germlines showing an identical CDR1 and CDR2 length and corresponding canonical folds. Subsequently the closest human germline was selected based on sequence homology in their framework regions. Non-matching amino acid residues were checked for their presence in other, related human germlines. In case there was no match, these residues were counted as foreign.

TABLE 10

Overall sequence homology of llama VH to human germline

| Closest Human Germline | Matching Clones | % Sequence Homology |
|---|---|---|
| IGHV1-2 | 1C2/2B7/2C12 | 93 |
|  | 2D8 | 94 |
|  | 1G5/2D7 | 93 |
|  | 2E12/2G7 | 94 |

TABLE 10-continued

Overall sequence homology of llama VH to human germline

| Closest Human Germline | Matching Clones | % Sequence Homology |
|---|---|---|
| IGHV3-23 | 1F2 | 98 |
|  | 1G4 | 92 |
|  | 5G7 | 95 |
|  | 5B12 | 92 |
|  | 1A1/2B8/2B9 | 98 |
|  | 1C3/1E3/2A7 | 98 |
| IGHV3-13 | 1E2 | 94 |
|  | 3A3/3B6/3E2/3E3 | 95 |
|  | 3B5/4F1 | 98 |
| IGHV3-20 | 4H1 | 94 |
|  | 4H4 | 93 |

TABLE 11

Overall sequence homology of llama VL to human germline

| Closest Human Germline | Matching Clones | % Sequence Homology |
|---|---|---|
| IGLV8-61 | 1E2 | 90 |
|  | 1F2 | 90 |
|  | 3E2/3E3/3A3 | 86 |
|  | 3B5/4F1 | 86 |
| IGLV2-18 | 3B6 | 91 |
| IGLV5-52 | 1G4 VL | 96 |
| IGLV3-19 | 1C2/2B7/2D7 | 95 |
|  | 2E12/2G7 | 96 |
|  | 2D8 | 95 |

Discussion And Conclusions

A total of 14 target specific VH families, 9 target specific Vλ families and 3 Vκ families were identified based on this very first selection This initial panel of 14 anti-IL-1Beta WT VH's and 12 anti-IL-1Beta WT VL's shows a remarkably high sequence homology to the human germline.

33% of those VH domains have a starting homology of 95% or more to the human situation and about 44% of the VL domains have a starting homology of 95% or more to the human situation, eliminating the need for further humanization.

VH domain 2D8 is a humanized version of VH 1C2 because it has one deviating amino acid residue less as compared to the closest human germline. Its corresponding VL domain (VL 2D8), had a starting homology of 95% which was further increased to 96% by 1 back mutation (VL 2G7) to the closest human germline.

All VH and VL domains, without a single exception, exhibited human 3-D binding site structures (i.e. identical combinations of canonical folds for CDR1 and CDR2 as occurring in the matching human germline segments) when assessed using the methodology described above (data not shown).

Humanization of Fabs 1E2 and 1 F2

Figure 2A:
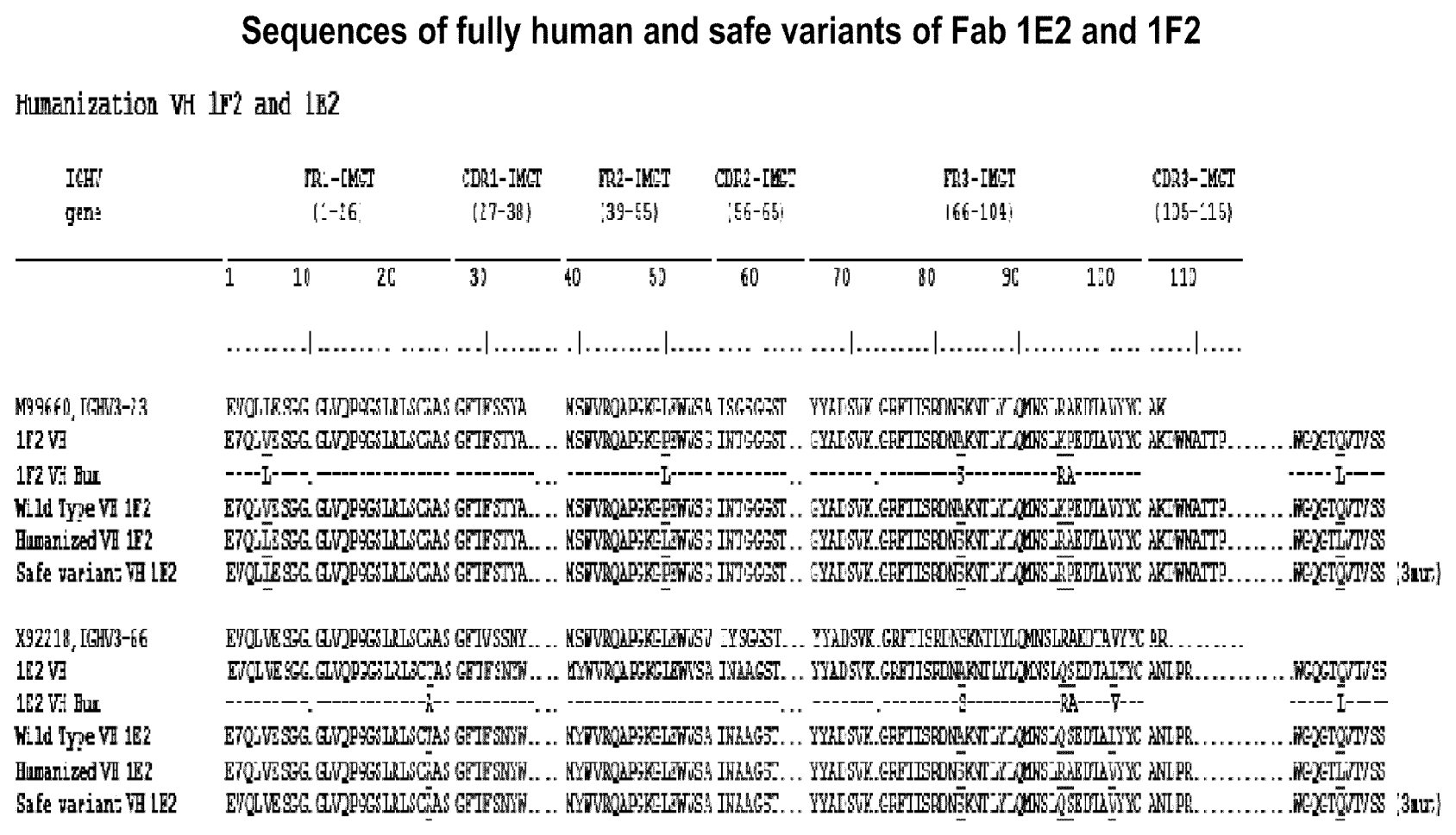
Figure 2B:
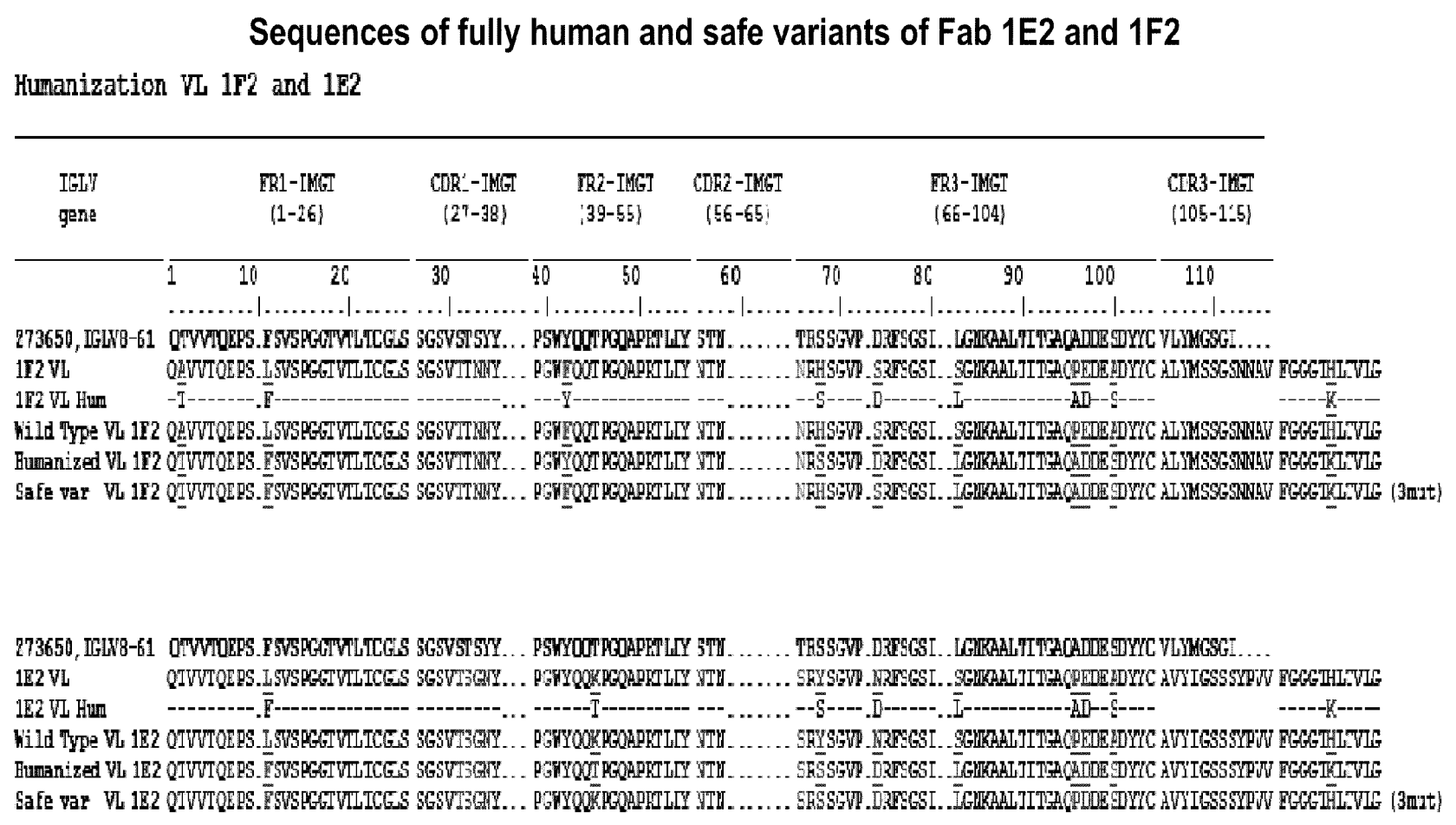

Humanization was performed on two IL-1Beta specific Fabs coded 1E2 and 1F2. Based on the alignment against the closest human germlines, mutations in their VH and Vλ framework regions were proposed (FIG. 2). The germlining of VH matching to the human VH3 family will often involve a number of residues, which already deviate in publically known *Lama glama, Lama pacos* or *Camelus dromedarius* derived germline sequences. For instance, Alanine on position 71 (numbering according to Kabat) and Lysine on 83 and Proline on 84 might be changed into Serine (although Alanine exists in certain human germline VH3 members), Arginine (although Lysine is used by a number of human VH3 germlines) and Alanine, respectively. For light chain variable sequences no germline sequences are available for Camelids, but it is very likely that a number of deviations in FRs from human germline exists that will be changed in the majority of lead antibodies. Besides the fully humanized (hum) and the wild type (wt) V regions, also a "safe variant" with only three wild type residues remaining was proposed (safe).

Fab 1E2 was formatted in a step-by-step approach, whereby the different versions (wt, safe and fully humanized) of the Vλ fused to the human constant domain were combined with various versions of the VH fused to the human constant CH1 domain to generate the Fabs indicated in Table 12.

TABLE 12

Fab 1E2 formats

|  |  | VH 1E2 + hum CH1 | | |
| --- | --- | --- | --- | --- |
|  |  | wt | safe | Hum |
| VL 1$^E$2 + humCL | wt | wt 1E2 | wt/safe | wt/hum |
|  | safe | safe/wt | safe 1E2 | safe/hum |
|  | hum | hum/wt | hum/safe | hum 1E2 |

Figure 3:
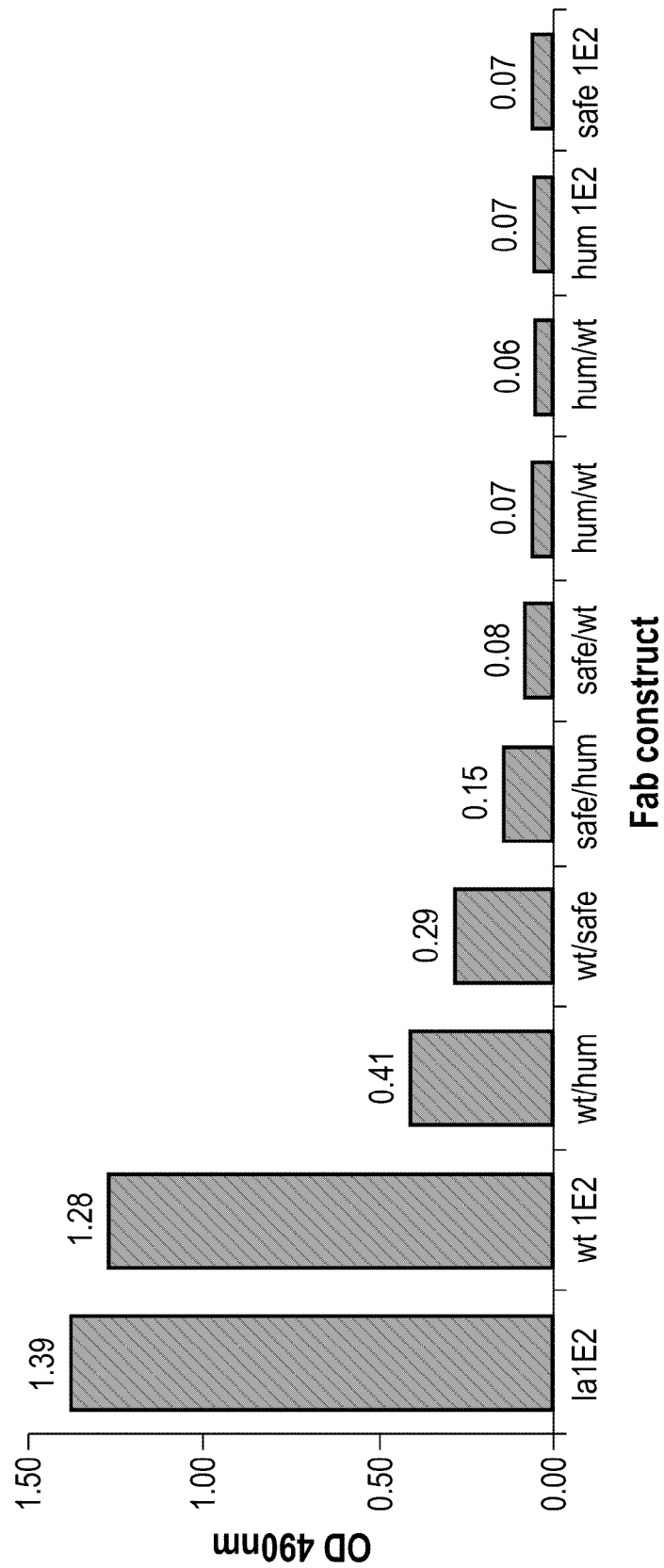
FIG. 3—shows the results of an ELISA in which recombinantly expressed Fabs were tested for their ability to bind biot-IL-1Beta. For this the Fabs were captured on an anti-myc coated Maxisorp plate. Biotinylated human IL-1Beta was added and bound cytokine was detected using HRP-conjugated streptavidin.

The genes of these Fabs were ordered as synthetic genes with GeneArt (Germany) and were subsequently produced in *E. coli*, purified and tested for their ability to bind biot-IL-1Beta. For this the Fabs were captured on an anti-myc coated Maxisorp plate. Biotinylated human IL-1Beta was added and bound cytokine was detected using HRP-conjugated streptavidin. The read out of this assay is represented in FIG. 3 below.

The replacement of the wild type constant domains CH1 and Cλ by their human counterpart did not affect the binding capacity.

Partial (wt Vλ/safe VH) and complete (wt Vλ/hum VH) humanization of the VH domain of 1E2 generated a functional Fab.

Figure 4:
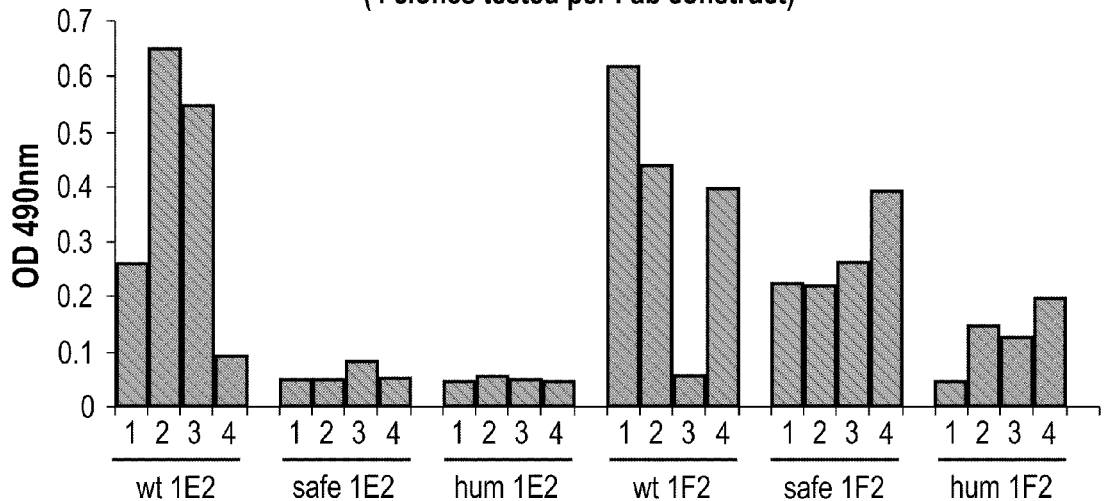
FIG. 4—shows the results of phage ELISA in which phage displaying humanized variants of Fabs 1E2 and 1F2 were tested for binding to IL-1Beta.

The humanized variants of clone 1F2 were tested with phage expressing gene3-Fabs fusions (FIG. 4). Phage were produced from 4 independent clones for each construct:

wt 1F2 and wt 1E2 (llama Vλ and VH fused to human Cλ and CH1)

safe variant 1F2 and safe variant 1E2 (partially humanized Vλ fused to human Cλ and CH1)

hum 1F2 and hum 1E2 (fully humanized Vλ and VH fused to human Cλ and CH1)

Four clones for each Fab were tested to overcome clonal variation (due to bacterial growth, phage production efficiency and toxicity etc. . . . ). Phage ELISA was performed by capturing of biotinylated IL-1Beta on neutravidin coated Maxisorp plate and subsequent incubation of crude phage extract (i.e. bacterial medium). After extensive washing, bound phages were detected with an anti-M13-HRP monoclonal antibody. The same phage preparations when tested on neutravidin coated wells (without biotinylated IL-1Beta) did not give signals (data not shown).

Back mutations in the framework regions of 1F2 VL and VH domains to the closest human germline successfully yield partially (safe) and fully (hum) humanized variants, maintaining antigen specificity.

Successful Formatting of Camelid Variable Domains with Human Constant Domains

The VL and VH variable domains of the IL-1Beta specific clone 1E2 were successfully fused to the human Cλ and CH1 constant domains, resulting in a "chimeric" Fab which was produced and purified.

This chimeric 1E2 Fab was produced by performing the induction for 4 h at 37° C. (o/d) or for 16 h and 28° C. (o/n) from the pCB5 phagemid (Δgene3). The wild type llama 1E2 Fab was produced by performing induction for 16 h at 30° C. from pCB3 (gene3 containing phagemid). After purification, these Fabs were loaded on SDS-PAGE with (reducing) or without (non-reducing) DTT. Coomassie staining was performed, nicely showing the presence of these Fabs or their composing light and heavy chains at the expected molecular weight band (not shown).

Figure 5:
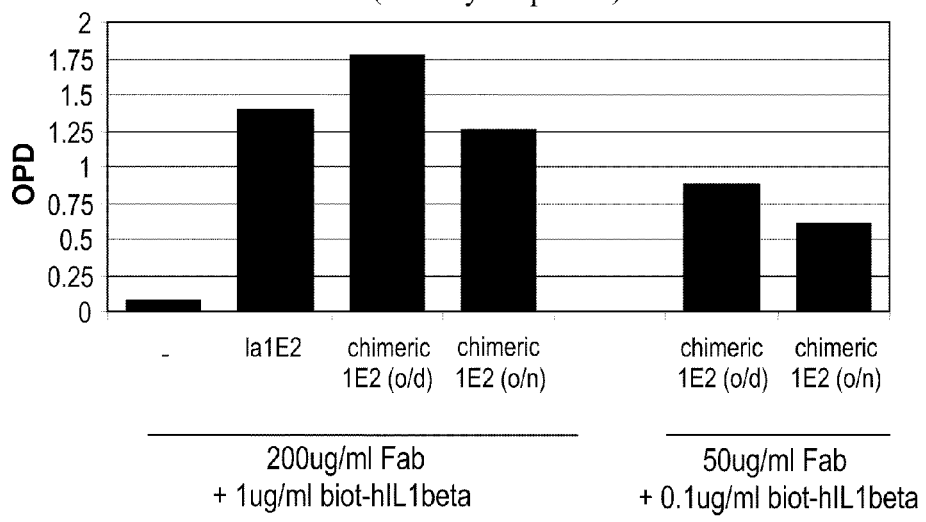
FIG. 5—shows the results of ELISA in which chimeric 1E2 was tested for binding to IL-1Beta.

The purified llama and chimeric 1E2 Fabs described above were captured on anti-myc coated maxisorp plates. After incubation with biotinylated human IL-1Beta and extensive washing, the biotinylated IL-1Beta bound to the Fab was detected using HRP-conjugated streptavidin. Both the purified llama and chimeric 1E2 Fabs exhibited functional target binding (FIG. 5). This finding demonstrates the feasibility to associate Camelid derived variable domains with the constant domains of human IgGs A Subset of Fabs Showed Functional Inhibition of the Target The table below shows the OD values resulting from the following ELISA experiment. Wells were coated with a mouse monoclonal antibody known to inhibit the binding of IL1-Beta with its receptor (provided by Diaclone SAS).

Biotinylated IL-1Beta was added to the wells together with periplasmic extracts of Fabs identified after 2 rounds of selection against biotinylated IL-1Beta. Detection of the bound biotinylated IL-1Beta happened through HRP labeled streptavidin. A reduced signal indicated the competition of a specific Fab with the blocking mouse monoclonal antibody, suggesting antagonism.

A positive control was included in well G12 by spiking in a large amount of the competing mouse monoclonal (well 12G in Table 13).

TABLE 13

Results of competition assay

|   | 6A | | | | | | 6C | | | | | |
|---|---|---|---|---|---|---|---|---|---|---|---|---|
|   | 1 | 2 | 3 | 4 | 5 | 6 | 7 | 8 | 9 | 10 | 11 | 12 |
| A | 0.205 | 0.621 | 0.670 | 0.691 | 0.704 | 0.823 | 0.353 | 0.737 | 0.726 | 0.544 | 0.551 | 0.626 |
| B | 0.668 | 0.546 | 0.444 | 0.632 | 0.614 | 0.627 | 0.442 | 0.641 | 0.558 | 0.693 | 0.565 | 0.548 |
| C | 0.756 | 0.541 | 0.386 | 0.572 | 0.763 | 0.593 | 0.517 | 0.537 | 0.518 | 0.588 | 0.473 | 0.435 |
| D | 0.521 | 0.790 | 0.203 | 0.792 | 0.801 | 0.263 | 0.619 | 0.483 | 0.631 | 0.592 | 0.455 | 0.603 |
| E | 0.798 | 0.545 | 0.359 | 0.528 | 0.281 | 0.655 | 0.618 | 0.516 | 0.651 | 0.493 | 0.575 | 0.367 |
| F | 0.747 | 0.611 | 0.520 | 0.599 | 0.203 | 0.204 | 0.605 | 0.373 | 0.550 | 0.516 | 0.602 | 0.392 |
| G | 0.498 | 0.477 | 0.539 | 0.693 | 0.663 | 0.197 | 0.554 | 0.589 | 0.807 | 0.528 | 0.634 | 0.063 |
| H | 0.628 | 0.493 | 0.552 | 0.900 | 0.858 | 0.635 | 0.170 | 0.574 | 0.559 | 0.598 | 0.593 | 0.378 |

A number of Fabs were identified which successfully compete with the blocking mouse monoclonal antibody (indicated by shaded cells in Table 13). Sequence analysis of the competing clones revealed the presence of three Fabs with different VH, which were present in 48 screened clones (part of the plate coded 6A in Table 13). The sequence alignments against the closest human germline and the structural homology analysis of the VH of the antagonistic Fab 1A1 (giving a signal of 0.205 in the competition assay of Table 13), 1B3 (signal of 0.444) and the related clone 1G1 (signal of 0.498) and finally 1C3 (signal of 0.386) are shown below.

All three have a very high degree of sequence homology with the matching human germline and have the identical canonical fold combinations as found in the human germline. This was also observed for the lambda light chain in the three antagonistic leads (data not shown). Fab 1A1 competes strongly with the antagonistic reference monoclonal antibody (IC50 of 12 µg/ml in ELISA based competition assay), whereas Fab 1C3 hardly shows competition (only at concentrations of more than 50 µg/ml). However, in the bioassay 1C3 is more potent (IC50 of 3 µg/ml) than 1A1 (IC50 of 10 µg/ml), which suggests a different epitope recognition. The high frequency of different antagonistic Fabs (3 different antibodies in 48 screened clones) and the difference in epitope recognition as found for two of these illustrates the high diversity of antibodies as the result of the outbred nature of the lama. The high degree of sequence homology with human germline V regions combined with the high diversity of (potent) antibodies and the broad epitope coverage enables the identification of panels of therapeutic antibodies from immunized camelids.

```
IGHV
gene
Kabat
FR/CDR          FR1-Kabat                         CDR1 Kabat     FR2-Kabat          CDR2 Kabat IMGT numbering  1         10        20        30            40             50                60         70
                .........|.........|.........|    ........|     .........|....    .....|.........|....
M99660, IGHV3-  EVQLLESGG.GLVQPGGSLRLSCAASGFTF    SSYA....MS    WVRQAPGKGLEWVS    AISGSGGST..YYADSVK.G
23 VH-1A1,      EVQLLESGG.GLVQPGGSLRLSCAASGFTF    DDYA....MS    WVRQAPGKGLEWVS    TISWNGGAT..YYAESMK.G
3E8,3D9

IGHV gene
Kabat FR/CDR    FR3-Kabat                              CDR3 Kabat          FR4 (IGHJ)

IMGT numbering        80        90        100            110       120          130
                 .....|.........|.........|......     ...|.........|.    .........|..
M99660, IGHV3-23 RFTISRDNSKNTLYLQMNSLRAEDTAVYYCAK                                              SEQ ID NO: 1
VH-1A1, 3E8,3D9  RFTISRDNAKNTLYLQMNSLKSEDTAVYYCAK     PYYSDYVGVEYDY      WGQGTQVTVSS        SEQ ID NO: 220

5 V    primer encoded and also in all other class 3 except 3-23
 53 A    occurs in all VH3 family members except 3-23
 95 K    also in IGHV3.13/49/66/72 and classes 5 and 7
 96 S    not in class 3 but in class 1
127 Q    not in human germline
Overall homology
84/86 framework residues = 98% homology
Canonical folds analysis
CDR H1 Class 1/10A [2fbj]
CDR H2 Class ?
!Similar to class 1/10B, but:
! H66 (Chothia Numbering) = A (allows: SYTNDR) SEQ ID NO: 221
```

| IGHV gene Kabat FR/CDR | FR1-Kabat | CDR1 Kabat | FR2-Kabat | CDR2 Kabat |
|---|---|---|---|---|
| IMGT numbering | 1        10        20        30 | 40 | 50 | 60        70 |
| | .........|.........|.........| | .........| | .........|.... | .....|.........|.... |
| M99660, IGHV3-23 | EVQLLESGG.GLVQPGGSLRLSCAASGFTF | SSYA....MS | WVRQAPGKGLEWVS | AISGSGGST..YYADSVK.G |
| VH-1C3, 1E3, 2A7 | EVQLVESGG.GLVQPGGSLRLSCAASGFTF | SSYW....MY | WVRQAPGKGLEWVS | AINTGGGRT..YYADSVK.G |

| IGHV gene Kabat FR/CDR | FR3-Kabat | CDR3 Kabat | FR4 (IGHJ) | |
|---|---|---|---|---|
| IMGT numbering | 80        90        100 | 110        120 | 130 | |
| | .....|.........|.........|...... | ...|.........|. | .........|.. | |
| M99660, IGHV3-23 | RFTISRDNSKNTLYLQMNSLRAEDTAVYYCAK | | | SEQ ID NO: 1 |
| VH-1C3, 1E3, 2A7 | RFTISRDNAKNTLYLQMNSLKSEDTAVYYCAK | GTSADGSSWYVPADPYDY | WGQGTQVTVSS | SEQ ID NO: 222 |

5 V    primer encoded and also in all other class3 except 3-23

83 A    occurs in all VH3 family members except 3-23

95 K    also in IGHV3.13/49/66/72 and classes 5 and 7

96 S    not in class 3 but in class 1

127 Q    not in human germline

Overall homology

94/86 framework residues = 98% homology

Canonical folds analysis

CDR H1 Class 1/10A [2fbj]

CDR H2 Class ?

!Similar to class 2/10A, but:

! H71 (Chothia Numbering) = R (allows: VAL)

| IGHV gene Kabat FR/CDR | FR1-Kabat | CDR1 Kabat | FR2-Kabat | CDR2 Kabat |
|---|---|---|---|---|
| IMGT numbering | 1        10        20        30        40 | 50 | 60        70 | |
| | .........|.........|.........|.........| | .........|.... | .....|........|.... | |
| X07448, IGHV1-2 | QVQLVQSGA.EVKKPGASVKVSCKASGYTFTGYYMH.. | WVRQAPGQGLEWMG | RINPNSGGT.NYAQKFQ.G | |
| VH-1B3, 1G2, | EVQLVQSGA.ELRNPGASVKVSCKASGYTFTSYYID.. | WVRQAPGQGLEWMG | RIDPEDGGT.KYAQKFQ.G | |
| 2D8 VH-1G1, 2B7 | EVQLVQSGA.ELRNPGASVKVSCKASGYTFTSYYTD.. | WVRQAPGQGLEWMG | RIDPEDGGT.KYAQKFQ.G | |

-continued

| IGHV gene Kabat FR/CDR | FR3-Kabat | CDR3 Kabat | FR4 (IGHJ) | |
|---|---|---|---|---|
| IMGT numbering | 80        90        100 | 110       120 | 130 | |
|  | .....\|.........\|.........\| | .........\|.........\|. | ........\|.. | |
| X07448, IGHV1-2 | RVTSTRDTSISTAYMELSRLRSDDTV-VYYCAR |  |  | SEQ ID NO: 223 |
| VH-1B3, 1G2, 2D8 | RVTFTADTSTSTAYVWLSSLRSED-TAVYYCAR | SGRYELDY....... | WGQGTQVTVSS | SEQ ID NO: 224 |
| VH-1G1, 2B7 | RVTFTADTSTSTAYVWLSSLRSED-TAVYYCLR | SGAYELDY....... | WGQGTQVTVSS | SEQ ID NO: 225 |

```
  1 E    Primer encoded, occurs as well in IGHV1-f
 11 L    occurs in class 2,3,4,6 and 7
 12 R    not in human germline
 13 N    not in human germline
 78 F    occurs in class 7
 85 G    occurs in class 7
 80 A    present in two class1 members
 84 T    occurs in half of class 1 members
 89 V    not in human germline
 93 S    present in majority of class 1 members
 97 E    present in majority of class 1 members
127 Q    not in human germline
Overall homology
79/86 framework residues = 92% homology
Canonical folds analysis
CDR H1 Class ?
!Similar to class 1/10A, but:
! H35 (Chothia Numbering) = D (allows: HENQSYT) SEQ ID NO: 226
! H80 (Chothia Numbering) = V (allows: LM)
CDR H2 Class ?
!Similar to class 2/10A, but:
! H53 (Chothia Numbering) = E (allows: AGYSKTN) SEQ ID NO: 227
```

Example 11

The following example demonstrates the functional diversity which can be achieved by immunisation of camelids, in comparison with the established mouse monoclonal antibody approach.

10 BALB/c mice were immunized with a recombinant produced cytokine with a small molecular weight. After completion of the immunization protocol, the animals were sacrificed, and hybridomas were generated by immortalizing their spleen cells. Supernatant of the resulting hybridomas was tested in the cytokine binding ELISA and subsequently in a suitable bioassay. One highly potent antagonist and one weaker antagonist could be identified.

Also, 4 llamas were immunized with the same recombinant produced cytokine, using the general protocol described herein. After completion of the immunization protocol, peripheral B lymphocytes were harvested and their RNA was extracted and purified. Using a set of llama specific primers, Fab libraries were generated using the phage display technique. Those Fabs were tested in the cytokine/cytokine receptor binding ELISA. 5 different VH families could be identified from the first 2 llamas, and 6 additional different VH families from the next 2 llamas, which blocked the cytokine/receptor interaction with high potency, meaning that those VH domains contained uniquely different CDRs, both in length and amino acid sequence.

Thus a higher functional diversity could be achieved from a small number of outbred llamas as opposed to a higher number of inbred BALB/c mice. All VH families obtained by active immunisation of llamas exhibited an extraordinary sequence homology as compared to the closest human germline and had the same canonical fold combinations for CDR1 and CDR2 as the matching human germlines.

Example 12

The following table summarises the results of amino acid sequence homology comparisons between germline VH domains of alpaca (*Lama pacos*) and the closest matching human germline VH domains. % homology was calculated using the same algorithm as described herein for *Lama glama*. Raw VH sequence data for *Lama pacos* is not shown:

TABLE 14 amino acid sequence homology germline
VH of *Lama pacos* vs human

| Alpaca (*Lama pacos*) germline VH family | Frequency | % amino acid sequence homology with closest matching human germline VH |
|---|---|---|
| VH3 | 70% (36/51) | ≥95% |
| VH1 | 10% (5/51) | 90-92% |
| VH2(NB *Lama pacos* VH2 aligns to human VH4) | 20% (10/51) | 81-88% |

Example 13

Derivation of Amino Acid Replacements for Humanisation

Multiple cDNA sequences encoding mature camelid VH domains were cloned and fully sequenced. In addition, the sequences of multiple camelid germline fragments encoding camelid Vλ/Vκ domains were obtained.

This vast amount of raw sequence information (not shown) was then processed bioinformatically. For each of the raw camelid sequences, the closest matching human germline sequence was derived, following the approach described elsewhere herein. This in turn permitted the derivation of consensus sequences for camelid VH and Vλ/Vκ domains belonging to different families or subfamilies, and also allowed direct comparison of members of each family or subfamily to their closest matching human germline. Consensus sequences for each camelid family or subfamily were then aligned and compared to consensus sequences for multiple different human germline families or subfamilies. These sequence alignments are shown in the accompanying figures.

In total 163 mature VH, 78 Vκ and 148 Vλ sequences were analyzed. For Vκ 75 out of 78 sequences contained a CDR3 with 9 AA as observed in the majority of somatically mutated human Vκ and all of these had proline at position 95 and 73 out of these 75 carried glutamine at position 90, which is associated with a canonical fold type 1 (Knappik et al., J. Mol. Biol. 296:57-86 (2000)) typical for human Vκs as well. Only two Vκ had a CDR3 of 8 residues and one Vκ with a CDR3 of 10 residues. The collection of camelid Vλ 80 out of 148 analyzed sequences carried a CDR3 with 10 amino acid residues, 23 with a CDR3 length of 9 residues, 2 with 8 residues, 30 with 11 residues, 8 with 12 residues, 4 with 13 residues and 1 with 14 residues. These observations correlate with the human system, in which there is a large variation in CDR3 length observed in the Vλ, with 92% of somatically mutated human Vλs having a CDR3 length between 9 and 11 residues (90% observed in the Llama immune system).

Based on the sequence comparisons outlined above, it was possible to 1) identify positions within camelid VH and Vλ/Vκ domains which commonly exhibit mismatches with human VH and Vλ/Vκ sequences, thereby identifying candidate residues to be considered for replacement, and 2) calculate % utilisation of different amino acids at each of these positions in human VH and Vλ/Vκ domain sequences, thereby identifying suitable replacement residues at each position. This % utilisation data is summarised in FIGS. 30 to 42.

Equivalents

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures, tables, appendices and/or annexes, regardless of the format of such literature and similar materials, are expressly incorporated by reference in their entirety. In the event that one or more of the incorporated literature and similar materials differs from or contradicts this application, including defined terms, term usage, described techniques, or the like, this application controls. Such equivalents are intended to be encompassed by the following claims.

The invention claimed is:

1. A chimeric antibody which specifically binds a target antigen, the chimeric antibody comprising a VH domain comprising HCDR1, HCDR2, and HCDR3 region amino acid sequences and a VL domain comprising LCDR1, LCDR2, and LCDR3 region sequences, wherein the HCDR1, HCDR2, HCDR3, LCDR1, LCDR2, and LCDR3 region sequences are obtained from a conventional camelid antibody, wherein the conventional camelid antibody is a heterotetrameric IgG antibody composed of two identical light chains and two identical heavy chains, wherein the heavy chains comprise a camelid VH domain paired with a camelid VL domain of said light chains, wherein the camelid VH domain has a sequence identity of 90% or more to a human VH domain germline sequence across the framework regions FR1, FR2, FR3 and FR4, wherein the VH domain amino acid sequence of the chimeric antibody is obtained by substituting one or more amino acid residues of the camelid VH domain at one or more positions selected from the group consisting of H1, H5, H7, H11, H12, H13, H14, H29, H30, H37, H40, H48, H67, H68, H69, H71, H74, H77, H78, H80, H81, H82b, H83, H84, H85, H86, H89, H93, H94 and H108, according to Kabat, with amino acids that are found at the corresponding positions in the human germline VH domain sequence, wherein the VH domain and the VL domain of the chimeric antibody are each fused to one or more IgG constant domains of a human antibody, and and wherein the HCDR1 and HCDR2 or the LCDR1 and LCDR2 of the conventional camelid antibody exhibit a combination of canonical fold structures which is identical or substantially identical to a combination of canonical fold structures for HCDR1 and HCDR2 or LCDR1 and LCDR2 of a human antibody.

2. The antibody of claim 1, wherein the human VH domain germline sequence is a human VH3 domain germline sequence, and wherein the one or more positions are selected from the group consisting of H1, H13, H14, H29, H30, H37, H40, H74, H77, H78, H82b, H83, H84, H86, H89, H93 and H94.

3. The antibody of claim 2, comprising one or more amino acid replacements selected from the group consisting of:
(a) amino acid at H74 replaced with S or A;
(b) amino acid at H83 replaced with R or K;
(c) amino acid at H84 replaced with A or T; and
(d) amino acid at H94 replaced with R.

4. The antibody of claim 3, comprising one or more amino acid replacements selected from the group consisting of:
(a) amino acid at H1 replaced with Q or E;
(b) amino acid at H13 replaced with Q, K or R;
(c) amino acid at H14 replaced with P
(d) amino acid at H29 replaced with F or V;
(e) amino acid at H30 replaced with S, D or G;

(f) amino acid at H37 replaced with V, F or I;
(g) amino acid at H40 replaced with A;
(h) amino acid at H77 replaced with T or S;
(i) amino acid at H78 replaced with L or A;
(j) amino acid at H82b replaced with S;
(k) amino acid at H86 replaced with D;
(l) amino acid at H89 replaced with V or L; and
(m) amino acid at H93 replaced with A or T.

5. The antibody of claim 1, wherein the human VH domain germline sequence is a human VH1 domain germline sequence, and wherein the one or more positions are selected from the group consisting of H1, H7, H11, H12, H13, H69, H71, H78, H80 and H86, according to Kabat.

6. The antibody of claim 5, comprising one or more amino acid replacements selected from the group consisting of:
(a) amino acid at H1 replaced with Q or E;
(b) amino acid at H7 replaced with S;
(c) amino acid at H11 replaced, with V;
(d) amino acid at H12 replaced with K;
(e) amino acid at H13 replaced with K;
(f) amino acid at H69 replaced with I, M or S;
(g) amino acid at H71 replaced with R, A, E or T;
(h) amino acid at H78 replaced with V or A;
(i) amino acid at H80 replaced with M; and
(j) amino acid at H86 replaced with D.

7. The antibody of claim 1, wherein the human VH domain germline sequence is a human VH4 domain germline sequence, and wherein the one or more positions are selected from the group consisting of H1, H16, H23, H30, H48, H49, H67, H68, H71, H81, H84, H85, and H86, according to Kabat.

8. The antibody of claim 7, comprising one or more amino acid replacements selected from the group consisting of:
(a) amino acid at H1 replaced with Q or E;
(b) amino acid at H16 replaced with E;
(c) amino acid at H23 replaced with A or T;
(d) amino acid at H30 replaced with S;
(e) amino acid at H48 replaced with I;
(f) amino acid at H67 replaced with V;
(g) amino acid at H68 replaced with T;
(h) amino acid at H71 replaced with V;
(i) amino acid at H81 replaced with K;
(j) amino acid at H84 replaced with A;
(k) amino acid at H85 replaced with A;
(l) amino acid at H86 replaced with D; and
(m) amino acid at H108 replaced with L.

9. The antibody of claim 1,
wherein the camelid VL domain has homology to a human Vλ domain germline sequence, and
wherein the VL domain sequence of the chimeric antibody is obtained by substituting one or more amino acids of the camelid VL domain at one or more positions selected from the group consisting of L1, L2, L3, L5, L7, L8, L9, L11, L14, L15, L18, L17, L19, L20, L38, L39, L40, L42, L44, L46, L47, L49, L58, L59, L60, L66, L67, L69, L70, L71, L72, L74, L76, L78, L80, L81, L84, L103, L104 and L108, according to Kabat, with amino acids that are found at the corresponding positions in the human Vλ domain germline sequence.

10. The antibody of claim 9, wherein the human Vλ domain germline sequence is a human Vλ1 domain germline sequence, and wherein the one or more positions in the camelid VL domain are selected from the group consisting of L11, L14, L18, L19, L38, L69, L74, L76 and L80, according to Kabat.

11. The antibody of claim 10, comprising one or more amino acid replacements selected from the group consisting of:
(a) amino acid at L11 replaced with A or V;
(b) amino acid at L14 replaced with A or T;
(c) amino acid at L18 replaced with R or K;
(d) amino acid at L19 replaced with V;
(e) amino acid at L38 replaced with Q;
(f) amino acid at L69 replaced with T;
(g) amino acid at L74 replaced with A or G;
(h) amino acid at L76 replaced with S or T; and
(i) amino acid at L80 replaced with S, T or A.

12. The antibody of claim 9, wherein the human Vλ domain germline sequence is a human Vλ2 domain germline sequence, and wherein the one or more positions in the camelid VL domain are selected from the group consisting of L3, L8, L14, L15, L17, L18, L39, L42, L47, L58, L59 and L80, according to Kabat.

13. The antibody of claim 12, comprising one or more amino acid replacements selected from the group consisting of:
(a) amino acid at L3 replaced with A;
(b) amino acid at L8 replaced with A, P or R;
(c) amino acid at L14 replaced with S;
(d) amino acid at L15 replaced with P;
(e) amino acid at L17 replaced with Q;
(f) amino acid at L18 replaced with S;
(g) amino acid at L39 replaced with H or P;
(h) amino acid at L42 replaced with K or T;
(i) amino acid at L47 replaced with M;
(j) amino acid at L58 replaced with V;
(k) amino acid at L59 replaced with P or S; and
(l) amino acid at L80 replaced with A.

14. The antibody of claim 9, wherein the human Vλ domain germline sequence is a human Vλ3 domain germline sequence, and wherein the one or more positions in the camelid VL domain are selected from the group consisting of L1, L2, L3, L5, L7, L8, L9, L11, L14, L15, L19, L20, L44, L46, L49, L60, L66, L67, L69, L70, L71, L72, L76, L78 and L84, according to Kabat.

15. The antibody of claim 14, comprising one or more o amino acid replacements selected from the group consisting of:
(a) amino acid at L1 replaced with S;
(b) amino acid at L2 replaced with Y;
(c) amino acid at L3 replaced with E;
(d) amino acid at L5 replaced with M;
(e) amino acid at L7 replaced with D, L or P;
(f) amino acid at L8 replaced with P, S, L or H;
(e) amino acid at L9 replaced with S or A;
(f) amino acid at L11 replaced with V;
(g) amino acid at L14 replaced with A or S;
(h) amino acid at L15 replaced with P, L or T;
(i) amino acid at L19 replaced with A or V;
(j) amino acid at L20 replaced with R or S;
(k) amino acid at L44 replaced with P;
(l) amino acid at L46 replaced with L;
(m) amino acid at L49 replaced with Y;
(n) amino acid at L60 replaced with E or D;
(o) amino acid at L66 replaced with S, N or T;
(p) amino acid at L67 replaced with S or P;
(q) amino acid at L69 replaced with T or N;
(r) amino acid at L70 replaced with T, M or I;
(s) amino acid at L71 replaced with A, V or T;
(t) amino acid at L72 replaced with T or S;
(u) amino acid at L76 replaced with S or T;
(v) amino acid at L78 replaced with V, A, T or I; and
(w) amino acid at L84 replaced with A.

16. The antibody of claim 9, wherein the human Vλ domain germline sequence is a human Vλ5 domain germline sequence, and wherein the one or more positions in the camelid VL domain are selected from the group consisting of L2, L11, L17, L19, L40, L70, L72 and L80, according to Kabat.

17. The antibody of claim 16, comprising one or more amino acid replacements selected from the group consisting of:
   (a) amino acid at L2 with P;
   (b) amino acid at L11 replaced with L, S or H;
   (c) amino acid at L17 replaced with A or E;
   (d) amino acid at L19 replaced with A or V;
   (e) amino acid at L40 replaced with P;
   (f) amino acid at L70 replaced with A or T;
   (g) amino acid at L72 replaced with I or L; and
   (h) amino acid at L80 replaced with S or P.

18. The antibody of claim 9, wherein the human Vλ domain germline sequence is a human Vλ8 domain germline sequence, and wherein the one or more positions in the camelid VL are selected from the group consisting of L2, L11, L60, L67, L80, L81 and L84, according to Kabat.

19. The antibody of claim 18, comprising one or more amino acid replacements selected from the group consisting of:
   (a) amino acid at L2 replaced with T;
   (b) amino acid at L11 replaced with F;
   (c) amino acid at L60 replaced with D;
   (d) amino acid at L67 replaced with L;
   (e) amino acid at L80 replaced with A;
   (f) amino acid at L81 replaced with D; and
   (g) amino acid at L84 replaced with S.

20. The antibody of claim 9, wherein the amino acid at L103 is replaced with K.

21. The antibody of claim 1,
   wherein the camelid VL domain has homology to a human Vκ domain germline sequence, and
   wherein the VL domain amino acid sequence of the chimeric antibody is obtained by substituting one or more amino acids of the camelid VL domain at one or more positions selected from the group consisting of K1, K2, K3, K4, K7, K9, K11, K12, K13, K14, K15, K18, K19, K36, K39, K42, K43, K45, K46, K58, K63, K68, K70, K77, K78, K79, K80, K83, K100, K103, K104 and K106, according to Kabat, with amino acids that are found at the corresponding positions in the human Vκ domain germline sequence.

22. The antibody of claim 21, wherein the human Vκ domain germline sequence is a human Vκ1 domain germline sequence, and wherein the one or more of positions in the camelid VL domain are selected from the group consisting of K1, K2, K4, K11, K12, K13, K15, K42, K43, K70, K77, K79, K80 and K83, according to Kabat.

23. The antibody of claim 22, comprising one or more amino acid replacements selected from the group consisting of:
   (a) amino acid at K2 replaced with D, A or N;
   (b) amino acid at K4 replaced with M or L;
   (c) amino acid at K11 replaced with V;
   (d) amino acid at K12 replaced with K;
   (e) amino acid at K13 replaced with K;
   (f) amino acid at K15 replaced with V or T;
   (g) amino acid at K42 replaced with K;
   (h) amino acid at K43 replaced with A or V;
   (i) amino acid at K70 replaced with D or E;
   (j) amino acid at K77 replaced with S or C;
   (k) amino acid at K79 replaced with Q;
   (l) amino acid at K80 replaced with P or S; and
   (m) amino acid at K83 replaced with F, I or V.

24. The antibody of claim 21, wherein the human Vκ domain germline sequence is a human Vk2 domain germline sequence, and wherein the one or more positions in the camelid VL domain are selected from the group consisting of K7, K9, K12, K14, K18, K36, K46, K63, K77, K79 and K83, according to Kabat.

25. The antibody of claim 24, comprising one or more amino acid replacements selected from the group consisting of:
   (a) amino acid at K7 replaced with T or S;
   (b) amino acid at K9 replaced with L;
   (c) amino acid at K12 replaced with P or S;
   (d) amino acid at K14 replaced with T;
   (e) amino acid at K18 replaced with P or Q;
   (f) amino acid at K36 replaced with Y, F or L;
   (g) amino acid at K46 replaced with L or R;
   (h) amino acid at K63 replaced with S;
   (i) amino acid at K77 replaced with R;
   (j) amino acid at K79 replaced with E; and
   (k) amino acid at K83 replaced with V or F.

26. (Withdrawn - Currently Amended) The antibody of claim 21, wherein the human Vκ domain germline sequence is a human Vk4 domain germline sequence, and wherein the one or more positions in the camelid VL domain are selected from the group consisting of K9, K11, K12, K13, K15, K18, K19, K39, K43, K45, K58, K68, K78, K80 and K83, according to Kabat.

27. The antibody of claim 26, comprising one or more amino acid replacements selected from the group consisting of:
   (a) amino acid at K9 replaced with D;
   (b) amino acid at K11 replaced with L;
   (c) amino acid at K12 replaced with A;
   (d) amino acid at K13 replaced with V;
   (e) amino acid at K15 replaced with L;
   (f) amino acid at K18 replaced with R;
   (g) amino acid at K19 replaced with A;
   (h) amino acid at K39 replaced with K;
   (i) amino acid at K43 replaced with P;
   (j) amino acid at K45 replaced with K;
   (k) amino acid at K58 replaced with V;
   (l) amino acid at K68 replaced with G;
   (j) amino acid at K78 replaced with L;
   (k) amino acid at K80 replaced with A; and
   (l) amino acid at K83 replaced with V.

28. The antibody of claim 21, further comprising amino acid replacements selected from the group consisting of
   (a) amino acid at K103 replaced with K;
   (b) amino acid at K104 replaced with V; and
   (c) amino acid At K106 replaced with I.

29. The antibody of claim 1, which is a Fab, Fab', F(ab')2, bi-specific Fab', linear antibody, or multispecific antibody.

30. The antibody of claim 1, wherein the conventional camelid antibody is from a camelid selected from the group consisting of camel, llama, dromedary, vicuna, guanaco and alpaca.

31. The antibody of claim 1, wherein the conventional camelid antibody is obtained by active immunisation of a camelid with a target antigen, or with a polynucleotide encoding said target antigen.

32. The antibody of claim 1, wherein the VH domain of the conventional camelid antibody exhibits a sequence identity of 95% or greater with the human VH domain germline sequence across the framework regions FR1, FR2, FR3 and FR4.

33. The antibody of claim 1 wherein the VH domain of the conventional camelid antibody exhibits a sequence identity of 97% or greater with the human VH domain germline sequence across the framework regions FRp1, FR2, FR3 and FR4.

* * * * *